(12) United States Patent
Ceccarelli et al.

(10) Patent No.: US 9,809,599 B2
(45) Date of Patent: Nov. 7, 2017

(54) ARYL-QUINOLINE DERIVATIVES

(71) Applicant: Hoffmann-La Roche Inc., Nutley, NJ (US)

(72) Inventors: Simona M. Ceccarelli, Basel (CH); Aurelia Conte, Shanghai (CN); Holger Kuehne, Loerrach (DE); Bernd Kuhn, Reinach (CH); Werner Neidhart, Hagenthal-le-Bas (FR); Ulrike Obst Sander, Reinach (CH); Markus Rudolph, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/938,005

(22) Filed: Nov. 11, 2015

(65) Prior Publication Data
US 2016/0060270 A1   Mar. 3, 2016

Related U.S. Application Data

(63) Continuation of application No. 13/666,202, filed on Nov. 1, 2012, now Pat. No. 9,199,938.

(30) Foreign Application Priority Data

Nov. 4, 2011   (EP) ..................... 11187967

(51) Int. Cl.
| | |
|---|---|
| C07D 215/00 | (2006.01) |
| C07D 215/02 | (2006.01) |
| C07D 215/54 | (2006.01) |
| C07D 401/04 | (2006.01) |
| C07D 413/04 | (2006.01) |
| C07D 491/048 | (2006.01) |
| C07D 401/14 | (2006.01) |
| C07D 215/227 | (2006.01) |
| C07D 413/14 | (2006.01) |

(52) U.S. Cl.
CPC ....... *C07D 491/048* (2013.01); *C07D 215/00* (2013.01); *C07D 215/02* (2013.01); *C07D 215/227* (2013.01); *C07D 215/54* (2013.01); *C07D 401/04* (2013.01); *C07D 401/14* (2013.01); *C07D 413/04* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 8,633,187 B2 | 1/2014 | Knight et al. | |
| 2010/0125091 A1* | 5/2010 | Abelman ............ | C07D 215/18 514/313 |
| 2012/0136018 A1 | 5/2012 | Kolczewski et al. | |

FOREIGN PATENT DOCUMENTS

| | | |
|---|---|---|
| WO | 2008049047 A2 | 4/2008 |
| WO | 2013/064465 A1 | 5/2013 |
| WO | 2013064520 A1 | 5/2013 |
| WO | 2013067423 A1 | 5/2013 |
| WO | 2013067434 A1 | 5/2013 |

OTHER PUBLICATIONS

STN search result (RN 307329-54-0, entry date Dec. 7, 2000).*
Tawada et al. (Chemical & Pharmaceutical Bulletin, 43(4):616-625, 1995).*
Ghorbani-Vaghei et al. (Tetrahedron Letters, 50(9): 1055-1058, 2009).*
The English translation of the Colombian Office Action, dated Dec. 17, 2015, in the related Colombian Patent Application No. 14-068.491.

* cited by examiner

*Primary Examiner* — Bong-Sook Baek

(57) ABSTRACT

The invention provides novel compounds having the general formula (I)

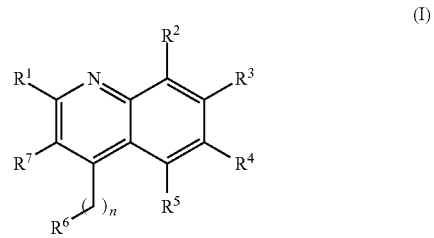

wherein $R^1$, $R^2$, $R^3$, $R^4$, $R^5$, $R^6$ and n are as described herein, compositions including the compounds and methods of using the compounds. The present compounds are useful as fatty-acid binding protein (FABP) 4 and/or 5 inhibitors and may be used for the treatment or prophylaxis of lipodystrophy, type 2 diabetes, dyslipidemia, atherosclerosis, liver diseases involving inflammation, steatosis and/or fibrosis, such as non-alcoholic fatty liver disease, in particular non-alcoholic steatohepatitis, metabolic syndrome, obesity, chronic inflammatory and autoimmune inflammatory diseases.

26 Claims, No Drawings

ARYL-QUINOLINE DERIVATIVES

PRIORITY TO RELATED APPLICATION(S)

This application is a Continuation of pending U.S. application Ser. No. 13/666,202, filed Nov. 1, 2012, which in turn claims the benefit of European Patent Application No. 11187967.2, filed Nov. 4, 2011, all of which are hereby incorporated by references in their entireties.

FIELD OF THE INVENTION

The present invention relates to organic compounds useful for therapy or prophylaxis in a mammal, and in particular to fatty-acid binding protein (FABP) 4 and/or 5 inhibitors, more particularly dual FABP 4/5 inhibitors for the treatment or prophylaxis of lipodystrophy, type 2 diabetes, dyslipidemia, atherosclerosis, liver diseases involving inflammation, steatosis and/or fibrosis, such as non-alcoholic fatty liver disease, in particular non-alcoholic steatohepatitis, metabolic syndrome, obesity, chronic inflammatory and autoimmune inflammatory diseases.

BACKGROUND OF THE INVENTION

FABP4 (aP2) and FABP5 (mal1) are members of the fatty acid binding protein family. FABPs are proteins of 14-15 KDa that act as chaperones for fatty acids in the aqueous cytosolic environment and facilitate their movement between cellular compartments. So far at least nine members of this family have been identified with a tissue-specific pattern of expression. FABP4 is mainly expressed in adipose tissue and macrophages, but also in other cell types, whereas FABP5 is expressed in a wide range of tissues and organs. FABPs are responsible for the transfer of fatty acids to different cell compartments and are thus implicated in key cellular functions such as lipid storage in adipocytes, fatty acid oxidation in mitochondria, ER signaling, fatty-acid-dependent gene expression, regulation of cytosolic enzymes activity, modulation of inflammatory response and leukotriene synthesis. Plasma FABP4 is secreted by adipose tissue in mice and secretion is de-regulated in obesity and blocking of plasma FABP4 in vivo by antibodies improves insulin sensitivity.

Several genetic evidences in human support a role of FABP4 and FABP5 in metabolic diseases. A mutation in the FABP4 promoter (SNP T-87C) leading to 50% reduction in gene expression is associated to reduced cardiovascular diseases (CVDs) and type 2 diabetes (T2D) risk and to reduced plasma triglycerides (TGs). Two mutations in FABP5 gene, one in the 5'UTR (rs454550), one in the promoter (nSNP), are associated, respectively to increased (OR 4.24) and decreased risk (OR 0.48) of T2D. In addition, it was shown that FABP4 protein and mRNA levels in atherosclerotic plaque macrophages are associated to plaques instability and CV death. Finally, a large number of publications report an association between FABP4 and FABP5 plasma levels and severity of metabolic diseases. Elevated FABP4 plasma levels are associated with atherogenic dyslipidemia, reduced endothelial function, increased intima-media (IM) thickness, metabolic syndrome, obesity and insulin resistance IR. Elevated FABP5 plasma levels are associated to metabolic syndrome.

Genetic and pharmacological studies in mice largely confirm the human evidences. It was demonstrated that loss-of-function in FABP4 and FABP5 improves insulin sensitivity, lowers glucose, and protects against atherosclerosis. FABP4 knockout mice on high fat diet showed metabolic improvement that was tempered by compensatory upregulation of FABP5 in adipose. Mice with a deletion of FABP5 gene on high fat (HF) diet showed body weight reduction and improved glucose and insulin tolerance. The FABP4/FABP5 double-knockout mice were strongly protected from hyperglycemia, insulin resistance, and hepatic steatosis. In addition, in an ApoE deficient background, FABP4 and FABP5 deletion was highly protective against the development of atherosclerosis and increased longevity. A specific FABP4 inhibitor (BMS309403), showed in a clamp study in ob/ob mice a reduction of hepatic glucose production, increased glucose uptake in muscle and adipose and reduction in hepatic steatosis, but no change in body weight and energy consumption. Also, it showed a decrease in atherosclerotic placques formation in ApoE KO mice. A dual FABP4/5 inhibitor, Compound 3 described in *J. Lipid Res.* 2011, 52, 646, showed in mice under HF diet a reduction in plasma triglycerides and free fatty acids, but no improvement in insulin and glucose tolerance.

SUMMARY OF THE INVENTION

The present invention relates to compounds according to formula (I),

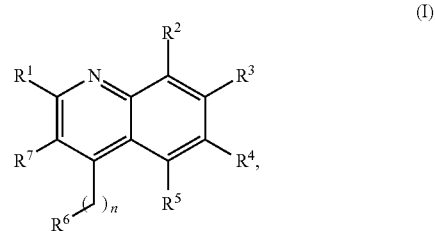

wherein
$R^1$ is selected from the group consisting of alkyl, haloalkyl, cycloalkyl, halocycloalkyl, alkoxy, haloalkoxy, cycloalkoxy, halocycloalkoxy, hydroxyalkyl, heterocycloalkyl, substituted heterocycloalkyl, substituted amino, aminocarbonyl or substituted aminocarbonyl, wherein substituted heterocycloalkyl is substituted with one to three substituents independently selected from the group consisting of oxo, halogen, alkyl, cycloalkyl and haloalkyl, and wherein substituted amino and substituted aminocarbonyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl, with the proviso that $R^1$ is not methyl or ethyl;
$R^2$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;
$R^3$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^4$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^5$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^6$ is selected from the group consisting of phenyl, substituted phenyl, pyridinyl and substituted pyridinyl, wherein substituted phenyl and substituted pyridinyl are substituted with one to three substituent independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, cyano, haloalkyl, hydroxy, hydroxyalkyl, alkoxy, alkoxyalkyl, haloalkoxy, hydroxyalkoxy, alkoxyalkoxy, alkoxyalkoxyalkyl, hydroxyhaloalkyl, amino and substituted amino, wherein substituted amino is substituted with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^7$ is selected from the group consisting of —COOH, tetrazol-5-yl, 3H-[1,3,4]oxadiazol-2-on-5-yl, 3H-[1,3,4]oxadiazole-2-thion-5-yl, 4H-[1,2,4]oxadiazol-5-on-3-yl, 4H-[1,2,4]oxadiazole-5-thion-3-yl, 3H-[1,2,3,5]oxathiadiazole-2-oxide-4-yl, 4H-[1,2,4]thiadiazol-5-on-3-yl, isoxazol-3-ol-5-yl, 5-alkylisoxazol-3-ol-4-yl, 5-cycloalkylisoxazol-3-ol-4-yl, furazan-3-ol-4-yl, 5-alkylsulfonylamino-[1,3,4]oxadiazol-2-yl, 5-cycloalkylsulfonylamino-[1,3,4]oxadiazol-2-yl, 5-alkylsulfonylamino-2H-[1,2,4]triazol-3-yl, 5-cycloalkylsulfonylamino-2H-[1,2,4]triazol-3-yl, 5-alkylisothiazol-3-ol-4-yl, 5-cycloalkylisothiazol-3-ol-4-yl, [1,2,5]thiadiazol-3-ol-4-yl, 1,4-dihydro-tetrazol-5-on-1-yl, 2H-tetrazol-5-ylcarbamoyl, 2H-tetrazole-5-carbonyl, [1,2,4]oxadiazolidine-3,5-dion-2-yl, 4H-[1,2,4]oxadiazol-5-on-3-yl, 2,4-dihydro-[1,2,4]triazol-3-on-5-sulfanyl, 4H-[1,2,4]triazole-3-sulfanyl, 4H-[1,2,4]triazole-3-sulfinyl, 4H-[1,2,4]triazole-3-sulfonyl, 4-alkyl-pyrazol-1-ol-5-yl, 4-cycloalkyl-pyrazol-1-ol-5-yl, 4-alkyl-[1,2,3]triazol-1-ol-5-yl, 4-cycloalkyl-[1,2,3]triazol-1-ol-5-yl, 5-alkyl-imidazol-1-ol-2-yl, 5-cycloalkyl-imidazol-1-ol-2-yl, 4-alkyl-imidazol-1-ol-5-yl, 4-cycloalkyl-imidazol-1-ol-5-yl, 4-alkyl-1,1-dioxo-1$\lambda^6$-[1,2,5]thiadiazolidin-3-on-5-yl, 4,4-dialkyl-1,1-dioxo-1$\lambda^6$-[1,2,5]thiadiazolidin-3-on-5-yl, 4-cycloalkyl-1,1-dioxo-1$\lambda^6$-[1,2,5]thiadiazolidin-3-on-5-yl, 4,4-dicycloalkyl-1,1-dioxo-1$\lambda^6$1,2,5]thiadiazolidin-3-on-5-yl, thiazolidine-2,4-dion-5-yl, oxazolidine-2,4-dion-5-yl, 3-[1-Hydroxy-meth-(E)-ylidene]-pyrrolidine-2,4-dion-1-yl, 3-[1-Hydroxy-meth-(Z)-ylidene]-pyrrolidine-2,4-dion-1-yl, 5-methyl-4-hydroxy-5H-furan-2-on-3-yl, 5,5-dialkyl-4-hydroxy-5H-furan-2-on-3-yl, 5-cycloalkyl-4-hydroxy-5H-furan-2-on-3-yl, 5,5-dicycloalkyl-4-hydroxy-5H-furan-2-on-3-yl, 3-hydroxy-cyclobut-3-ene-1,2-dion-4-yl and 3-hydroxy-cyclobut-3-ene-1,2-dion-4-amino; and n is zero or 1;

with the proviso that at least one of $R^2$, $R^3$, $R^4$ and $R^5$ is different from hydrogen and that said compound is not 6-methoxy-4-phenyl-2-trifluoromethyl-quinoline-3-carboxylic acid or 4-(3,4-dimethoxy-phenyl)-2-hydroxymethyl-6,7-dimethoxy-quinoline-3-carboxylic acid;

or pharmaceutically acceptable salts or esters thereof.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of lipodystrophy, type 2 diabetes, dyslipidemia, atherosclerosis, liver diseases involving inflammation, steatosis and/or fibrosis, such as non-alcoholic fatty liver disease, in particular non-alcoholic steatohepatitis, metabolic syndrome, obesity, chronic inflammatory and autoimmune inflammatory diseases and the use of the said compounds, salts or esters for the production of medicaments for the treatment or prophylaxis of lipodystrophy, type 2 diabetes, dyslipidemia, atherosclerosis, liver diseases involving inflammation, steatosis and/or fibrosis, such as non-alcoholic fatty liver disease, in particular non-alcoholic steatohepatitis, metabolic syndrome, obesity, chronic inflammatory and autoimmune inflammatory diseases.

Objects of the present invention are also the compounds of formula (I) and their aforementioned salts and esters and their use as therapeutically active substances, pharmaceutical compositions, medicaments containing the said compounds, their pharmaceutically acceptable salts or esters, the use of the said compounds, salts or esters for the treatment or prophylaxis of illnesses, especially in the treatment or prophylaxis of lipodystrophy, such as genetic and iatrogenic lipodystrophy, cancer, eye diseases supported by endothelial proliferation and angiogenesis, such as macular degeneration and retinopathy, lung diseases, such as asthma, bronchopulmonary dysplasia and chronic obstructive pulmonary disease, sarcoidosis, chronic renal diseases, such as vasculitis, focal segmental glomerulosclerosis, diabetic nephropathy, lupus nephritis, polycystic kidney disease and drug or toxin-induced chronic tubulointerstitial nephritis, preeclampsia and polycystic ovary syndrome, and the use of the said compounds, salts or esters for the production of medicaments for the treatment or prophylaxis of lipodystrophy, such as genetic and iatrogenic lipodystrophy, cancer, eye diseases supported by endothelial proliferation and angiogenesis, such as macular degeneration and retinopathy, lung diseases, such as asthma, bronchopulmonary dysplasia and chronic obstructive pulmonary disease, sarcoidosis, chronic renal diseases, such as vasculitis, focal segmental glomerulosclerosis, diabetic nephropathy, lupus nephritis, polycystic kidney disease and drug or toxin-induced chronic tubulointerstitial nephritis, preeclampsia and polycystic ovary syndrome Compounds of the present invention are FABP 4 and/or 5 inhibitors, more particularly dual FABP 4 and 5 inhibitors.

In particular, they are also selective FABP 4 and/or 5 inhibitors compared to FABP3 and/or 1.

DETAILED DESCRIPTION OF THE INVENTION

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy and isopropoxy. More particular alkoxy group is isopropoxy.

The term "alkoxyalkoxy" denotes an alkoxy group wherein at least one of the hydrogen atoms of the alkoxy group has been replaced by another alkoxy group. Examples of alkoxyalkoxy group include methoxymethoxy, ethoxymethoxy, methoxyethoxy, ethoxyethoxy, methoxypropoxy and ethoxypropoxy. Particular alkoxyalkoxy groups include methoxymethoxy and methoxyethoxy.

The term "alkoxyalkoxyalkyl" denotes an alkyl group wherein at least one of the hydrogen atoms of the alkyl group has been replaced by an alkoxyalkoxy group. Examples of alkoxyalkoxyalkyl group include methoxymethoxymethyl, ethoxymethoxymethyl, methoxyethoxymethyl, ethoxyethoxymethyl, methoxypropoxymethyl, ethoxypropoxymethyl, methoxymethoxyethyl, ethoxymethoxyethyl, methoxyethoxyethyl, ethoxyethoxyethyl, methoxypropoxyethyl and ethoxypropoxyethyl.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl and ethoxypropyl. Particular alkoxyalkyl group include methoxymethyl and methoxyethyl. More particular alkoxyalkyl group is methoxyethyl.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, and tert-butyl. Particular alkyl groups include methyl, ethyl and isopropyl.

The term "alkylcycloalkyl" denotes a cycloalkyl group wherein at least one of the hydrogen atoms of the cycloalkyl group is replaced by an alkyl group. Examples of alkylcycloalkyl include methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular alkylcycloalkyl groups include methyl-cyclopropyl and dimethyl-cyclopropyl.

The term "alkylcycloalkylalkyl" denotes an alkyl group wherein at least one of the hydrogen atoms of the alkyl group is replaced by an alkylcycloalkyl group. Examples of alkylcycloalkylalkyl include methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "alkylsulfonylamino" denotes a group of formula —NH—S(O)$_2$—R' wherein R' is an alkyl group. Examples of alkylsulfonylamino include methylsulfonylamino, ethylsulfonylamino, propylsulfonylamino, isopropylsulfonylamino, n-butylsulfonylamino, iso-butylsulfonylamino, sec-butylsulfonylamino, and tert-butylsulfonylamino The term "amino" denotes a —NH$_2$ group.

The term "aminoalkyl" denotes an alkyl group wherein at least one of the hydrogen atoms of the alkyl group has been replaced by an amino group. Examples of aminoalkyl include aminomethyl, aminoethyl, aminopropyl, aminomethylpropyl and diaminopropyl.

The term "aminocarbonyl" of the formula —C(O)—NH$_2$

The term "carbonyl" denotes a —C(O)— group.

The term "carboxylic" denotes a —C(O)OH group.

The term "cyano" denotes a —C≡N group.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopentyloxy.

The term "cycloalkoxyalkyl" denotes an alkyl group wherein at least one of the hydrogen atoms of the alkyl group has been replaced by a cycloalkoxy group. Examples of cycloalkoxyalkyl group include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkoxycarbonyl" denotes a group of the formula —C(O)—R', wherein R' is a cycloalkoxy group. Examples of cycloalkoxycarbonyl groups include groups of the formula —C(O)—R', wherein R' is cyclopropoxy, cyclobutoxy, cyclopentyloxy, cyclohexyloxy, cycloheptyloxy and cyclooctyloxy. Particular cycloalkoxycarbonyl group is a group of the formula —C(O)—R', wherein R' is cyclopropoxy.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl group is cyclopropyl and cyclopentyl.

The term "cycloalkylalkoxy" denotes an alkoxy group wherein at least one of the hydrogen atoms of the alkoxy group is replaced by a cycloalkyl group. Examples of cycloalkylalkoxy include cyclopropylmethoxy, cyclobutylmethoxy, cyclopentylmethoxy, cyclohexylmethoxy, cycloheptylmethoxy and cyclooctylmethoxy.

The term "cycloalkylalkoxyalkyl" denotes an alkyl group wherein at least one of the hydrogen atoms of the alkyl group is replaced by a cycloalkylalkoxy group. Examples of cycloalkylalkoxyalkyl include cyclopropylmethoxymethyl, cyclopropylmethoxyethyl, cyclobutylmethoxymethyl, cyclobutylmethoxyethyl, cyclopentylmethoxymethyl, cyclopentylmethoxyethyl, cyclohexylmethoxymethyl, cyclohexylmethoxyethyl, cycloheptylmethoxymethyl, cycloheptylmethoxyethyl, cyclooctylmethoxymethyl and cyclooctylmethoxyethyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "cycloalkylsulfonylamino" denotes a group of formula —NH—S(O)$_2$— wherein R' is a cycloalkyl group. Examples of cycloalkylsulfonylamino cyclopropylsulfonylamino, cyclobutanylsulfonylamino, cyclopentylsulfonylamino or cyclohexylsulfonylamino.

The term "haloalkoxy" denotes an alkoxy group wherein at least one of the hydrogen atoms of the alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy, trifluoroethoxy and trifluoromethylethoxy.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl and trifluoroethyl.

The term "halocycloalkoxy" denotes a cycloalkoxy group wherein at least one of the hydrogen atoms of the cycloalkoxy group has been replaced by same or different halogen atoms, particularly fluoro atoms. Examples of halocycloalkoxyl include fluorocyclopropoxy, difluorocyclopropoxy, fluorocyclobutoxy and difluorocyclobutoxy.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halocycloalkylalkyl" denotes an alkyl group wherein at least one of the hydrogen atoms of the alkyl group has been replaced by a halocycloalkyl. Examples of halocycloalkylalkyl groups include fluorocyclopropylmethyl, fluorocyclopropylethyl, difluorocyclopropylmethyl, difluorocyclopropylethyl, fluorocyclobutylmethyl, fluorocyclobutylethyl, difluorocyclobutylmethyl and difluorocyclobutylethyl.

The term "halogen" and "halo" are used interchangeably herein and denote fluoro, chloro, bromo, or iodo. Particular halogens are chloro and fluoro.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are oxetanyl, azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl. Further particular examples of heterocycloalkyl group are pyrrolidinyl, piperidinyl and morpholinyl. More particular examples of heterocycloalkyl are pyrrolidinyl and piperidinyl.

The term "hydroxy" denotes a —OH group.

The term "hydroxyalkoxy" an alkoxy group wherein at least one of the hydrogen atoms of the alkoxy group has been replaced by a hydroxy group. Examples of hydroxyalkoxy include hydroxyethoxy, hydroxypropoxy, hydroxymethylpropoxy and dihydroxypropoxy.

The term "hydroxyhaloalkyl" denotes an alkyl wherein at least one of the hydrogen atoms of the alkyl has been replaced by a hydroxy group and wherein at least one of the hydrogen atoms of the alkyl has been replaced by a halogen. Examples of hydroxyhaloalkyl include hydroxytrifluoroethyl, hydroxytrifluoropropyl and hydroxyhexafluoropropyl.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl. Particular examples are hydroxymethyl and hydroxyethyl.

The term "nitro" denotes a —NO$_2$ group.

The term "oxo" denotes a =O group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The term "sulfonyl" denotes a —S(O)$_2$— group.

The term "sulfonylamino" denotes a —NH—S(O)$_2$— group.

The term "tetrazol-5-yl" encompasses 1H-tetrazol-5-yl and 2H-tetrazol-5-yl.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

The present invention relates to compounds according to formula (I),

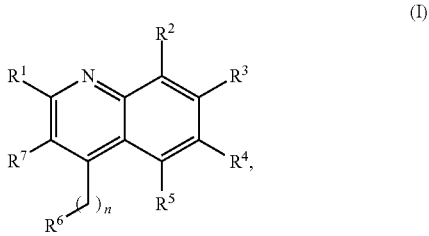

wherein $R^1$ is selected from the group consisting of alkyl, haloalkyl, cycloalkyl, halocycloalkyl, alkoxy, haloalkoxy, cycloalkoxy, halocycloalkoxy, hydroxyalkyl, heterocycloalkyl, substituted heterocycloalkyl, substituted amino, aminocarbonyl or substituted aminocarbonyl, wherein substituted heterocycloalkyl is substituted with one to three substituents independently selected from the group consisting of oxo, halogen, alkyl, cycloalkyl and haloalkyl, and wherein substituted amino and substituted aminocarbonyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl, with the proviso that $R^1$ is not methyl or ethyl;

$R^2$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^3$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^4$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^5$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^6$ is selected from the group consisting of phenyl, substituted phenyl, pyridinyl and substituted pyridinyl, wherein substituted phenyl and substituted pyridinyl are substituted with one to three substituent independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, cyano, haloalkyl, hydroxy, hydroxyalkyl, alkoxy, alkoxyalkyl, haloalkoxy, hydroxyhaloalkoxy, alkoxyalkoxy, alkoxyalkoxyalkyl, hydroxyhaloalkyl, amino and substituted amino, wherein substituted amino is substituted with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^7$ is selected from the group consisting of —COOH, tetrazol-5-yl, 3H-[1,3,4]oxadiazol-2-on-5-yl, 3H-[1,3,4]oxadiazole-2-thion-5-yl, 4H-[1,2,4]oxadiazol-5-on-3-yl, 4H-[1,2,4]oxadiazole-5-thion-3-yl, 3H-[1,2,3,5]oxathiadiazole-2-oxide-4-yl, 4H-[1,2,4]thiadiazol-5-on-3-yl, isoxazol-3-ol-5-yl, 5-alkylisoxazol-3-ol-4-yl, 5-cycloalkylisoxazol-3-ol-4-yl, furazan-3-ol-4-yl, 5-alkylsulfonylamino-[1,3,4]oxadiazol-2-yl, 5-cycloalkylsulfonylamino-[1,3,4]oxadiazol-2-yl, 5-alkylsulfonylamino-2H-[1,2,4]triazol-3-yl, 5-cycloalkylsulfonylamino-2H-[1,2,4]triazol-3-yl, 5-alkylisothiazol-3-ol-4-yl, 5-cycloalkylisothiazol-3-ol-4-yl, [1,2,5]thiadiazol-3-ol-4-yl, 1,4-dihydro-tetrazol-5-on-1-yl, 2H-tetrazol-5-ylcarbamoyl, 2H-tetrazole-5-carbonyl, [1,2,4]oxadiazolidine-3,5-dion-2-yl, 4H-[1,2,4]oxadiazol-5-on-3-yl, 2,4-dihydro-[1,2,4]triazol-3-on-5-sulfanyl, 4H-[1,2,4]triazole-3-sulfanyl, 4H-[1,2,4]triazole-3-sulfinyl, 4H-[1,2,4]triazole-3-sulfonyl, 4-alkyl-pyrazol-1-ol-5-yl, 4-cycloalkyl-pyrazol-1-ol-5-yl, 4-alkyl-[1,2,3]triazol-1-ol-5-yl, 4-cycloalkyl-[1,2,3]triazol-1-ol-5-yl, 5-alkyl-imidazol-1-ol-2-yl, 5-cycloalkyl-imidazol-1-ol-2-yl, 4-alkyl-imidazol-1-ol-5-yl, 4-cycloalkyl-imidazol-1-ol-5-yl, 4-alkyl-1,1-dioxo-1λ$^6$-[1,2,5]thiadiazolidin-3-on-5-yl, 4,4-dialkyl-1,1- dioxo-1λ⁶-[1,2,5]thiadiazolidin-3-on-5-yl, 4-cycloalkyl-1,1-dioxo-1λ⁶-[1,2,5]thiadiazolidin-3-on-5-yl, 4,4-dicycloalkyl-1,1-dioxo-1λ⁶1,2,5]thiadiazolidin-3-on-5-yl, thiazolidine-2,4-dion-5-yl, oxazolidine-2,4-dion-5-yl, 3-[1-Hydroxy-meth-(E)-ylidene]-pyrrolidine-2,4-dion-1-yl, 3-[1-Hydroxy-meth-(Z)-ylidene]-pyrrolidine-2,4-dion-1-yl, 5-methyl-4-hydroxy-5H-furan-2-on-3-yl, 5,5-dialkyl-4-hydroxy-5H-furan-2-on-3-yl, 5-cycloalkyl-4-hydroxy-5H-furan-2-on-3-yl, 5,5-dicycloalkyl-4-hydroxy-5H-furan-2-on-3-yl, 3-hydroxy-cyclobut-3-ene-1,2-dion-4-yl and 3-hydroxy-cyclobut-3-ene-1,2-dion-4-amino; and n is zero or 1;

with the proviso that at least one of $R^2$, $R^3$, $R^4$ and $R^5$ is different from hydrogen and that said compound is not 6-methoxy-4-phenyl-2-trifluoromethyl-quinoline-3-carboxylic acid or 4-(3,4-dimethoxy-phenyl)-2-hydroxymethyl-6,7-dimethoxy-quinoline-3-carboxylic acid;

or pharmaceutically acceptable salts or esters thereof.

Also an embodiment of the present invention are compounds according to formula (I) as described herein and pharmaceutically acceptable salts thereof, more particularly compounds according to formula (I) as described herein.

A further embodiment of the present invention are compounds according to formula (I) as described herein, wherein $R^1$ is selected from the group consisting of alkyl, haloalkyl, cycloalkyl, alkoxy, haloalkoxy, cycloalkoxy, hydroxyalkyl, heterocycloalkyl, substituted heterocycloalkyl, substituted amino and substituted aminocarbonyl, wherein substituted heterocycloalkyl is substituted with one to three substituents independently selected from the group consisting of oxo, halogen and alkyl, and wherein substituted amino and substituted aminocarbonyl are substituted on the nitrogen atom with one to two substituents independently selected from the group consisting of alkyl, hydroxyalkyl and alkoxyalkyl, with the proviso that $R^1$ is not methyl or ethyl.

A particular embodiment of the present invention are compounds according to formula (I) as described herein, wherein $R^1$ is selected from the group consisting of alkoxy, heterocycloalkyl, substituted heterocycloalkyl and substituted amino, wherein substituted heterocycloalkyl is substituted with one to three substituents independently selected from the group consisting of oxo, halogen and alkyl, and wherein substituted amino and substituted aminocarbonyl are substituted on the nitrogen atom with one to two substituents independently selected from alkyl, hydroxyalkyl and alkoxyalkyl.

In a further embodiment of the present invention are compounds according to formula (I) as described herein, wherein $R^1$ is selected from the group consisting of alkoxy, heterocycloalkyl, substituted heterocycloalkyl and substituted amino, wherein substituted heterocycloalkyl is substituted with one to three alkyl, and wherein substituted amino is substituted on the nitrogen atom with one to two alkyl.

Another further embodiment of the present invention are compounds according to formula (I) as described herein, wherein $R^1$ is selected from the group consisting of alkoxy, heterocycloalkyl, substituted heterocycloalkyl and substituted amino, wherein substituted heterocycloalkyl is substituted with one alkyl, and wherein substituted amino is substituted on the nitrogen atom with two alkyl.

Another embodiment of the present invention are compounds according to formula (I) as described herein, wherein $R^1$ is alkoxy.

Another particular embodiment of the present invention are compounds according to formula (I) as described herein, wherein $R^1$ is isopropoxy.

The present invention also relates to compounds according to formula (I) as described herein, wherein $R^1$ is heterocycloalkyl or substituted heterocycloalkyl, wherein substituted heterocycloalkyl is substituted with one to three alkyl.

A further particular embodiment of the present invention are compounds according to formula (I) as described herein, wherein $R^1$ is substituted heterocycloalkyl, wherein substituted heterocycloalkyl is substituted with one to three alkyl.

A more particular embodiment of the present invention are compounds according to formula (I) as described herein, wherein $R^1$ is piperidinyl or methylpyrrolidinyl.

Also an embodiment of the present invention are compounds according to formula (I) as described herein, wherein $R^1$ is piperidin-1-yl or 2-methylpyrrolidin-1-yl.

The present invention also relates to compounds according to formula (I) as described herein, wherein $R^1$ is substituted amino, wherein substituted amino is substituted on the nitrogen atom with one to two alkyl.

Another embodiment of the present invention are compounds according to formula (I) as described herein, wherein $R^1$ is substituted amino, wherein substituted amino is substituted on the nitrogen atom with two alkyl.

A further particular embodiment of the present invention are compounds according to formula (I) as described herein, wherein is $R^1$ is N,N-diethylamino.

A particular embodiment of the present invention are compounds according to formula (I) as described herein, wherein $R^2$ is selected from the group consisting of hydrogen, halogen, alkyl, haloalkyl, alkoxy and substituted amino, wherein substituted amino is substituted on the nitrogen atom with one to two alkyl.

Also an embodiment of the present invention are compounds according to formula (I) as described herein, wherein $R^2$ is hydrogen or halogen.

The present invention also relates to compounds according to formula (I) as described herein, wherein $R^2$ is hydrogen.

Another embodiment of the present invention are compounds according to formula (I) as described herein, wherein $R^2$ is halogen.

The present invention also relates to compounds according to formula (I) as described herein, wherein $R^2$ is chloro.

Also an embodiment of the present invention are compounds according to formula (I) as described herein, wherein $R^3$ is selected from the group consisting of hydrogen, alkoxy and halogen.

Also an embodiment of the present invention are compounds according to formula (I) as described herein, wherein $R^3$ is hydrogen or halogen.

Also an embodiment of the present invention are compounds according to formula (I) as described herein, wherein $R^3$ is hydrogen.

Another embodiment of the present invention are compounds according to formula (I) as described herein, wherein $R^4$ is selected from the group consisting of hydrogen, halogen, alkyl, nitro and cyano.

A particular embodiment of the present invention are compounds according to formula (I) as described herein, wherein $R^4$ is halogen.

A further particular embodiment of the present invention are compounds according to formula (I) as described herein, wherein $R^4$ is chloro.

Also a particular embodiment of the present invention are compounds according to formula (I) as described herein, wherein $R^5$ is hydrogen.

Also a particular embodiment of the present invention are compounds according to formula (I) as described herein, wherein $R^6$ is phenyl or phenyl substituted with one to three substituent independently selected from the group consisting of alkyl, halogen, haloalkyl, alkoxy and haloalkoxy.

A more particular embodiment of the present invention are compounds according to formula (I) as described herein, wherein $R^6$ is phenyl.

Also a particular embodiment of the present invention are compounds according to formula (I) as described herein, wherein $R^6$ is phenyl substituted with one to three substituent independently selected from the group consisting of alkyl, halogen, haloalkyl, alkoxy and haloalkoxy.

Also a particular embodiment of the present invention are compounds according to formula (I) as described herein, wherein $R^6$ is phenyl substituted with one halogen.

Another embodiment of the present invention are compounds according to formula (I) as described herein, wherein $R^6$ is 2-halophenyl or 3-halophenyl.

Another embodiment of the present invention are compounds according to formula (I) as described herein, wherein $R^6$ is chlorophenyl.

Also an embodiment of the present invention are compounds according to formula (I) as described herein, wherein $R^6$ is 2-chlorophenyl or 3-chlorophenyl.

Another embodiment of the present invention are compounds according to formula (I) as described herein, wherein $R^6$ is pyridinyl or pyridinyl substituted with one to three substituents independently selected from the group consisting of alkyl, halogen, haloalkyl, alkoxy or haloalkoxy.

Another embodiment of the present invention are compounds according to formula (I) as described herein, wherein $R^6$ is pyridinyl substituted with one alkyl.

Also an embodiment of the present invention are compounds according to formula (I) as described herein, wherein $R^7$ is selected from the group consisting of —COOH, tetrazol-5-yl, 3H-[1,3,4]oxadiazol-2-on-5-yl, 3H-[1,3,4]oxadiazole-2-thion-5-yl, 4H-[1,2,4]oxadiazol-5-on-3-yl, 4H-[1,2,4]oxadiazole-5-thion-3-yl, 3H-[1,2,3,5]oxathiadiazole-2-oxide-4-yl and 4H-[1,2,4]thiadiazol-5-on-3-yl.

Also an embodiment of the present invention are compounds according to formula (I) as described herein, wherein $R^7$ is selected from the group consisting of —COOH, 1H-tetrazol-5-yl, 3H-[1,3,4]oxadiazol-2-on-5-yl, 3H-[1,3,4]oxadiazole-2-thion-5-yl, 4H-[1,2,4]oxadiazol-5-on-3-yl, 4H-[1,2,4]oxadiazole-5-thion-3-yl, 3H-[1,2,3,5]oxathiadiazole-2-oxide-4-yl and 4H-[1,2,4]thiadiazol-5-on-3-yl.

Another embodiment of the present invention are compounds according to formula (I) as described herein, wherein $R^7$ is selected from the group consisting of —COOH, tetrazol-5-yl, 3H-[1,3,4]oxadiazol-2-on-5-yl and 3H-[1,3,4]oxadiazole-2-thion-5-yl.

A further embodiment of the present invention are compounds according to formula (I) as described herein, wherein $R^7$ is selected from the group consisting of —COOH, 1H-tetrazol-5-yl, 3H-[1,3,4]oxadiazol-2-on-5-yl and 3H-[1,3,4]oxadiazole-2-thion-5-yl.

A further embodiment of the present invention are compounds according to formula (I) as described herein, wherein $R^7$ is —COOH, tetrazol-5-yl or 3H-[1,3,4]oxadiazole-2-thion-5-yl.

Another embodiment of the present invention are compounds according to formula (I) as described herein, wherein $R^7$ is selected from the group consisting of —COOH, 1H-tetrazol-5-yl and 3H-[1,3,4]oxadiazole-2-thion-5-yl.

A further embodiment of the present invention are compounds according to formula (I) as described herein, wherein $R^7$ is —COOH.

A particular embodiment of the present invention are compounds according to formula (I) as described herein, wherein $R^7$ is tetrazol-5-yl.

A particular embodiment of the present invention are compounds according to formula (I) as described herein, wherein $R^7$ is 1H-tetrazol-5-yl.

A further particular embodiment of the present invention are compounds according to formula (I) as described herein, wherein $R^7$ is 3H-[1,3,4]oxadiazole-2-thion-5-yl.

A more particular embodiment of the present invention are compounds according to formula (I) as described herein, wherein n is zero.

Another embodiment of the present invention are compounds according to formula (I) as described herein, wherein n is 1.

Particular examples of compounds of formula (I) as described herein are selected from the group consisting of
6-Chloro-2-cyclopropyl-4-phenyl-quinoline-3-carboxylic acid;
6-Chloro-2-isopropyl-4-phenyl-quinoline-3-carboxylic acid;
2-Ethoxy-6-nitro-4-phenyl-quinoline-3-carboxylic acid;
6-Chloro-2-ethoxy-4-phenyl-quinoline-3-carboxylic acid;
6-Chloro-4-phenyl-2-piperidin-1-yl-quinoline-3-carboxylic acid;
6-Chloro-4-(3-chloro-phenyl)-2-cyclopropyl-quinoline-3-carboxylic acid;
7-Chloro-4-(2-fluoro-phenyl)-2-isopropyl-quinoline-3-carboxylic acid;
7-Chloro-2-cyclopropyl-4-(2-fluoro-phenyl)-quinoline-3-carboxylic acid;
6-Chloro-2-methylcarbamoyl-4-phenyl-quinoline-3-carboxylic acid;
6-Chloro-4-(2-chloro-benzyl)-2-cyclopropyl-quinoline-3-carboxylic acid;
6-Chloro-4-phenyl-2-(2,2,2-trifluoro-ethoxy)-quinoline-3-carboxylic acid;
6-Chloro-2-morpholin-4-yl-4-phenyl-quinoline-3-carboxylic acid;
6-Chloro-2-cyclopropyl-4-(2-trifluoromethyl-benzyl)-quinoline-3-carboxylic acid;
6-Chloro-4-(2-chloro-benzyl)-2-isopropyl-quinoline-3-carboxylic acid;
6-Chloro-2-isopropoxy-4-phenyl-quinoline-3-carboxylic acid;
6-Chloro-2-cyclopentyloxy-4-phenyl-quinoline-3-carboxylic acid;
6-Chloro-2-(4,4-difluoro-piperidin-1-yl)-4-phenyl-quinoline-3-carboxylic acid;
6,7-Dichloro-2-cyclopropyl-4-phenyl-quinoline-3-carboxylic acid;
6-Chloro-2-cyclopropyl-8-methyl-4-phenyl-quinoline-3-carboxylic acid;
6-Chloro-2-isopropyl-4-(3-trifluoromethoxy-phenyl)-quinoline-3-carboxylic acid;
6,8-Dichloro-4-phenyl-2-piperidin-1-yl-quinoline-3-carboxylic acid;
6,8-Dichloro-4-phenyl-2-pyrrolidin-1-yl-quinoline-3-carboxylic acid;
6,8-Dichloro-2-dimethylamino-4-phenyl-quinoline-3-carboxylic acid;
6,8-Dichloro-2-diethylamino-4-phenyl-quinoline-3-carboxylic acid;

6,7-Dichloro-4-phenyl-2-piperidin-1-yl-quinoline-3-carboxylic acid;
6,7-Dichloro-4-phenyl-2-pyrrolidin-1-yl-quinoline-3-carboxylic acid;
6-Chloro-4-phenyl-2-pyrrolidin-1-yl-3-(1H-tetrazol-5-yl)-quinoline;
6-Chloro-4-phenyl-2-piperidin-1-yl-3-(1H-tetrazol-5-yl)-quinoline;
6-Chloro-4-(2-chloro-benzyl)-2-dimethylamino-quinoline-3-carboxylic acid;
6-Chloro-2-hydroxymethyl-4-phenyl-quinoline-3-carboxylic acid;
6-Chloro-2-isopropyl-4-(3-isopropyl-phenyl)-quinoline-3-carboxylic acid;
6-Chloro-4-(3-ethoxy-phenyl)-2-isopropyl-quinoline-3-carboxylic acid;
6-Chloro-2-isopropyl-4-(3-trifluoromethyl-phenyl)-quinoline-3-carboxylic acid;
6-Chloro-4-phenyl-2-(2,2,2-trifluoro-ethyl)-quinoline-3-carboxylic acid;
6-Chloro-4-(3-chloro-4-fluoro-phenyl)-2-isopropyl-quinoline-3-carboxylic acid;
6-Chloro-2-cyclopentyl-4-phenyl-quinoline-3-carboxylic acid;
6-Chloro-4-phenyl-2-pyrrolidin-1-yl-quinoline-3-carboxylic acid;
6-Chloro-2-(2-oxo-pyrrolidin-1-yl)-4-phenyl-quinoline-3-carboxylic acid;
6-Chloro-2-isopropyl-4-(2-methoxy-benzyl)-quinoline-3-carboxylic acid;
6-Chloro-8-methyl-4-phenyl-2-piperidin-1-yl-quinoline-3-carboxylic acid;
6-Chloro-8-methyl-4-phenyl-2-pyrrolidin-1-yl-quinoline-3-carboxylic acid;
6-Chloro-2-(isopropyl-methyl-amino)-4-phenyl-quinoline-3-carboxylic acid;
8-Ethyl-4-phenyl-2-piperidin-1-yl-quinoline-3-carboxylic acid;
6-Chloro-2-diethylamino-8-methyl-4-phenyl-quinoline-3-carboxylic acid;
6,8-Dichloro-2-(isopropyl-methyl-amino)-4-phenyl-quinoline-3-carboxylic acid;
6-Chloro-2-[(2-hydroxy-ethyl)-methyl-amino]-4-phenyl-quinoline-3-carboxylic acid;
8-Ethyl-4-phenyl-2-pyrrolidin-1-yl-quinoline-3-carboxylic acid;
2-Dimethylamino-8-ethyl-4-phenyl-quinoline-3-carboxylic acid;
6-Chloro-2-[(2-methoxy-ethyl)-methyl-amino]-4-phenyl-quinoline-3-carboxylic acid;
6,8-Dichloro-2-(ethyl-methyl-amino)-4-phenyl-quinoline-3-carboxylic acid;
6,8-Dichloro-2-(2-methyl-pyrrolidin-1-yl)-4-phenyl-quinoline-3-carboxylic acid;
6-Chloro-2-diethylamino-4-phenyl-quinoline-3-carboxylic acid;
6-Chloro-4-phenyl-2-(2,2,2-trifluoro-1-methyl-ethoxy)-quinoline-3-carboxylic acid;
6-Ethyl-8-methyl-4-phenyl-2-piperidin-1-yl-quinoline-3-carboxylic acid;
6-Chloro-2-(ethyl-methyl-amino)-8-methyl-4-phenyl-quinoline-3-carboxylic acid;
6-Chloro-8-methyl-2-(2-methyl-pyrrolidin-1-yl)-4-phenyl-quinoline-3-carboxylic acid;
6,8-Dichloro-2-(4,4-difluoro-piperidin-1-yl)-4-phenyl-quinoline-3-carboxylic acid;
6-Chloro-2-(4,4-difluoro-piperidin-1-yl)-8-methyl-4-phenyl-quinoline-3-carboxylic acid;
[6-Chloro-4-phenyl-3-(1H-tetrazol-5-yl)-quinolin-2-yl]-diethyl-amine;
6-Cyano-8-methyl-4-phenyl-2-piperidin-1-yl-quinoline-3-carboxylic acid;
6-Chloro-4-(2-chloro-benzyl)-2-dimethylamino-8-fluoro-quinoline-3-carboxylic acid;
6-Chloro-4-(2-chloro-benzyl)-2,8-bis-dimethylamino-quinoline-3-carboxylic acid;
6-Chloro-4-(2-chloro-benzyl)-8-fluoro-2-methylamino-quinoline-3-carboxylic acid;
6-Ethyl-8-methyl-2-(2-methyl-pyrrolidin-1-yl)-4-phenyl-quinoline-3-carboxylic acid;
6-Ethyl-2-(ethyl-methyl-amino)-8-methyl-4-phenyl-quinoline-3-carboxylic acid;
6-Cyano-2-(ethyl-methyl-amino)-8-methyl-4-phenyl-quinoline-3-carboxylic acid;
[6-Chloro-4-phenyl-3-(1H-tetrazol-5-yl)-quinolin-2-yl]-ethyl-methyl-amine;
[6-Chloro-4-phenyl-3-(1H-tetrazol-5-yl)-quinolin-2-yl]-isopropyl-methyl-amine;
6-Chloro-4-(2-chloro-benzyl)-2-(2,2,2-trifluoro-ethyl)-quinoline-3-carboxylic acid;
6-Chloro-2-(2-methyl-pyrrolidin-1-yl)-4-phenyl-3-(1H-tetrazol-5-yl)-quinoline;
6-Chloro-2-isopropyl-4-(2-trifluoromethoxy-benzyl)-quinoline-3-carboxylic acid;
6,8-Dichloro-4-(3-chloro-4-fluoro-phenyl)-2-isopropyl-quinoline-3-carboxylic acid;
6,8-Dichloro-4-(3-ethoxy-phenyl)-2-isopropyl-quinoline-3-carboxylic acid;
6,8-Dichloro-2-isopropyl-4-(3-isopropyl-phenyl)-quinoline-3-carboxylic acid;
6-Chloro-4-(2-chloro-benzyl)-2-(ethyl-methyl-amino)-8-fluoro-quinoline-3-carboxylic acid;
6-Chloro-4-(2-chloro-benzyl)-2-isopropyl-8-methyl-quinoline-3-carboxylic acid;
5-(6-Chloro-4-phenyl-2-piperidin-1-yl-quinolin-3-yl)-3H-[1,3,4]oxadiazol-2-one;
6-Chloro-2-diethylamino-4-(3-isopropyl-phenyl)-quinoline-3-carboxylic acid;
6-Chloro-4-(3-isopropyl-phenyl)-2-pyrrolidin-1-yl-quinoline-3-carboxylic acid;
6-Chloro-4-(3-isopropyl-phenyl)-2-piperidin-1-yl-quinoline-3-carboxylic acid;
6-Chloro-2-dimethylamino-4-(3-isopropyl-phenyl)-quinoline-3-carboxylic acid;
6-Chloro-4-(3-isopropyl-phenyl)-2-(2,2,2-trifluoro-1-methyl-ethoxy)-quinoline-3-carboxylic acid;
6-Chloro-4-(2-chloro-benzyl)-2-isopropyl-8-methoxy-quinoline-3-carboxylic acid;
6-Chloro-4-(2-chloro-benzyl)-2-dimethylamino-8-trifluoromethyl-quinoline-3-carboxylic acid;
5-(6-Chloro-4-phenyl-2-piperidin-1-yl-quinolin-3-yl)-3H-[1,3,4]oxadiazole-2-thione;
6-Chloro-4-(2-chloro-benzyl)-2-diethylamino-quinoline-3-carboxylic acid;
6-Chloro-4-(2-chloro-benzyl)-2-pyrrolidin-1-yl-quinoline-3-carboxylic acid;
6-Chloro-4-(2-chloro-benzyl)-2-piperidin-1-yl-quinoline-3-carboxylic acid;
6-Chloro-2-piperidin-1-yl-4-(2-trifluoromethyl-benzyl)-quinoline-3-carboxylic acid;
6-Chloro-4-(2-chloro-benzyl)-2-isopropoxy-quinoline-3-carboxylic acid;

6-Chloro-4-(3-chloro-phenyl)-2-diethylamino-quinoline-3-carboxylic acid;
6-Chloro-4-(3-chloro-phenyl)-2-pyrrolidin-1-yl-quinoline-3-carboxylic acid;
6-Chloro-4-(3-chloro-phenyl)-2-piperidin-1-yl-quinoline-3-carboxylic acid;
6-Chloro-4-(3-chloro-phenyl)-2-dimethylamino-quinoline-3-carboxylic acid;
6-Chloro-4-(2-chloro-benzyl)-2-(2,2,2-trifluoro-1-methyl-ethoxy)-quinoline-3-carboxylic acid;
6-Chloro-4-(3-chloro-phenyl)-2-(2,2,2-trifluoro-1-methyl-ethoxy)-quinoline-3-carboxylic acid;
6-Chloro-4-(3-chloro-phenyl)-2-isopropoxy-quinoline-3-carboxylic acid;
[6-Chloro-4-(3-isopropyl-phenyl)-3-(1H-tetrazol-5-yl)-quinolin-2-yl]-diethyl-amine;
[6-Chloro-4-(3-isopropyl-phenyl)-3-(1H-tetrazol-5-yl)-quinolin-2-yl]-ethyl-methyl-amine;
and pharmaceutically acceptable salts thereof.

Other particular examples of compounds of formula (I) as described herein are selected from the group consisting of
6-Chloro-8-fluoro-4-phenyl-2-(piperidin-1-yl)-3-(2H-tetrazol-5-yl)quinoline;
6-Chloro-2-(pentan-3-yl)-4-phenyl-3-(1H-tetrazol-5-yl)quinoline;
4-Phenyl-2-(piperidin-1-yl)-3-(1H-tetrazol-5-yl)-6-(trifluoromethyl)quinoline;
Diethyl-[4-phenyl-3-(2H-tetrazol-5-yl)-6-trifluoromethyl-quinolin-2-yl]-amine;
6-Chloro-2-cyclobutyl-4-phenyl-3-(1H-tetrazol-5-yl)quinoline;
6-Chloro-2-cyclopentyl-7-fluoro-4-phenyl-3-(2H-tetrazol-5-yl)quinoline;
6-Chloro-7-fluoro-2-(pentan-3-yl)-4-phenyl-3-(2H-tetrazol-5-yl)quinoline;
6-Chloro-7-fluoro-4-phenyl-2-(piperidin-1-yl)-3-(2H-tetrazol-5-yl)quinoline;
6-Chloro-N,N-diethyl-7-fluoro-4-phenyl-3-(2H-tetrazol-5-yl)quinolin-2-amine;
6-Chloro-4-(3-chlorophenyl)-2-(pentan-3-yl)-3-(1H-tetrazol-5-yl)quinoline;
6-Chloro-2-cyclohexyl-4-phenyl-3-(1H-tetrazol-5-yl)quinoline;
6-chloro-4-(3-chlorophenyl)-2-cyclobutyl-3-(1H-tetrazol-5-yl)quinoline;
2-(Pentan-3-yl)-4-phenyl-3-(2H-tetrazol-5-yl)-6-(trifluoromethyl)quinoline;
2-Cyclopentyl-4-phenyl-3-(2H-tetrazol-5-yl)-6-(trifluoromethyl)quinoline;
6-Chloro-2-cyclohexyl-7-fluoro-4-phenyl-3-(2H-tetrazol-5-yl)quinoline;
2-Cyclohexyl-4-phenyl-3-(2H-tetrazol-5-yl)-6-(trifluoromethyl)quinoline;
6-Chloro-4-(3-chlorophenyl)-2-isopropyl-3-(1H-tetrazol-5-yl)quinoline;
6-Chloro-4-(3-chlorophenyl)-2-cyclopropyl-3-(1H-tetrazol-5-yl)quinoline;
6-Chloro-2-(3,3-difluoropiperidin-1-yl)-7-fluoro-4-phenyl-3-(2H-tetrazol-5-yl)quinoline;
6-Chloro-2-(3,3-difluoroazetidin-1-yl)-7-fluoro-4-phenyl-3-(2H-tetrazol-5-yl)quinoline;
1-(6-Chloro-4-phenyl-3-(2H-tetrazol-5-yl)quinolin-2-yl)piperidin-2-one;
7-Methoxy-2-(pentan-3-yl)-4-phenyl-3-(1H-tetrazol-5-yl)quinoline;
2-Cyclopentyl-7-methoxy-4-phenyl-3-(1H-tetrazol-5-yl)quinoline;
7-Methoxy-4-phenyl-2-(piperidin-1-yl)-3-(2H-tetrazol-5-yl)quinoline;
1-(6-Chloro-4-phenyl-3-(2H-tetrazol-5-yl)quinolin-2-yl)pyrrolidin-2-one;
2-Cyclopentyl-4-(2-methylpyridin-4-yl)-3-(2H-tetrazol-5-yl)-6-(trifluoromethyl)quinoline;
6-Chloro-2-cyclohexyl-4-(2-methyl-pyridin-4-yl)-3-(2H-tetrazol-5-yl)-quinoline;
6-Chloro-2-cyclopentyl-4-(2-methyl-pyridin-4-yl)-3-(2H-tetrazol-5-yl)-quinoline;
6-Chloro-4-(2-methylpyridin-4-yl)-2-(pentan-3-yl)-3-(2H-tetrazol-5-yl)quinoline;
and pharmaceutically acceptable salts thereof.

Further particular examples of compounds of formula (I) as described herein are selected from the group consisting of
6-Chloro-4-phenyl-2-piperidin-1-yl-quinoline-3-carboxylic acid;
6-Chloro-4-phenyl-2-piperidin-1-yl-3-(1H-tetrazol-5-yl)-quinoline;
6,8-Dichloro-2-(2-methyl-pyrrolidin-1-yl)-4-phenyl-quinoline-3-carboxylic acid;
6-Chloro-2-(2-methyl-pyrrolidin-1-yl)-4-phenyl-3-(1H-tetrazol-5-yl)-quinoline;
5-(6-Chloro-4-phenyl-2-piperidin-1-yl-quinolin-3-yl)-3H-[1,3,4]oxadiazole-2-thione;
6-Chloro-4-(2-chloro-benzyl)-2-diethylamino-quinoline-3-carboxylic acid;
6-Chloro-4-(3-chloro-phenyl)-2-diethylamino-quinoline-3-carboxylic acid;
6-Chloro-4-(3-chloro-phenyl)-2-isopropoxy-quinoline-3-carboxylic acid;
and pharmaceutically acceptable salts thereof.

Also further particular examples of compounds of formula (I) as described herein are selected from the group consisting of
6-Chloro-8-fluoro-4-phenyl-2-(piperidin-1-yl)-3-(2H-tetrazol-5-yl)quinoline;
6-Chloro-2-cyclopentyl-7-fluoro-4-phenyl-3-(2H-tetrazol-5-yl)quinoline;
6-Chloro-4-(2-methylpyridin-4-yl)-2-(pentan-3-yl)-3-(2H-tetrazol-5-yl)quinoline;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

The following abbreviations are used in the present text: DBU=1,8-Diazabicyclo[5.4.0]undec-7-en, DCM=Dichloromethane, DMAP=N,N-Dimethylpyridine, DMF=N,N-Dimethylformamide, DMSO=Dimethylsulfoxide, EtOAc=Ethyl acetate, EtOH=Ethanol, MeOH=Methanol, pTsOH=p-Toluenesulfonic acid, TBAF=Tetrabutylammonium fluoride, TEA=Triethylamine, TF=Trifluoromethanesulfonyl, TFA=Trifluoroacetic acid, THF=Tetrahydrofuran.

Compounds of formula (I), wherein $R^7$ is —COOH and n is 0 may be prepared as illustrated in scheme 1.

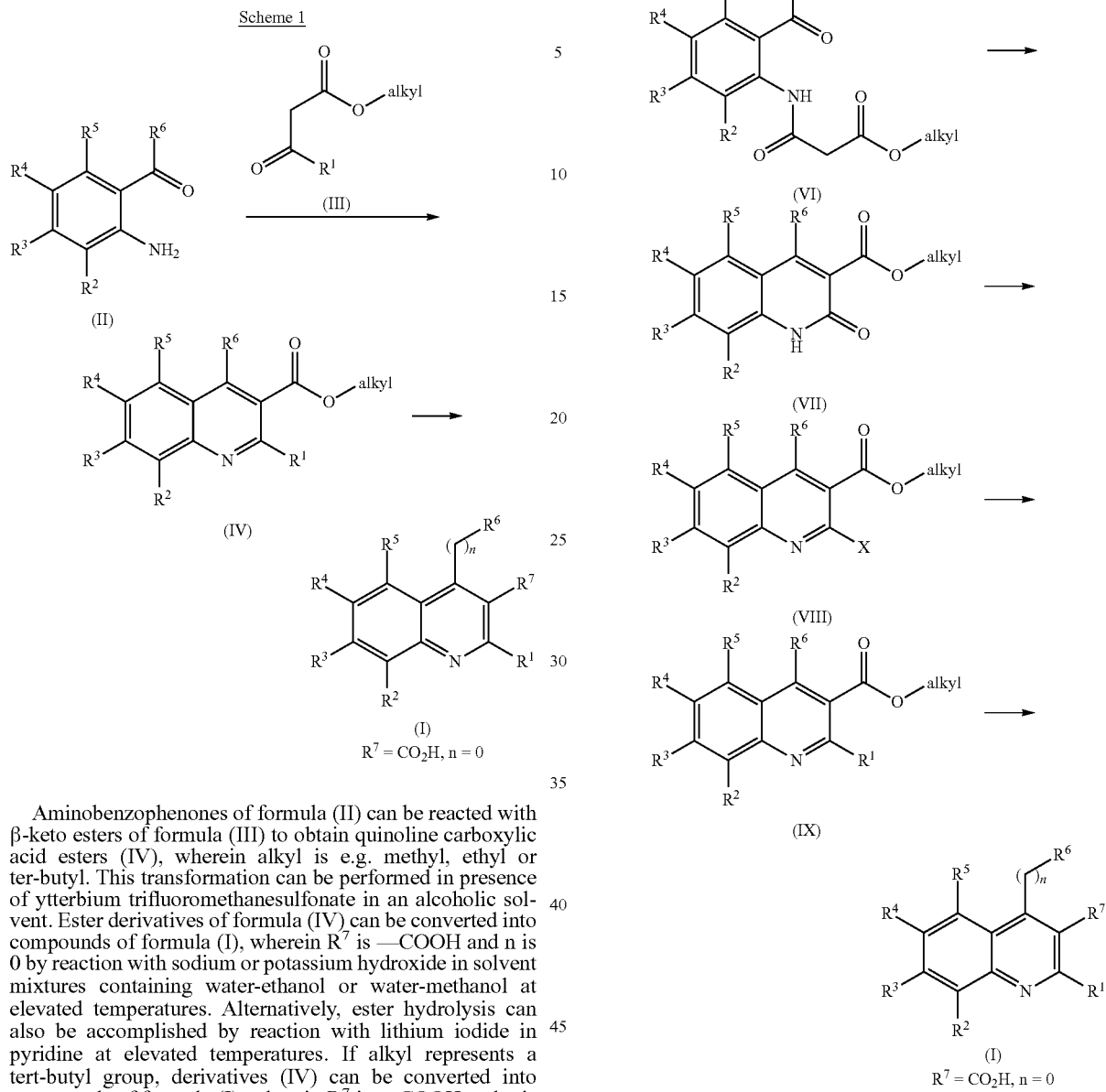

Aminobenzophenones of formula (II) can be reacted with β-keto esters of formula (III) to obtain quinoline carboxylic acid esters (IV), wherein alkyl is e.g. methyl, ethyl or ter-butyl. This transformation can be performed in presence of ytterbium trifluoromethanesulfonate in an alcoholic solvent. Ester derivatives of formula (IV) can be converted into compounds of formula (I), wherein $R^7$ is —COOH and n is 0 by reaction with sodium or potassium hydroxide in solvent mixtures containing water-ethanol or water-methanol at elevated temperatures. Alternatively, ester hydrolysis can also be accomplished by reaction with lithium iodide in pyridine at elevated temperatures. If alkyl represents a tert-butyl group, derivatives (IV) can be converted into compounds of formula (I), wherein $R^7$ is —COOH and n is 0 by reaction with an acid such as HCl in a solvent such as dioxane or with TFA in a solvent such as DCM.

Compounds of formula (I), wherein $R^7$ is —COOH and n is 0 can also be prepared as illustrated in scheme 2.

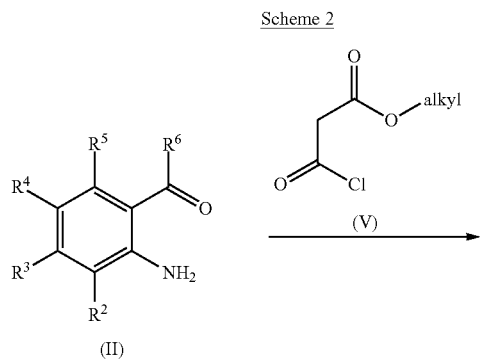

Aminobenzophenones of formula (II) can be converted into compounds of formula (VI) by reaction with alkyl malonyl chlorides (V). Derivatives of formula (VI) can subsequently be cyclized to quinolinones of formula (VII) by reaction with a suitable base such as sodium methylate, sodium ethylate or potassium tert-butylate. Quinolinones of formula (VII) can be elaborated into quinoline derivatives of formula (IV) in 2 steps. Reaction of compounds of formula (VII) with phosphorus oxychloride delivers chloro quinolines of formula (VIII), wherein X is Cl. Alternatively, compounds of formula (VII) can be reacted with N-phenyl-bis(trifluoromethanesulphonimide) in presence of a base such as sodium hydride to obtain derivatives of formula (VIII), wherein X is OTf. Compounds of formula (VIII), wherein X is Cl or OTf can be reacted with alcohols in presence of a base such as sodium hydride to obtain compounds of formula (IV), wherein $R^1$ represents alkoxy, haloalkoxy, cycloalkoxy or halocycloalkoxy. Compounds of formula (VIII), wherein X is Cl or OTf can also be reacted with amines or amides, optionally in presence of a base such as triethylamine, potassium carbonate or sodium hydride to obtain compounds of formula (IV), wherein $R^1$ represents heterocycloalkyl, substituted heterocycloalkyl or substituted amino. By reaction of compounds of formula (VIII), wherein X is Cl with Grignard reagents $R^1MgX'$ (X' is Cl, Br or I), derivatives of formula (IV) can be obtained wherein $R^1$ represents alkyl or cycloalkyl. Conversion of derivatives of formula (IV) into compounds of formula (I), wherein $R^7$ is —COOH and n is 0 can be accomplished as discussed for scheme 1.

Compounds of formula (VII) can also be obtained from aminobenzophenones of formula (II) as illustrated in scheme 3 by reaction of derivatives of formula (II) with malonic esters of formula (IX) in presence of a base such as potassium hydroxide or DBU.

Scheme 3

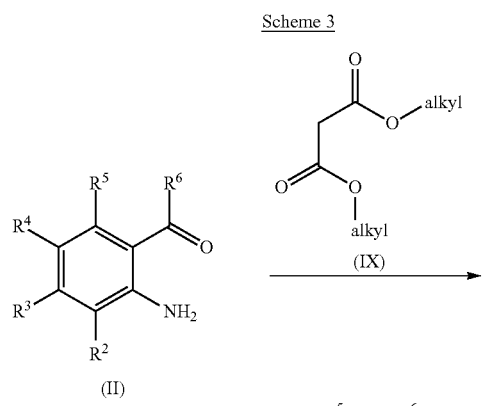

(II)

(IX)

(VII)

Compounds of formula (I), wherein $R^7$ is —COOH, n is 0 and $R^1$ represents substituted amino, heterocycloalky or substituted heterocycloalkyl can also be directly obtained by reaction of derivatives of formula (VIII), wherein X is Cl with suitable acyclic or cyclic secondary amines in pyridine at elevated temperatures.

Compounds of formula (I), wherein $R^7$ is —COOH, n is 0 and $R^1$ represents alkoxy, haloalkoxy, cycloalkoxy or halocycloalkoxy can also be obtained from derivatives (VII) as illustrated in scheme 4.

Scheme 4

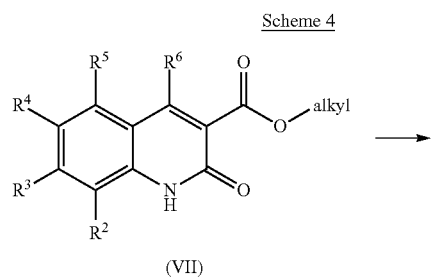

(VII)

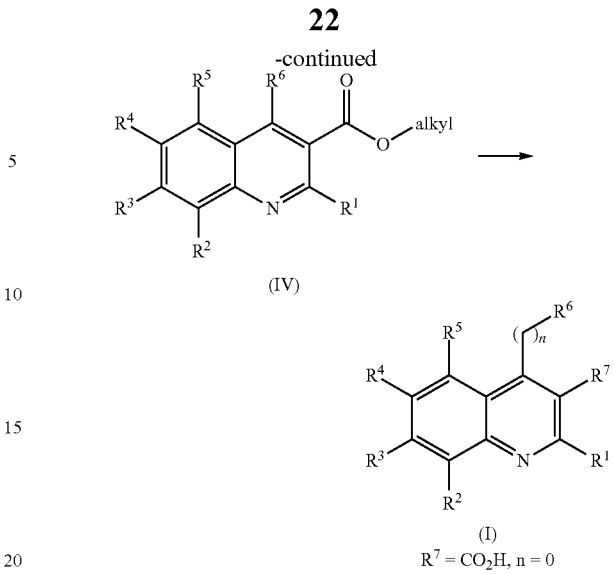

(IV)

(I)
$R^7 = CO_2H$, n = 0

Quinolinones of formula (VII) can be elaborated into derivatives of formula (IV) by O-alkylation with an appropriate alkylating reagent, such as alkyl-X, haloalkyl-X, cycloalkyl-X or halocycloalkyl-X, wherein X is Br or I, in presence of a base such as sodium hydride in a polar aprotic solvent. Conversion of derivatives of formula (IV) into compounds of formula (I), wherein $R^7$ is —COOH, n is 0 and $R^1$ represents alkoxy, haloalkoxy, cycloalkoxy or halocycloalkoxy can be accomplished as discussed for scheme 1.

Compounds of formula (I), wherein $R^7$ is —COOH, n is 0 may also be prepared as illustrated in scheme 5.

Scheme 5

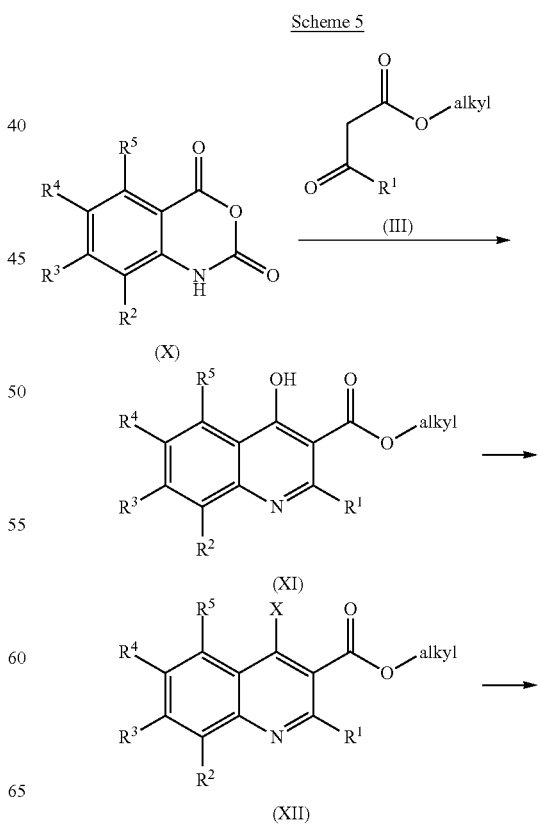

(X)

(III)

(XI)

(XII)

-continued

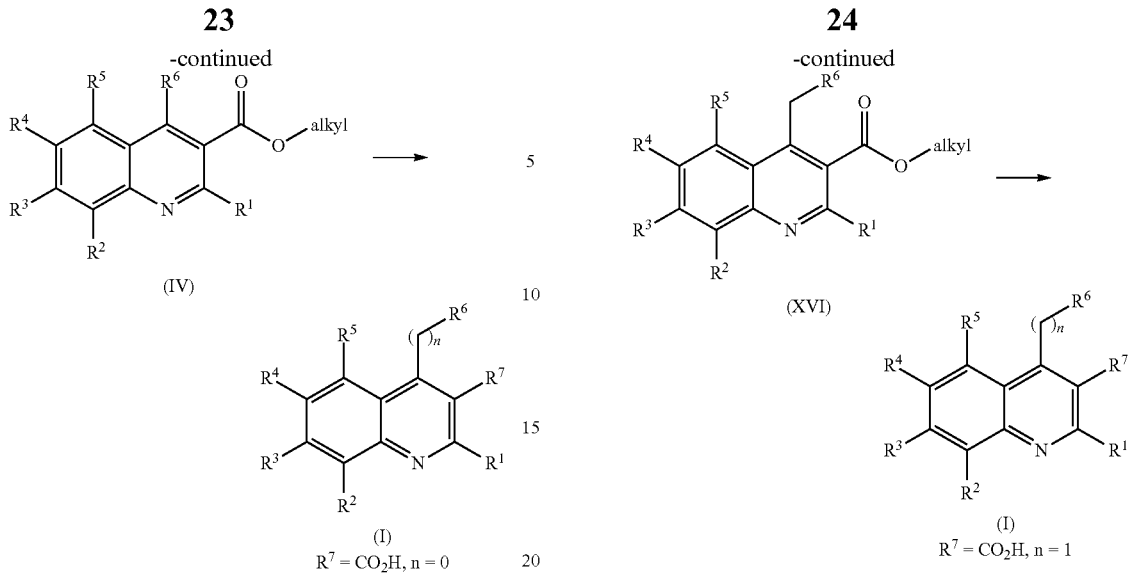

1H-Benzo[d][1,3]oxazine-2,4-diones of formula (X) can be reacted with j-keto esters of formula (III) in presence of a base such as sodium hydride to obtain compounds of formula (XI). Derivatives of formula (XI) can be either reacted with phosphorus oxychloride or phosphorus oxybromide to obtain compounds of formula (XII) wherein X represents Cl or Br respectively, or they can be reacted with N-phenylbis(trifluoromethanesulphonimide) in presence of a base such as sodium hydride to obtain derivatives of formula (XII), wherein X is OTf. Compounds of formula (XII), wherein X is Cl, Br or OTf can be converted into compounds of formula (IV) by reaction with arylboronic acid or arylboronic acid ester derivatives using Suzuki reaction conditions, employing a palladium catalysts such as tetrakis(triphenylphosphine)palladium(0) and a base such as potassium carbonate or potassium phosphate. Transformation of derivatives of formula (IV) into compounds of formula (I), wherein $R^7$ is —COOH, n is 0 can be accomplished as discussed for scheme 1.

Compounds of formula (I), wherein $R^7$ is —COOH, n is 1 may be prepared as illustrated in scheme 6.

Scheme 6

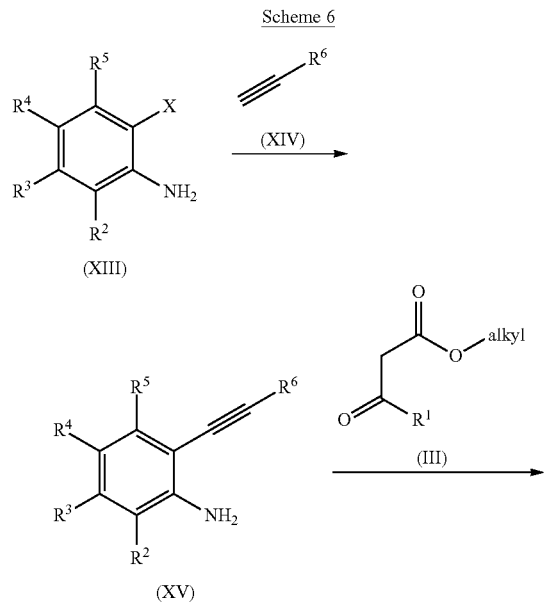

Aniline derivatives of formula (XIII), wherein X is Br or I, can be reacted with phenyl acetylenes of formula (XIV) in presence of a palladium catalyst such as bis(triphenylphosphine)palladium(II) chloride, copper(I)iodide and a base such as diethylamine to obtain compounds of formula (XV). Derivatives of formula (XV) can be converted into quinolines of formula (XVI) by reaction with β-keto esters of formula (III) in presence of toluene-4-sulfonic acid in anhydrous methanol or ethanol. Conversion of derivatives of formula (XVI) into compounds of formula (I), wherein $R^7$ is —COOH, n is 1 can be accomplished as discussed for scheme 1.

Compounds of formula (I, $R^7$=CO₂H, n=1) can also be prepared as illustrated in scheme 7.

Scheme 7

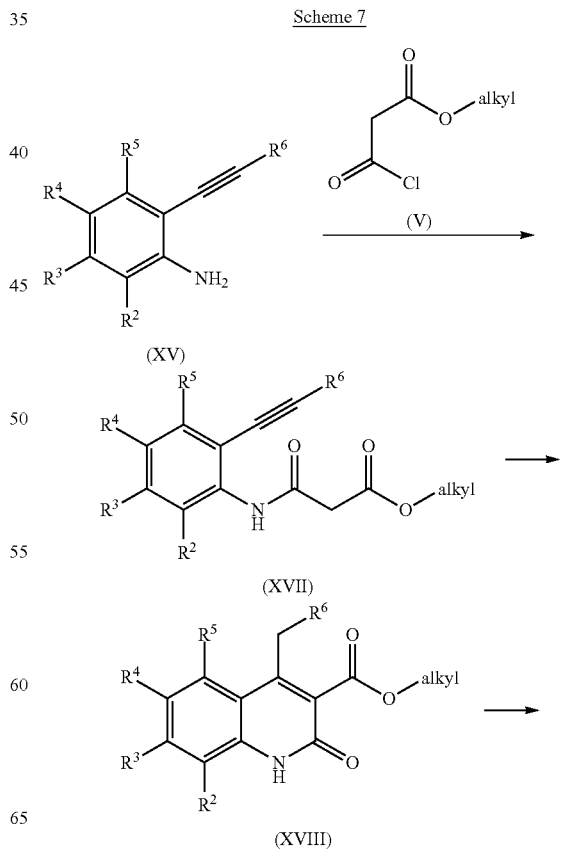

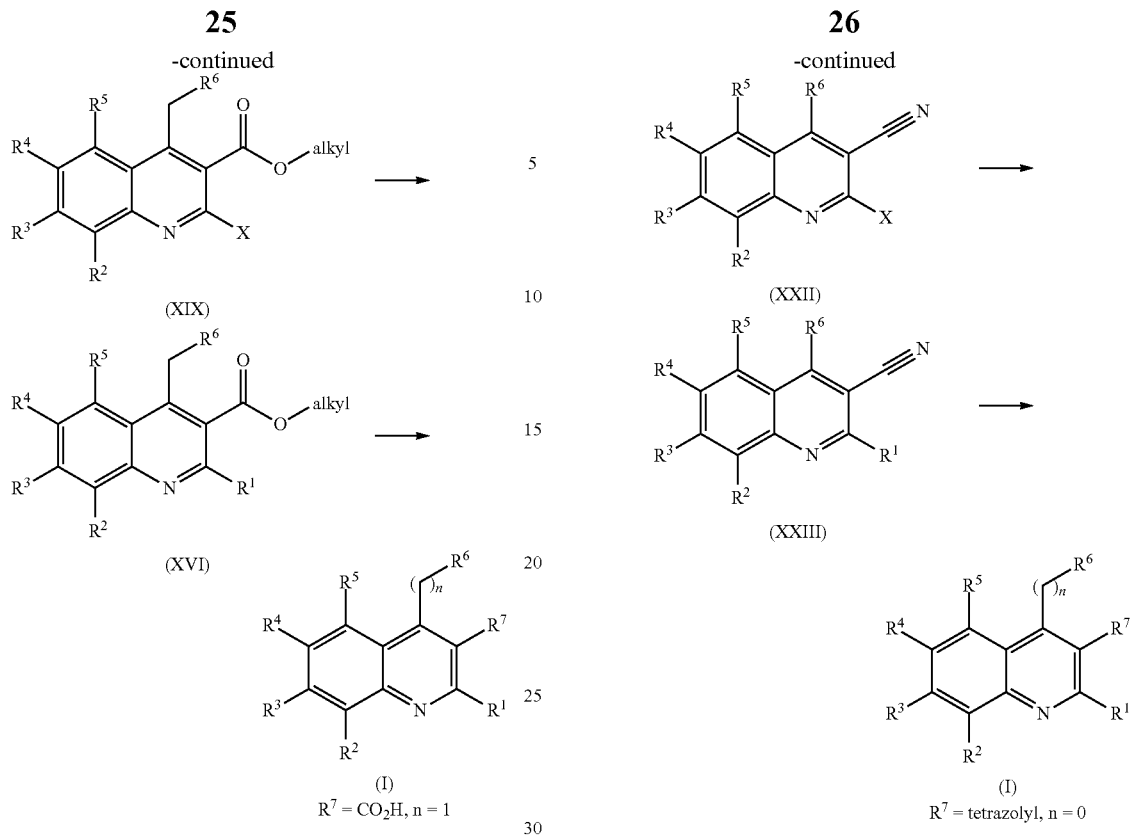

Reaction of derivatives of formula (XV) with alkyl malonyl chlorides of formula (V) in presence of a base such as triethylamine delivers compounds of formula (XVII) that can be cyclized to quinolinones of formula (XVIII). This cyclization can be accomplished with sodium hydride in a polar aprotic solvent such as DMSO. Elaboration of compounds of formula (XVIII) into derivatives of formula (XIX), wherein X is Cl or OTf and subsequent conversion to derivatives of formula (XVI) and finally into compounds of formula (I), wherein $R^7$ is —COOH and n is 1 can be accomplished as discussed for scheme 2.

Compounds of formula (I), wherein $R^7$ is tetrazolyl and n is 0 can be prepared as described in scheme 8.

Scheme 8

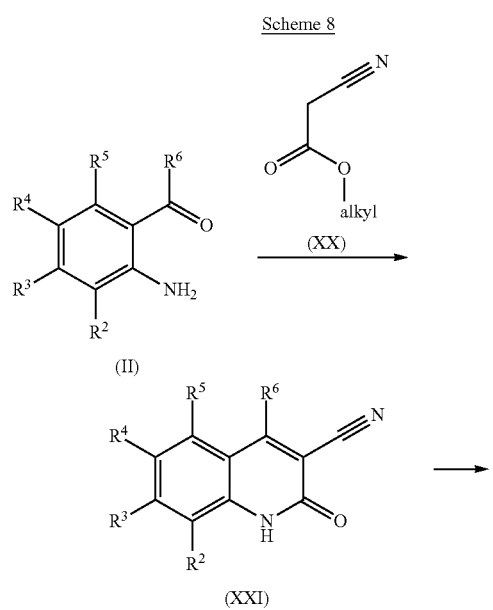

Aminobenzophenones of formula (II) can be reacted with cyanoacetic acid esters of formula (XX) to obtain quinolinones of formula (XXI). This transformation can be performed in presence of cerium (III) chloride heptahydrate at elevated temperatures optionally in a microwave oven. Conversion of quinolinones of formula (XXI) into compounds of formula (XXII), wherein X is Cl or OTf and the subsequent nucleophilic displacement reaction to introduce $R^1$ substituents can be accomplished as discussed for scheme 2. Reaction of derivatives of formula (XXIII) with trimethyltin azide in an inert solvent such as xylene at elevated temperatures delivers compounds of formula (I), wherein $R^7$ is tetrazolyl and n is 0.

An alternative preparation of compounds of formula (XXI) is illustrated in scheme 9.

Scheme 9

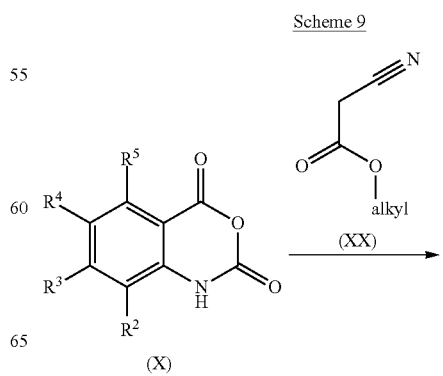

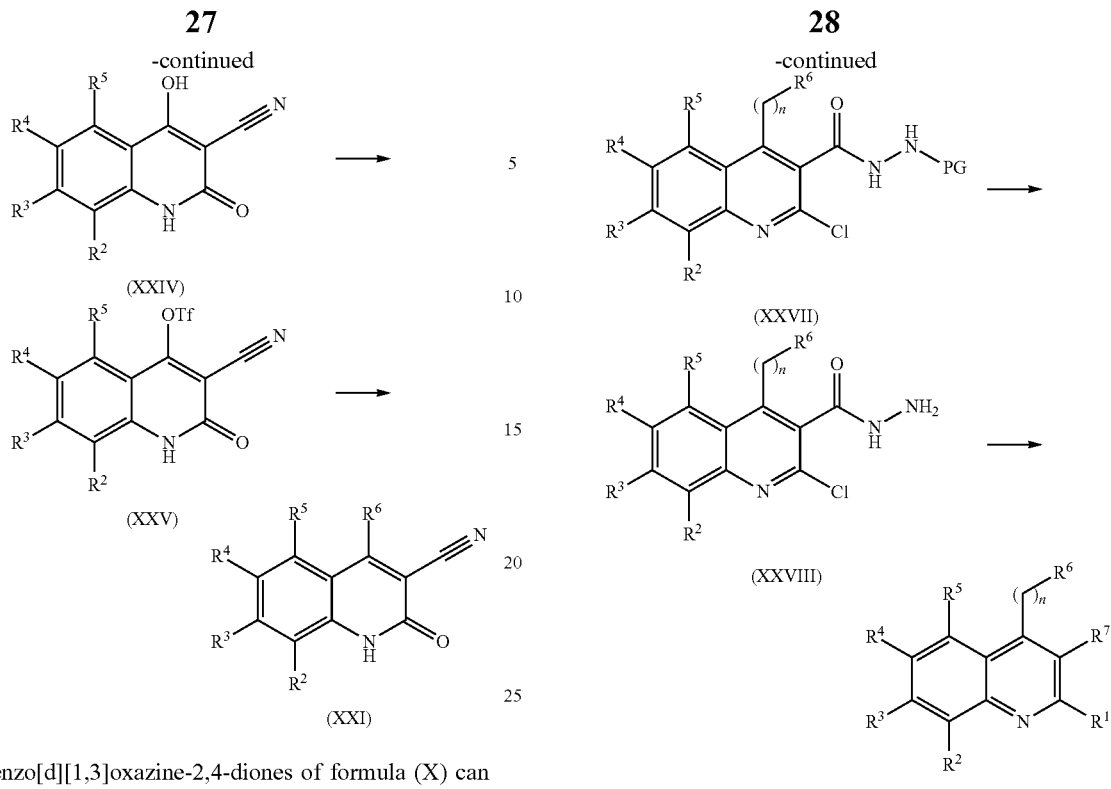

1H-Benzo[d][1,3]oxazine-2,4-diones of formula (X) can be reacted with cyanoacetic acid esters of formula (XX) to obtain quinolones of formula (XXIV) which can be reacted with N-phenylbis(trifluoromethanesulphonimide) in presence of a base such as sodium hydride to obtain derivatives of formula (XXV). Compounds of formula (XXV) can be converted into compounds of formula (XXI) by reaction with arylboronic acid or arylboronic acid ester derivatives using Suzuki reaction conditions, employing a palladium catalysts such as tetrakis(triphenylphosphine)palladium(0) and a base such as potassium carbonate or potassium phosphate. Elaboration of derivatives of formula (XXI) into compounds of formula (I), wherein $R^7$ is tetrazolyl and n is 0 is discussed in scheme 8.

Compounds of formula (I), wherein $R^7$ is [1,3,4]-oxadiazol-2-on-yl or a [1,3,4]-oxadiazol-2-thion-yl may be prepared as described in scheme 10.

Scheme 10

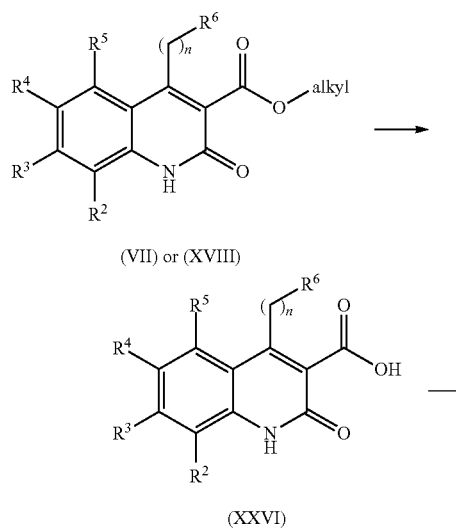

Derivatives of formula (VII) or (XVIII) can be reacted with lithium hydroxide in a solvent such as methanol or ethanol at elevated temperatures to obtain carboxylic acids of formula (XXVI). To elaborate compounds of formula (XXVI) into derivatives of formula (XXVII), wherein PG is protecting group they can be reacted first with phosphorus oxychloride and then with suitably protected hydrazine. If PG represents a 9-fluorenylmethoxycarbonyl (Fmoc) group and acyclic or cyclic secondary amines are introduced as $R^1$ substituents, cleavage of the protecting group and nucleophilic displacement can be performed in one step to obtain compounds formula (XXVIII). Compounds of formula (XXVIII) can be reacted with N,N'-carbonyldiimidazole or 1,1'-thiocarbonyldiimidazole in presence of a base such as triethylamine and in a solvent such as THF to obtain compounds of formula (I), wherein $R^7$ is [1,3,4]-oxadiazol-2-on-yl or [1,3,4]-oxadiazol-2-thion-yl.

Alternative to the route described in scheme 8, formula (XXIII) compounds can be prepared as illustrated in scheme 11.

Scheme 11:

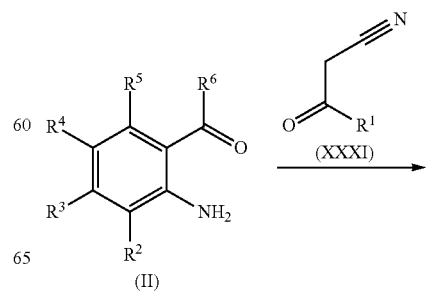

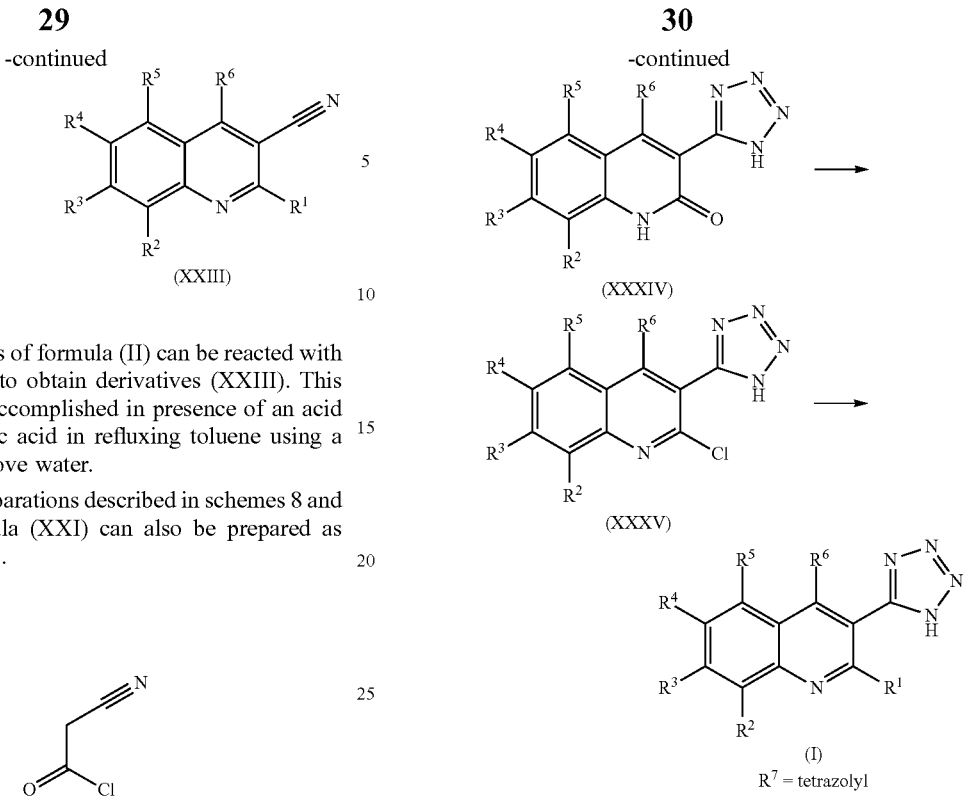

Aminobenzophenones of formula (II) can be reacted with β-keto nitriles (XXXI) to obtain derivatives (XXIII). This transformation can be accomplished in presence of an acid such as methanesulfonic acid in refluxing toluene using a Dean-Stark-trap to remove water.

Alternative to the preparations described in schemes 8 and 9, quinolones of formula (XXI) can also be prepared as illustrated in scheme 12.

Scheme 12:

Aminobenzophenones of formula (II) can be reacted with cyano-acetyl chloride (XXXII) in presence of a base such as triethylamine to obtain compounds of formula (XXI). Compounds of formula (I), wherein $R^7$ is tetrazolyl and n is 0 can be prepared as described in scheme 13.

Scheme 13:

Aminobenzophenones of formula (II) can be reacted with (1H-tetrazol-5-yl)-acetic acid (XXXIII) in the presence of 1-propanephosphonic acid cyclic anhydride in ethyl acetate as a solvent to obtain compounds of formula (XXXIV). Derivatives (XXXIV) can be converted into compounds of formula (XXXV) by reaction with phosphorus oxychloride. Compounds of formula (XXXV) can be reacted with amines, optionally in presence of a base such as triethylamine, to obtain compounds of formula (I), wherein $R^1$ represents heterocycloalkyl, substituted heterocycloalkyl or substituted amino.

Alternative to the routes described in schemes 8 and 11, formula (XXIII) compounds can be prepared as illustrated in scheme 14.

Scheme 14:

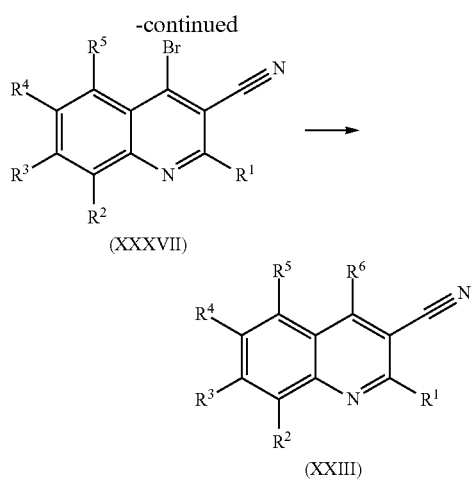

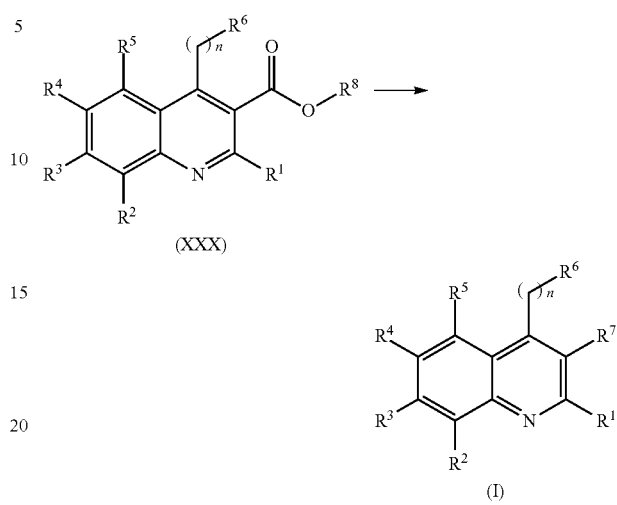

1H-Benzo[d][1,3]oxazine-2,4-diones of formula (X) can be reacted with β-keto nitriles (XXXI) in the presence of a base such as triethylamine to obtain compounds of formula (XXXVI) which can be reacted with phosphorus tribromide to obtain derivatives of formula (XXXVII). Compounds of formula (XXXVII) can be converted into compounds of formula (XXIII) by reaction with arylboronic acid or arylboronic acid ester derivatives using Suzuki reaction conditions, employing a palladium catalysts such as tetrakis(triphenylphosphine)palladium(0) and a base such as cesium carbonate.

Also an embodiment of the present invention is a process to prepare a compound of formula (I) as defined above comprising the reaction of a) a compound of formula (XXIII) in the presence of a compound of formula (XXIX);

b) a compound of formula (XXX) in the presence of base or and acid;

In particular in the presence of sodium or potassium hydroxide in solvent mixtures containing water-ethanol or water-methanol, or in the presence of lithium iodide in pyridine, at a temperature comprised between RT and reflux, or wherein $R^8$ is tert-butyl, in the presence of an acid such as HCl in a solvent such as dioxane or with TFA in a solvent such as DCM, wherein $R^1$, $R^2$, $R^3$, $R^4$, $R^5$, $R^6$ and n are as defined herein and wherein $R^7$ is —COOH and $R^8$ is alkyl, particularly methyl, ethyl or tert-butyl; or c) a compound of formula (XXVIII) in the presence of N,N'-carbonyldiimidazole or 1,1'-thiocarbonyldiimidazole;

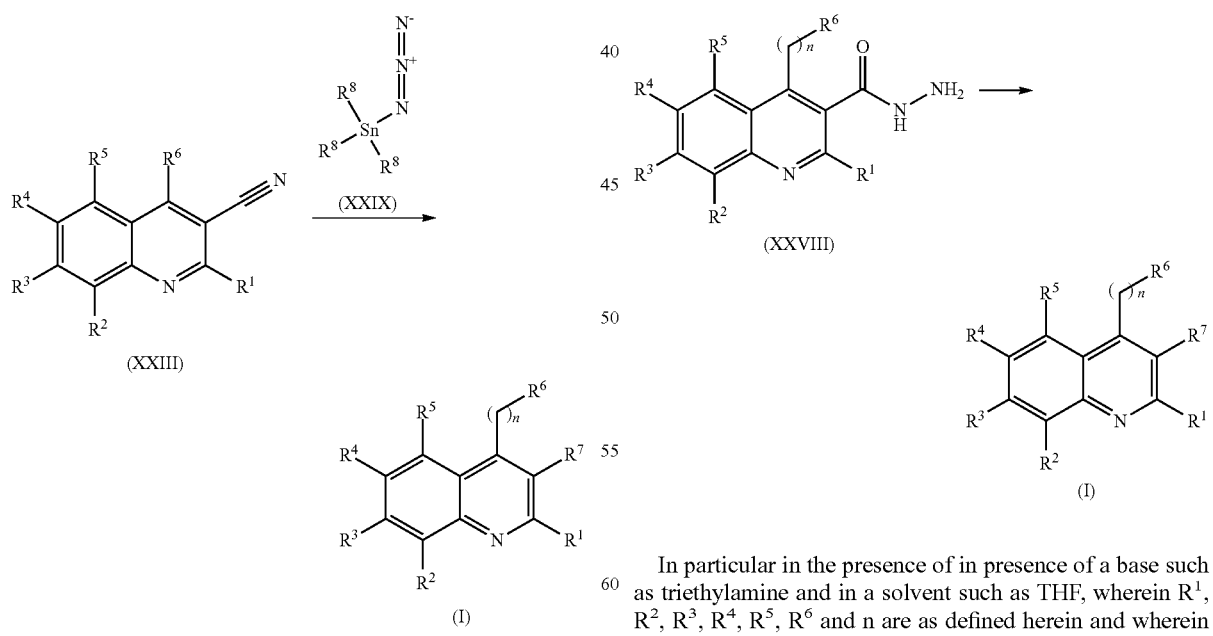

In particular in a solvent, particularly xylene, at a temperature comprised between 50 and reflux, wherein $R^1$, $R^2$, $R^3$, $R^4$, $R^5$, $R^6$ and n are as defined herein and wherein $R^7$ is tetrazolyl and $R^8$ is alkyl, particularly methyl; or In particular in the presence of in presence of a base such as triethylamine and in a solvent such as THF, wherein $R^1$, $R^2$, $R^3$, $R^4$, $R^5$, $R^6$ and n are as defined herein and wherein $R^7$ is 3H-[1,3,4]-oxadiazol-2-on-yl or 3H-[1,3,4]-oxadiazol-2-thion-yl.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

In accordance with the invention, the compounds of formula (I) or their pharmaceutically acceptable salts and esters can be used for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

Particular liver diseases are liver diseases involving inflammation, steatosis and/or fibrosis, such non-alcoholic fatty liver disease, more particularly non-alcoholic steatohepatitis.

Particular lipodystrophy are genetic and iatrogenic lipodystrophy.

Particular eye diseases are eye diseases supported by endothelial proliferation and angiogenesis, particularly macular degeneration and retinopathy.

Particular lung diseases are asthma, bronchopulmonary dysplasia and chronic obstructive pulmonary disease.

Particular chronic renal diseases are vasculitis, focal segmental glomerulosclerosis, diabetic nephropathy, lupus nephritis, polycystic kidney disease and drug or toxin-induced chronic tubulointerstitial nephritis.

The present invention also relates to the use of a compound according to formula (I) as described herein for the treatment or prophylaxis of lipodystrophy, type 2 diabetes, dyslipidemia, atherosclerosis, liver diseases involving inflammation, steatosis and/or fibrosis, metabolic syndrome, obesity, chronic inflammatory and autoimmune inflammatory diseases.

The present invention also relates to the use of a compound according to formula (I) as described herein for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

The present invention particularly relates to the use of a compound according to formula (I) as described herein for the treatment or prophylaxis of type 2 diabetes, atherosclerosis, cancer, chronic renal disease and non-alcoholic steatohepatitis.

The present invention also relates to the use of a compound according to formula (I) as described herein for the treatment or prophylaxis of non-alcoholic steatohepatitis.

The present invention also relates to the use of a compound according to formula (I) as described herein for the treatment or prophylaxis of lipodystrophy.

A particular embodiment of the present invention is a compound according to formula (I) as described herein for the treatment or prophylaxis of lipodystrophy, type 2 diabetes, dyslipidemia, atherosclerosis, liver diseases involving inflammation, steatosis and/or fibrosis, metabolic syndrome, obesity, chronic inflammatory and autoimmune inflammatory diseases.

A particular embodiment of the present invention is a compound according to formula (I) as described herein for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

Another particular embodiment of the present invention is a compound according to formula (I) as described herein for the treatment or prophylaxis of type 2 diabetes, atherosclerosis, cancer, chronic renal disease and non-alcoholic steatohepatitis.

Also a particular embodiment of the present invention is a compound according to formula (I) as described herein for the treatment or prophylaxis of non-alcoholic steatohepatitis.

Also a particular embodiment of the present invention is a compound according to formula (I) as described herein for the treatment or prophylaxis of lipodystrophy.

The present invention also relates to the use of a compound according to formula (I) as described herein for the preparation of a medicament for the treatment or prophylaxis of lipodystrophy, type 2 diabetes, dyslipidemia, atherosclerosis, liver diseases involving inflammation, steatosis and/or fibrosis, metabolic syndrome, obesity, chronic inflammatory and autoimmune inflammatory diseases.

The present invention also relates to the use of a compound according to formula (I) as described herein for the preparation of a medicament for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

The present invention particularly relates to the use of a compound according to formula (I) as described herein for the preparation of a medicament for the treatment or prophylaxis of type 2 diabetes, atherosclerosis, cancer, chronic renal disease and non-alcoholic steatohepatitis.

Also an embodiment of the present invention is the use of a compound according to formula (I) as described herein for the preparation of a medicament for the treatment or prophylaxis of non-alcoholic steatohepatitis.

Also an embodiment of the present invention is the use of a compound according to formula (I) as described herein for the preparation of a medicament for the treatment or prophylaxis of lipodystrophy.

Also an object of the invention is a method for the treatment or prophylaxis of lipodystrophy, type 2 diabetes, dyslipidemia, atherosclerosis, liver diseases involving inflammation, steatosis and/or fibrosis, metabolic syndrome, obesity, chronic inflammatory and autoimmune inflammatory diseases, which method comprises administering an effective amount of a compound according to formula (I) as described herein.

Also an object of the invention is a method for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome, which method comprises administering an effective amount of a compound according to formula (I) as described herein.

Another object of the invention is a method for the treatment or prophylaxis of type 2 diabetes, atherosclerosis, cancer, chronic renal disease and non-alcoholic steatohepatitis, which method comprises administering an effective amount of a compound according to formula (I) as described herein.

Also an embodiment of the present invention is a method for the treatment or prophylaxis of lipodystrophy, which method comprises administering an effective amount of a compound according to formula (I) as described herein.

Also an embodiment of the present invention is a method for the treatment or prophylaxis of non-alcoholic steatohepatitis, which method comprises administering an effective amount of a compound according to formula (I) as described herein.

Also an embodiment of the present invention is a method for the treatment or prophylaxis of lipodystrophy, which method comprises administering an effective amount of a compound according to formula (I) as described herein.

Also a particular embodiment of the present invention is a compound according to formula (I) as described herein, when manufactured according to any one of the described processes.

Assay Procedures

Compounds were profiled for activity against human FABP4 (huFABP4) and/or human FABP5 (huFABP5) in Terbium (Tb) time resolved-fluorescence energy transfer (TR-FRET) assays monitoring the direct binding of Bodipy labeled fatty acid to His6 tagged FABP proteins (huFABP4 was expressed in house in *E. Coli* and purified, huFABP5 was purchased from Cayman Chemical Co., cat. no. 10010364), bound to Terbium labeled anti His6 tag antibody. Assay read-outs reflected energy transfer, upon binding of the ligand to the FABP protein, from the Terbium donor molecule to the acceptor Bodipy moiety. Final ligand concentration (125 nM) approximated the Kd for each protein.

Stock DMSO solutions (1.8 mM) of compounds were serially diluted 3-fold for ten concentrations with 100% DMSO (50 µM to 0.003 µM final compound concentration). 1 µl of these compound dilutions and 1 µl of Bodipy labeled fatty acid 4.5 µM in 100% DMSO (Bodipy FL C11, cat. no. D3862, Invitrogen) were sequentially pipetted in wells of 384-well black polypropylene plates (Thermo Matrix cat. no. 4344). FABP4 or FABP5 protein was then added (28 µl of 64 nM protein in 25 mM Tris pH 7.5, 0.4 mg/ml γ-globulin, 1 mM DTT, 0.012% NP40, final protein concentration: 50 nM). Assay blanks contained ligand, but no protein. Neutral controls contained ligand, but no compound. After adding the detection reagent (Tb antiHis6 antibody, Columbia Biosciences, TB-110, 6 µl of a 24 nM Ab solution in 25 mM Tris pH 7.5, 0.4 mg/ml γ-globulin, final Tb antiHis6 Ab concentration: 4 nM), plates were spun one minute at 1000 rpm. Following an incubation at room temperature with shaking for 30 minutes, plates were read using an Envision reader (Perkin Elmer, Extinction wavelength: 340 nm, Emission: 490 nm and 520 nm, time delay: 100 µs; time window: 200 µs, 50 flashes).

Final assay conditions were: 50 nM FABP protein, 125 nM Bodipy labeled fatty acid, 0.009% (vol/vol) NP40, 5.5% (vol/vol) DMSO in a total final assay volume of 36 µl. The assay was performed in triplicate.

The relative fluorescence units (RFU) ratio (520 nm*10000/488 nm) were used to calculate the percent inhibition: 100−(RFU ratio compound−blank)/neutral control−blank)*100. These percent inhibition values were then fit to dose response curves using a 4 parameter logistic model (Hill sigmoidal dose-response model). $IC_{50}$s reflected compound concentrations associated with 50% inhibition of protein activity compared to that of neutral controls.

| Example | IC50 h-fabp4-ecoli-r µM | IC50 h-fabp5-ecoli-r µM |
| --- | --- | --- |
| 1 | 0.0424 | 4.786 |
| 2 | 0.0512 | 2.62 |
| 3 | 0.216 | 20.98 |
| 4 | 0.125 | 6.41 |
| 5 | 0.0755 | 1.0935 |
| 6 | 0.057 | 2.802 |
| 7 | 3.964 | |
| 8 | 0.0671 | 7.101 |
| 9 | 0.729 | 10.34 |
| 10 | 0.112 | 3.218 |
| 11 | 0.131 | 18.56 |
| 12 | 0.283 | |
| 13 | 0.165 | 2.685 |
| 14 | 0.0821 | 4.891 |
| 15 | 0.0449 | 4.329 |
| 16 | 0.0947 | 5.195 |
| 17 | 0.169 | 19.87 |
| 18 | 0.0429 | 10.7 |
| 19 | 0.0275 | 0.618 |
| 20 | 0.152 | 16.47 |
| 21 | 0.0617 | 0.294 |
| 22 | 0.0534 | 0.459 |
| 23 | 0.0517 | 0.952 |
| 24 | 0.074 | 0.179 |
| 25 | 0.114 | 5.798 |
| 26 | 0.172 | 8.54 |
| 27 | 0.0828 | 0.518 |
| 28 | 0.0505 | 0.211 |
| 29 | 0.0974 | 3.678 |
| 30 | 2.055 | |
| 31 | 0.06115 | 9.227 |
| 32 | 0.07035 | 28.575 |
| 33 | 0.212 | 18.98 |
| 34 | 0.0822 | 17.96 |
| 35 | 0.0889 | 10.8 |
| 36 | 0.166 | 6.182 |
| 37 | 0.22 | 15.19 |
| 38 | 9.248 | |
| 39 | 0.999 | 19.32 |
| 40 | 0.0548 | 0.251 |
| 41 | 0.0533 | 0.587 |
| 42 | 0.0561 | 4.56 |
| 43 | 0.0819 | 1.334 |
| 44 | 0.0677 | 0.128 |
| 45 | 0.0591 | 0.136 |
| 46 | 0.127 | 10.09 |
| 47 | 0.0654 | 4.054 |
| 48 | 0.0769 | 7.54 |
| 49 | 0.0859 | 39.28 |
| 50 | 0.0361 | 0.183 |
| 51 | 0.0352 | 0.266 |
| 52 | 0.0445 | 1.402 |
| 53 | 0.0956 | 8.392 |
| 54 | 0.0561 | 0.181 |
| 55 | 0.0507 | 0.235 |
| 56 | 0.0498 | 0.365 |
| 57 | 0.0477 | 1.555 |
| 58 | 0.0476 | 1.558 |
| 59 | 0.0603 | 0.159 |
| 60 | 0.0603 | 10.12 |
| 61 | 0.109 | 3.695 |
| 62 | 0.272 | 19.27 |
| 63 | 0.124 | 14.19 |
| 64 | 0.0608 | 0.285 |
| 65 | 0.0665 | 0.235 |
| 66 | 0.0445 | 8.424 |
| 67 | 0.0454 | 0.182 |
| 68 | 0.0408 | 0.205 |
| 69 | 0.294 | 16.34 |
| 70 | 0.0619 | 0.257 |
| 71 | 2.909 | 10.83 |
| 72 | 0.0343 | 0.615 |
| 73 | 0.0468 | 1.237 |
| 74 | 0.0405 | 0.694 |
| 75 | 0.0937 | 0.765 |
| 76 | 0.0602 | 0.184 |

| Example | IC50 h-fabp4-ecoli-r μM | IC50 h-fabp5-ecoli-r μM |
|---|---|---|
| 77 | 0.0705 | 0.386 |
| 78 | 0.0398 | 1.8073 |
| 79 | 0.246 | 13.95 |
| 80 | 0.093 | 6.09 |
| 81 | 0.0635 | 9.956 |
| 82 | 0.126 | 11.33 |
| 83 | 0.093 | 14.5 |
| 84 | 0.0683 | 0.134 |
| 85 | 0.0423 | 0.314 |
| 86 | 0.0524 | 0.414 |
| 87 | 0.785 | 4.016 |
| 88 | 0.423 | 1.939 |
| 89 | 0.902 | 1.381 |
| 90 | 0.3772 | 3.0951 |
| 91 | 0.0193 | 1.0644 |
| 92 | 0.0867 | 4.3067 |
| 93 | 0.0256 | 2.385 |
| 94 | 0.0289 | 2.1291 |
| 95 | 0.765 | 7.8007 |
| 96 | 0.0663 | 2.2954 |
| 97 | 0.0317 | 1.4315 |
| 98 | 1.392 | 2.1168 |
| 99 | 1.339 | 3.01 |
| 100 | 0.0439 | 0.1634 |
| 101 | 0.0103 | 0.1637 |
| 102 | 0.0326 | 0.0961 |
| 103 | 0.025 | 0.0638 |
| 104 | 0.0218 | 0.1753 |
| 105 | 0.0273 | 0.1396 |
| 106 | 0.0165 | 0.0798 |
| 107 | 0.0133 | 0.0623 |
| 108 | 0.0132 | 0.0512 |
| 109 | 0.0128 | 0.2784 |
| 110 | 0.0336 | 0.336 |
| 111 | 0.0205 | 0.4147 |
| 112 | 0.0247 | 0.1311 |
| 113 | 0.0255 | 0.1521 |
| 114 | 0.0255 | 0.2438 |
| 115 | 0.1677 | 0.2618 |
| 116 | 0.0123 | 0.4593 |
| 117 | 0.0316 | 0.6545 |
| 118 | 0.0184 | 0.3302 |
| 119 | 0.0209 | 0.6975 |
| 120 | 0.0214 | 0.9824 |
| 121 | 0.0111 | 0.2039 |
| 122 | 0.0356 | 0.2178 |
| 123 | 0.0867 | 2.9036 |
| 124 | 0.028 | 5.7926 |
| 125 | 0.0297 | 4.5218 |
| 126 | 0.0176 | 2.3833 |
| 127 | 0.0846 | 2.5497 |
| 128 | 0.1693 | 0.0689 |

Compounds of formula (I) and their pharmaceutically acceptable salts or esters thereof as described herein have IC$_{50}$ (FABP4 inhibition) values between 0.000001 μM and 1000 μM, particular compounds have IC$_{50}$ values between 0.000005 μM and 500 μM, further particular compounds have IC$_{50}$ values between 0.00005 μM and 5 μM.

Compounds of formula (I) and their pharmaceutically acceptable salts or esters thereof as described herein have IC$_{50}$ (FABP5 inhibition) values between 0.000001 μM and 1000 μM, particular compounds have IC$_{50}$ values between 0.000005 μM and 500 μM, further particular compounds have IC$_{50}$ values between 0.00005 μM and 50 μM.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of type 2 diabetes related microvascular complications (such as, but not limited to diabetic retinopathy, diabetic neuropathy and diabetic nephropathy), coronary artery disease, obesity and underlying inflammatory diseases, chronic inflammatory and autoimmune/inflammatory diseases The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Example 1

6-Chloro-2-cyclopropyl-4-phenylquinoline-3-carboxylic acid

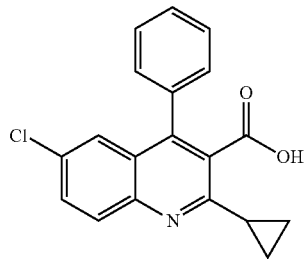 [SMILES: O=C(O)c1c(C2CC2)nc2ccc(Cl)cc2c1-c1ccccc1]

Step A: 6-Chloro-2-cyclopropyl-4-phenyl-quinoline-3-carboxylic acid methyl ester

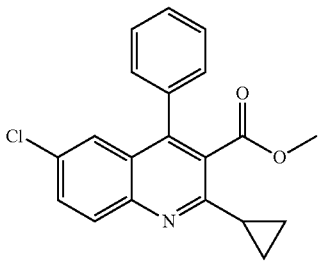 [SMILES: COC(=O)c1c(C2CC2)nc2ccc(Cl)cc2c1-c1ccccc1]

In a 5 ml round-bottomed flask, (2-amino-5-chlorophenyl)(phenyl)methanone (100 mg, 432 µmol, Eq: 1.00) and methyl 3-cyclopropyl-3-oxopropanoate (79.8 mg, 561 µmol, Eq: 1.3) were combined with EtOH (1.5 ml) to give a light yellow solution. Ytterbium triflate (26.9 mg, 43.2 µmol, Eq: 0.1) was added. The mixture was stirred at room temperature overnight, upon which a white precipitate formed. The precipitate was filtered and washed with ethanol to provide the title compound (67 mg, 46%) as a white powder.

Step B: 6-Chloro-2-cyclopropyl-4-phenylquinoline-3-carboxylic acid

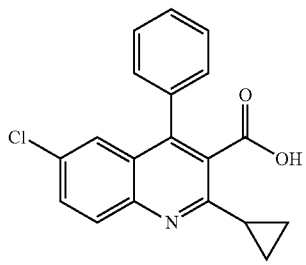 [SMILES: O=C(O)c1c(C2CC2)nc2ccc(Cl)cc2c1-c1ccccc1]

6-Chloro-2-cyclopropyl-4-phenyl-quinoline-3-carboxylic acid methyl ester (67 mg, 198 µmol, Eq: 1.00) was combined with methanol (1.6 ml) to give a white suspension. Two drops of THF were added to help solubilization. KOH (91 mg, 1.62 mmol, Eq: 8.18) was dissolved in water (140 µl) and was added to the reaction mixture. The reaction mixture was heated to 65° C. to give a colorless solution and stirred at 65° C. for 50 h. The reaction mixture was concentrated in vacuo and the residue dissolved in water. Acidification with HCl (6N) to pH 1 yielded a white precipitate, which was filtered and dried under high vacuum to yield 6-chloro-2-cyclopropyl-4-phenylquinoline-3-carboxylic acid (50 mg, 77%) as a white powder. MS (ESI): 324.2 (M+H)$^+$.

Example 2

6-Chloro-2-isopropyl-4-phenyl-quinoline-3-carboxylic acid

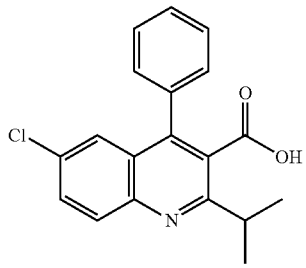 [SMILES: CC(C)c1nc2ccc(Cl)cc2c(-c2ccccc2)c1C(=O)O]

Step A: 6-Chloro-2-isopropyl-4-phenyl-quinoline-3-carboxylic acid ethyl ester

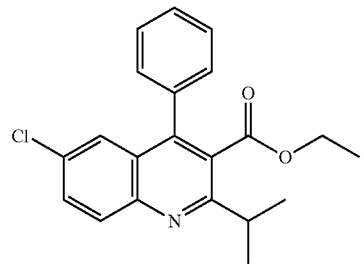 [SMILES: CCOC(=O)c1c(C(C)C)nc2ccc(Cl)cc2c1-c1ccccc1]

The title compound was prepared in analogy to example 1 step A using (2-amino-5-chlorophenyl)(phenyl)methanone and ethyl 3-isopropyl-3-oxopropanoate as starting materials.

Step B: 6-Chloro-2-isopropyl-4-phenyl-quinoline-3-carboxylic acid

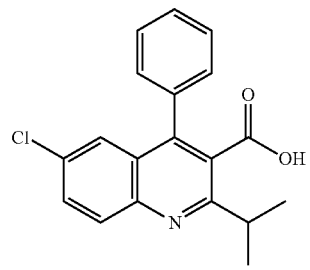 [SMILES: CC(C)c1nc2ccc(Cl)cc2c(-c2ccccc2)c1C(=O)O]

The title compound was prepared in analogy to example 1 step B from 6-chloro-2-isopropyl-4-phenyl-quinoline-3-carboxylic acid ethyl ester. MS (ESI): 326.2 (M+H)$^+$.

Example 3

2-Ethoxy-6-nitro-4-phenyl-quinoline-3-carboxylic acid

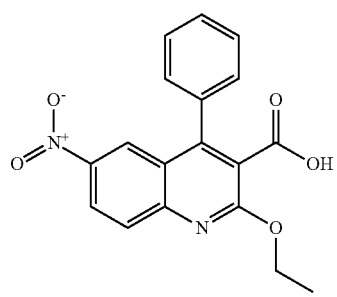 [SMILES: CCOc1nc2ccc([N+](=O)[O-])cc2c(-c2ccccc2)c1C(=O)O]

A solution of 2-chloro-6-nitro-4-phenyl-quinoline-3-carboxylic acid ethyl ester (10 mg, 0.028 mmol) was suspended in ethanol and treated with 3N KOH (0.1 ml, 10.7 Eq). The mixture was warmed to 80° C. for 24 h, then further 3N KOH (0.1 ml, 10.7 Eq.) was added and stirring at 80° C. was continued for further 24 h. The mixture was diluted with water and acidified to pH 1 with HCl 1N. The slurry was extracted with dichloromethane and the extracts were evaporated to yield the title compound (7.6 mg, 82%) as a white powder. MS (ESI): 339.2 (M+H)$^+$.

Example 4

2-Ethoxy-6-chloro-4-phenyl-quinoline-3-carboxylic acid

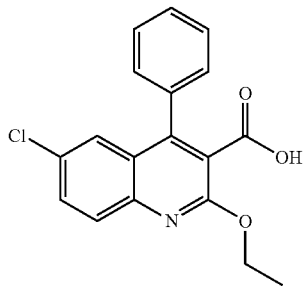 [SMILES: CCOc1nc2ccc(Cl)cc2c(-c2ccccc2)c1C(=O)O]

The title compound was obtained in analogy to example 3 using 2,6-dichloro-4-phenyl-quinoline-3-carboxylic acid ethyl ester (prepared as described in example 11 step B) as starting material. MS (ESI): 328.2 (M+H)$^+$.

Example 5

6-Chloro-4-phenyl-2-piperidin-1-yl-quinoline-3-carboxylic acid

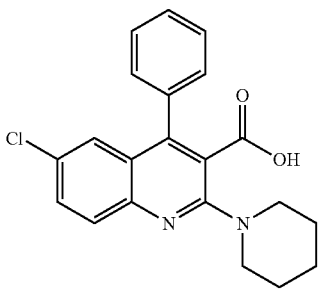 [SMILES: O=C(O)c1c(N2CCCCC2)nc2ccc(Cl)cc2c1-c1ccccc1]

Step A: 6-Chloro-4-phenyl-2-piperidin-1-yl-quinoline-3-carboxylic acid ethyl ester

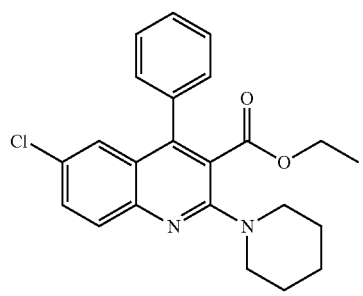 [SMILES: CCOC(=O)c1c(N2CCCCC2)nc2ccc(Cl)cc2c1-c1ccccc1]

The title compound was prepared in analogy to example 12 step A from 2,6-dichloro-4-phenyl-quinoline-3-carboxylic acid ethyl ester (prepared as described in example 11 step B) and piperidine.

Step B

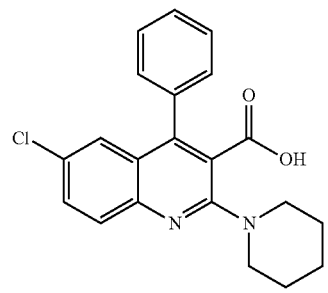 [SMILES: O=C(O)c1c(N2CCCCC2)nc2ccc(Cl)cc2c1-c1ccccc1]

The title compound was prepared in analogy to example 1 step B from 6-chloro-4-phenyl-2-piperidin-1-yl-quinoline-3-carboxylic acid ethyl ester. MS (ESI): 367.3 (M+H)$^+$.

Example 6

6-Chloro-4-(3-chloro-phenyl)-2-cyclopropyl-quinoline-3-carboxylic acid

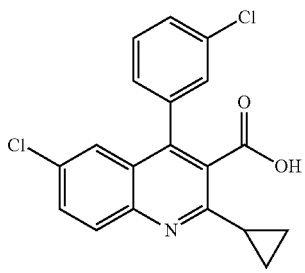 [SMILES: O=C(O)c1c(C2CC2)nc2ccc(Cl)cc2c1-c1cccc(Cl)c1]

Step A: 6-Chloro-4-(3-chloro-phenyl)-2-cyclopropyl-quinoline-3-carboxylic acid methyl ester

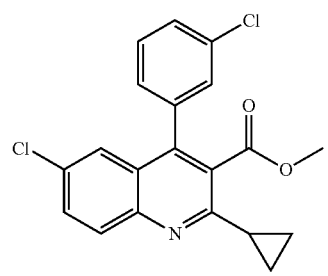 [SMILES: COC(=O)c1c(C2CC2)nc2ccc(Cl)cc2c1-c1cccc(Cl)c1]

To a mixture of (2-amino-5-chlorophenyl)(3-chlorophenyl) methanone (81 mg, 0.31 mmol, 1 eq) and methyl 3-cyclopropyl-3-oxopropanoate (56.2 mg, 0.40 mmol, 1.3 eq) in ethanol (3 ml) was added ytterbium triflate (19 mg, 0.03 mmol, 0.1 eq) and the yellow solution was stirred overnight at room temperature. The resultant precipitate was filtered and washed with a small amount of ethanol to give the desired product (49 mg, 43%) as a white solid which did not require any further purification. MS (ESI): 372.1 (M+H)$^+$.

Step B: 6-Chloro-4-(3-chloro-phenyl)-2-cyclopropyl-quinoline-3-carboxylic acid

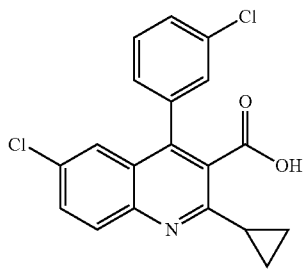 [SMILES: O=C(O)c1c(C2CC2)nc2ccc(Cl)cc2c1-c1cccc(Cl)c1]

To a white suspension of methyl 6-chloro-4-(3-chloro-phenyl)-2-cyclopropylquinoline-3-carboxylate (45 mg, 0.12 mmol, 1 eq) in ethanol (2 ml) was added 1N NaOH (604 µl, 0.60 mmol, 5 eq) and the reaction mixture was refluxed overnight. The clear solution was then cooled to room temperature and concentrated in vacuo. The residue was diluted with water and the pH was adjusted to 3 with 1N HCl. The aqueous layer was extracted with ethyl acetate (×3) and the organic phases were combined and washed with brine, dried (Na$_2$SO$_4$), filtered and concentrated in vacuo to give a crude residue which was purified by flash column chromatography (1:1 ethyl acetate:heptane with 5% AcOH) to give 6-chloro-4-(3-chloro-phenyl)-2-cyclopropyl-quinoline-3-carboxylic acid (32 mg, 74%) as a white solid. MS (ESI): 358.1 (M+H)$^+$.

Example 7

7-Chloro-4-(2-fluoro-phenyl)-2-isopropyl-quinoline-3-carboxylic acid

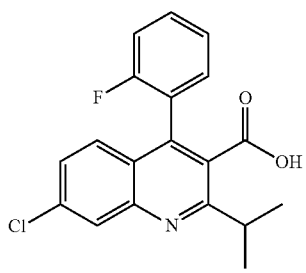 [SMILES: CC(C)c1nc2cc(Cl)ccc2c(-c2ccccc2F)c1C(=O)O]

Step A: 7-Chloro-4-(2-fluoro-phenyl)-2-isopropyl-quinoline-3-carboxylic acid ethyl ester

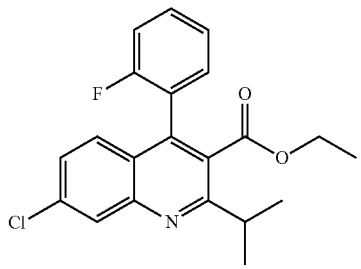 [SMILES: CCOC(=O)c1c(C(C)C)nc2cc(Cl)ccc2c1-c1ccccc1F]

The title compound was prepared in analogy to example 6 step A from a mixture of (2-amino-4-chloro-phenyl)-(2-fluoro-phenyl)-methanone and 4-methyl-3-oxo-pentanoic acid ethyl ester. White solid. MS (ESI): 372.1 (M+H)$^+$.

Step B: 7-Chloro-4-(2-fluoro-phenyl)-2-isopropyl-quinoline-3-carboxylic acid

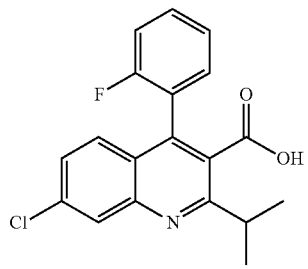 [SMILES: CC(C)c1nc2cc(Cl)ccc2c(-c2ccccc2F)c1C(=O)O]

The title compound was prepared in analogy to example 6 step B from a mixture of 7-chloro-4-(2-fluoro-phenyl)-2-isopropyl-quinoline-3-carboxylic acid ethyl ester and 1N NaOH in ethanol. White solid. MS (ESI): 344.1 (M+H)$^+$.

Example 8

7-Chloro-2-cyclopropyl-4-(2-fluoro-phenyl)-quinoline-3-carboxylic acid

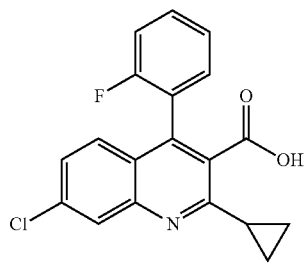 [SMILES: O=C(O)c1c(C2CC2)nc2cc(Cl)ccc2c1-c1ccccc1F]

Step A: 7-Chloro-4-(2-fluoro-phenyl)-2-isopropyl-quinoline-3-carboxylic acid methyl ester

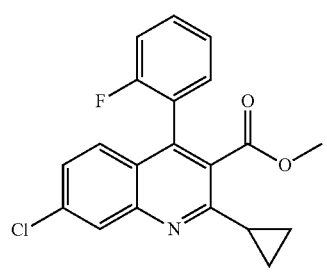 [SMILES: COC(=O)c1c(C2CC2)nc2cc(Cl)ccc2c1-c1ccccc1F]

The title compound was prepared in analogy to example 6 step A from a mixture of (2-amino-4-chloro-phenyl)-(2-fluoro-phenyl)-methanone and 3-cyclopropyl-3-oxo-propionic acid methyl ester. White solid. MS (ESI): 356.1 (M+H)$^+$.

Step B: 7-Chloro-4-(2-fluoro-phenyl)-2-isopropyl-quinoline-3-carboxylic acid

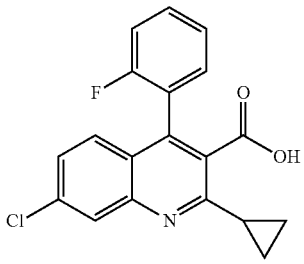 [SMILES: O=C(O)c1c(C2CC2)nc2cc(Cl)ccc2c1-c1ccccc1F]

The title compound was prepared in analogy to example 6 step B from a mixture of 7-chloro-4-(2-fluoro-phenyl)-2-isopropyl-quinoline-3-carboxylic acid methyl ester and 1N NaOH in ethanol. White solid. MS (ESI): 342.0 (M+H)$^+$.

Example 9

6-Chloro-2-methylcarbamoyl-4-phenyl-quinoline-3-carboxylic acid

Step A: 7-Chloro-9-phenyl-furo[3,4-b]quinoline-1,3-dione

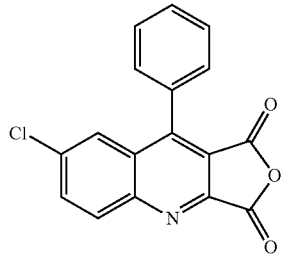 [SMILES: O=C1OC(=O)c2c1nc1ccc(Cl)cc1c2-c1ccccc1]

Acetic anhydride (288 µl, 3.0 mmol) was added to a stirred suspension of 6-chloro-4-phenylquinoline-2,3-dicarboxylic acid (100 mg, 0.31 mmol) in dimethoxyethane (1 ml) in an inert N$_2$ atmosphere followed by the addition of pyridine (49 µl, 0.61 mmol) at room temperature.

The reaction mixture was then stirred at room temperature overnight and the resulting solid filtered off, washed with ether and air dried to give 68 mg (72%) as a white solid.

Step B 6-Chloro-2-methylcarbamoyl-4-phenyl-quinoline-3-carboxylic acid

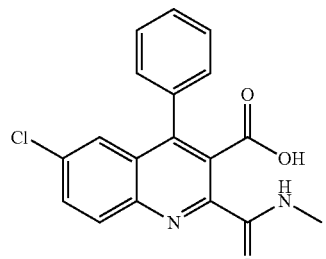

To a solution of 7-chloro-9-phenylfuro[3,4-b]quinoline-1,3-dione (100 mg, 0.32 mmol, 1 eq) in THF (2 ml) was added methyl amine (2M in THF, 807 µl, 1.61 mmol, 5 eq) and the reaction mixture was stirred overnight. The resultant precipitate was filtered and washed with ether. The solid was purified by flash column chromatography (10% AcOH in ethyl acetate) to give the title compound as a white solid. MS (ESI): 338.9 (M−H)$^−$.

Example 10

6-Chloro-4-(2-chloro-benzyl)-2-cyclopropyl-quinoline-3-carboxylic acid

Step A: 4-Chloro-2-(2-chloro-phenylethynyl)-phenylamine

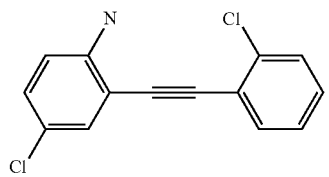 [SMILES: Nc1ccc(Cl)cc1C#Cc1ccccc1Cl]

To a stirred solution of 4-chloro-2-iodo-phenylamine (500 mg, 1.97 mmol) in dimethylformamide (4 ml) was added PdCl$_2$(PPh$_3$)$_2$ (7 mg, 0.02 mmol) followed by copper(I) iodide (3.7 mg, 0.02 mmol), 1-chloro-2-ethynyl-benzene (0.28 ml, 2.36 mmol) and diethylamine (1.65 ml, 15.78 mmol) under nitrogen at RT. The resulting reaction mixture was purged with nitrogen and then heated to 50° C. for 5 h. After cooling to room temperature, the mixture was diluted with water and extracted with ethyl acetate. The combined organic layers were washed with brine, dried over sodium sulfate and concentrated in vacuo to give a crude residue which was purified by flash column chromatography (elution with 4% EtOAc in hexane) to yield 4-chloro-2-(2-chloro-phenylethynyl)-phenylamine (320 mg, 62% yield) as an off white solid. LC-MS: 262 (M+H)$^+$.

Step B: 6-chloro-4-(2-chloro-benzyl)-2-cyclopropyl-quinoline-3-carboxylic acid ethyl ester

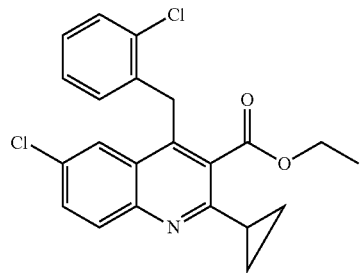 [SMILES: CCOC(=O)c1c(C2CC2)nc2ccc(Cl)cc2c1Cc1ccccc1Cl]

To a solution of 4-chloro-2-(2-chloro-phenylethynyl)-phenylamine (100 mg, 0.38 mmol, 1 eq) and ethyl 3-cyclopropyl-3-oxopropanoate (89.4 mg, 0.57 mmol, 1.5 eq) in anhydrous EtOH (5 ml), was added p-TsOH.H$_2$O (72.6 mg, 0.38 mmol, 1 eq) and the mixture was refluxed for 16 h. After cooling, the reaction mixture was concentrated in vacuo and then diluted with ethyl acetate. The mixture was washed with saturated sodium bicarbonate solution, brine, dried over sodium sulfate and concentrated in vacuo to give a crude residue which was purified by flash column chromatography (elution with 3% ethyl acetate in hexane) to give 6-chloro-4-(2-chloro-benzyl)-2-cyclopropyl-quinoline-3-carboxylic acid ethyl ester (33 mg, 22%) as a pale yellow solid. MS (ESI): 400.0 (M+H)+.

Step C: 6-Chloro-4-(2-chloro-benzyl)-2-cyclopropyl-quinoline-3-carboxylic acid

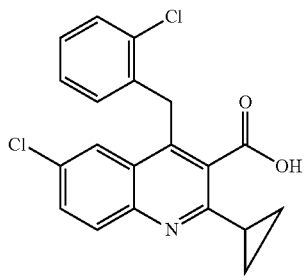

The title compound was prepared in analogy to example 6 step B from a mixture of 6-chloro-4-(2-chloro-benzyl)-2-cyclopropyl-quinoline-3-carboxylic acid ethyl ester and 1N NaOH in ethanol. White solid. MS (ESI): 372.0 (M+H)+.

Example 11

6-Chloro-4-phenyl-2-(2,2,2-trifluoro-ethoxy)-quinoline-3-carboxylic acid

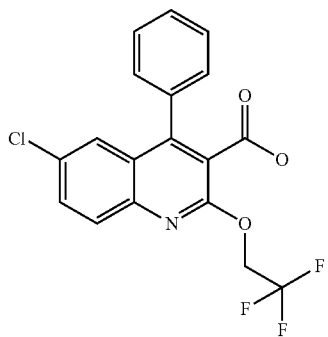 [SMILES: O=C(O)c1c(OCC(F)(F)F)nc2ccc(Cl)cc2c1-c1ccccc1]

Step A: 6-Chloro-2-oxo-4-phenyl-1,2-dihydro-quinoline-3-carboxylic acid ethyl ester

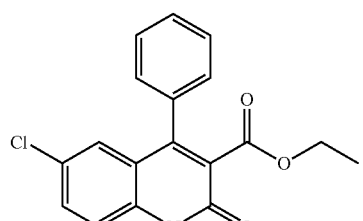

To a mixture of (2-amino-5-chloro-phenyl)-phenyl-methanone (5 g, 21.58 mmol) and malonic acid diethyl ester (4.565 ml, 30.21 mmol) was added DBU (0.45 ml, 3.02 mmol) under nitrogen and the mixture was stirred at 180-190° C. for 16 h. After cooling, the crude residue was purified by flash column chromatography (100-200 mesh silica, eluting with 50% ethyl acetate in hexane) to afford pure 6-chloro-2-oxo-4-phenyl-1,2-dihydro-quinoline-3-carboxylic acid ethyl ester (3.5 g, 49%) as off white solid. LC-MS: 328 (M+H)+.

Step B:
2,6-Dichloro-4-phenyl-quinoline-3-carboxylic acid ethyl ester

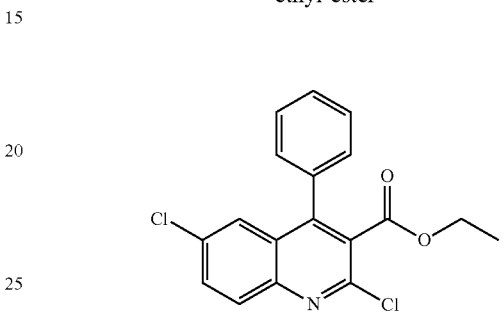

POCl3 (15 ml) was added to 6-chloro-2-oxo-4-phenyl-1,2-dihydro-quinoline-3-carboxylic acid ethyl ester (3 g, 9.15 mmol) and refluxed for 1 h. Then the reaction mixture was cooled to room temperature and diluted with cold water and the pH was adjusted to 7 with ammonia solution and extracted with ethyl acetate. The organic layer was washed with brine, dried over sodium sulfate, concentrated in vacuo to afford a crude residue which was purified by flash column chromatography (100-200 mesh silica, eluting with 5-10% ethyl acetate in hexane) to afford pure 2,6-dichloro-4-phenyl-quinoline-3-carboxylic acid ethyl ester (2 g, 63%) as pale yellow solid. LC-MS: 346 (M+H)+.

Step C: 6-Chloro-4-phenyl-2-(2,2,2-trifluoro-ethoxy)-quinoline-3-carboxylic acid ethyl ester

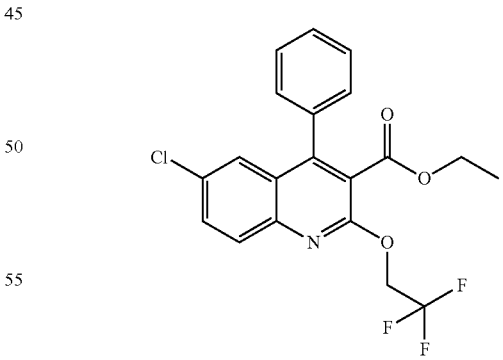

To the stirred solution of 2,2,2-trifluoro-ethanol (0.051 ml, 0.69 mmol) in 4 ml of DMF, was added NaH (28 mg, 0.69 mmol) portion wise at 0° C. The mixture was stirred for 30 min at room temperature and then a solution of 2,6-dichloro-4-phenyl-quinoline-3-carboxylic acid ethyl ester (200 mg, 0.58 mmol) in 2 ml dry DMF was added. The resulting reaction mixture was stirred for 5 h at room temperature. The reaction mixture was quenched with saturated aqueous NH₄Cl solution and then diluted with further water, and extracted with EtOAc. The organic layer was washed with brine, dried over anhydrous Na₂SO₄ and concentrated in vacuo to give a crude residue which was purified by flash column chromatography (5% ethyl acetate in hexane) to obtain 6-chloro-4-phenyl-2-(2,2,2-trifluoro-ethoxy)-quinoline-3-carboxylic acid ethyl ester (140 mg, 59%) as off white solid. LC-MS: 410 (M+H)⁺.

Step C: 6-Chloro-4-phenyl-2-(2,2,2-trifluoro-ethoxy)-quinoline-3-carboxylic acid

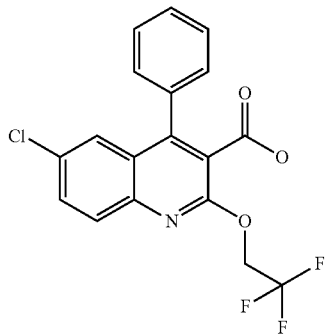 [SMILES: O=C(O)c1c(OCC(F)(F)F)nc2ccc(Cl)cc2c1-c1ccccc1]

The title compound was prepared in analogy to example 6 step B from a mixture of 6-chloro-4-phenyl-2-(2,2,2-trifluoro-ethoxy)-quinoline-3-carboxylic acid ethyl ester and 1N NaOH in ethanol. Off white solid (19.2 mg, 17%). LC-MS: 382 (M+H)⁺.

Example 12

6-Chloro-2-morpholin-4-yl-4-phenyl-quinoline-3-carboxylic acid

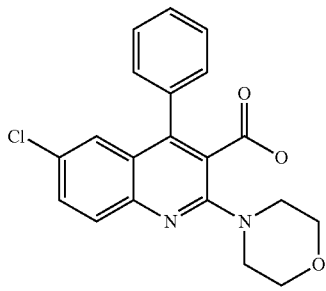 [SMILES: O=C(O)c1c(N2CCOCC2)nc2ccc(Cl)cc2c1-c1ccccc1]

Step A: 6-Chloro-2-morpholin-4-yl-4-phenyl-quinoline-3-carboxylic acid ethyl ester

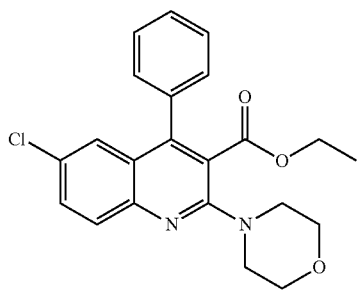

To a stirred solution of 2,6-dichloro-4-phenyl-quinoline-3-carboxylic acid ethyl ester (prepared as described in example 11 step B, 100 mg, 0.29 mmol) in a sealed tube was added morpholine (0.038 ml, 0.43 mmol). Then the mixture was stirred at 150° C. for 3 h. After cooling, this reaction mixture was diluted with water and extracted with ethyl acetate. The organic layer was washed with brine, dried over sodium sulfate and concentrated in vacuo to afford a crude residue which was purified by flash column chromatography (100-200 mesh silica, eluting with 10% ethyl acetate in hexane) to give 6-chloro-2-morpholin-4-yl-4-phenyl-quinoline-3-carboxylic acid ethyl ester (65 mg, 57%) as pale yellow solid. LC-MS: 397 (M+H)⁺.

Step B: 6-Chloro-2-morpholin-4-yl-4-phenyl-quinoline-3-carboxylic acid

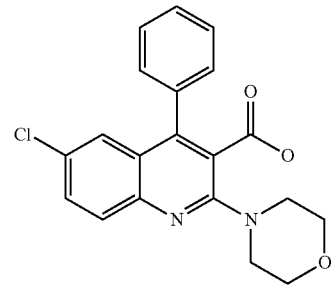 [SMILES: O=C(O)c1c(N2CCOCC2)nc2ccc(Cl)cc2c1-c1ccccc1]

To a stirred solution of 6-chloro-2-morpholin-4-yl-4-phenyl-quinoline-3-carboxylic acid ethyl ester (100 mg, 0.25 mmol) in ethanol (10 ml) was added 1N NaOH (1.26 ml, 1.26 mmol) solution at RT. The reaction mixture was refluxed for 24 h. The volatiles were removed under vacuum to afford a crude residue which was diluted with water. The aqueous layer was washed with ethyl acetate to remove non-polar impurities and then the pH was adjusted to 4-3 with 10% citric acid under cooling. Then the aqueous layer was extracted with ethyl acetate. The organic layer was washed with brine, dried over Na₂SO₄ and concentrated in vacuo to give a crude residue which was purified via Prep-HPLC followed by Prep-TLC to obtain pure 6-chloro-2-morpholin-4-yl-4-phenyl-quinoline-3-carboxylic acid as pale yellow solid (14 mg, 15%). LC-MS: 369 (M+H)⁺.

Example 13

6-Chloro-2-cyclopropyl-4-(2-trifluoromethyl-benzyl)-quinoline-3-carboxylic acid

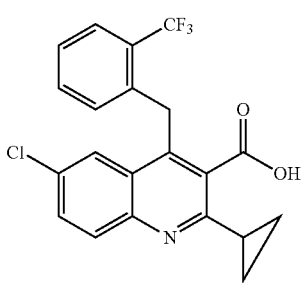 [SMILES: O=C(O)c1c(C2CC2)nc2ccc(Cl)cc2c1Cc1ccccc1C(F)(F)F]

Step A: 6-Chloro-4-(2-chloro-benzyl)-2-cyclopropyl-quinoline-3-carboxylic acid ethyl ester

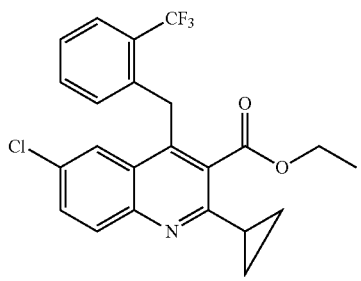

The title compound was prepared in analogy to example 10 step B from a mixture of 4-chloro-2-((2-(trifluoromethyl)phenyl)ethynyl)aniline (prepared in analogy to example 10 step A, from 1-ethynyl-2-(trifluoromethyl)benzene and 4-chloro-2-iodoaniline) and ethyl 3-cyclopropyl-3-oxopropanoate and pTsOH-H$_2$O in dry ethanol. Off white solid (25 mg, 11%). MS (ESI): 434.4 (M+H)$^+$.

Step B: 6-Chloro-2-cyclopropyl-4-(2-trifluoromethyl-benzyl)-quinoline-3-carboxylic acid

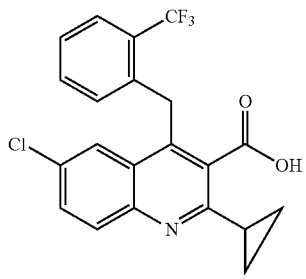 [SMILES: O=C(O)c1c(C2CC2)nc2ccc(Cl)cc2c1Cc1ccccc1C(F)(F)F]

The title compound was prepared in analogy to example 6 step B from a mixture of 6-chloro-4-(2-chloro-benzyl)-2-cyclopropyl-quinoline-3-carboxylic acid ethyl ester and 1N NaOH in ethanol. White solid. MS (ESI): 406.3 (M+H)$^+$.

Example 14

6-Chloro-4-(2-chloro-benzyl)-2-isopropyl-quinoline-3-carboxylic acid

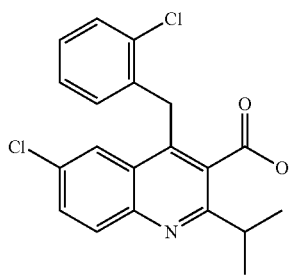 [SMILES: CC(C)c1nc2ccc(Cl)cc2c(Cc2ccccc2Cl)c1C(=O)O]

Step A: 6-Chloro-4-(2-chloro-benzyl)-2-isopropyl-quinoline-3-carboxylic acid ethyl ester

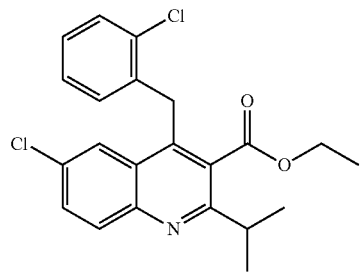 [SMILES: CCOC(=O)c1c(C(C)C)nc2ccc(Cl)cc2c1Cc1ccccc1Cl]

To a solution of 4-chloro-2-(2-chloro-phenylethynyl)-phenylamine (prepared as described in example 10 step A, 100 mg, 0.38 mmol) and 4-methyl-3-oxo-pentanoic acid ethyl ester (0.092 ml, 0.57 mmol) in anhydrous EtOH (10 ml), was added p-TsOH-H$_2$O (72.56 mg, 0.38 mmol) and the mixture was refluxed for 72 h. After cooling, the reaction mixture was diluted with ethyl acetate and the organic layer was washed with saturated sodium bicarbonate solution and brine, dried over sodium sulfate, concentrated in vacuo. The crude residue was purified by flash column chromatography (elution with 3% EtOAc in hexane) to give 6-chloro-4-(2-chloro-benzyl)-2-isopropyl-quinoline-3-carboxylic acid ethyl ester (35 mg, 23% yield) as a yellow sticky solid. LC-MS: 402 (M+H)$^+$.

Step B: 6-Chloro-4-(2-chloro-benzyl)-2-isopropyl-quinoline-3-carboxylic acid

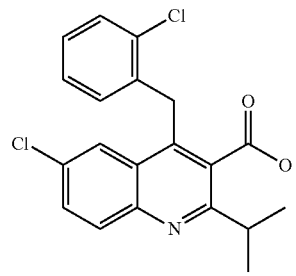 [SMILES: CC(C)c1nc2ccc(Cl)cc2c(Cc2ccccc2Cl)c1C(=O)O]

The title compound was prepared in analogy to example 6 step B from a mixture of 6-chloro-4-(2-chloro-benzyl)-2-isopropyl-quinoline-3-carboxylic acid ethyl ester (30 mg, 0.074 mmol) and 1N NaOH in ethanol. White solid (16 mg, 57%) LC-MS: 374 (M+H)$^+$.

Example 15

6-Chloro-2-isopropoxy-4-phenyl-quinoline-3-carboxylic acid

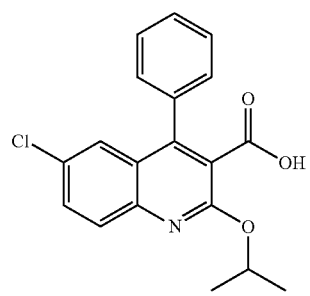 [SMILES: CC(C)Oc1nc2ccc(Cl)cc2c(-c2ccccc2)c1C(=O)O]

53

Step A: 6-Chloro-2-isopropoxy-4-phenyl-quinoline-3-carboxylic acid ethyl ester

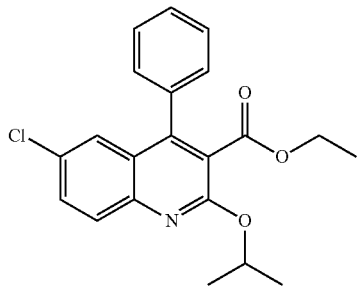 [SMILES: CCOC(=O)c1c(OC(C)C)nc2ccc(Cl)cc2c1-c1ccccc1]

The title compound was prepared in analogy to example 11 step C from 2,6-dichloro-4-phenyl-quinoline-3-carboxylic acid ethyl ester (prepared as described in example 11 step B) and propan-2-ol. Yellow solid (35 mg, 33%). LC-MS: 370 (M+H)$^+$.

Step B: 6-Chloro-2-isopropoxy-4-phenyl-quinoline-3-carboxylic acid

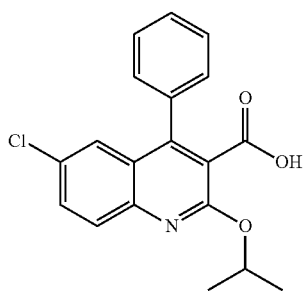

The title compound was prepared in analogy to example 6 step B from a mixture of 6-chloro-2-isopropoxy-4-phenyl-quinoline-3-carboxylic acid ethyl ester and 1N NaOH in ethanol. Off white solid (17.2 mg, 47%). LC-MS: 342 (M+H)$^+$.

Example 16

6-Chloro-2-cyclopentyloxy-4-phenyl-quinoline-3-carboxylic acid

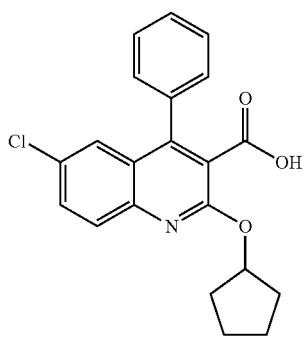 [SMILES: O=C(O)c1c(OC2CCCC2)nc2ccc(Cl)cc2c1-c1ccccc1]

54

Step A: 6-Chloro-2-cyclopentyloxy-4-phenyl-quinoline-3-carboxylic acid ethyl ester

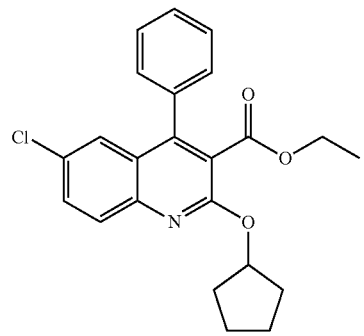 [SMILES: CCOC(=O)c1c(OC2CCCC2)nc2ccc(Cl)cc2c1-c1ccccc1]

The title compound was prepared in analogy to example 11 step C from 2,6-dichloro-4-phenyl-quinoline-3-carboxylic acid ethyl ester (prepared as described in example 11 step B) and cyclopentanol. Colorless sticky liquid. (50 mg, 44%). LC-MS: 396 (M+H)$^+$.

Step B: 6-Chloro-2-cyclopentyloxy-4-phenyl-quinoline-3-carboxylic acid

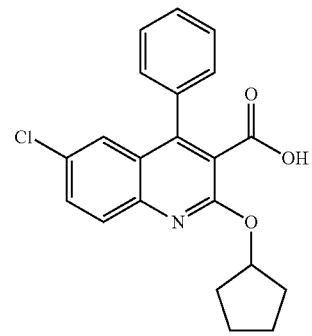 [SMILES: O=C(O)c1c(OC2CCCC2)nc2ccc(Cl)cc2c1-c1ccccc1]

The title compound was prepared in analogy to example 6 step B from a mixture of 6-chloro-2-cyclopentyloxy-4-phenyl-quinoline-3-carboxylic acid ethyl ester and 1N NaOH in ethanol. Off white solid (28.5 mg, 77%). LC-MS: 368 (M+H)$^+$.

Example 17

6-Chloro-2-(4,4-difluoro-piperidin-1-yl)-4-phenyl-quinoline-3-carboxylic acid

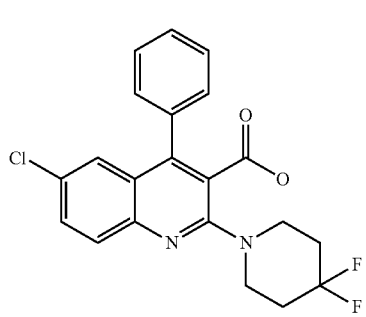 [SMILES: O=C(O)c1c(N2CCC(F)(F)CC2)nc2ccc(Cl)cc2c1-c1ccccc1]

Step A: 6-Chloro-2-(4,4-difluoro-piperidin-1-yl)-4-phenyl-quinoline-3-carboxylic acid ethyl ester

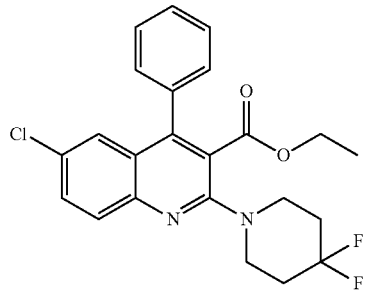 [SMILES: CCOC(=O)c1c(N2CCC(F)(F)CC2)nc2ccc(Cl)cc2c1-c1ccccc1]

The title compound was prepared in analogy to example 11 step C from 2,6-dichloro-4-phenyl-quinoline-3-carboxylic acid ethyl ester (prepared as described in example 11 step B) and 4,4-difluoro-piperidine. Pale yellow solid (110 mg, 44%). LC-MS: 431 (M+H)$^+$.

Step B: 6-Chloro-2-(4,4-difluoro-piperidin-1-yl)-4-phenyl-quinoline-3-carboxylic acid

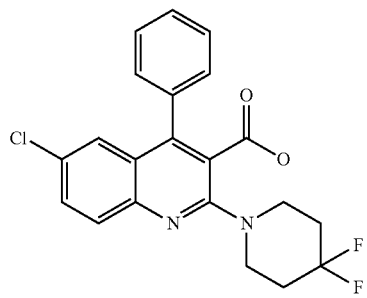 [SMILES: O=C(O)c1c(N2CCC(F)(F)CC2)nc2ccc(Cl)cc2c1-c1ccccc1]

The title compound was prepared in analogy to example 12 step B from a mixture of 6-chloro-2-(4,4-difluoro-piperidin-1-yl)-4-phenyl-quinoline-3-carboxylic acid ethyl ester and 1N NaOH in ethanol. Pale yellow solid (55 mg, 74%). LC-MS: 403 (M+H)$^+$.

Example 18

6,7-Dichloro-2-cyclopropyl-4-phenyl-quinoline-3-carboxylic acid

Step A: 6,7-Dichloro-2-cyclopropyl-4-phenyl-quinoline-3-carboxylic acid methyl ester

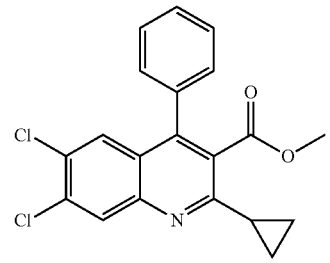 [SMILES: COC(=O)c1c(C2CC2)nc2cc(Cl)c(Cl)cc2c1-c1ccccc1]

The title compound was prepared in analogy to example 6 step A from a mixture of (2-amino-4,5-dichloro-phenyl)-phenyl-methanone and methyl 3-cyclopropyl-3-oxopropanoate. Yellow solid. MS (ESI): 372.1 (M+H)$^+$.

Step B: 6,7-Dichloro-2-cyclopropyl-4-phenyl-quinoline-3-carboxylic acid

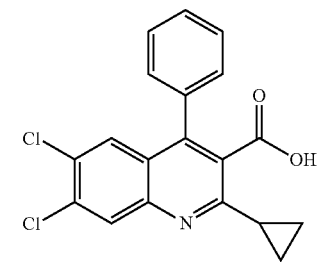 [SMILES: O=C(O)c1c(C2CC2)nc2cc(Cl)c(Cl)cc2c1-c1ccccc1]

The title compound was prepared in analogy to example 6 step B from a mixture of 6,7-dichloro-2-cyclopropyl-4-phenyl-quinoline-3-carboxylic acid methyl ester and KOH in a mixture of ethanol/water. White solid. MS (ESI): 358.0 (M+H)$^+$.

Example 19

6-Chloro-2-cyclopropyl-8-methyl-4-phenyl-quinoline-3-carboxylic acid

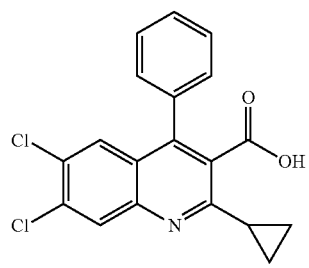

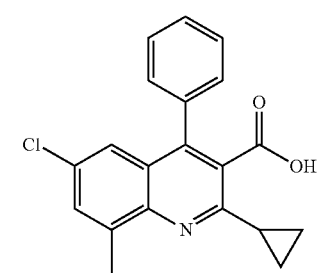 [SMILES: Cc1cc(Cl)cc2c(-c3ccccc3)c(C(=O)O)c(C3CC3)nc12]

Step A: 6-Chloro-2-cyclopropyl-8-methyl-4-phenyl-quinoline-3-carboxylic acid methyl ester

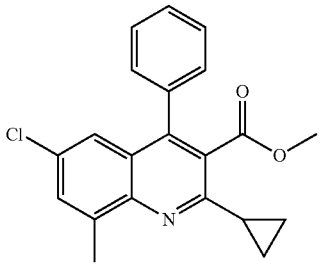 [SMILES: COC(=O)c1c(C2CC2)nc2c(C)cc(Cl)cc2c1-c1ccccc1]

The title compound was prepared in analogy to example 6 step A from a mixture of (2-amino-5-chloro-3-methyl-phenyl)-phenyl-methanone and methyl 3-cyclopropyl-3-oxopropanoate. Off-white solid. MS (ESI): 352.2 (M+H)+.

Step B: 6-Chloro-2-cyclopropyl-8-methyl-4-phenyl-quinoline-3-carboxylic acid

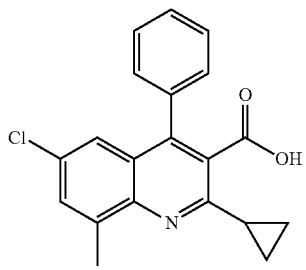 [SMILES: Cc1cc(Cl)cc2c(-c3ccccc3)c(C(=O)O)c(C3CC3)nc12]

The title compound was prepared in analogy to example 6 step B from a mixture of 6-chloro-2-cyclopropyl-8-methyl-4-phenyl-quinoline-3-carboxylic acid methyl ester and KOH in a mixture of ethanol/water. White solid. MS (ESI): 338.2 (M+H)+.

Example 20

6-Chloro-2-isopropyl-4-(3-trifluoromethoxy-phenyl)-quinoline-3-carboxylic acid

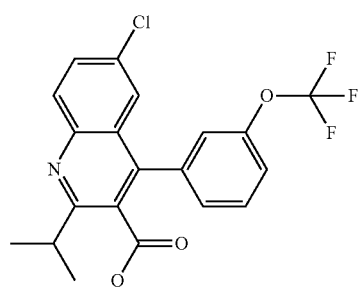 [SMILES: CC(C)c1nc2ccc(Cl)cc2c(-c2cccc(OC(F)(F)F)c2)c1C(=O)O]

Step A: 6-Chloro-4-hydroxy-2-isopropyl-quinoline-3-carboxylic acid methyl ester

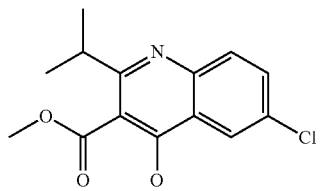

To the stirred solution of 4-methyl-3-oxo-pentanoic acid methyl ester (34.8 ml, 242.94 mmol) in 30 ml of dimethyl acetamide under nitrogen was added sodium hydride (60%, 972 mg, 24.9 mmol) portion wise at 0° C., stirred for 30 min at RT followed by addition of 6-chloro-1H-benzo[d][1,3] oxazine-2,4-dione (4.0 g, 20.24 mmol) in dimethyl acetamide (34 ml). The resulting reaction mixture was stirred at 120° C. for 1 h, monitored by TLC, cooled to room temperature, diluted with water and extracted with ethyl acetate. The combined organic phases were washed with brine, dried over sodium sulfate, concentrated in vacuo and purified by flash column chromatography (100-200 mesh silica, eluting with 40% EtOAc in hexane) to afford pure 6-chloro-4-hydroxy-2-isopropyl-quinoline-3-carboxylic acid methyl ester (2.2 g, 39%) as an off white solid. LC-MS: 280 (M+H)+.

Step B: 4-Bromo-6-chloro-2-isopropyl-quinoline-3-carboxylic acid methyl ester

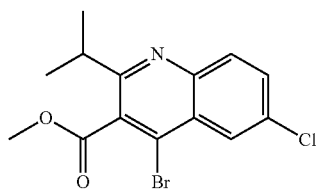

To a stirred solution of 6-chloro-4-hydroxy-2-isopropyl-quinoline-3-carboxylic acid methyl ester (800 mg, 2.86 mmol) in DCM (15 ml) was added POBr3 (1.23 g, 4.3 mmol) at 25° C. and the resulting reaction mixture was refluxed for 6 h. The reaction mixture was diluted with cold water, extracted with DCM, washed with brine, dried over sodium sulfate and concentrated in vacuo to give a crude residue which was purified by flash column chromatography (eluting with 5% EtOAc in hexane on 100-200 mesh silica gel column chromatography) to afford pure 4-bromo-6-chloro-2-isopropyl-quinoline-3-carboxylic acid methyl ester (500 mg, 51%) as an off white solid. LC-MS: 343 (M+H)+.

Step C: 6-Chloro-2-isopropyl-4-(3-trifluoromethoxy-phenyl)-quinoline-3-carboxylic acid methyl ester

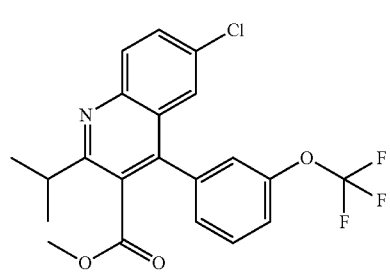 [SMILES: COC(=O)c1c(C(C)C)nc2ccc(Cl)cc2c1-c1cccc(OC(F)(F)F)c1]

A mixture of 4-bromo-6-chloro-2-isopropyl-quinoline-3-carboxylic acid methyl ester (150 mg, 0.44 mmol), K₂CO₃ (183 mg, 1.31 mmol) and 3-trifluoromethoxyphenylboronic acid (61 mg, 0.35 mmol) in dimethyl formamide (4 ml) in a sealed tube was purged with argon for 20 min followed by addition of Pd(PPh₃)₄ (51 mg, 0.04 mmol), again purged with argon for 10 min and the reaction mixture was heated at 90° C. for 5 h under stirring. After cooling, the reaction mixture was filtered through celite bed and washed with ethyl acetate. The organic phase was concentrated in vacuo and then partitioned between water and ethyl acetate. The organic phase was separated and washed with brine, dried over sodium sulfate and concentrated in vacuo to afford a crude residue. This crude residue was purified by flash column chromatography (100-200 mesh silica, eluting with 2% EtOAc in hexane) to afford pure 6-chloro-2-isopropyl-4-(3-trifluoromethoxy-phenyl)-quinoline-3-carboxylic acid methyl ester (65 mg, 35%) as pale yellow sticky liquid. LC-MS: 424 (M+H)⁺.

Step D: 6-Chloro-2-isopropyl-4-(3-trifluoromethoxy-phenyl)-quinoline-3-carboxylic acid

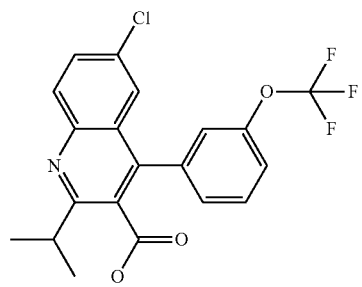 [SMILES: CC(C)c1nc2ccc(Cl)cc2c(-c2cccc(OC(F)(F)F)c2)c1C(=O)O]

To the stirred solution of 6-chloro-2-isopropyl-4-(3-trifluoromethoxy-phenyl)-quinoline-3-carboxylic acid methyl ester (50 mg, 0.118 mmol) in 3 ml of pyridine under nitrogen was added lithium iodide (158 mg, 1.18 mmol) at RT. Then the reaction mixture was refluxed for 16 h. Volatiles were removed under vacuo to afford a crude residue which was diluted with water and ethyl acetate. The organic phase was discarded and the aqueous layer was made acidic to pH 3 with 10% aqueous citric acid under cooling. The aqueous phase was then extracted with ethyl acetate and the combined organic layers were washed with brine, dried over sodium sulfate and concentrated in vacuo to give a crude residue which was purified by prep TLC (mobile phase: 5% MeOH in DCM) to afford 6-chloro-2-isopropyl-4-(3-trifluoromethoxy-phenyl)-quinoline-3-carboxylic acid (25 mg, 52%) as an off white solid. LC-MS: 410 (M+H)⁺.

Example 21

6,8-Dichloro-4-phenyl-2-piperidin-1-yl-quinoline-3-carboxylic acid

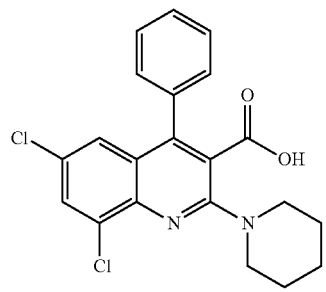 [SMILES: O=C(O)c1c(N2CCCCC2)nc2c(Cl)cc(Cl)cc2c1-c1ccccc1]

Step A:
N-(2-Benzoyl-4,6-dichloro-phenyl)-malonamic acid methyl ester

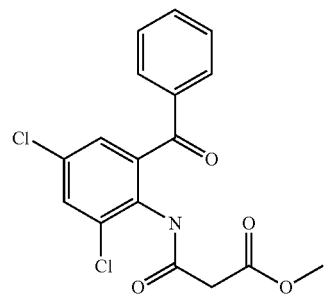 [SMILES: COC(=O)CC(=O)Nc1c(Cl)cc(Cl)cc1C(=O)c1ccccc1]

Methyl 3-chloro-3-oxopropanoate (317 mg, 249 µl, 2.25 mmol, Eq: 1.2) was added dropwise to a yellow solution of (2-amino-3,5-dichloro-phenyl)-phenyl-methanone (500 mg, 1.88 mmol, Eq: 1.00) in DCM (5 ml) at 0° C. The yellow solution was then allowed to warm slowly to RT. After completion of the reaction the mixture was washed with sat. NaHCO₃ solution and brine, dried with Na₂SO₄ and evaporated. The remaining light brown residue (603 mg) was used in the next reaction step without further purification. MS (ESI): 366.0 (M+H)⁺.

Step B: 6,8-Dichloro-2-oxo-4-phenyl-1,2-dihydro-quinoline-3-carboxylic acid methyl ester

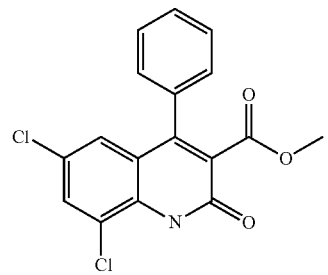 [SMILES: COC(=O)c1c(-c2ccccc2)c2cc(Cl)cc(Cl)c2[nH]c1=O]

Crude N-(2-benzoyl-4,6-dichloro-phenyl)-malonamic acid methyl ester (600 mg, 1.64 mmol, Eq: 1.00) from step A was suspended in methanol (16 ml) and a solution of sodium methanolate in methanol (13.8 ml, 0.5 M, 6.88 mmol, Eq: 4.2) was added. The reaction mixture was stirred at reflux for 1 h and was then allowed to cool to RT overnight. Most of the methanol was removed in vacuo and the remaining residue was poured onto ice. The mixture was acidified to pH 6 with 1N and 0.1N HCl and a light brown solid precipitated. The solid was filtered off, washed with water and a small amount of MeOH and dried. The resulting title compound (522 mg, light brown solid) was used in the next reaction step without further purification. MS (ESI): 348.0 (M+H)⁺.

Step C:
2,6,8-Trichloro-4-phenyl-quinoline-3-carboxylic acid methyl ester

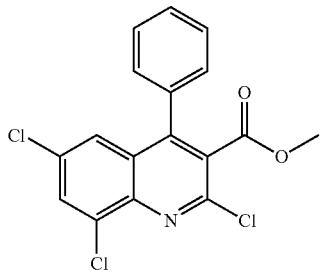 [SMILES: COC(=O)c1c(Cl)nc2c(Cl)cc(Cl)cc2c1-c1ccccc1]

The title compound was prepared in analogy to example 11 step B from 6,8-dichloro-2-oxo-4-phenyl-1,2-dihydroquinoline-3-carboxylic acid methyl ester and POCl₃. Light brown solid. MS (ESI): 366.0 (M+H)⁺.

Step D: 6,8-Dichloro-4-phenyl-2-piperidin-1-yl-quinoline-3-carboxylic acid

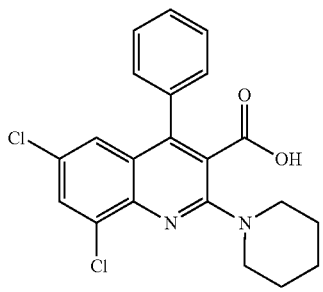 [SMILES: O=C(O)c1c(N2CCCCC2)nc2c(Cl)cc(Cl)cc2c1-c1ccccc1]

A solution of 2,6,8-trichloro-4-phenyl-quinoline-3-carboxylic acid methyl ester (115 mg, 0.314 mmol, Eq: 1.00) and piperidine (150 mg, 174 µl, 1.76 mmol, Eq: 5.6) in pyridine (1.5 ml) was stirred at 135° C. for 3 h in a sealed tube. The solution was allowed to cool to RT and cold water and ice were added. A light yellow solid precipitated which was filtered off, washed with water and dried (42 mg, 6,8-dichloro-4-phenyl-2-piperidin-1-yl-quinoline-3-carboxylic acid methyl ester, MS (ESI): 415.3 (M+H)⁺). The mother liquor was evaporated, water was added to the remaining residue and the pH was adjusted to 2 with 0.1N HCl. The mixture was extracted with chloroform and the combined organic extracts were dried with Na₂SO₄ and evaporated to yield the title compound (64 mg, yellow solid). MS (ESI): 401.2 (M+H)⁺.

Example 22

6,8-Dichloro-4-phenyl-2-pyrrolidin-1-yl-quinoline-3-carboxylic acid

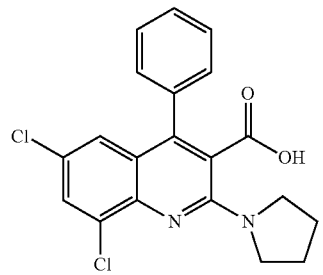 [SMILES: O=C(O)c1c(N2CCCC2)nc2c(Cl)cc(Cl)cc2c1-c1ccccc1]

The title compound was prepared in analogy to example 21 step D from 2,6,8-trichloro-4-phenyl-quinoline-3-carboxylic acid methyl ester (prepared as described in example 21 step C) and pyrrolidine. Yellow solid. MS (ESI): 387.2 (M+H)⁺.

Example 23

6,8-Dichloro-2-dimethylamino-4-phenyl-quinoline-3-carboxylic acid

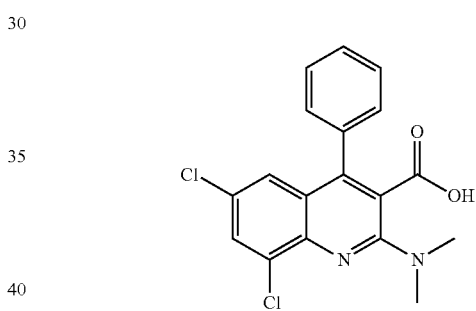

The title compound was prepared in analogy to example 21 step D from 2,6,8-trichloro-4-phenyl-quinoline-3-carboxylic acid methyl ester (prepared as described in example 21 step C) and dimethylamine (40% in H₂O). Light yellow solid. MS (ESI): 361.1 (M+H)⁺.

Example 24

6,8-Dichloro-2-diethylamino-4-phenyl-quinoline-3-carboxylic acid

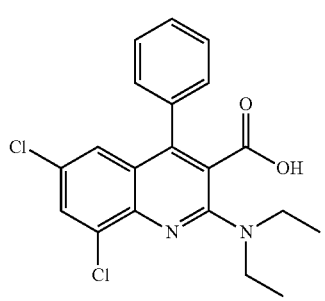 [SMILES: CCN(CC)c1nc2c(Cl)cc(Cl)cc2c(-c2ccccc2)c1C(=O)O]

The title compound was prepared in analogy to example 21 step D from 2,6,8-trichloro-4-phenyl-quinoline-3-carboxylic acid methyl ester (prepared as described in example 21 step C) and diethylamine. Brown foam. MS (ESI): 389.0 (M+H)⁺.

Example 25

6,7-Dichloro-4-phenyl-2-piperidin-1-yl-quinoline-3-carboxylic acid

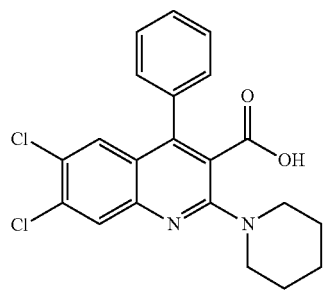 [SMILES: O=C(O)c1c(N2CCCCC2)nc2cc(Cl)c(Cl)cc2c1-c1ccccc1]

Step A:
N-(2-Benzoyl-4,5-dichloro-phenyl)-malonamic acid methyl ester

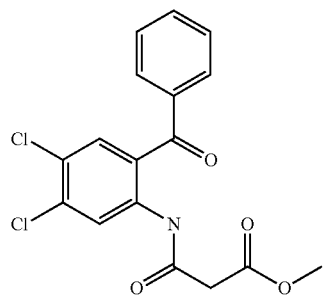 [SMILES: COC(=O)CC(=O)Nc1cc(Cl)c(Cl)cc1C(=O)c1ccccc1]

The title compound was prepared in analogy to example 21 step A from (2-amino-4,5-dichloro-phenyl)-phenyl-methanone and methyl 3-chloro-3-oxopropanoate. MS (ESI): 366.0 (M+H)⁺.

Step B: 6,7-Dichloro-2-oxo-4-phenyl-1,2-dihydro-quinoline-3-carboxylic acid methyl ester

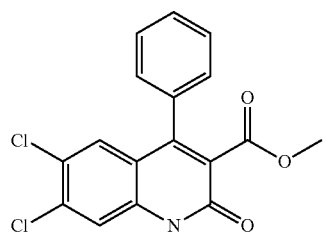 [SMILES: COC(=O)c1c(-c2ccccc2)c2cc(Cl)c(Cl)cc2[nH]c1=O]

The title compound was prepared in analogy to example 21 step B from N-(2-benzoyl-4,5-dichloro-phenyl)-malonamic acid methyl ester. MS (ESI): 348.0 (M+H)⁺.

Step C:
2,6,7-Trichloro-4-phenyl-quinoline-3-carboxylic acid methyl ester

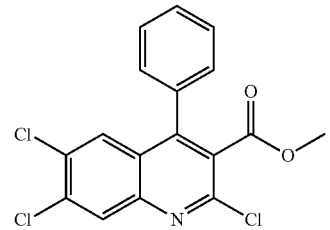 [SMILES: COC(=O)c1c(Cl)nc2cc(Cl)c(Cl)cc2c1-c1ccccc1]

The title compound was prepared in analogy to example 21 step C from 6,7-dichloro-2-oxo-4-phenyl-1,2-dihydro-quinoline-3-carboxylic acid methyl ester. MS (ESI): 348.0 (M+H)⁺.

Step D: 6,7-Dichloro-4-phenyl-2-piperidin-1-yl-quinoline-3-carboxylic acid

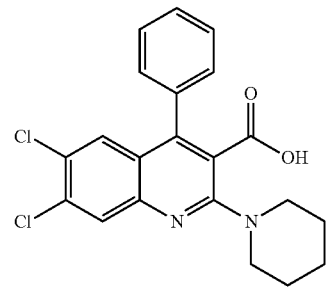 [SMILES: O=C(O)c1c(N2CCCCC2)nc2cc(Cl)c(Cl)cc2c1-c1ccccc1]

The title compound was prepared in analogy to example 21 step D from 2,6,7-trichloro-4-phenyl-quinoline-3-carboxylic acid methyl ester and piperidine. Brown solid. MS (ESI): 401.1 (M+H)⁺.

Example 26

6,7-Dichloro-4-phenyl-2-pyrrolidin-1-yl-quinoline-3-carboxylic acid

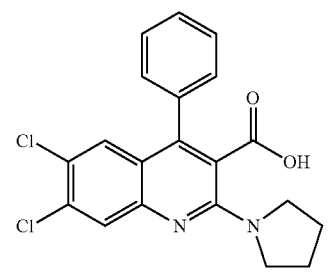 [SMILES: O=C(O)c1c(N2CCCC2)nc2cc(Cl)c(Cl)cc2c1-c1ccccc1]

The title compound was prepared in analogy to example 25 step D from 2,6,7-trichloro-4-phenyl-quinoline-3-carboxylic acid methyl ester (prepared as described in example 25 step C) and pyrrolidine. Brown solid. MS (ESI): 387.1 (M+H)⁺.

Example 27

6-Chloro-4-phenyl-2-pyrrolidin-1-yl-3-(1H-tetrazol-5-yl)-quinoline

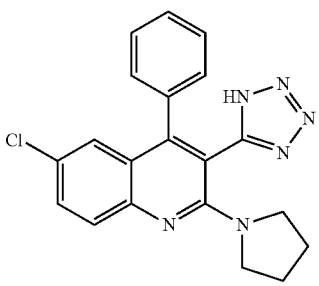 [SMILES: Clc1ccc2nc(N3CCCC3)c(-c3nnn[nH]3)c(-c3ccccc3)c2c1]

Step A: 6-Chloro-2-oxo-4-phenyl-1,2-dihydro-quinoline-3-carbonitrile

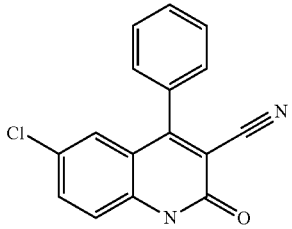 [SMILES: N#Cc1c(-c2ccccc2)c2cc(Cl)ccc2[nH]c1=O]

A mixture of (2-amino-5-chlorophenyl)(phenyl)methanone (1 g, 4.32 mmol, Eq: 1.00), ethyl 2-cyanoacetate (2.44 g, 2.3 ml, 21.6 mmol, Eq: 5) and cerium (III) chloride heptahydrate (322 mg, 863 µmol, Eq: 0.2) was heated to 200° C. for 30 min in a microwave. Then water was added and the mixture was acidified to pH 2-3 with 0.1N HCl. The mixture was then extracted with ethyl acetate (3×) and the combined extracts were washed with water and brine, dried with Na₂SO₄, filtered and evaporated. The remaining residue was triturated with a mixture of DCM (5 ml) and heptane (2 ml) for 2 h. Filtration yielded the title compound (389 mg, light yellow solid). MS (ESI): 281.1 (M+H)⁺.

Step B: 2,6-Dichloro-4-phenyl-quinoline-3-carbonitrile

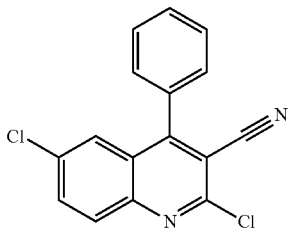 [SMILES: N#Cc1c(Cl)nc2ccc(Cl)cc2c1-c1ccccc1]

POCl₃ (1.64 g, 1 ml, 10.7 mmol, Eq: 30.1) was added to 6-chloro-2-oxo-4-phenyl-1,2-dihydro-quinoline-3-carbonitrile (100 mg, 356 µmol, Eq: 1.00) and the mixture was refluxed for 1 h. The reaction mixture was then allowed to cool to RT, poured onto cold water and extracted with DCM (3×). The combined organic layers were washed with brine, dried with Na₂SO₄ and evaporated to dryness. The remaining residue was purified by column chromatography (silica gel, DCM/heptane 1:1) to afford the title compound as white solid (81 mg). MS (ESI): 299.0 (M+H)⁺.

Step C: 6-Chloro-4-phenyl-2-pyrrolidin-1-yl-quinoline-3-carbonitrile

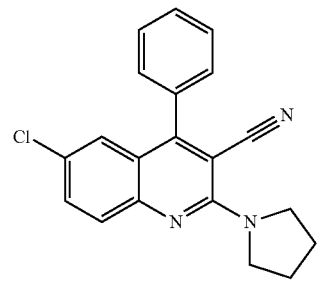 [SMILES: N#Cc1c(N2CCCC2)nc2ccc(Cl)cc2c1-c1ccccc1]

2,6-Dichloro-4-phenyl-quinoline-3-carbonitrile (30 mg, 100 µmol, Eq: 1.00), pyrrolidine (14.3 mg, 16.6 µl, 201 µmol, Eq: 2) and triethylamine (30.4 mg, 41.9 µl, 301 µmol, Eq: 3) were dissolved in DMF (0.5 ml) and the reaction mixture was heated to 120° C. for 20 min in a microwave. Then water was added and the mixture was extracted with ethyl acetate (3×). The combined organic layers were dried with Na₂SO₄ and evaporated to dryness. The remaining residue was purified by column chromatography (silica gel, DCM/heptane 1:1) to afford the title compound as yellow solid (28 mg). MS (ESI): 334.2 (M+H)⁺.

Step D: 6-Chloro-4-phenyl-2-pyrrolidin-1-yl-3-(1H-tetrazol-5-yl)-quinoline

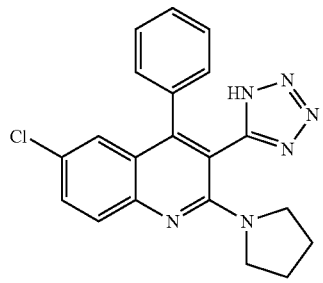 [SMILES: Clc1ccc2nc(N3CCCC3)c(-c3nnn[nH]3)c(-c3ccccc3)c2c1]

6-Chloro-4-phenyl-2-pyrrolidin-1-yl-quinoline-3-carbonitrile (25 mg, 74.9 µmol, Eq: 1.00) and azidotrimethyltin (30.8 mg, 150 µmol, Eq: 2) were dissolved in xylene (1 ml) and the reaction mixture was heated to 120° C. for 40 h. The mixture was allowed to cool to RT and the solid was filtered off, washed with boiling toluene and suspended in water. The pH was adjusted to 1 by addition of 0.1N HCl and the mixture was extracted with ethyl acetate (3×). The combined organic layers were dried with Na₂SO₄ and evaporated and the remaining residue was purified by column chromatography (silica gel, DCM/MeOH 9:1) to afford the title compound as yellow solid (5.8 mg). MS (ESI): 377.3 (M+H)+.

Example 28

6-Chloro-4-phenyl-2-piperidin-1-yl-3-(1H-tetrazol-5-yl)-quinoline

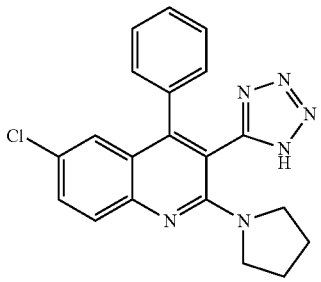 [SMILES: Clc1ccc2nc(N3CCCC3)c(-c3nnn[nH]3)c(-c3ccccc3)c2c1]

Step A: 6-Chloro-4-phenyl-2-piperidin-1-yl-quinoline-3-carbonitrile

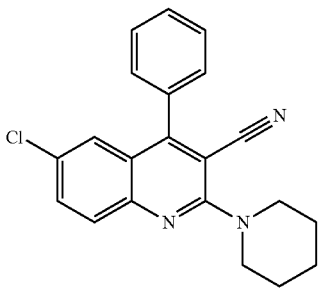 [SMILES: N#Cc1c(N2CCCCC2)nc2ccc(Cl)cc2c1-c1ccccc1]

The title compound was prepared in analogy to example 27 step C from 2,6-dichloro-4-phenyl-quinoline-3-carbonitrile (prepared as described in example 27 step B) and piperidine. Yellow solid. MS (ESI): 348.2 (M+H)+.

Step B: 6-Chloro-4-phenyl-2-piperidin-1-yl-3-(1H-tetrazol-5-yl)-quinoline

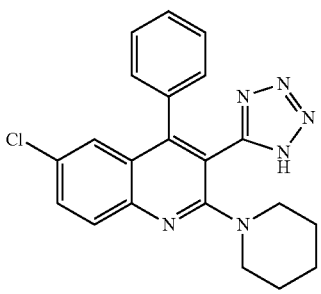 [SMILES: Clc1ccc2nc(N3CCCCC3)c(-c3nnn[nH]3)c(-c3ccccc3)c2c1]

The title compound was prepared in analogy to example 27 step D from 6-chloro-4-phenyl-2-piperidin-1-yl-quinoline-3-carbonitrile. Light yellow solid. MS (ESI): 391.2 (M+H)+.

Example 29

6-Chloro-4-(2-chloro-benzyl)-2-dimethylamino-quinoline-3-carboxylic acid

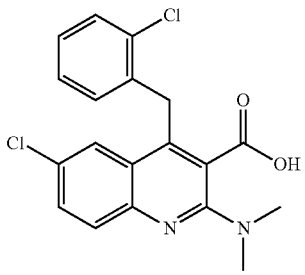 [SMILES: CN(C)c1nc2ccc(Cl)cc2c(Cc2ccccc2Cl)c1C(=O)O]

Step A: N-[4-Chloro-2-(2-chloro-phenylethynyl)-phenyl]-malonamic acid ethyl ester

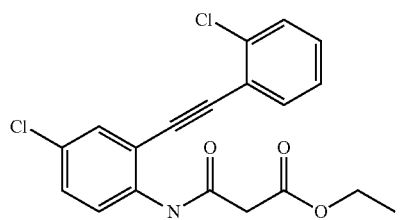 [SMILES: CCOC(=O)CC(=O)Nc1ccc(Cl)cc1C#Cc1ccccc1Cl]

To a solution of 4-chloro-2-(2-chloro-phenylethynyl)-phenylamine (prepared as described in example 10 step A, 4 g, 15.26 mmol) in THF (25 ml) at 0° C. was added chlorocarbonyl-acetic acid ethyl ester followed by triethyl amine (3.2 ml, 22.89 mmol) drop wise under nitrogen, then the reaction mixture was stirred for 4 h at 25° C. The reaction mixture was diluted with water (50 ml), and extracted with EtOAc (3×75 ml). The organic phases were combined and washed with brine (40 ml), dried over anhydrous Na2SO4, filtered, and concentrated in vacuo to give a crude residue which was purified by flash column chromatography (5-10% EtOAc/hexane) to afford N-[4-chloro-2-(2-chloro-phenylethynyl)-phenyl]-malonamic acid ethyl ester (3.6 g, 62.71%) as an off white solid. LC-MS (ESI): 376 (M+H)+.

Step B: 6-Chloro-4-(2-chloro-benzyl)-2-hydroxy-quinoline-3-carboxylic acid ethyl ester

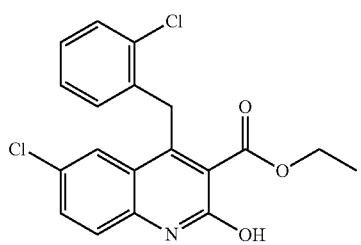 [SMILES: CCOC(=O)c1c(O)nc2ccc(Cl)cc2c1Cc1ccccc1Cl]

To a suspension of sodium hydride (60%; 32 mg, 0.8 mmol) in DMSO (3 ml) was added a solution of N-[4- chloro-2-(2-chloro-phenylethynyl)-phenyl]-malonamic acid ethyl ester (200 mg, 0.532 mmol) in DMSO (2 ml) under nitrogen at 25° C., and the reaction mixture was stirred for 2 h at 80° C. The reaction mixture was diluted with ethyl acetate (15 ml), and the organic layer was washed with brine (3×10 ml), dried over anhydrous Na$_2$SO$_4$, filtered, and concentrated in vacuo to give a crude residue which was purified by flash column chromatography (20% EtOAc in hexane) to afford 6-chloro-4-(2-chloro-benzyl)-2-hydroxy-quinoline-3-carboxylic acid ethyl ester (63 mg, 32%) as an off white solid. LC-MS (ESI): 376 (M+H)$^+$.

Step C: 6-Chloro-4-(2-chloro-benzyl)-2-trifluoromethanesulfonyloxy-quinoline-3-carboxylic acid ethyl ester

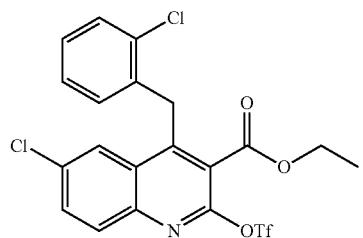 [SMILES: CCOC(=O)c1c(OS(=O)(=O)C(F)(F)F)nc2ccc(Cl)cc2c1Cc1ccccc1Cl]

To a solution of 6-chloro-4-(2-chloro-benzyl)-2-hydroxy-quinoline-3-carboxylic acid ethyl ester (200 mg, 0.532 mmol) in DMF (3 ml) was added sodium hydride (60%; 32 mg, 0.8 mmol) portion wise at 0° C., and the resulting reaction mixture was stirred for 1.5 h at 25° C. Then it was cooled to 0° C., and a solution of N-phenylbis(trifluoromethanesulfonimide) (285 mg, 0.8 mmol) in DMF (2 ml) was added drop wise. The resulting reaction mixture was stirred for 3 h at 25° C. and then quenched with saturated aqueous ammonium chloride solution (30 ml), and then extracted with EtOAc (3×20 ml). The combined organic layer was washed with brine (3×10 ml), dried over anhydrous Na$_2$SO$_4$, filtered, and concentrated in vacuo to give a crude residue which was purified by flash column chromatography (2% EtOAc in hexane) to give 6-chloro-4-(2-chloro-benzyl)-2-trifluoromethanesulfonyloxy-quinoline-3-carboxylic acid ethyl ester (87.5 mg, 32%) as an off white solid. LC-MS (ESI): 508 (M+H)$^+$.

Step D: 6-Chloro-4-(2-chloro-benzyl)-2-dimethylamino-quinoline-3-carboxylic acid ethyl ester

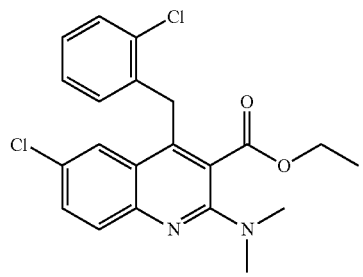

To a solution of 6-chloro-4-(2-chloro-benzyl)-2-trifluoromethanesulfonyloxy-quinoline-3-carboxylic acid ethyl ester (100 mg, 0.2 mmol) in THF (2 ml) was added potassium carbonate (109 mg, 0.79 mmol) and dimethylamine (2M solution in THF; 0.5 ml, 0.98 mmol) at 25° C. and the resulting reaction mixture was stirred at 70° C. for 3 h. The mixture was diluted with water (5 ml), and extracted with EtOAc (3×15 ml) and the organic phases were combined and washed with brine (15 ml), dried over anhydrous Na$_2$SO$_4$, filtered, and concentrated under reduced pressure. The crude residue was purified by column chromatography (3% EtOAc/hexane) to give 6-chloro-4-(2-chloro-benzyl)-2-dimethylamino-quinoline-3-carboxylic acid ethyl ester (55 mg, 69%) as pale yellow solid. LC-MS (ESI): 403 (M+H)$^+$.

Step E: 6-Chloro-4-(2-chloro-benzyl)-2-dimethylamino-quinoline-3-carboxylic acid

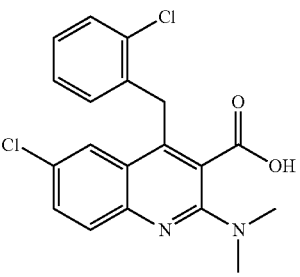 [SMILES: CN(C)c1nc2ccc(Cl)cc2c(Cc2ccccc2Cl)c1C(=O)O]

The title compound was prepared in analogy to example 12 step B from a mixture of 6-chloro-4-(2-chloro-benzyl)-2-dimethylamino-quinoline-3-carboxylic acid ethyl ester and 1N NaOH in ethanol. Pale yellow solid. LC-MS (ESI): 375 (M+H)$^+$.

Example 30

6-Chloro-2-hydroxymethyl-4-phenyl-quinoline-3-carboxylic acid

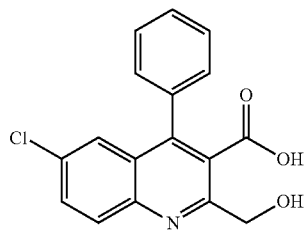 [SMILES: O=C(O)c1c(CO)nc2ccc(Cl)cc2c1-c1ccccc1]

To a solution of 7-chloro-9-phenylfuro[3,4-b]quinoline-1,3-dione (prepared as described in example 9 step A, 250 mg, 0.81 mmol) in THF was added NaBH$_4$ (30.5 mg, 0.81 mmol) at 15° C., then AcOH (92.4 µl, 1.61 mmol) was added drop wise and stirring was continued for 4 hr at room temperature. The reaction mixture was dissolved in water and the pH was adjusted to ca. 2 and extracted with ethyl acetate. The organic phases were combined and washed with brine, dried over anhydrous Na$_2$SO$_4$, filtered, and concentrated under reduced pressure. The crude residue was purified by flash column chromatography, and then further triturated with ether to give the desired product as an off-white solid (25 mg, 10%). MS (ESI): 314 (M+H)$^+$.

Example 31

6-Chloro-2-isopropyl-4-(3-isopropyl-phenyl)-quinoline-3-carboxylic acid

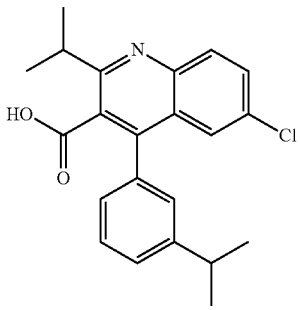 [SMILES: CC(C)c1cccc(-c2c(C(=O)O)c(C(C)C)nc3ccc(Cl)cc23)c1]

Step A:
4,6-Dichloro-2-isopropyl-quinoline-3-carboxylic acid methyl ester

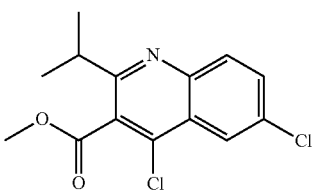 [SMILES: COC(=O)c1c(C(C)C)nc2ccc(Cl)cc2c1Cl]

A mixture of 6-chloro-4-hydroxy-2-isopropyl-quinoline-3-carboxylic acid methyl ester (prepared as described in example 20 step A, 2 g, 7.15 mmol) and phosphorous oxychloride (10 ml) under nitrogen was refluxed for 1 h. After cooling the reaction mixture to room temperature, the mixture was poured onto ice cold water and the pH of the aqueous phase was adjusted to 7 with aqueous ammonia solution. The aqueous phase was extracted with ethyl acetate and the combined organic phases were washed with brine, dried over sodium sulfate and concentrated in vacuo to give a crude residue which was purified by flash column chromatography (100-200 mesh silica, eluting with 5-10% EtOAc in hexane) to afford pure 4,6-dichloro-2-isopropyl-quinoline-3-carboxylic acid methyl ester (1.3 g, 61%) as pale yellow solid. LC-MS: 298 (M+H)+.

Step B: 6-Chloro-2-isopropyl-4-(3-isopropyl-phenyl)-quinoline-3-carboxylic acid methyl ester

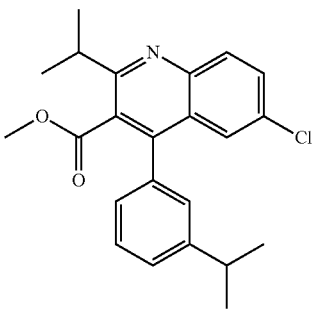 [SMILES: COC(=O)c1c(C(C)C)nc2ccc(Cl)cc2c1-c1cccc(C(C)C)c1]

The title compound was prepared in analogy to example 20 step C from 4,6-dichloro-2-isopropyl-quinoline-3-carboxylic acid methyl ester (200 mg, 0.67 mmol) and 3-isopropylphenylboronic acid (99 mg, 0.6 mmol). Off-white sticky liquid (90 mg, 35%). LC-MS: 382 (M+H)+.

Step C: 6-Chloro-2-isopropyl-4-(3-isopropyl-phenyl)-quinoline-3-carboxylic acid

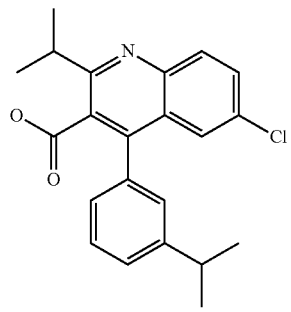 [SMILES: CC(C)c1cccc(-c2c(C(=O)O)c(C(C)C)nc3ccc(Cl)cc23)c1]

The title compound was prepared in analogy to example 20 step D from 6-chloro-2-isopropyl-4-(3-isopropyl-phenyl)-quinoline-3-carboxylic acid methyl ester (50 mg, 0.13 mmol) and lithium iodide in pyridine. Off-white solid (18 mg, 37%). LC-MS: 366 (M−H)−.

Example 32

6-Chloro-4-(3-ethoxy-phenyl)-2-isopropyl-quinoline-3-carboxylic acid

Step A: 6-Chloro-4-(3-ethoxy-phenyl)-2-isopropyl-quinoline-3-carboxylic acid methyl ester

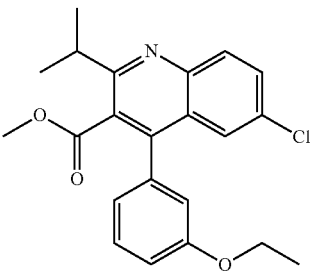 [SMILES: CCOc1cccc(-c2c(C(=O)OC)c(C(C)C)nc3ccc(Cl)cc23)c1]

The title compound was prepared in analogy to example 20 step C from 4,6-dichloro-2-isopropyl-quinoline-3-carboxylic acid methyl ester (prepared as described in example 31 step A, 200 mg, 0.67 mmol) and 3-ethoxyphenylboronic acid (72 mg, 0.54 mmol). Sticky liquid (105 mg, 41%). LC-MS: 384 (M+H)+.

Step B: 6-Chloro-4-(3-ethoxy-phenyl)-2-isopropyl-quinoline-3-carboxylic acid

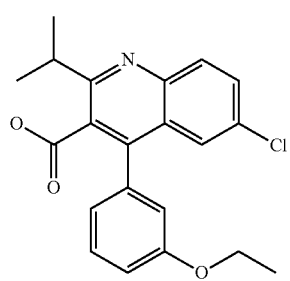 [SMILES: CCOc1cccc(-c2c(C(=O)O)c(C(C)C)nc3ccc(Cl)cc23)c1]

The title compound was prepared in analogy to example 6 step B from a mixture of 6-chloro-4-(3-ethoxy-phenyl)-2-isopropyl-quinoline-3-carboxylic acid methyl (80 mg, 0.21 mmol) and 1N NaOH in ethanol. Off white solid (16 mg, 21%). LC-MS: 368 (M−H)⁻.

Example 33

6-Chloro-2-isopropyl-4-(3-trifluoromethyl-phenyl)-quinoline-3-carboxylic acid

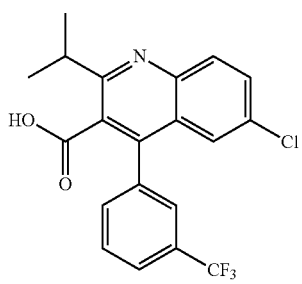 [SMILES: CC(C)c1nc2ccc(Cl)cc2c(-c2cccc(C(F)(F)F)c2)c1C(=O)O]

Step A: 6-Chloro-2-isopropyl-4-(3-isopropyl-phenyl)-quinoline-3-carboxylic acid methyl ester

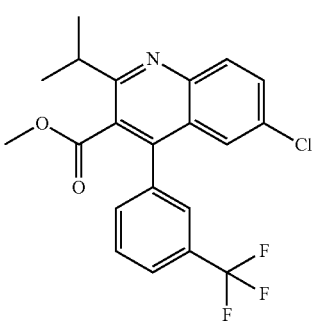 [SMILES: COC(=O)c1c(C(C)C)nc2ccc(Cl)cc2c1-c1cccc(C(F)(F)F)c1]

The title compound was prepared in analogy to example 20 step C from 4,6-dichloro-2-isopropyl-quinoline-3-carboxylic acid methyl ester (prepared as described in example 31 step A, 100 mg, 0.34 mmol) and 3-trifluoromethylphenylboronic acid (52 mg, 0.27 mmol). Sticky liquid (60 mg, 44%). LC-MS: 408 (M+H)⁺.

Step B: 6-Chloro-2-isopropyl-4-(3-trifluoromethyl-phenyl)-quinoline-3-carboxylic acid

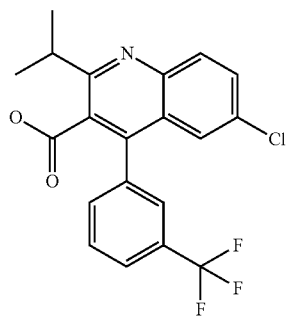 [SMILES: CC(C)c1nc2ccc(Cl)cc2c(-c2cccc(C(F)(F)F)c2)c1C(=O)O]

The title compound was prepared in analogy to example 20 step D from 6-chloro-2-isopropyl-4-(3-trifluoromethyl-phenyl)-quinoline-3-carboxylic acid methyl ester (50 mg, 0.12 mmol) and lithium iodide in pyridine. Off-white solid (19 mg, 39.35%). LC-MS: 392 (M−H)⁻.

Example 34

6-Chloro-4-phenyl-2-(2,2,2-trifluoro-ethyl)-quinoline-3-carboxylic acid

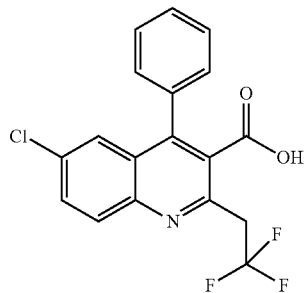 [SMILES: O=C(O)c1c(CC(F)(F)F)nc2ccc(Cl)cc2c1-c1ccccc1]

Step A: 5,5,5-Trifluoro-3-oxo-pentanoic acid methyl ester

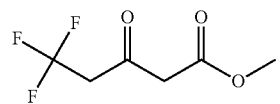

To a stirred solution of 2,2-dimethyl-[1,3]dioxane-4,6-dione (200 mg, 1.41 mmol), pyridine (0.125 ml, 1.55 mmol) and DMAP (344 mg, 2.81 mmol) in dichloromethane (10 ml), was added 3,3,3-trifluoro-propionyl chloride (0.16 ml, 1.55 mmol) at 0° C. The resulting reaction mixture was stirred under nitrogen for 1 h at 0° C. and then allowed to warm to room temperature and stirred for 2 h. Volatiles were removed under reduced pressure, and the crude residue was diluted with diethyl ether and washed with 1 N HCl. The organic layer was dried and concentrated to get the intermediate, which was diluted with 10 ml of methanol and refluxed for 5 h. Volatiles were removed under reduced pressure to afford the crude 5,5,5-trifluoro-3-oxo-pentanoic acid methyl ester (120 mg, 46%) as brown liquid which was used in the following step without further purification. FIA-MS: 183 (M−H)⁻.

Step B: 6-Chloro-4-phenyl-2-(2,2,2-trifluoro-ethyl)-quinoline-3-carboxylic acid methyl ester

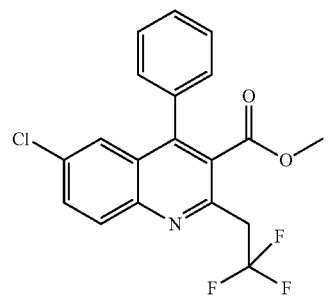 [SMILES: COC(=O)c1c(CC(F)(F)F)nc2ccc(Cl)cc2c1-c1ccccc1]

To a solution of (2-amino-5-chloro-phenyl)-phenyl-methanone (120 mg, 0.52 mmol) and 5,5,5-trifluoro-3-oxo-pentanoic acid methyl ester (124 mg, 0.67 mmol) in 5 ml ethanol at room temperature was added ytterbium triflate (32 mg, 0.05 mmol). The reaction mixture was stirred for 16 h at room temperature, upon which a white precipitate was formed. The precipitated solid was filtered and washed with ethanol to afford 6-chloro-4-phenyl-2-(2,2,2-trifluoro-ethyl)-quinoline-3-carboxylic acid methyl ester (70 mg, 36%) as an off white solid. LC-MS: 380 (M+H)$^+$.

Step C: 6-Chloro-4-phenyl-2-(2,2,2-trifluoro-ethyl)-quinoline-3-carboxylic acid

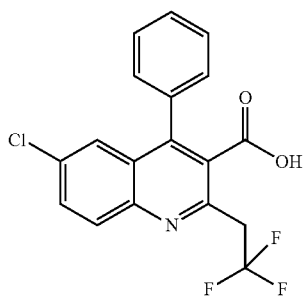 [SMILES: O=C(O)c1c(CC(F)(F)F)nc2ccc(Cl)cc2c1-c1ccccc1]

The title compound was prepared in analogy to example 20 step D from 6-chloro-4-phenyl-2-(2,2,2-trifluoro-ethyl)-quinoline-3-carboxylic acid methyl ester (60 mg, 0.16 mmol) and lithium iodide (212 mg, 1.58 mmol) in pyridine. Off white solid (9.5 mg, 16%). LC-MS: 364 (M−H)$^-$.

Example 35

6-Chloro-4-(3-chloro-4-fluoro-phenyl)-2-isopropyl-quinoline-3-carboxylic acid

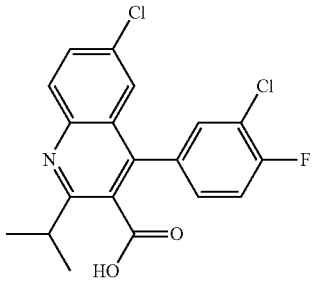 [SMILES: CC(C)c1nc2ccc(Cl)cc2c(-c2ccc(F)c(Cl)c2)c1C(=O)O]

Step A: 6-Chloro-4-(3-chloro-4-fluoro-phenyl)-2-isopropyl-quinoline-3-carboxylic acid methyl ester

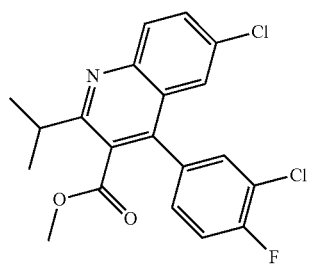 [SMILES: COC(=O)c1c(C(C)C)nc2ccc(Cl)cc2c1-c1ccc(F)c(Cl)c1]

The title compound was prepared in analogy to example 20 step C from 4-bromo-6-chloro-2-isopropyl-quinoline-3-carboxylic acid methyl ester (prepared as described in example 20 step B, 150 mg, 0.44 mmol) and 3-chloro-4-fluorophenylboronic acid (62 mg, 0.35 mmol) as off white solid (70 mg, 41%). LC-MS: 392 (M+H)$^+$.

Step B: 6-Chloro-4-(3-chloro-4-fluoro-phenyl)-2-isopropyl-quinoline-3-carboxylic acid

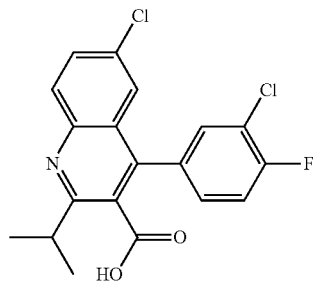 [SMILES: CC(C)c1nc2ccc(Cl)cc2c(-c2ccc(F)c(Cl)c2)c1C(=O)O]

The title compound was prepared in analogy to example 20 step D from 6-chloro-4-(3-chloro-4-fluoro-phenyl)-2-isopropyl-quinoline-3-carboxylic acid methyl ester (60 mg, 0.15 mmol) and lithium iodide in pyridine. Off white solid (43 mg, 74%). LC-MS: 376 (M−H)$^-$.

Example 36

6-Chloro-2-cyclopentyl-4-phenyl-quinoline-3-carboxylic acid

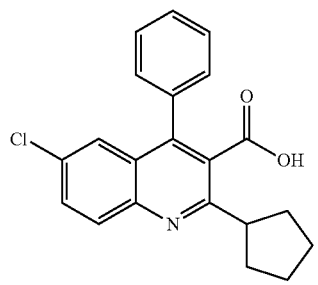

Step A 6-Chloro-2-cyclopentyl-4-phenyl-quinoline-3-carboxylic acid ethyl ester

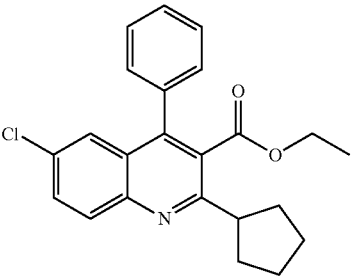 [SMILES: CCOC(=O)c1c(C2CCCC2)nc2ccc(Cl)cc2c1-c1ccccc1]

To a stirred solution of 2,6-dichloro-4-phenyl-quinoline-3-carboxylic acid ethyl ester (prepared as described in example 11 step B, 100 mg, 0.29 mmol) in 2 ml THF, was added cyclopentyl magnesium bromide (2 M solution in diethyl ether) (0.72 ml, 1.44 mmol) drop wise at 25° C. under nitrogen. The resulting reaction mixture was stirred for 40 min at 50° C. in a microwave. The reaction mixture was then quenched with saturated aqueous NH₄Cl solution and extracted with ethyl acetate. The combined organic phases were dried over anhydrous sodium sulfate and concentrated in vacuo to give a crude residue which was purified by flash column chromatography (2% ethyl acetate in hexane) to afford 6-chloro-2-cyclopentyl-4-phenyl-quinoline-3-carboxylic acid ethyl ester (16.5 mg, 15%) as pale yellow sticky solid. LC-MS: 380 (M+H)⁺.

Step B 6-Chloro-2-cyclopentyl-4-phenyl-quinoline-3-carboxylic acid

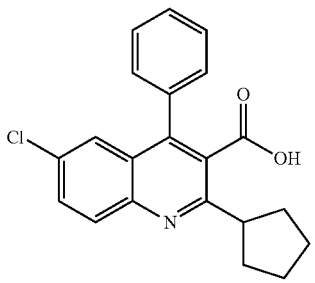 [SMILES: O=C(O)c1c(C2CCCC2)nc2ccc(Cl)cc2c1-c1ccccc1]

The title compound was prepared in analogy to example 20 step D from 6-chloro-2-cyclopentyl-4-phenyl-quinoline-3-carboxylic acid ethyl ester (35 mg, 0.09 mmol) and lithium iodide in pyridine. Off-white solid (15 mg, 46%). LC-MS: 350 (M−H)⁻.

Example 37

6-Chloro-4-phenyl-2-pyrrolidin-1-yl-quinoline-3-carboxylic acid

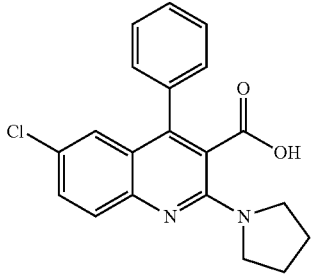 [SMILES: O=C(O)c1c(N2CCCC2)nc2ccc(Cl)cc2c1-c1ccccc1]

Step A 6-Chloro-4-phenyl-2-pyrrolidin-1-yl-quinoline-3-carboxylic acid ethyl ester

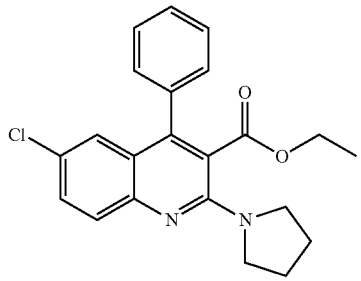 [SMILES: CCOC(=O)c1c(N2CCCC2)nc2ccc(Cl)cc2c1-c1ccccc1]

To a stirred solution of 2,6-dichloro-4-phenyl-quinoline-3-carboxylic acid ethyl ester (prepared as described in example 11 step B, 200 mg, 0.58 mmol) in DMSO (2 ml) in sealed tube, was added pyrrolidine (0.073 ml, 0.89 mmol), K₂CO₃ (153 mg, 1.11 mmol) and the mixture was stirred at 90° C. for 3 h. After cooling, the crude mixture was diluted with water and extracted with ethyl acetate. The organic phases were combined and washed with brine, dried over sodium sulfate and concentrated in vacuo to give a crude residue which was purified by flash column chromatography (100-200 mesh silica, eluting with 10% ethyl acetate in hexane) to obtain 6-chloro-4-phenyl-2-pyrrolidin-1-yl-quinoline-3-carboxylic acid ethyl ester (150 mg, 68%) as pale yellow solid. LC-MS: 381 (M+H)⁺.

Step B 6-Chloro-4-phenyl-2-pyrrolidin-1-yl-quinoline-3-carboxylic acid

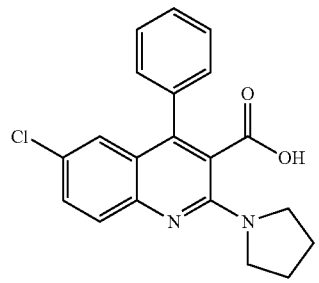

The title compound was prepared in analogy to example 20 step D from 6-chloro-4-phenyl-2-pyrrolidin-1-yl-quinoline-3-carboxylic acid ethyl ester (100 mg, 0.26 mmol) and LiI (351.4 mg, 2.63 mmol) in pyridine. Pale yellow solid (74 mg, 80%). LC-MS: 351 (M−H)⁻.

Example 38

6-Chloro-2-(2-oxo-pyrrolidin-1-yl)-4-phenyl-quinoline-3-carboxylic acid

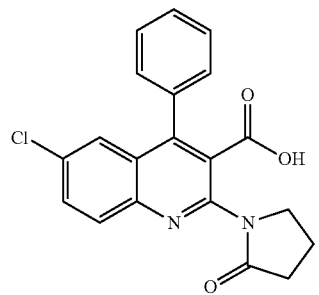

Step A 6-Chloro-2-(2-oxo-pyrrolidin-1-yl)-4-phenyl-quinoline-3-carboxylic acid ethyl ester

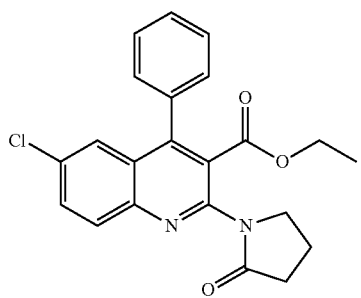 [SMILES: CCOC(=O)c1c(N2CCCC2=O)nc2ccc(Cl)cc2c1-c1ccccc1]

To a solution of pyrrolidin-2-one (0.054 ml, 0.69 mmol) in THF in a microwave vessel under nitrogen, was added NaH (28 mg, 0.69 mmol) portion wise at 25° C. The reaction mixture was stirred for 30 min followed by the addition of a solution of 2,6-dichloro-4-phenyl-quinoline-3-carboxylic acid ethyl ester (prepared as described in example 11 step B, 200 mg, 0.58 mmol) in 2 ml THF at 25° C. Then the resulting reaction mixture was stirred for 1 h at 60° C. in a microwave. After cooling, reaction mixture was quenched with saturated aqueous NH₄Cl solution and extracted with ethyl acetate. The organic layer was washed with brine, dried over anhydrous sodium sulfate and concentrated in vacuo to afford a crude residue which was purified by flash column chromatography (eluting with 20% ethyl acetate in hexane) to obtain 6-chloro-2-(2-oxo-pyrrolidin-1-yl)-4-phenyl-quinoline-3-carboxylic acid ethyl ester (15 mg, 7%) as an off white solid. LC-MS: 395 (M+H)$^+$.

Step B 6-Chloro-2-(2-oxo-pyrrolidin-1-yl)-4-phenyl-quinoline-3-carboxylic acid

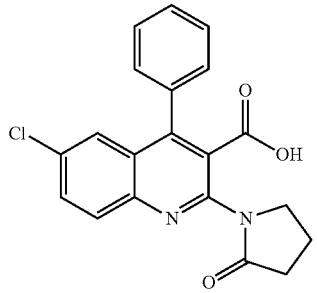 [SMILES: O=C(O)c1c(N2CCCC2=O)nc2ccc(Cl)cc2c1-c1ccccc1]

The title compound was prepared in analogy to example 20 step D from 6-chloro-2-(2-oxo-pyrrolidin-1-yl)-4-phenyl-quinoline-3-carboxylic acid ethyl ester (50 mg, 0.13 mmol) and LiI in pyridine. Yellow solid (11 mg, 24%). LC-MS: 367 (M+H)$^+$.

Example 39

6-Chloro-2-isopropyl-4-(2-methoxy-benzyl)-quinoline-3-carboxylic acid

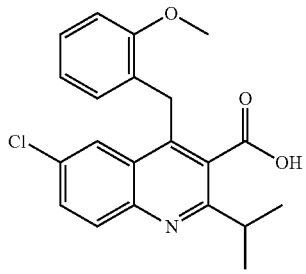 [SMILES: COc1ccccc1Cc1c(C(=O)O)c(C(C)C)nc2ccc(Cl)cc12]

Step A
4-Chloro-2-(2-methoxy-phenylethynyl)-phenylamine

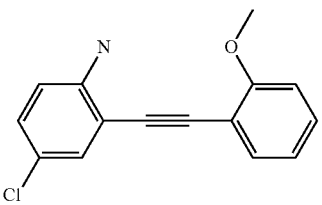 [SMILES: COc1ccccc1C#Cc1cc(Cl)ccc1N]

The title compound was prepared in analogy to example 10 step A from 4-chloro-2-iodo-phenylamine (1 g, 3.95 mmol) and 1-ethynyl-2-methoxy-benzene (625 mg, 4.73 mmol). Off white solid (635 mg, 62% yield). LC-MS (ESI): 258 (M+H)$^+$.

Step B 6-Chloro-2-isopropyl-4-(2-methoxy-benzyl)-quinoline-3-carboxylic acid ethyl ester

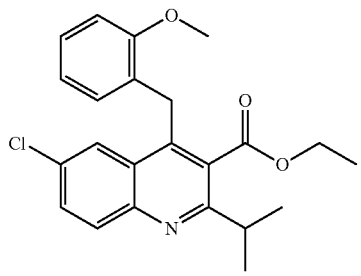 [SMILES: CCOC(=O)c1c(C(C)C)nc2ccc(Cl)cc2c1Cc1ccccc1OC]

The title compound was prepared in analogy to example 10 step B from 4-chloro-2-(2-methoxy-phenylethynyl)-phenylamine (200 mg, 0.78 mmol) and 4-methyl-3-oxo-pentanoic acid ethyl ester (0.2 ml, 1.16 mmol) in anhydrous EtOH (8 ml). Light green liquid. (100 mg, 32% yield). LC-MS (ESI): 398 (M+H)$^+$.

Step C 6-Chloro-2-isopropyl-4-(2-methoxy-benzyl)-quinoline-3-carboxylic acid

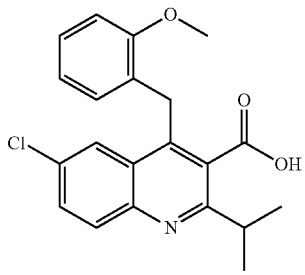 [SMILES: COc1ccccc1Cc1c(C(=O)O)c(C(C)C)nc2ccc(Cl)cc12]

The title compound was prepared in analogy to example 20 step D from 6-chloro-2-isopropyl-4-(2-methoxy-benzyl)-quinoline-3-carboxylic acid ethyl ester (80 mg, 0.2 mmol) and lithium iodide (134.5 mg, 1.01 mmol) in pyridine. Off white solid (24 mg, 32%). LC-MS (ESI): 368 (M−H)$^−$.

Example 40

6-Chloro-8-methyl-4-phenyl-2-piperidin-1-yl-quinoline-3-carboxylic acid

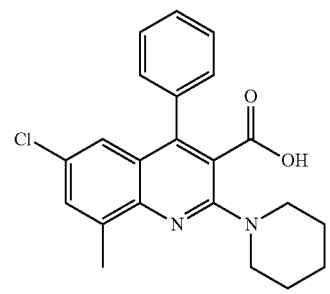

Step A: N-(2-Benzoyl-4-chloro-6-methyl-phenyl)-malonamic acid methyl ester

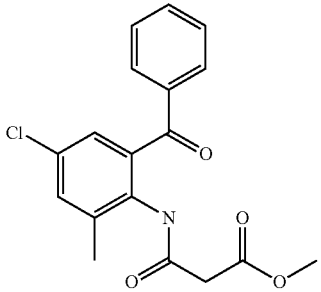 [SMILES: COC(=O)CC(=O)Nc1c(C)cc(Cl)cc1C(=O)c1ccccc1]

The title compound was prepared in analogy to example 21 step A from (2-amino-5-chloro-3-methyl-phenyl)-phenyl-methanone and methyl 3-chloro-3-oxopropanoate. Brown oil. MS (ESI): 346.1 (M+H)⁺.

Step B: 6-Chloro-8-methyl-2-oxo-4-phenyl-1,2-dihydro-quinoline-3-carboxylic acid methyl ester

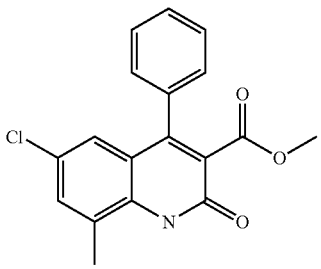 [SMILES: COC(=O)c1c(-c2ccccc2)c2cc(Cl)cc(C)c2[nH]c1=O]

The title compound was prepared in analogy to example 21 step B from N-(2-benzoyl-4-chloro-6-methyl-phenyl)-malonamic acid methyl ester. Light brown solid. MS (ESI): 328.2 (M+H)⁺.

Step C: 2,6-Dichloro-8-methyl-4-phenyl-quinoline-3-carboxylic acid methyl ester

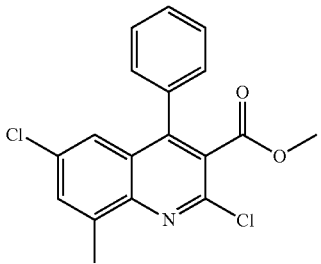 [SMILES: COC(=O)c1c(Cl)nc2c(C)cc(Cl)cc2c1-c1ccccc1]

The title compound was prepared in analogy to example 21 step C from 6-chloro-8-methyl-2-oxo-4-phenyl-1,2-dihydro-quinoline-3-carboxylic acid methyl ester. Off-white solid. MS (ESI): 346.0 (M+H)⁺.

Step D: 6-Chloro-8-methyl-4-phenyl-2-piperidin-1-yl-quinoline-3-carboxylic acid

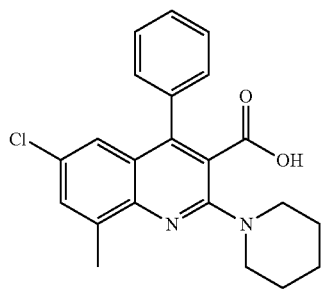

The title compound was prepared in analogy to example 21 step D from 2,6-dichloro-8-methyl-4-phenyl-quinoline-3-carboxylic acid methyl ester and piperidine. Brown solid. MS (ESI): 381.2 (M+H)⁺.

Example 41

6-Chloro-8-methyl-4-phenyl-2-pyrrolidin-1-yl-quinoline-3-carboxylic acid

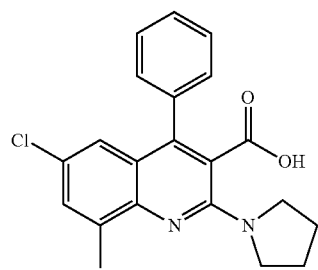 [SMILES: Cc1cc(Cl)cc2c(-c3ccccc3)c(C(=O)O)c(N3CCCC3)nc12]

The title compound was prepared in analogy to example 40 step D from 2,6-dichloro-8-methyl-4-phenyl-quinoline-3-carboxylic acid methyl ester (prepared as described in example 40 step C) and pyrrolidine. Brown foam. MS (ESI): 367.0 (M+H)⁺.

Example 42

6-Chloro-2-(isopropyl-methyl-amino)-4-phenyl-quinoline-3-carboxylic acid

Step A: 6-Chloro-2-(isopropyl-methyl-amino)-4-phenyl-quinoline-3-carboxylic acid tert-butyl ester

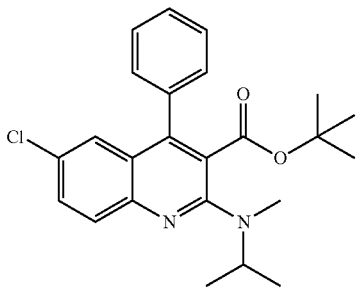 [SMILES: CC(C)N(C)c1nc2ccc(Cl)cc2c(-c2ccccc2)c1C(=O)OC(C)(C)C]

The title compound was prepared in analogy to example 92 step A from tert-butyl 6-chloro-4-phenyl-2-(trifluoromethylsulfonyloxy)quinoline-3-carboxylate (prepared in analogy to example 91 step A to C, 100 mg, 0.21 mmol) and N-methylpropan-2-amine (0.213 ml, 2.05 mmol). Pale yellow solid (75 mg, 89%). MS (ESI): 411 (M+H)⁺.

Step B 6-Chloro-2-(isopropyl-methyl-amino)-4-phenyl-quinoline-3-carboxylic acid

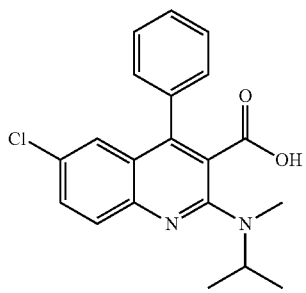 [SMILES: CC(C)N(C)c1nc2ccc(Cl)cc2c(-c2ccccc2)c1C(=O)O]

A solution of tert-butyl 6-chloro-2-(isopropyl(methyl)amino)-4-phenylquinoline-3-carboxylate (75 mg, 183 µmol), in DCM (1 ml) and TFA (1 ml) was stirred at room temperature for 2 h followed by a further 2 h at 40° C. The reaction mixture was concentrated in vacuo and the crude residue was dissolved in ethyl acetate and washed with water. The ethyl acetate layer was washed with 0.1N NaOH solution (2×) and then the aqueous layer was made acidic (pH 3-4) with 1N HCl and then further extracted with ethyl acetate. The organic layers were combined, dried over Na₂SO₄, filtered and concentrated in vacuo to give the desired product as a light yellow solid (48 mg, 74%). MS (ESI): 355 (M+H)⁺.

Example 43

8-Ethyl-4-phenyl-2-piperidin-1-yl-quinoline-3-carboxylic acid

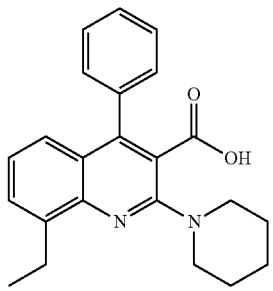 [SMILES: CCc1cccc2c(-c3ccccc3)c(C(=O)O)c(N3CCCCC3)nc12]

Step A:
(2-Amino-3-ethyl-phenyl)-phenyl-methanone

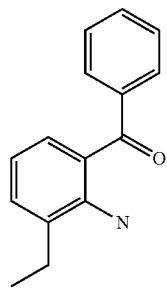 [SMILES: CCc1cccc(C(=O)c2ccccc2)c1N]

To a solution of boron trichloride (9.9 ml, 9.9 mmol, Eq: 1.2) in 1,1,2,2-tetrachloroethane (20.0 ml) was added 2-ethylaniline (1 g, 1.02 ml, 8.25 mmol, Eq: 1.00) dropwise at 0° C. and the resulting mixture was stirred for 30 min at RT. Then benzonitrile (1.7 g, 1.7 ml, 16.5 mmol, Eq: 2) and aluminum chloride (1.21 g, 9.08 mmol, Eq: 1.1) were added successively and the reaction mixture was heated to reflux for 44 h. Then 2N HCl (20 ml) was added at 0° C. and the mixture was heated to 80° C. for 30 min. Additional water was added and the mixture was extracted with DCM (3×). The combined extracts were dried with Na₂SO₄ and evaporated. The remaining residue was purified by column chromatography (silica gel, DCM/heptane 1:1) to afford the title compound as yellow oil (930 mg, containing 20% 2-ethylaniline). MS (ESI): 226.2 (M+H)⁺.

Step B: N-(2-Benzoyl-6-ethyl-phenyl)-malonamic acid methyl ester

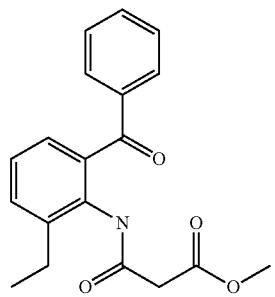 [SMILES: CCc1cccc(C(=O)c2ccccc2)c1NC(=O)CC(=O)OC]

The title compound was prepared in analogy to example 21 step A from (2-amino-3-ethyl-phenyl)-phenyl-methanone and methyl 3-chloro-3-oxopropanoate. White solid. MS (ESI): 326.2 (M+H)⁺.

Step C: 8-Ethyl-2-oxo-4-phenyl-1,2-dihydro-quinoline-3-carboxylic acid methyl ester

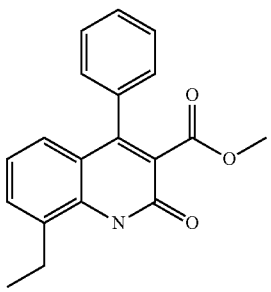 [SMILES: CCc1cccc2c(-c3ccccc3)c(C(=O)OC)c(=O)[nH]c12]

The title compound was prepared in analogy to example 21 step B from N-(2-benzoyl-6-ethyl-phenyl)-malonamic acid methyl ester. White solid. MS (ESI): 306.2 (M+H)⁺.

Step D:
2-Chloro-8-ethyl-4-phenyl-quinoline-3-carboxylic acid methyl ester

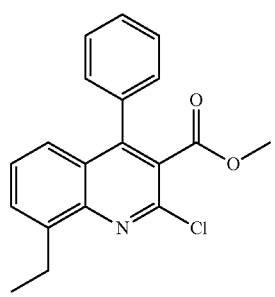 [SMILES: CCc1cccc2c(-c3ccccc3)c(C(=O)OC)c(Cl)nc12]

The title compound was prepared in analogy to example 21 step C from 8-ethyl-2-oxo-4-phenyl-1,2-dihydro-quinoline-3-carboxylic acid methyl ester. Light yellow oil. MS (ESI): 326.1 (M+H)⁺.

Step E: 8-Ethyl-4-phenyl-2-piperidin-1-yl-quinoline-3-carboxylic acid

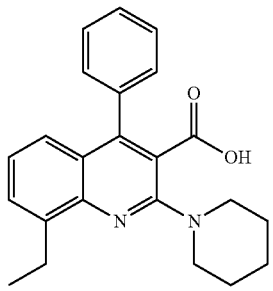 [SMILES: CCc1cccc2c(-c3ccccc3)c(C(=O)O)c(N3CCCCC3)nc12]

The title compound was prepared in analogy to example 21 step D from 2-chloro-8-ethyl-4-phenyl-quinoline-3-carboxylic acid methyl ester and piperidine. Yellow oil. MS (ESI): 361.2 (M+H)⁺.

Example 44

6-Chloro-2-diethylamino-8-methyl-4-phenyl-quinoline-3-carboxylic acid

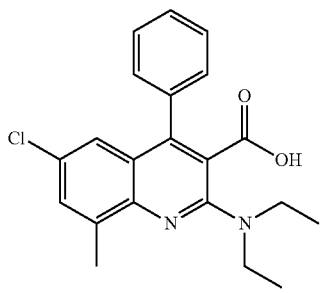 [SMILES: CCN(CC)c1nc2c(C)cc(Cl)cc2c(-c2ccccc2)c1C(=O)O]

The title compound was prepared in analogy to example 40 step D from 2,6-dichloro-8-methyl-4-phenyl-quinoline-3-carboxylic acid methyl ester (prepared as described in example 40 step C) and diethylamine. Brown solid. MS (ESI): 369.1 (M+H)⁺.

Example 45

6,8-Dichloro-2-(isopropyl-methyl-amino)-4-phenyl-quinoline-3-carboxylic acid

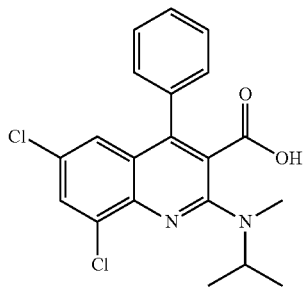 [SMILES: CC(C)N(C)c1nc2c(Cl)cc(Cl)cc2c(-c2ccccc2)c1C(=O)O]

The title compound was prepared in analogy to example 21 step D from 2,6,8-trichloro-4-phenyl-quinoline-3-carboxylic acid methyl ester (prepared as described in example 21 step C) and isopropyl-methyl-amine. Light brown foam. MS (ESI): 389.2 (M+H)⁺.

Example 46

6-Chloro-2-[(2-hydroxy-ethyl)-methyl-amino]-4-phenyl-quinoline-3-carboxylic acid Step A: 6-Chloro-2-[(2-hydroxy-ethyl)-methyl-amino]-4-phenyl-quinoline-3-carboxylic acid tert-butyl ester

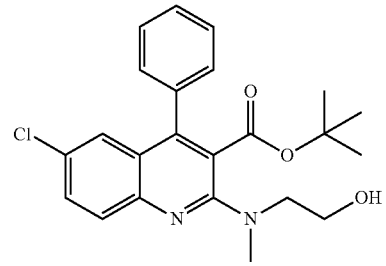 [SMILES: CN(CCO)c1nc2ccc(Cl)cc2c(-c2ccccc2)c1C(=O)OC(C)(C)C]

The title compound was prepared in analogy to example 92 step A from tert-butyl 6-chloro-4-phenyl-2-(trifluoromethylsulfonyloxy)quinoline-3-carboxylate (prepared in analogy to example 91 step A to C, 100 mg, 0.21 mmol) and 2-(methylamino)ethanol (0.164 ml, 2.05 mmol). Pale yellow solid (65 mg, 77%). MS (ESI): 413 (M+H)⁺.

Step B: 6-Chloro-2-[(2-hydroxy-ethyl)-methyl-amino]-4-phenyl-quinoline-3-carboxylic acid

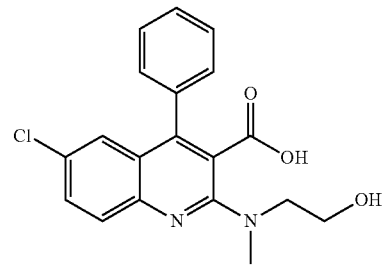 [SMILES: CN(CCO)c1nc2ccc(Cl)cc2c(-c2ccccc2)c1C(=O)O]

The title compound was prepared in analogy to example 42 step B from 6-chloro-2-[(2-hydroxy-ethyl)-methyl-amino]-4-phenyl-quinoline-3-carboxylic acid tert-butyl ester and TFA. Light yellow solid. MS (ESI): 355 (M−H)⁻.

Example 47

8-Ethyl-4-phenyl-2-pyrrolidin-1-yl-quinoline-3-carboxylic acid

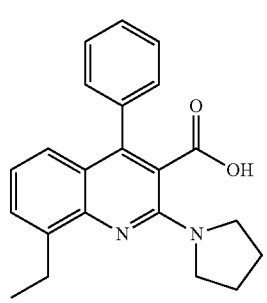 [SMILES: CCc1cccc2c(-c3ccccc3)c(C(=O)O)c(N3CCCC3)nc12]

The title compound was prepared in analogy to example 43 step E from 2-chloro-8-ethyl-4-phenyl-quinoline-3-carboxylic acid methyl ester (prepared as described in example 43 step D) and pyrrolidine. Yellow solid. MS (ESI): 347.2 (M+H)+.

Example 48

2-Dimethylamino-8-ethyl-4-phenyl-quinoline-3-carboxylic acid

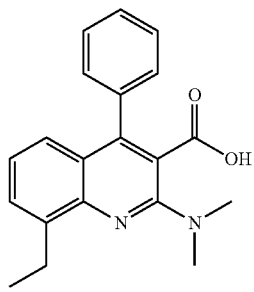 [SMILES: CCc1cccc2c(-c3ccccc3)c(C(=O)O)c(N(C)C)nc12]

The title compound was prepared in analogy to example 43 step E from 2-chloro-8-ethyl-4-phenyl-quinoline-3-carboxylic acid methyl ester (prepared as described in example 43 step D) and dimethylamine (40% in water). Yellow solid. MS (ESI): 321.2 (M+H)+.

Example 49

6-Chloro-2-[(2-methoxy-ethyl)-methyl-amino]-4-phenyl-quinoline-3-carboxylic acid Step A: 6-Chloro-2-[(2-methoxy-ethyl)-methyl-amino]-4-phenyl-quinoline-3-carboxylic acid tert-butyl ester

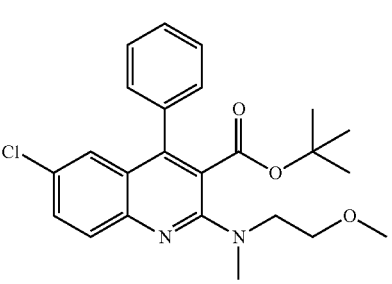 [SMILES: COCCN(C)c1nc2ccc(Cl)cc2c(-c2ccccc2)c1C(=O)OC(C)(C)C]

The title compound was prepared in analogy to example 92 step A from tert-butyl 6-chloro-4-phenyl-2-(trifluoromethylsulfonyloxy)quinoline-3-carboxylate (prepared in analogy to example 91 step A to C, 100 mg, 0.21 mmol) and 2-methoxy-N-methylethanamine (183 mg, 2.05 mmol). Pale yellow solid (75 mg, 86%). MS (ESI): 427 (M+H)+.

Step B: 6-Chloro-2-[(2-methoxy-ethyl)-methyl-amino]-4-phenyl-quinoline-3-carboxylic acid

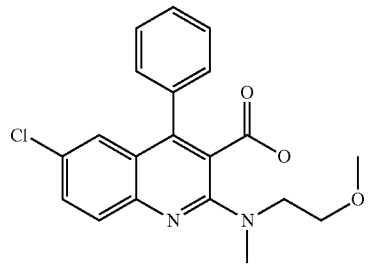 [SMILES: COCCN(C)c1nc2ccc(Cl)cc2c(-c2ccccc2)c1C(=O)O]

The title compound was prepared in analogy to example 42 step B from 6-chloro-2-[(2-methoxy-ethyl)-methyl-amino]-4-phenyl-quinoline-3-carboxylic acid tert-butyl ester and TFA. Light yellow foam. MS (ESI): 369 (M−H)−.

Example 50

6,8-Dichloro-2-(ethyl-methyl-amino)-4-phenyl-quinoline-3-carboxylic acid

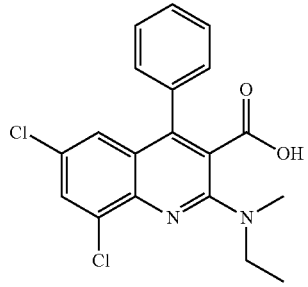 [SMILES: CCN(C)c1nc2c(Cl)cc(Cl)cc2c(-c2ccccc2)c1C(=O)O]

The title compound was prepared in analogy to example 21 step D from 2,6,8-trichloro-4-phenyl-quinoline-3-carboxylic acid methyl ester (prepared as described in example 21 step C) and ethyl-methyl-amine. Brown foam. MS (ESI): 375.1 (M+H)+.

Example 51

6,8-Dichloro-2-(2-methyl-pyrrolidin-1-yl)-4-phenyl-quinoline-3-carboxylic acid

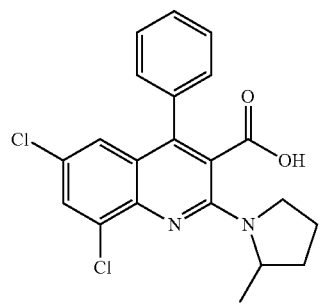 [SMILES: CC1CCCN1c1nc2c(Cl)cc(Cl)cc2c(-c2ccccc2)c1C(=O)O]

The title compound was prepared in analogy to example 21 step D from 2,6,8-trichloro-4-phenyl-quinoline-3-carboxylic acid methyl ester (prepared as described in example 21 step C) and 2-methylpyrrolidine. Brown foam. MS (ESI): 401.2 (M+H)⁺.

Example 52

6-Chloro-2-diethylamino-4-phenyl-quinoline-3-carboxylic acid

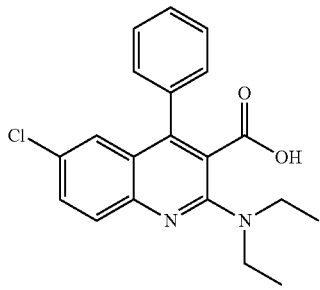 [SMILES: CCN(CC)c1nc2ccc(Cl)cc2c(-c2ccccc2)c1C(=O)O]

Step A: 6-Chloro-2-diethylamino-4-phenyl-quinoline-3-carboxylic acid ethyl ester

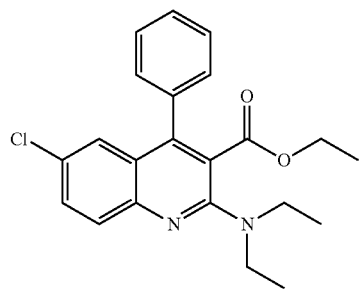 [SMILES: CCOC(=O)c1c(N(CC)CC)nc2ccc(Cl)cc2c1-c1ccccc1]

The title compound was prepared in analogy to example 37 step A from 2,6-dichloro-4-phenyl-quinoline-3-carboxylic acid ethyl ester (prepared as described in example 11 step B, 100 mg, 0.29 mmol) and diethyl-amine (0.06 ml, 0.58 mmol). Sticky liquid (70 mg, 63%). LC-MS: 383 (M+H)⁺.

Step B: 6-Chloro-2-diethylamino-4-phenyl-quinoline-3-carboxylic acid

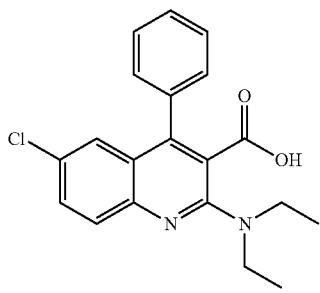 [SMILES: CCN(CC)c1nc2ccc(Cl)cc2c(-c2ccccc2)c1C(=O)O]

The title compound was prepared in analogy to example 20 step D from 6-chloro-2-diethylamino-4-phenyl-quinoline-3-carboxylic acid ethyl ester (50 mg, 0.13 mmol) and LiI in pyridine. Pale yellow solid (30 mg, 65%). LC-MS: 355 (M+H)⁺.

Example 53

6-Chloro-4-phenyl-2-(2,2,2-trifluoro-1-methyl-ethoxy)-quinoline-3-carboxylic acid

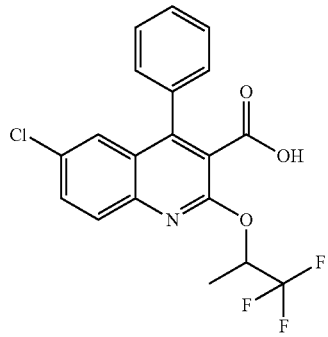 [SMILES: CC(Oc1nc2ccc(Cl)cc2c(-c2ccccc2)c1C(=O)O)C(F)(F)F]

Step A: 6-Chloro-4-phenyl-2-(2,2,2-trifluoro-1-methyl-ethoxy)-quinoline-3-carboxylic acid ethyl ester

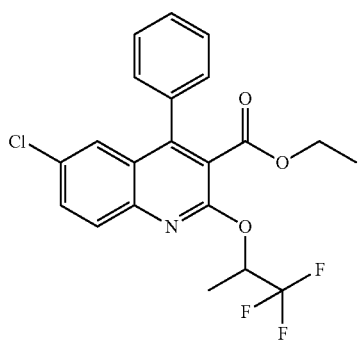 [SMILES: CCOC(=O)c1c(OC(C)C(F)(F)F)nc2ccc(Cl)cc2c1-c1ccccc1]

The title compound was prepared in analogy to example 37 step A from 2,6-dichloro-4-phenyl-quinoline-3-carboxylic acid ethyl ester (prepared as described in example 11 step B, 100 mg, 0.29 mmol) and 1,1,1-trifluoro-propan-2-ol (40 mg, 0.35 mmol). Pale yellow solid (76 mg, 62%). LC-MS: 424 (M+H)⁺.

Step B: 6-Chloro-4-phenyl-2-(2,2,2-trifluoro-1-methyl-ethoxy)-quinoline-3-carboxylic acid

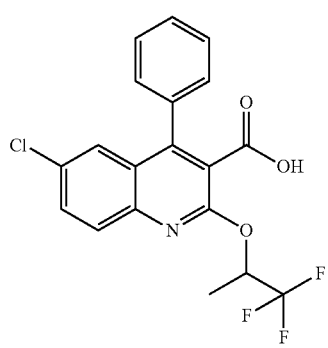 [SMILES: CC(Oc1nc2ccc(Cl)cc2c(-c2ccccc2)c1C(=O)O)C(F)(F)F]

The title compound was prepared in analogy to example 20 step D from 6-chloro-4-phenyl-2-(2,2,2-trifluoro-1- methyl-ethoxy)-quinoline-3-carboxylic acid ethyl ester (100 mg, 0.26 mmol) and LiI in pyridine. Off white solid (55 mg, 53%). LC-MS: 396 (M+H)⁺.

Example 54

6-Ethyl-8-methyl-4-phenyl-2-piperidin-1-yl-quinoline-3-carboxylic acid

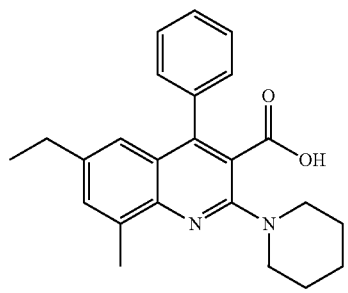 [SMILES: CCc1cc(C)c2nc(N3CCCCC3)c(C(=O)O)c(-c3ccccc3)c2c1]

Step A:
(2-Amino-5-bromo-3-methyl-phenyl)-phenyl-methanone

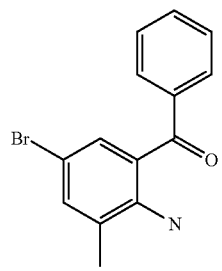

The title compound was prepared in analogy to example 43 step A from 4-bromo-2-methylaniline and benzonitrile. Yellow oil. MS (ESI): 392.0 (M+H)⁺.

Step B:
N-(2-Benzoyl-4-bromo-6-methyl-phenyl)-malonamic acid methyl ester

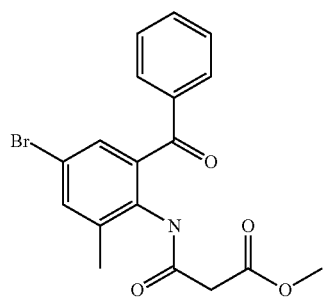 [SMILES: COC(=O)CC(=O)Nc1c(C)cc(Br)cc1C(=O)c1ccccc1]

The title compound was prepared in analogy to example 21 step A from (2-amino-5-bromo-3-methyl-phenyl)-phenyl-methanone and methyl 3-chloro-3-oxopropanoate. Light yellow solid. MS (ESI): 392.1 (M+H)⁺.

Step C: 6-Bromo-8-methyl-2-oxo-4-phenyl-1,2-dihydro-quinoline-3-carboxylic acid methyl ester

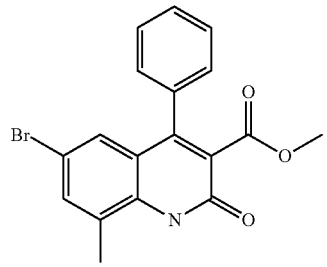

The title compound was prepared in analogy to example 21 step B from N-(2-benzoyl-4-bromo-6-methyl-phenyl)-malonamic acid methyl ester. White solid. MS (ESI): 374.2 (M+H)⁺.

Step D: 6-Ethyl-8-methyl-2-oxo-4-phenyl-1,2-dihydro-quinoline-3-carboxylic acid methyl ester

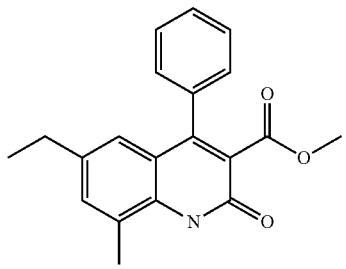 [SMILES: CCc1cc(C)c2[nH]c(=O)c(C(=O)OC)c(-c3ccccc3)c2c1]

A mixture of 6-bromo-8-methyl-2-oxo-4-phenyl-1,2-dihydro-quinoline-3-carboxylic acid methyl ester (25 mg, 67.2 µmol, Eq: 1.00), triethylborane (134 µl, 134 µmol, Eq: 2), potassium carbonate (18.6 mg, 134 µmol, Eq: 2) and 1,1'-bis(diphenylphosphino)ferrocene-palladium(II)dichloride dichloromethane complex (5.49 mg, 6.72 µmol, Eq: 0.1) in DMF was heated to 65° C. for 16 h in a sealed tube. Then water was added and the reaction mixture was extracted with ethyl acetate (3×). The combined extracts were washed with water and brine, dried with Na₂SO₄ and evaporated. The remaining residue was purified by column chromatography (silica gel, DCM/EtOAc 4:1) to afford the title compound as light brown solid (15 mg). MS (ESI): 322.2 (M+H)⁺.

Step E: 2-Chloro-6-ethyl-8-methyl-4-phenyl-quinoline-3-carboxylic acid methyl ester

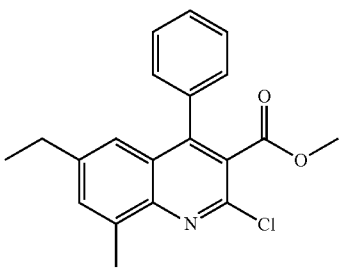 [SMILES: CCc1cc(C)c2nc(Cl)c(C(=O)OC)c(-c3ccccc3)c2c1]

The title compound was prepared in analogy to example 21 step C from 6-ethyl-8-methyl-2-oxo-4-phenyl-1,2-dihydro-quinoline-3-carboxylic acid methyl ester. White solid. MS (ESI): 340.1 (M+H)⁺.

Step F: 6-Ethyl-8-methyl-4-phenyl-2-piperidin-1-yl-quinoline-3-carboxylic acid

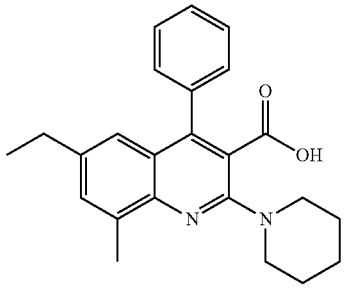 [SMILES: CCc1cc(C)c2nc(N3CCCCC3)c(C(=O)O)c(-c3ccccc3)c2c1]

The title compound was prepared in analogy to example 21 step D from 2-chloro-6-ethyl-8-methyl-4-phenyl-quinoline-3-carboxylic acid methyl ester and piperidine. Light brown solid. MS (ESI): 375.4 (M+H)⁺.

Example 55

6-Chloro-2-(ethyl-methyl-amino)-8-methyl-4-phenyl-quinoline-3-carboxylic acid

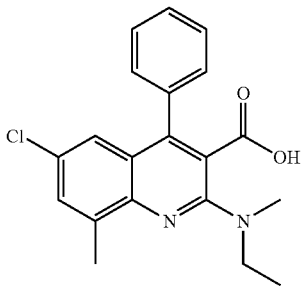 [SMILES: CCN(C)c1nc2c(C)cc(Cl)cc2c(-c2ccccc2)c1C(=O)O]

The title compound was prepared in analogy to example 40 step D from 2,6-dichloro-8-methyl-4-phenyl-quinoline-3-carboxylic acid methyl ester (prepared as described in example 40 step C) and ethyl-methyl-amine. Yellow foam. MS (ESI): 355.1 (M+H)⁺.

Example 56

6-Chloro-8-methyl-2-(2-methyl-pyrrolidin-1-yl)-4-phenyl-quinoline-3-carboxylic acid

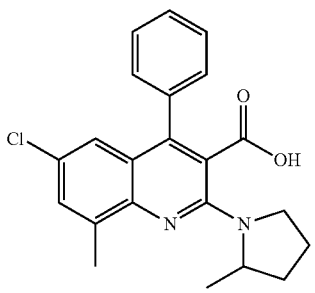 [SMILES: Cc1cc(Cl)cc2c(-c3ccccc3)c(C(=O)O)c(N3CCCC3C)nc12]

The title compound was prepared in analogy to example 40 step D from 2,6-dichloro-8-methyl-4-phenyl-quinoline-3-carboxylic acid methyl ester (prepared as described in example 40 step C) and 2-methylpyrrolidine. Yellow foam. MS (ESI): 381.2 (M+H)⁺.

Example 57

6,8-Dichloro-2-(4,4-difluoro-piperidin-1-yl)-4-phenyl-quinoline-3-carboxylic acid

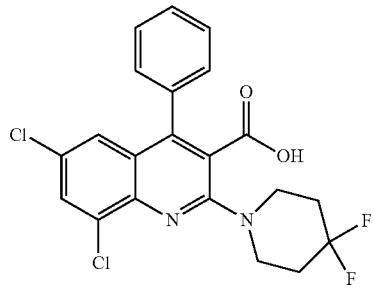 [SMILES: O=C(O)c1c(N2CCC(F)(F)CC2)nc2c(Cl)cc(Cl)cc2c1-c1ccccc1]

The title compound was prepared in analogy to example 21 step D from 2,6,8-trichloro-4-phenyl-quinoline-3-carboxylic acid methyl ester (prepared as described in example 21 step C) and 4,4-difluoro-piperidine. Yellow foam. MS (ESI): 437.1 (M+H)⁺.

Example 58

6-Chloro-2-(4,4-difluoro-piperidin-1-yl)-8-methyl-4-phenyl-quinoline-3-carboxylic acid

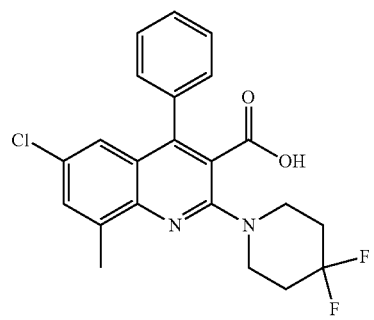 [SMILES: Cc1cc(Cl)cc2c(-c3ccccc3)c(C(=O)O)c(N3CCC(F)(F)CC3)nc12]

The title compound was prepared in analogy to example 40 step D from 2,6-dichloro-8-methyl-4-phenyl-quinoline-3-carboxylic acid methyl ester (prepared as described in example 40 step C) and 4,4-difluoro-piperidine. Light yellow foam. MS (ESI): 417.2 (M+H)⁺.

Example 59

[6-Chloro-4-phenyl-3-(1H-tetrazol-5-yl)-quinolin-2-yl]-diethyl-amine

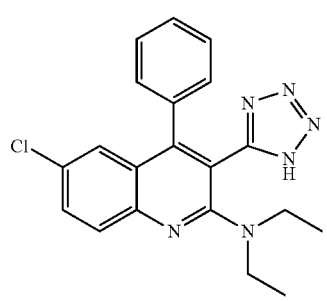 [SMILES: CCN(CC)c1nc2ccc(Cl)cc2c(-c2ccccc2)c1-c1nnn[nH]1]

Step A: 6-Chloro-2-diethylamino-4-phenyl-quinoline-3-carbonitrile

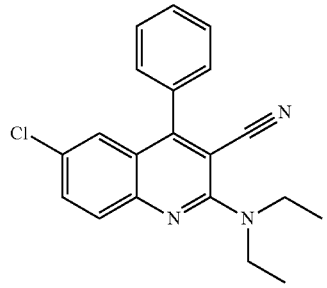 [SMILES: CCN(CC)c1nc2ccc(Cl)cc2c(-c2ccccc2)c1C#N]

The title compound was prepared in analogy to example 27 step C from 2,6-dichloro-4-phenyl-quinoline-3-carbonitrile (prepared as described in example 27 step B) and diethylamine. Yellow solid. MS (ESI): 336.2 (M+H)+.

Step B: [6-Chloro-4-phenyl-3-(1H-tetrazol-5-yl)-quinolin-2-yl]-diethyl-amine

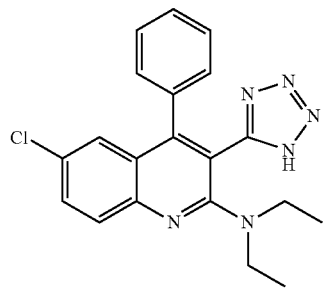 [SMILES: CCN(CC)c1nc2ccc(Cl)cc2c(-c2ccccc2)c1-c1nnn[nH]1]

The title compound was prepared in analogy to example 27 step D from 6-chloro-2-diethylamino-4-phenyl-quinoline-3-carbonitrile. Light yellow solid. MS (ESI): 379.2 (M+H)+.

Example 60

6-Cyano-8-methyl-4-phenyl-2-piperidin-1-yl-quinoline-3-carboxylic acid

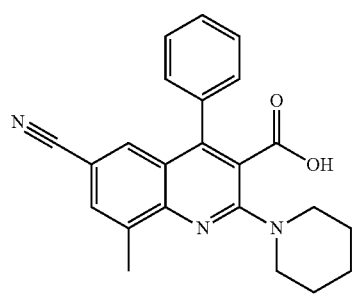 [SMILES: Cc1cc(C#N)cc2c(-c3ccccc3)c(C(=O)O)c(N3CCCCC3)nc12]

Step A: 6-Cyano-8-methyl-2-oxo-4-phenyl-1,2-dihydro-quinoline-3-carboxylic acid methyl ester

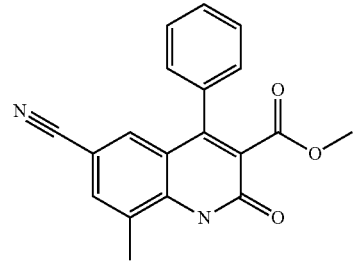 [SMILES: COC(=O)c1c(-c2ccccc2)c2cc(C#N)cc(C)c2[nH]c1=O]

A suspension of 6-bromo-8-methyl-2-oxo-4-phenyl-1,2-dihydro-quinoline-3-carboxylic acid methyl ester (prepared as described in example 54 step C) (140 mg, 376 μmol, Eq: 1.00) and copper(I) cyanide (121 mg, 41.5 μl, 1.35 mmol, Eq: 3.6) in DMF (2.8 ml) was heated to 130° C. for 2 d. Then water was added and the mixture was extracted with DCM (3×). The combined extracts were washed with water and brine, dried with Na$_2$SO$_4$ and evaporated to give the title compound as off-white solid (120 mg). MS (ESI): 317.2 (M−H)−

Step B: 2-Chloro-6-cyano-8-methyl-4-phenyl-quinoline-3-carboxylic acid methyl ester

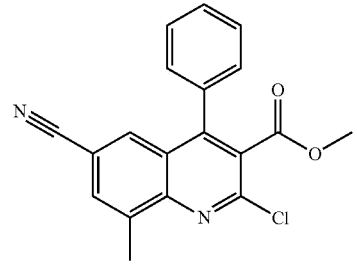 [SMILES: COC(=O)c1c(Cl)nc2c(C)cc(C#N)cc2c1-c1ccccc1]

The title compound was prepared in analogy to example 21 step C from 6-cyano-8-methyl-2-oxo-4-phenyl-1,2-dihydro-quinoline-3-carboxylic acid methyl ester. Yellow solid. MS (ESI): 338.9 (M+H)+.

Step C: 6-Cyano-8-methyl-4-phenyl-2-piperidin-1-yl-quinoline-3-carboxylic acid

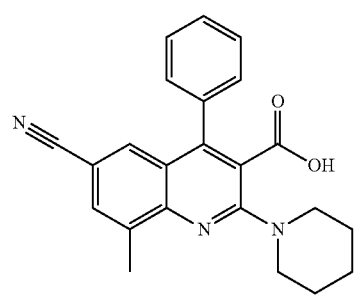 [SMILES: Cc1cc(C#N)cc2c(-c3ccccc3)c(C(=O)O)c(N3CCCCC3)nc12]

The title compound was prepared in analogy to example 21 step D from 2-chloro-6-cyano-8-methyl-4-phenyl-quinoline-3-carboxylic acid methyl ester and piperidine. Yellow solid. MS (ESI): 372.2 (M+H)+.

Example 61

6-Chloro-4-(2-chloro-benzyl)-2-dimethylamino-8-fluoro-quinoline-3-carboxylic acid

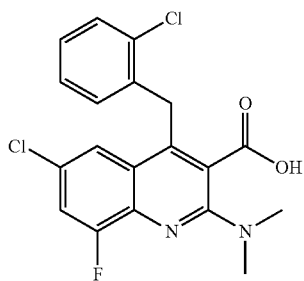

Step A: 4-Chloro-2-(2-chloro-phenylethynyl)-6-fluoro-phenylamine

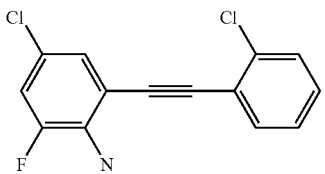 [SMILES: Nc1c(F)cc(Cl)cc1C#Cc1ccccc1Cl]

The title compound was prepared in analogy to example 10 step A from 4-chloro-2-fluoro-6-iodoaniline (500 mg, 1.84 mmol) and 1-chloro-2-ethynyl-benzene (302 mg, 2.21 mmol). Brown solid (1.05 g, 68%). Rf 0.3 (1:9 Ethyl acetate:heptane) as a bright blue spot under UV light.

Step B: N-[4-Chloro-2-(2-chloro-phenylethynyl)-6-fluoro-phenyl]-malonamic acid ethyl ester

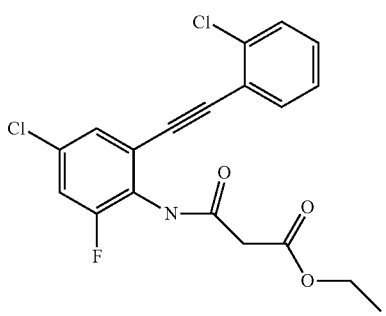 [SMILES: CCOC(=O)CC(=O)Nc1c(F)cc(Cl)cc1C#Cc1ccccc1Cl]

The title compound was prepared in analogy to example 29 step A from 4-chloro-2-(2-chloro-phenylethynyl)-6-fluoro-phenylamine (570 mg, 2.03 mmol) and chlorocarbonyl-acetic acid ethyl ester (460 mg, 3.05 mmol). White solid (440 mg, 55%) MS (ESI): 394 (M+H)+.

Step C: 6-Chloro-4-(2-chloro-benzyl)-8-fluoro-2-oxo-1,2-dihydro-quinoline-3-carboxylic acid ethyl ester

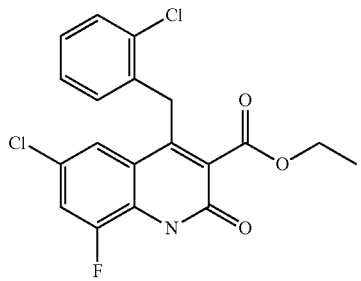 [SMILES: CCOC(=O)c1c(Cc2ccccc2Cl)c2cc(Cl)cc(F)c2[nH]c1=O]

The title compound was prepared in analogy to example 29 step B from N-[4-Chloro-2-(2-chloro-phenylethynyl)-6-fluoro-phenyl]-malonamic acid ethyl ester (217 mg, 0.55 mmol) and NaH (33 mg, 0.83 mmol) in DMSO. Off white solid (120 mg, 55%). MS (ESI): 394 (M+H)+.

Step D: 6-Chloro-4-(2-chloro-benzyl)-2-dimethylamino-8-trifluoromethyl-quinoline-3-carboxylic acid ethyl ester and 6-chloro-4-(2-chloro-benzyl)-2,8-bis-dimethylamino-quinoline-3-carboxylic acid ethyl ester

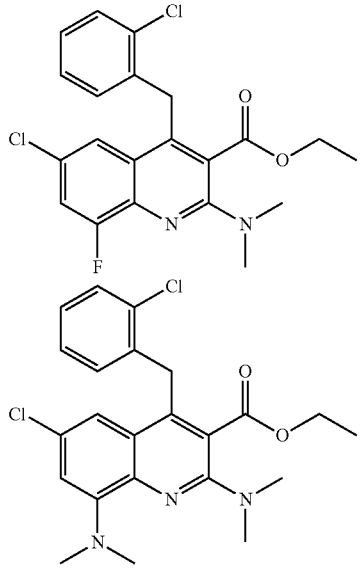

The title compounds were prepared in analogy to example 29 step D from a crude mixture of 6-chloro-4-(2-chloro-benzyl)-8-fluoro-2-trifluoromethanesulfonyloxy-quinoline-3-carboxylic acid ethyl ester (prepared in analogy to example 29 step C from 6-Chloro-4-(2-chloro-benzyl)-8-fluoro-2-oxo-1,2-dihydro-quinoline-3-carboxylic acid ethyl ester and N-phenylbis(trifluoromethanesulfonimide) and dimethylamine to give a mixture of products which were separated by flash column chromatography: 6-chloro-4-(2-chloro-benzyl)-2-dimethylamino-8-trifluoromethyl-quinoline-3-carboxylic acid ethyl ester (off white solid. MS (ESI): 421 (M+H)+) and 6-chloro-4-(2-chloro-benzyl)-2,8-bis-dimethylamino-quinoline-3-carboxylic acid ethyl ester (off white solid. MS (ESI): 446 (M+H)+).

Step E: 6-Chloro-4-(2-chloro-benzyl)-2-dimethyl-amino-8-fluoro-quinoline-3-carboxylic acid

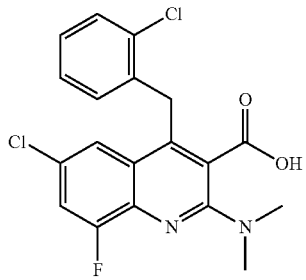 [SMILES: CN(C)c1nc2c(F)cc(Cl)cc2c(Cc2ccccc2Cl)c1C(=O)O]

The title compound was prepared in analogy to example 12 step B from a mixture of 6-chloro-4-(2-chloro-benzyl)-2-dimethylamino-8-trifluoromethyl-quinoline-3-carboxylic acid ethyl ester and 1N NaOH in ethanol. Off white solid. MS (ESI): 393 (M+H)$^+$.

Example 62

6-Chloro-4-(2-chloro-benzyl)-2,8-bis-dimethyl-amino-quinoline-3-carboxylic acid

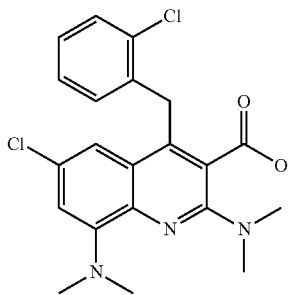 [SMILES: CN(C)c1nc2c(N(C)C)cc(Cl)cc2c(Cc2ccccc2Cl)c1C(=O)O]

The title compound was prepared in analogy to example 12 step B from a mixture of 6-chloro-4-(2-chloro-benzyl)-2,8-bis-dimethylamino-quinoline-3-carboxylic acid ethyl ester (prepared as described in example 61 step D) and 1N NaOH in ethanol. Light yellow solid. MS (ESI): 418 (M+H)$^+$.

Example 63

6-Chloro-4-(2-chloro-benzyl)-8-fluoro-2-methyl-amino-quinoline-3-carboxylic acid

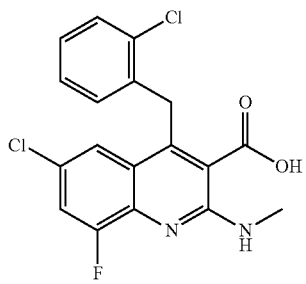 [SMILES: CNc1nc2c(F)cc(Cl)cc2c(Cc2ccccc2Cl)c1C(=O)O]

Step A: 6-Chloro-4-(2-chloro-benzyl)-8-fluoro-2-methylamino-quinoline-3-carboxylic acid ethyl ester

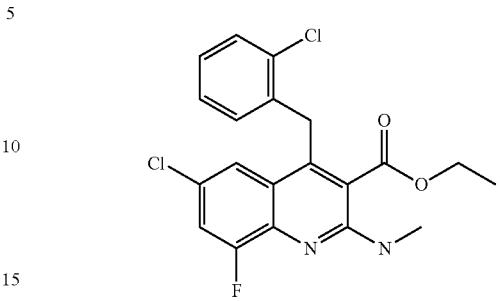

The title compound was prepared in analogy to example 61 step D from a crude mixture of 6-chloro-4-(2-chloro-benzyl)-8-fluoro-2-trifluoromethanesulfonyloxy-quinoline-3-carboxylic acid ethyl ester and N-phenylbis(trifluoromethanesulfonimide) and methylamine. Off white solid. MS (ESI): 407 (M+H)$^+$.

Step B: 6-Chloro-4-(2-chloro-benzyl)-8-fluoro-2-methylamino-quinoline-3-carboxylic acid

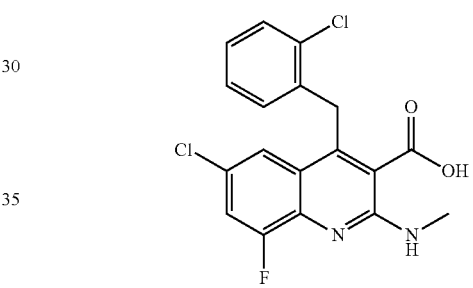

The title compound was prepared in analogy to example 12 step B from a mixture of 6-chloro-4-(2-chloro-benzyl)-8-fluoro-2-methylamino-quinoline-3-carboxylic acid ethyl ester and 1N NaOH in ethanol. Light yellow solid. MS (ESI): 379 (M+H)$^+$.

Example 64

6-Ethyl-8-methyl-2-(2-methyl-pyrrolidin-1-yl)-4-phenyl-quinoline-3-carboxylic acid

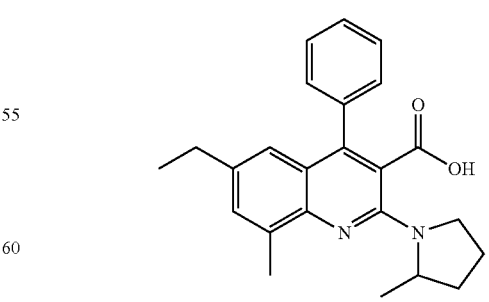

The title compound was prepared in analogy to example 54 step F from 2-chloro-6-ethyl-8-methyl-4-phenyl-quinoline-3-carboxylic acid methyl ester (prepared as described in example 54 step E) and 2-methylpyrrolidine. Light brown solid. MS (ESI): 375.3 (M+H)$^+$.

Example 65

6-Ethyl-2-(ethyl-methyl-amino)-8-methyl-4-phenyl-quinoline-3-carboxylic acid

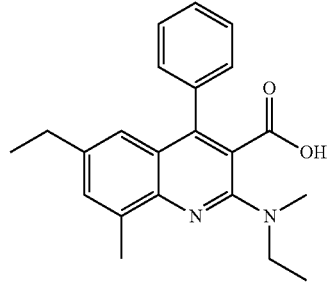 [SMILES: CCc1cc(C)c2nc(N(C)CC)c(C(=O)O)c(-c3ccccc3)c2c1]

The title compound was prepared in analogy to example 54 step F from 2-chloro-6-ethyl-8-methyl-4-phenyl-quinoline-3-carboxylic acid methyl ester (prepared as described in example 54 step E) and ethyl-methyl-amine. Light brown solid. MS (ESI): 349.3 (M+H)$^+$.

Example 66

6-Cyano-2-(ethyl-methyl-amino)-8-methyl-4-phenyl-quinoline-3-carboxylic acid

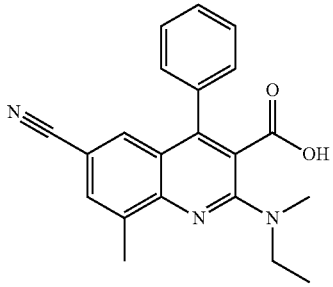 [SMILES: CCN(C)c1nc2c(C)cc(C#N)cc2c(-c2ccccc2)c1C(=O)O]

The title compound was prepared in analogy to example 60 step C from 2-chloro-6-cyano-8-methyl-4-phenyl-quinoline-3-carboxylic acid methyl ester (prepared as described in example 60 step B) and ethyl-methyl-amine. Off-white solid. MS (ESI): 346.2 (M+H)$^+$.

Example 67

[6-Chloro-4-phenyl-3-(1H-tetrazol-5-yl)-quinolin-2-yl]-ethyl-methyl-amine

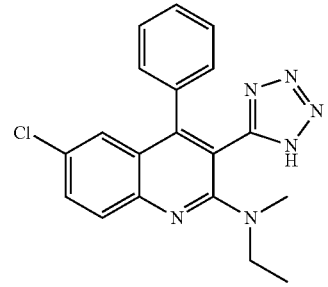 [SMILES: CCN(C)c1nc2ccc(Cl)cc2c(-c2ccccc2)c1-c1nnn[nH]1]

Step A: 6-Chloro-2-(ethyl-methyl-amino)-4-phenyl-quinoline-3-carbonitrile

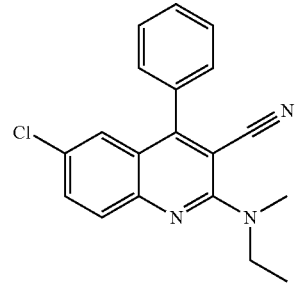 [SMILES: CCN(C)c1nc2ccc(Cl)cc2c(-c2ccccc2)c1C#N]

The title compound was prepared in analogy to example 27 step C from 2,6-dichloro-4-phenyl-quinoline-3-carbonitrile (prepared as described in example 27 step B) and ethyl-methyl-amine. Yellow solid. MS (ESI): 322.2 (M+H)$^+$.

Step B: [6-Chloro-4-phenyl-3-(1H-tetrazol-5-yl)-quinolin-2-yl]-ethyl-methyl-amine

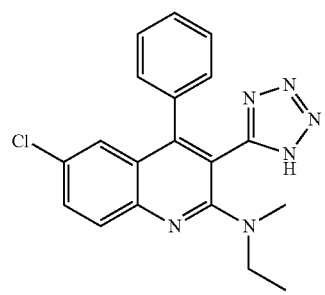 [SMILES: CCN(C)c1nc2ccc(Cl)cc2c(-c2ccccc2)c1-c1nnn[nH]1]

The title compound was prepared in analogy to example 27 step D from 6-chloro-2-(ethyl-methyl-amino)-4-phenyl-quinoline-3-carbonitrile. Yellow solid. MS (ESI): 365.1 (M+H)$^+$.

Example 68

[6-Chloro-4-phenyl-3-(1H-tetrazol-5-yl)-quinolin-2-yl]-isopropyl-methyl-amine

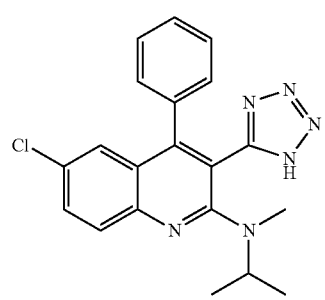 [SMILES: CC(C)N(C)c1nc2ccc(Cl)cc2c(-c2ccccc2)c1-c1nnn[nH]1]

Step A: 6-Chloro-2-(isopropyl-methyl-amino)-4-phenyl-quinoline-3-carbonitrile

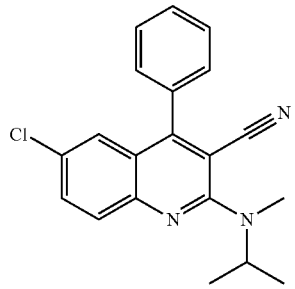 [SMILES: CC(C)N(C)c1nc2ccc(Cl)cc2c(-c2ccccc2)c1C#N]

The title compound was prepared in analogy to example 27 step C from 2,6-dichloro-4-phenyl-quinoline-3-carbonitrile (prepared as described in example 27 step B) and isopropyl-methyl-amine. Yellow solid. MS (ESI): 336.2 (M+H)$^+$.

Step B: [6-Chloro-4-phenyl-3-(1H-tetrazol-5-yl)-quinolin-2-yl]-isopropyl-methyl-amine

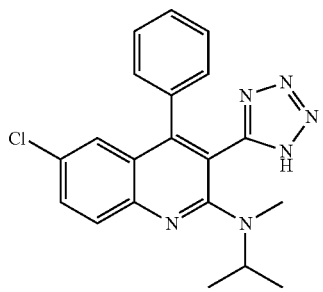 [SMILES: CC(C)N(C)c1nc2ccc(Cl)cc2c(-c2ccccc2)c1-c1nnn[nH]1]

The title compound was prepared in analogy to example 27 step D from 6-chloro-2-(isopropyl-methyl-amino)-4-phenyl-quinoline-3-carbonitrile. Yellow solid. MS (ESI): 379.2 (M+H)$^+$.

Example 69

6-Chloro-4-(2-chloro-benzyl)-2-(2,2,2-trifluoro-ethyl)-quinoline-3-carboxylic acid

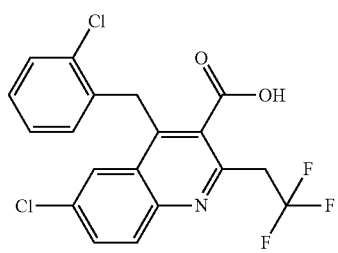 [SMILES: O=C(O)c1c(CC(F)(F)F)nc2ccc(Cl)cc2c1Cc1ccccc1Cl]

Step A: 6-Chloro-4-(2-chloro-benzyl)-2-(2,2,2-trifluoro-ethyl)-quinoline-3-carboxylic acid ethyl ester

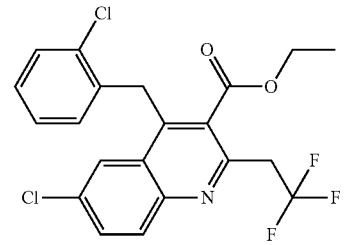 [SMILES: CCOC(=O)c1c(CC(F)(F)F)nc2ccc(Cl)cc2c1Cc1ccccc1Cl]

The title compound was prepared in analogy to example 10 step B from 4-chloro-2-(2-chloro-phenylethynyl)-phenylamine (prepared as described in example 10 step A, 300 mg, 1.14 mmol), 5,5,5-trifluoro-3-oxo-pentanoic acid methyl ester (prepared as described in example 34 step A, 421.4 mg, 2.29 mmol) and p-TsOH.H$_2$O (326.54 mg, 1.72 mmol). Yellow solid (90 mg, 18% yield). LC-MS: 442 (M+H)$^+$.

Step B: 6-Chloro-4-(2-chloro-benzyl)-2-(2,2,2-trifluoro-ethyl)-quinoline-3-carboxylic acid

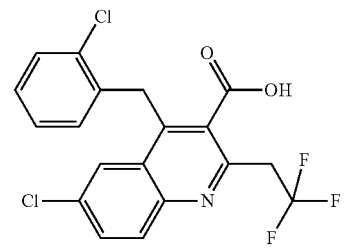 [SMILES: O=C(O)c1c(CC(F)(F)F)nc2ccc(Cl)cc2c1Cc1ccccc1Cl]

The title compound was prepared in analogy to example 20 step D from 6-chloro-4-(2-chloro-benzyl)-2-(2,2,2-trifluoro-ethyl)-quinoline-3-carboxylic acid ethyl ester (70 mg, 0.16 mmol) and LiI (212 mg, 1.58 mmol) in pyridine. Off white solid (15 mg, 23%). LC-MS: 412 (M−H)$^−$.

Example 70

6-Chloro-2-(2-methyl-pyrrolidin-1-yl)-4-phenyl-3-(1H-tetrazol-5-yl)-quinoline

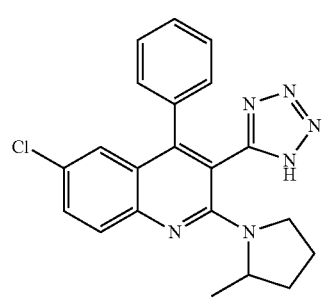 [SMILES: CC1CCCN1c1nc2ccc(Cl)cc2c(-c2ccccc2)c1-c1nnn[nH]1]

Step A: 6-Chloro-2-(2-methyl-pyrrolidin-1-yl)-4-phenyl-quinoline-3-carbonitrile

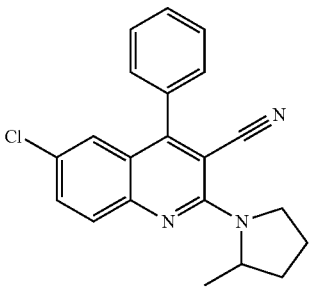 [SMILES: CC1CCCN1c1nc2ccc(Cl)cc2c(-c2ccccc2)c1C#N]

The title compound was prepared in analogy to example 27 step C from 2,6-dichloro-4-phenyl-quinoline-3-carbonitrile (prepared as described in example 27 step B) and 2-methylpyrrolidine. Yellow solid. MS (ESI): 348.2 (M+H)⁺.

Step B: 6-Chloro-2-(2-methyl-pyrrolidin-1-yl)-4-phenyl-3-(1H-tetrazol-5-yl)-quinoline

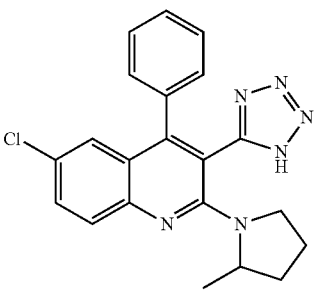 [SMILES: CC1CCCN1c1nc2ccc(Cl)cc2c(-c2ccccc2)c1-c1nnn[nH]1]

The title compound was prepared in analogy to example 27 step D from 6-chloro-2-(2-methyl-pyrrolidin-1-yl)-4-phenyl-quinoline-3-carbonitrile. Yellow solid. MS (ESI): 391.2 (M+H)⁺.

Example 71

6-Chloro-2-isopropyl-4-(2-trifluoromethoxy-benzyl)-quinoline-3-carboxylic acid

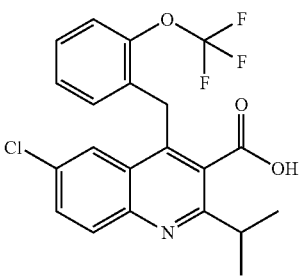 [SMILES: CC(C)c1nc2ccc(Cl)cc2c(Cc2ccccc2OC(F)(F)F)c1C(=O)O]

Step A: 4-Chloro-2-trimethylsilanylethynyl-phenylamine

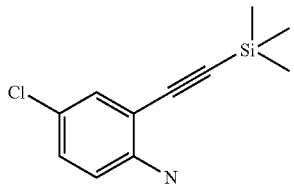

To a stirred solution of 4-chloro-2-iodo-phenylamine (5 g, 19.73 mmol) in THF (40 ml) was added triethyl amine (6.836 ml, 49.32 mmol), and ethynyl-trimethyl-silane (5.576 ml, 39.45 mmol) at 25° C. The mixture was purged with argon for 10 min, followed by the addition of PdCl₂(PPh₃)₂ (0.692 g, 0.99 mmol) and CuI (113 mg, 0.59 mmol) at 25° C. The reaction mixture was stirred at room temperature for 2 h and was subsequently diluted with water and extracted with ethyl acetate. The combined organic layers were washed with brine, dried over anhydrous sodium sulfate and concentrated in vacuo to afford a crude residue which was purified by flash column chromatography (2-5% ethyl acetate in hexane) to afford 4-chloro-2-trimethylsilanylethynyl-phenylamine (3.6 g, 82%) as a brown solid. GC-MS: 223 (M).

Step B: 4-Chloro-2-(2-trifluoromethoxy-phenylethynyl)-phenylamine

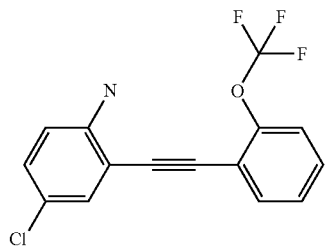 [SMILES: Nc1ccc(Cl)cc1C#Cc1ccccc1OC(F)(F)F]

To a solution of 4-chloro-2-trimethylsilanylethynyl-phenylamine (300 mg, 1.34 mmol) in THF (10 ml) was added triethylamine (0.6 ml, 4.02 mmol), and 1-bromo-2-trifluoromethoxy-benzene (0.3 ml, 2.01 mmol). The mixture was purged with argon for 10 min and then PdCl₂ (PPh₃)₂ (47 mg, 0.07 mmol) was added followed by CuI (7.7 mg, 0.04 mmol). The reaction mixture was then heated to 70° C. TBAF (1M solution in THF) (1.54 ml, 1.54 mmol) was added and the reaction mixture was stirred for 1 h at 70° C. After cooling, the mixture was filtered through celite bed, washed with ethyl acetate. The filtrate was concentrated in vacuo and the residue was purified by flash column chromatography (2-3% ethyl acetate in hexane) to obtain 4-chloro-2-(2-trifluoromethoxy-phenylethynyl)-phenylamine (210 mg, 50% yield) as a brown solid. GC-MS: 311 (M).

Step C: 6-Chloro-2-isopropyl-4-(2-trifluoromethoxy-benzyl)-quinoline-3-carboxylic acid ethyl ester

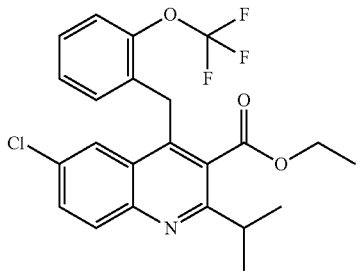 [SMILES: CCOC(=O)c1c(C(C)C)nc2ccc(Cl)cc2c1Cc1ccccc1OC(F)(F)F]

The title compound was prepared in analogy to example 10 step B from 4-chloro-2-(2-trifluoromethoxy-phenylethynyl)-phenylamine (240 mg, 0.77 mmol) and methyl-3-oxopentanoic acid ethyl ester (0.186 ml, 1.15 mmol). Off white solid (80 mg, 23% yield). LC-MS (ESI): 452 (M+H)$^+$.

Step D: 6-Chloro-2-isopropyl-4-(2-trifluoromethoxy-benzyl)-quinoline-3-carboxylic acid

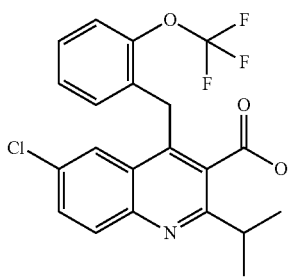 [SMILES: CC(C)c1nc2ccc(Cl)cc2c(Cc2ccccc2OC(F)(F)F)c1C(=O)O]

The title compound was prepared in analogy to example 20 step D from 6-chloro-2-isopropyl-4-(2-trifluoromethoxy-benzyl)-quinoline-3-carboxylic acid ethyl ester (70 mg, 0.16 mmol) and lithium iodide. Off white solid (18 mg, 27%). LC-MS (ESI): 422 (M−H)$^-$.

Example 72

6,8-Dichloro-4-(3-chloro-4-fluoro-phenyl)-2-isopropyl-quinoline-3-carboxylic acid

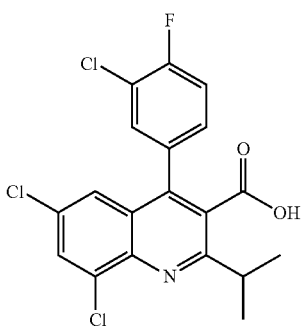 [SMILES: CC(C)c1nc2c(Cl)cc(Cl)cc2c(-c2ccc(F)c(Cl)c2)c1C(=O)O]

Step A: 6,8-Dichloro-4-hydroxy-2-isopropyl-quinoline-3-carboxylic acid methyl ester

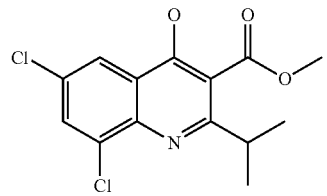 [SMILES: COC(=O)c1c(C(C)C)nc2c(Cl)cc(Cl)cc2c1O]

To the stirred solution of methyl 4-methyl-3-oxopentanoate (6.21 g, 6.13 ml, 40.9 mmol, Eq: 10) in DMA (6 ml) was added sodium hydride (55% in mineral oil, 223 mg, 5.12 mmol, Eq: 1.25) in two portions at 0° C. After 30 min at RT a solution of 6,8-dichloro-1H-benzo[d][1,3]oxazine-2,4-dione (1 g, 4.09 mmol, Eq: 1.00) in DMA (6 ml) was added. The resulting mixture was stirred at 120° C. for 1 h. The solution was cooled to RT, diluted with water and extracted with ethyl acetate (3×). The combined organic layers were washed with water and brine, dried with Na$_2$SO$_4$ and evaporated. The remaining residue was purified by column chromatography (silica gel, heptane/EtOAc 90:10-80:20) to afford the title compound as off-white gum (686 mg). MS (ESI): 313.9 (M+H)$^+$.

Step B: 6,8-Dichloro-2-isopropyl-4-trifluoromethanesulfonyloxy-quinoline-3-carboxylic acid methyl ester

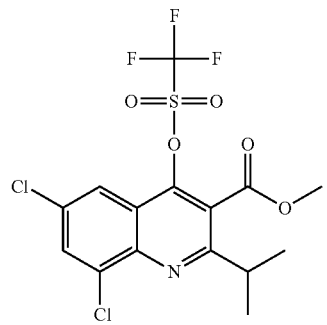 [SMILES: COC(=O)c1c(C(C)C)nc2c(Cl)cc(Cl)cc2c1OS(=O)(=O)C(F)(F)F]

Sodium hydride (55% in mineral oil, 130 mg, 2.98 mmol, Eq: 1.3) was added to a solution of 6,8-dichloro-4-hydroxy-2-isopropyl-quinoline-3-carboxylic acid methyl ester (720 mg, 2.29 mmol, Eq: 1.00) in DMF (7 ml) at RT. The mixture was stirred for 30 min, then a solution of 1,1,1-trifluoro-N-phenyl-N-(trifluoromethylsulfonyl)methanesulfonamide (1.06 g, 2.98 mmol, Eq: 1.3) in DMF (4 ml) was added. After 4 h the reaction mixture was diluted with water and extracted with ethyl acetate (3×). The combined organic layers were washed with water (3×) and brine, dried with Na$_2$SO$_4$ and evaporated. The remaining residue was purified by column chromatography (silica gel, heptane/EtOAc 98:2) to afford the title compound as colorless oil (1019 mg). MS (ESI): 446.0 (M+H)$^+$.

Step C: 6,8-Dichloro-4-(3-chloro-4-fluoro-phenyl)-2-isopropyl-quinoline-3-carboxylic acid methyl ester

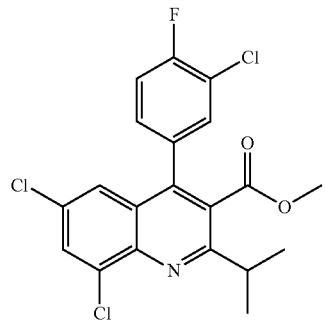 [SMILES: COC(=O)c1c(C(C)C)nc2c(Cl)cc(Cl)cc2c1-c1ccc(F)c(Cl)c1]

A suspension of 6,8-dichloro-2-isopropyl-4-trifluoromethanesulfonyloxy-quinoline-3-carboxylic acid methyl ester (85.0 mg, 0.181 mmol, Eq: 1.00), 3-chloro-4-fluorophenylboronic acid (34.7 mg, 0.199 mmol, Eq: 1.1), potassium phosphate tribasic (57.7 mg, 0.272 mmol, Eq: 1.5) and tetrakis(triphenylphosphine)palladium (0) (6.27 mg, 0.00543 mmol, Eq: 0.0300) in dioxane (2.5 ml) was heated to 100° C. for 4 h. The suspension was cooled to RT overnight, then diluted with sat. NH$_4$Cl solution and extracted with ethyl acetate (3×). The combined organic layers were washed with sat. NH$_4$Cl solution and brine, dried with Na$_2$SO$_4$ and evaporated. The remaining residue was purified by column chromatography (silica gel, heptane/EtOAc 99:1) to afford the title compound as white solid (46 mg). MS (ESI): 426.0 (M+H)$^+$.

Step D: 6,8-Dichloro-4-(3-chloro-4-fluoro-phenyl)-2-isopropyl-quinoline-3-carboxylic acid

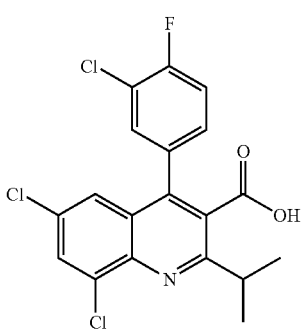 [SMILES: CC(C)c1nc2c(Cl)cc(Cl)cc2c(-c2ccc(F)c(Cl)c2)c1C(=O)O]

A solution of 6,8-dichloro-4-(3-chloro-4-fluoro-phenyl)-2-isopropyl-quinoline-3-carboxylic acid methyl ester (42.0 mg, 0.0984 mmol, Eq: 1.00) and lithium iodide (132 mg, 0.984 mmol, Eq: 10.0) in pyridine (1.5 ml) was heated to 135° C. overnight. The pyridine was then removed in vacuo and the remaining residue was diluted with water. The pH was adjusted to 12 by addition of 0.1N NaOH and the mixture was extracted with diethylether/heptane (60:40) (3×). The aqueous layer was acidified with 0.1N HCl to pH 3 and extracted with CHCl$_3$ (3×). The combined CHCl$_3$ layers were dried with Na$_2$SO$_4$ and evaporated to yield the title compound as white foam (35 mg). MS (ESI): 412.1 (M+H)$^+$.

Example 73

6,8-Dichloro-4-(3-ethoxy-phenyl)-2-isopropyl-quinoline-3-carboxylic acid

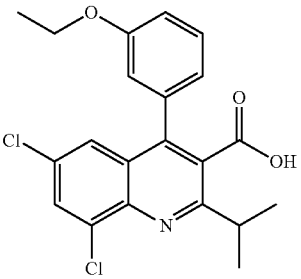 [SMILES: CCOc1cccc(-c2c(C(=O)O)c(C(C)C)nc3c(Cl)cc(Cl)cc23)c1]

Step A: 6,8-Dichloro-4-(3-ethoxy-phenyl)-2-isopropyl-quinoline-3-carboxylic acid methyl ester

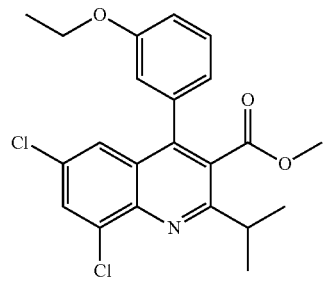 [SMILES: CCOc1cccc(-c2c(C(=O)OC)c(C(C)C)nc3c(Cl)cc(Cl)cc23)c1]

The title compound was prepared in analogy to example 72 step C from 6,8-dichloro-2-isopropyl-4-trifluoromethanesulfonyloxy-quinoline-3-carboxylic acid methyl ester (prepared as described in example 72 step B) and 3-ethoxyphenylboronic acid. White solid. MS (ESI): 418.2 (M+H)$^+$.

Step B: 6,8-Dichloro-4-(3-ethoxy-phenyl)-2-isopropyl-quinoline-3-carboxylic acid

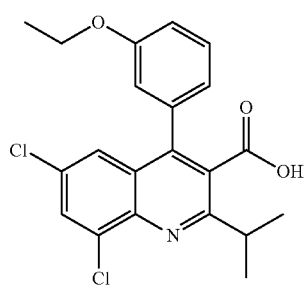 [SMILES: CCOc1cccc(-c2c(C(=O)O)c(C(C)C)nc3c(Cl)cc(Cl)cc23)c1]

The title compound was prepared in analogy to example 72 step D from 6,8-dichloro-4-(3-ethoxy-phenyl)-2-isopropyl-quinoline-3-carboxylic acid methyl ester. Light yellow foam. MS (ESI): 404.1 (M+H)$^+$.

Example 74

6,8-Dichloro-2-isopropyl-4-(3-isopropyl-phenyl)-quinoline-3-carboxylic acid

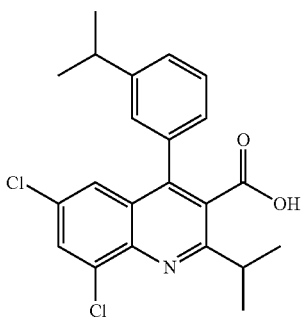 [SMILES: CC(C)c1cccc(-c2c(C(=O)O)c(C(C)C)nc3c(Cl)cc(Cl)cc23)c1]

Step A: 6,8-Dichloro-2-isopropyl-4-(3-isopropyl-phenyl)-quinoline-3-carboxylic acid methyl ester

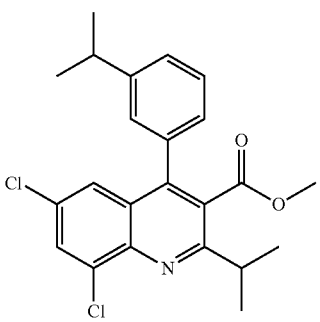 [SMILES: COC(=O)c1c(C(C)C)nc2c(Cl)cc(Cl)cc2c1-c1cccc(C(C)C)c1]

The title compound was prepared in analogy to example 72 step C from 6,8-dichloro-2-isopropyl-4-trifluoromethanesulfonyloxy-quinoline-3-carboxylic acid methyl ester (prepared as described in example 72 step B) and 3-isopropylphenylboronic acid. Colorless semisolid. MS (ESI): 416.1 (M+H)$^+$.

Step B: 6,8-Dichloro-2-isopropyl-4-(3-isopropyl-phenyl)-quinoline-3-carboxylic acid

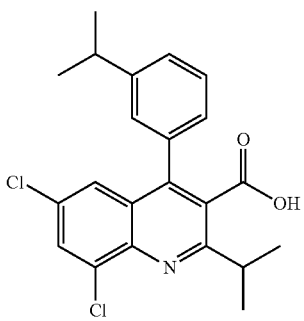 [SMILES: CC(C)c1cccc(-c2c(C(=O)O)c(C(C)C)nc3c(Cl)cc(Cl)cc23)c1]

The title compound was prepared in analogy to example 72 step D from 6,8-dichloro-2-isopropyl-4-(3-isopropyl-phenyl)-quinoline-3-carboxylic acid methyl ester. White foam. MS (ESI): 402.1 (M+H)$^+$.

Example 75

6-Chloro-4-(2-chloro-benzyl)-2-(ethyl-methyl-amino)-8-fluoro-quinoline-3-carboxylic acid

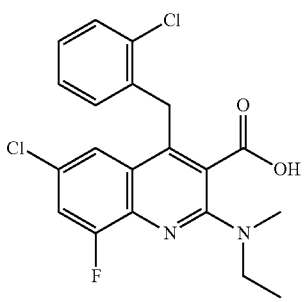 [SMILES: CCN(C)c1nc2c(F)cc(Cl)cc2c(Cc2ccccc2Cl)c1C(=O)O]

Step A: 6-Chloro-4-(2-chloro-benzyl)-8-fluoro-2-trifluoromethanesulfonyloxy-quinoline-3-carboxylic acid ethyl ester

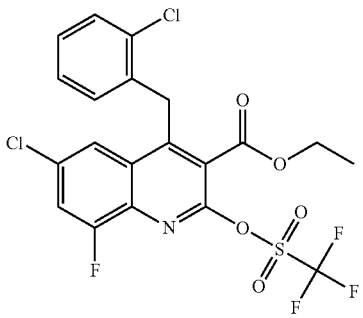 [SMILES: CCOC(=O)c1c(OS(=O)(=O)C(F)(F)F)nc2c(F)cc(Cl)cc2c1Cc1ccccc1Cl]

Sodium hydride (55% in mineral oil, 21.6 mg, 0.496 mmol, Eq: 1.2) was added to a solution of 6-chloro-4-(2-chloro-benzyl)-8-fluoro-2-oxo-1,2-dihydro-quinoline-3-carboxylic acid ethyl ester (prepared as described in example 61 step C) (163 mg, 0.413 mmol, Eq: 1.00) in DMF (2 ml) at RT. The mixture was stirred for 20 min, then a solution of 1,1,1-trifluoro-N-phenyl-N-(trifluoromethylsulfonyl)methanesulfonamide (177 mg, 0.496 mmol, Eq: 1.2) in DMF (2 ml) was added and the mixture was stirred for 1.5 h. Then water was added and the mixture was extracted with ethyl acetate (3×). The combined organic layers were washed with water (3×) and brine, dried with Na$_2$SO$_4$ and evaporated. The crude title compound was used in the next reaction step without further purification (248 mg, yellow gum). MS (ESI): 526.0 (M+H)$^+$.

Step B: 6-Chloro-4-(2-chloro-benzyl)-2-(ethyl-methyl-amino)-8-fluoro-quinoline-3-carboxylic acid ethyl ester

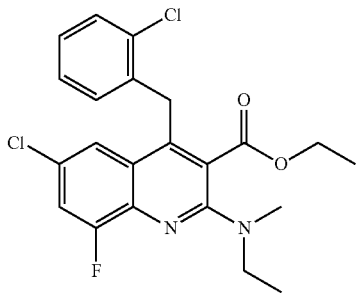 [SMILES: CCOC(=O)c1c(N(C)CC)nc2c(F)cc(Cl)cc2c1Cc1ccccc1Cl]

A solution of 6-chloro-4-(2-chloro-benzyl)-8-fluoro-2-trifluoromethanesulfonyloxy-quinoline-3-carboxylic acid ethyl ester (108 mg, 0.205 mmol, Eq: 1.00) and ethyl-methyl-amine (12.7 mg, 18.5 µl, 0.215 mmol, Eq: 1.05) in DMSO (1.5 ml) was heated to 40° C. for 65 h. Additional ethyl-methyl-amine (60.6 mg, 88.1 µl, 1.02 mmol, Eq: 5) was added and the solution was heated to 80° C. for 1.5 h. The solution was cooled to RT, diluted with water and extracted with ethyl acetate (3×). The combined organic layers were washed with water (3×) and brine, dried with Na$_2$SO$_4$ and evaporated. The remaining residue was purified by column chromatography (silica gel, heptane/EtOAc 96.5:3.5) to afford the title compound as yellow solid (48 mg). MS (ESI): 435.2 (M+H)$^+$.

Step C: 6-Chloro-4-(2-chloro-benzyl)-2-(ethyl-methyl-amino)-8-fluoro-quinoline-3-carboxylic acid

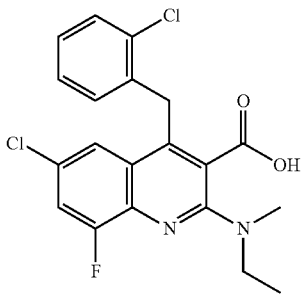 [SMILES: CCN(C)c1nc2c(F)cc(Cl)cc2c(Cc2ccccc2Cl)c1C(=O)O]

The title compound was prepared in analogy to example 72 step D from 6-chloro-4-(2-chloro-benzyl)-2-(ethyl-methyl-amino)-8-fluoro-quinoline-3-carboxylic acid ethyl ester. Yellow foam. MS (ESI): 407.2 (M+H)$^+$.

Example 76

6-Chloro-4-(2-chloro-benzyl)-2-isopropyl-8-methyl-quinoline-3-carboxylic acid

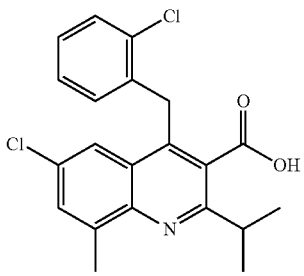 [SMILES: Cc1cc(Cl)cc2c(Cc3ccccc3Cl)c(C(=O)O)c(C(C)C)nc12]

Step A: 4-Chloro-2-iodo-6-methyl-phenylamine

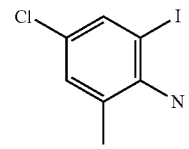

To a solution of 4-chloro-2-methyl-phenylamine (1 g, 7.06 mmol) in acetic acid (20 ml) was added N-iodo succinimide (2.38 g, 10.59 mmol) portion wise at 25° C. under nitrogen. The reaction mixture was stirred at 25° C. for 16 h. The volatiles were removed in vacuo and the resultant crude residue was diluted with EtOAc (40 ml). The organic layer was washed with aqueous 1N NaOH solution (2×15 ml), followed by aqueous Na$_2$S$_2$O$_3$ solution (2×15 ml), and brine (20 ml). The organic layer was dried over anhydrous Na$_2$SO$_4$, filtered, and concentrated in vacuo to give a crude residue which was purified by flash column chromatography (5-10% EtOAc in hexane) to yield 4-chloro-2-iodo-6-methyl-phenylamine (1.5 g, 79%) as brown solid. GC-MS: 267 (M).

Step B: 4-Chloro-2-(2-chloro-phenylethynyl)-6-methyl-phenylamine

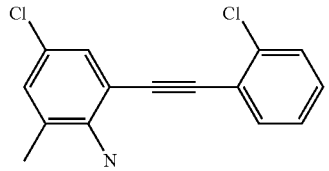 [SMILES: Cc1cc(Cl)cc(C#Cc2ccccc2Cl)c1N]

The title compound was prepared in analogy to example 10 step A from 4-chloro-2-iodo-6-methyl-phenylamine (1.5 g, 5.61 mmol) and 1-chloro-2-ethynyl-benzene (920 mg, 6.73 mmol) to afford 4-chloro-2-(2-chloro-phenylethynyl)-6-methyl-phenylamine (1.06 g, 68%) as an off white solid. LC-MS (ESI): 276 (M+H)$^+$.

Step C: 6-Chloro-4-(2-chloro-benzyl)-2-isopropyl-8-methyl-quinoline-3-carboxylic acid ethyl ester

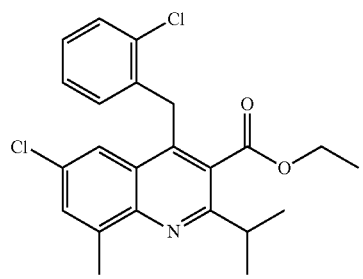 [SMILES: CCOC(=O)c1c(C(C)C)nc2c(C)cc(Cl)cc2c1Cc1ccccc1Cl]

The title compound was prepared in analogy to example 10 step B from 4-chloro-2-(2-chloro-phenylethynyl)-6-methyl-phenylamine (400 mg, 1.45 mmol) and 4-methyl-3-oxo-pentanoic acid ethyl ester (0.351 ml, 2.17 mmol). Brown solid. LC-MS (ESI): 416 (M+H)$^+$.

Step D: 6-Chloro-4-(2-chloro-benzyl)-2-isopropyl-8-methyl-quinoline-3-carboxylic acid

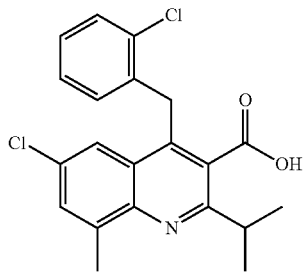 [SMILES: Cc1cc(Cl)cc2c(Cc3ccccc3Cl)c(C(=O)O)c(C(C)C)nc12]

The title compound was prepared in analogy to example 6 step B from a mixture of 6-chloro-4-(2-chloro-benzyl)-2-isopropyl-8-methyl-quinoline-3-carboxylic acid ethyl ester (50 mg, 0.12 mmol) and 1N NaOH in ethanol. Off white solid (18 mg, 39%). LC-MS (ESI): 388 (M+H)+.

Example 77

5-(6-Chloro-4-phenyl-2-piperidin-1-yl-quinolin-3-yl)-3H-[1,3,4]oxadiazol-2-one

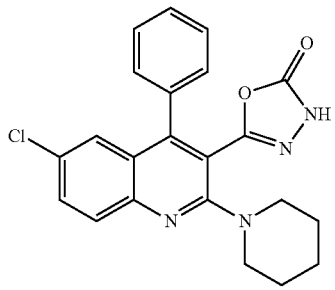 [SMILES: O=c1[nH]nc(-c2c(N3CCCCC3)nc3ccc(Cl)cc3c2-c2ccccc2)o1]

Step A: N-(2-Benzoyl-4-chloro-phenyl)-malonamic acid methyl ester

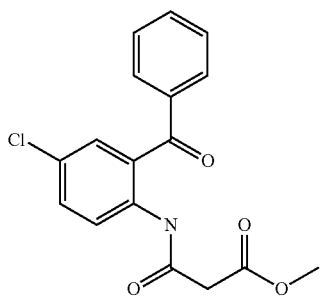 [SMILES: COC(=O)CC(=O)Nc1ccc(Cl)cc1C(=O)c1ccccc1]

The title compound was prepared in analogy to example 21 step A from (2-amino-5-chloro-phenyl)-phenyl-methanone and methyl 3-chloro-3-oxopropanoate. Off-white solid. MS (ESI): 330.1 (M–H)−.

Step B: 6-Chloro-2-oxo-4-phenyl-1,2-dihydro-quinoline-3-carboxylic acid methyl ester

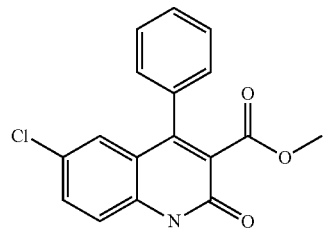 [SMILES: COC(=O)c1c(-c2ccccc2)c2cc(Cl)ccc2[nH]c1=O]

The title compound was prepared in analogy to example 21 step B from N-(2-benzoyl-4-chloro-phenyl)-malonamic acid methyl ester. Off-white solid. MS (ESI): 312.2 (M–H)−.

Step C: 6-Chloro-2-oxo-4-phenyl-1,2-dihydro-quinoline-3-carboxylic acid

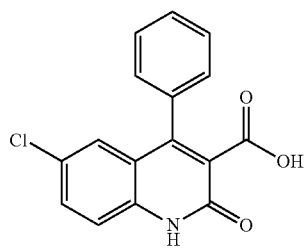 [SMILES: O=C(O)c1c(-c2ccccc2)c2cc(Cl)ccc2[nH]c1=O]

A mixture of 6-chloro-2-oxo-4-phenyl-1,2-dihydro-quinoline-3-carboxylic acid methyl ester (380 mg, 1.21 mmol, Eq: 1.00) and lithium hydroxide (3.8 ml, 3.8 mmol, Eq: 3.14) in ethanol (7.6 ml) was heated to 50° C. for 72 h in a sealed tube. Then water was added and the mixture was extracted with diethylether (3×). The pH of the aqueous layer was then adjusted to 1 by addition of 1N HCl and the mixture was extracted with ethyl acetate (3×). The combined ethyl acetate extracts were washed with brine, dried with Na2SO4 and evaporated to yield the title compound (378 mg) as off-white solid. MS (ESI): 300.0 (M+H)+.

Step D: N'-(2,6-Dichloro-4-phenyl-quinoline-3-carbonyl)-hydrazinecarboxylic acid 9H-fluoren-9-ylmethyl ester

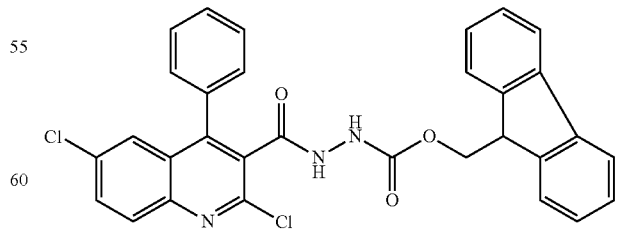

A mixture of 6-chloro-2-oxo-4-phenyl-1,2-dihydro-quinoline-3-carboxylic acid (100 mg, 334 µmol, Eq: 1.00) and phosphorus oxychloride (3.29 g, 2 ml, 21.5 mmol, Eq: 64.3) was heated to 120° C. for 3 h. The reaction mixture was evaporated to dryness and the remaining residue was co-evaporated with toluene (2×). The residue was dissolved in DCM (1 ml) and 9-fluorenylmethyl carbazate (127 mg, 500 μmol, Eq: 1.5) was added. The reaction mixture was stirred at RT for 4 h. Then water was added and the mixture was extracted with ethyl acetate (3×). The combined extracts were washed with water and brine, dried with Na₂SO₄ and evaporated. The remaining residue was purified by column chromatography (silica gel, DCM/EtOAc 9:1) to afford the title compound as off-white solid (102 mg). MS (ESI): 554.1 (M+H)⁺.

Step E: 6-Chloro-4-phenyl-2-piperidin-1-yl-quinoline-3-carboxylic acid hydrazide

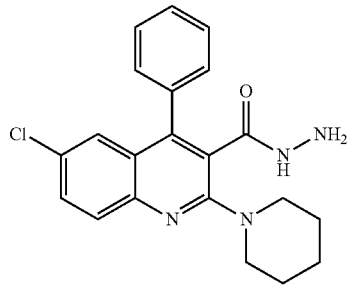 [SMILES: NNC(=O)c1c(N2CCCCC2)nc2ccc(Cl)cc2c1-c1ccccc1]

A mixture of N'-(2,6-dichloro-4-phenyl-quinoline-3-carbonyl)-hydrazinecarboxylic acid 9H-fluoren-9-ylmethyl ester (130 mg, 211 μmol, Eq: 1.00), piperidine (180 mg, 209 μl, 2.11 mmol, Eq: 10) and triethylamine (64.1 mg, 88.2 μl, 633 μmol, Eq: 3) in DMF (2 ml) was heated to 120° C. for 20 min in a microwave. Water was added and the mixture was extracted with ethyl acetate (3×). The combined extracts were washed with water and brine, dried with Na₂SO₄ and evaporated. The remaining residue was purified by column chromatography (silica gel, DCM/EtOAc 9:1-4:1) to afford the title compound as light yellow solid (31 mg). MS (ESI): 381.2 (M+H)⁺.

Step F: 5-(6-Chloro-4-phenyl-2-piperidin-1-yl-quinolin-3-yl)-3H-[1,3,4]oxadiazol-2-one

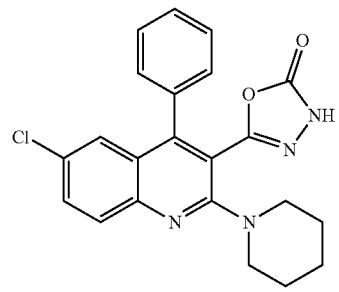 [SMILES: O=c1[nH]nc(-c2c(N3CCCCC3)nc3ccc(Cl)cc3c2-c2ccccc2)o1]

6-Chloro-4-phenyl-2-piperidin-1-yl-quinoline-3-carboxylic acid hydrazide (30 mg, 70.9 μmol, Eq: 1.00) and N,N'-carbonyldiimidazole (13.8 mg, 85.1 μmol, Eq: 1.2) were dissolved in THF (1 ml). Then triethylamine (10.0 mg, 13.8 μL, 99.2 μmol, Eq: 1.4) was added and the reaction mixture was stirred for 2 h at RT. Water was added and the mixture was extracted with ethyl acetate (3×). The combined extracts were washed with water and brine, dried with Na₂SO₄ and evaporated. The remaining residue was purified by column chromatography (silica gel, DCM/EtOAc 97:3) to afford the title compound as yellow solid (25 mg). MS (ESI): 407.2 (M+H)⁺.

Example 78

6-Chloro-2-diethylamino-4-(3-isopropyl-phenyl)-quinoline-3-carboxylic acid

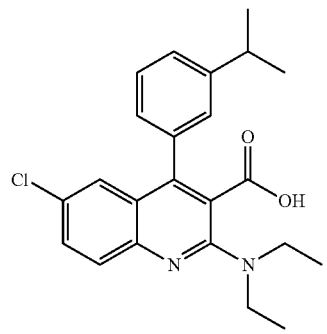 [SMILES: CCN(CC)c1nc2ccc(Cl)cc2c(-c2cccc(C(C)C)c2)c1C(=O)O]

Step A: (2-Amino-5-chloro-phenyl)-(3-isopropyl-phenyl)-methanone

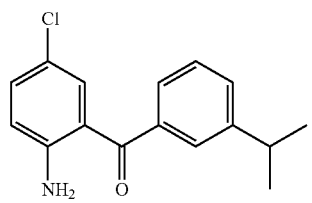 [SMILES: CC(C)c1cccc(C(=O)c2cc(Cl)ccc2N)c1]

To a solution of 2-amino-5-chloro-benzonitrile (1 g, 6.55 mmol) in diethyl ether (20 ml) was added 3-isopropyl phenyl magnesium bromide (prepared freshly as a 1M solution in diethyl ether; 20 ml, 19.66 mmol) drop wise at 0° C., and the resulting reaction mixture was stirred for 1 h under reflux conditions followed by another 16 h at room temperature. The reaction mixture was cooled to 5° C., quenched with water followed by 2N aqueous HCl solution. The reaction mixture was then stirred at 45° C. for an additional 5 h. The reaction mixture was made basic (pH 8-9) with aqueous solution of NaOH, and then extracted with diethyl ether (2×30 ml). The organic phases were combined and washed with brine (25 ml), dried over anhydrous Na₂SO₄, concentrated in vacuo to give a crude residue which was purified by flash column chromatography (5% EtOAc in hexane) to afford (2-amino-5-chloro-phenyl)-(3-isopropyl-phenyl)-methanone (1.1 g, 61%) as a yellow sticky liquid. LC-MS (ESI): 274 (M+H)⁺.

Step B: 6-Chloro-4-(3-isopropyl-phenyl)-2-oxo-1,2-dihydro-quinoline-3-carboxylic acid tert-butyl ester

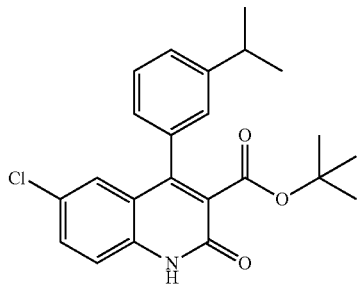 [SMILES: CC(C)c1cccc(-c2c(C(=O)OC(C)(C)C)c(=O)[nH]c3ccc(Cl)cc23)c1]

To a mixture of (2-amino-5-chloro-phenyl)-(3-isopropyl-phenyl)-methanone (1.1 g, 4.02 mmol), and malonic acid di-tert-butyl ester (1.344 ml, 6.03 mmol) was added potassium hydroxide (113 mg, 2.01 mmol) at 25° C., and the resulting reaction mixture was stirred at 110° C. for 16 h. It was cooled to 0° C., and directly purified by column chromatography over silica gel (20-30% EtOAc/hexane) to afford 6-chloro-4-(3-isopropyl-phenyl)-2-oxo-1,2-dihydro-quinoline-3-carboxylic acid tert-butyl ester (700 mg, 44%) as pale yellow solid. LC-MS (ESI): 398 (M+H)$^+$.

Step C: 6-Chloro-4-(3-isopropyl-phenyl)-2-trifluoromethanesulfonyloxy-quinoline-3-carboxylic acid tert-butyl ester

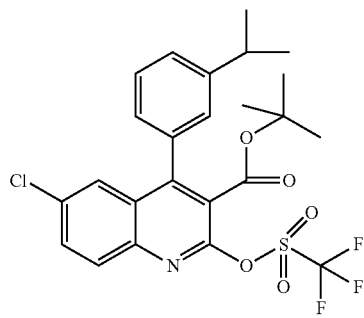 [SMILES: CC(C)c1cccc(-c2c(C(=O)OC(C)(C)C)c(OS(=O)(=O)C(F)(F)F)nc3ccc(Cl)cc23)c1]

To a solution of 6-chloro-4-(3-isopropyl-phenyl)-2-oxo-1,2-dihydro-quinoline-3-carboxylic acid tert-butyl ester (500 mg, 1.26 mmol) in DMF (10 ml) was added sodium hydride (60%, 76 mg, 1.88 mmol) portion wise at 0° C., and the resulting reaction mixture was stirred at 25° C. for 1.5 h. The reaction mixture was cooled to 0° C., and a solution of N-phenylbis(trifluoromethanesulfonimide) (673 mg, 1.88 mmol) in DMF (5 ml) was added drop wise. The reaction mixture was stirred for 3 h at 25° C. and then quenched with saturated aqueous ammonium chloride solution (20 ml), and extracted with EtOAc (2×30 ml). The organic layers were combined and dried over anhydrous Na$_2$SO$_4$, filtered, and concentrated in vacuo to give a crude residue which was purified by flash column chromatography (1-2% EtOAc in hexane) to afford 6-chloro-4-(3-isopropyl-phenyl)-2-trifluoromethanesulfonyloxy-quinoline-3-carboxylic acid tert-butyl ester (420 mg, 63%) as a pale yellow solid. LC-MS (ESI): 530 (M+H)$^+$.

Step D: 6-Chloro-2-diethylamino-4-(3-isopropyl-phenyl)-quinoline-3-carboxylic acid tert-butyl ester

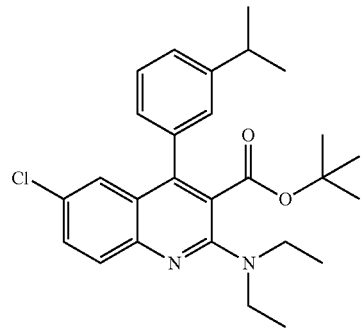 [SMILES: CCN(CC)c1nc2ccc(Cl)cc2c(-c2cccc(C(C)C)c2)c1C(=O)OC(C)(C)C]

To a solution of diethyl amine (0.078 ml, 0.75 mmol) in THF (5 ml) was added 6-chloro-4-(3-isopropyl-phenyl)-2-trifluoromethanesulfonyloxy-quinoline-3-carboxylic acid tert-butyl ester (200 mg, 0.38 mmol) and potassium carbonate (208 mg, 1.51 mmol) at 25° C. The resulting reaction mixture was stirred at 70° C. for 3 h. Volatiles were removed in vacuo and the resulting crude mixture was diluted with water (15 ml), and extracted with EtOAc (2×30 ml). The combined organic layers were dried over anhydrous Na$_2$SO$_4$, filtered, and concentrated in vacuo to give a crude residue which was purified by flash column chromatography (3% EtOAc in hexane) to afford 6-chloro-2-diethylamino-4-(3-isopropyl-phenyl)-quinoline-3-carboxylic acid tert-butyl ester (110 mg, 64%) as a pale yellow solid. LC-MS (ESI): 453 (M+H)$^+$.

Step E: 6-Chloro-2-diethylamino-4-(3-isopropyl-phenyl)-quinoline-3-carboxylic acid

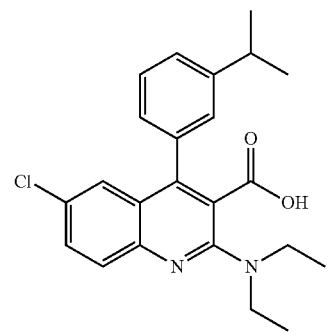 [SMILES: CCN(CC)c1nc2ccc(Cl)cc2c(-c2cccc(C(C)C)c2)c1C(=O)O]

To 6-chloro-2-diethylamino-4-(3-isopropyl-phenyl)-quinoline-3-carboxylic acid tert-butyl ester (75 mg, 0.17 mmol) was added a solution of HCl in dioxane (4N, 3 ml), and the mixture was heated to reflux for 4 h. The reaction mixture was then cooled to room temperature and then concentrated in vacuo to give a crude residue which was diluted with EtOAc (20 ml). The organic layer was washed with brine (10 ml), dried over anhydrous Na$_2$SO$_4$, filtered, and concentrated in vacuo to afford 6-chloro-2-diethylamino-4-(3-isopropyl-phenyl)-quinoline-3-carboxylic acid (55 mg, 84%) as a pale yellow solid. LC-MS (ESI): 397 (M+H)$^+$.

Example 79

6-Chloro-4-(3-isopropyl-phenyl)-2-pyrrolidin-1-yl-quinoline-3-carboxylic acid

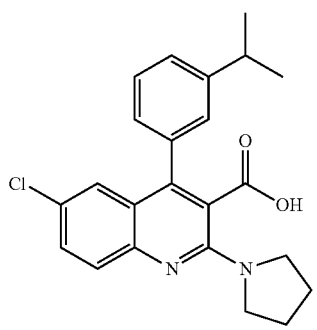 [SMILES: CC(C)c1cccc(-c2c(C(=O)O)c(N3CCCC3)nc3ccc(Cl)cc23)c1]

Step A: 6-Chloro-4-(3-isopropyl-phenyl)-2-pyrrolidin-1-yl-quinoline-3-carboxylic acid tert-butyl ester

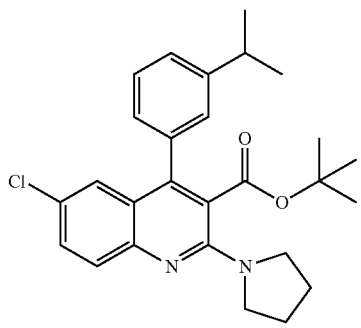 [SMILES: CC(C)c1cccc(-c2c(C(=O)OC(C)(C)C)c(N3CCCC3)nc3ccc(Cl)cc23)c1]

To a solution of pyrrolidine (0.093 ml, 1.13 mmol) in DMSO (7 ml) was added 6-chloro-4-(3-isopropyl-phenyl)-2-trifluoromethanesulfonyloxy-quinoline-3-carboxylic acid tert-butyl ester (prepared as described in example 78 step C, 400 mg, 0.76 mmol) and potassium carbonate (313 mg, 2.026 mmol) at 25° C. The resulting reaction mixture was stirred at 90° C. for 3 h. The reaction mixture was diluted with water (15 ml), and extracted with EtOAc (2×30 ml). The combined organic layers were dried over anhydrous Na$_2$SO$_4$, filtered, and concentrated in vacuo to give a crude residue which was purified by flash column chromatography (5-10% EtOAc in hexane) to afford 6-chloro-4-(3-isopropyl-phenyl)-2-pyrrolidin-1-yl-quinoline-3-carboxylic acid tert-butyl ester (250 mg, 73%) as pale yellow solid. LC-MS (ESI): 451 (M+H)$^+$.

Step B: 6-Chloro-4-(3-isopropyl-phenyl)-2-pyrrolidin-1-yl-quinoline-3-carboxylic acid

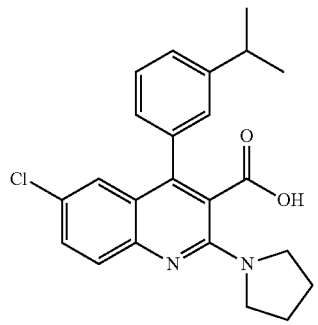 [SMILES: CC(C)c1cccc(-c2c(C(=O)O)c(N3CCCC3)nc3ccc(Cl)cc23)c1]

The title compound was prepared in analogy to example 78 step E from 6-chloro-4-(3-isopropyl-phenyl)-2-pyrrolidin-1-yl-quinoline-3-carboxylic acid tert-butyl ester (50 mg, 0.11 mmol) and 4N HCl in dioxane. White solid (16 mg, 37%). LC-MS (ESI): 395 (M+H)$^+$.

Example 80

6-Chloro-4-(3-isopropyl-phenyl)-2-piperidin-1-yl-quinoline-3-carboxylic acid

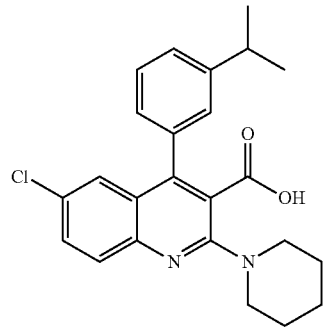 [SMILES: CC(C)c1cccc(-c2c(C(=O)O)c(N3CCCCC3)nc3ccc(Cl)cc23)c1]

Step A: 6-Chloro-4-(3-isopropyl-phenyl)-2-piperidin-1-yl-quinoline-3-carboxylic acid tert-butyl ester

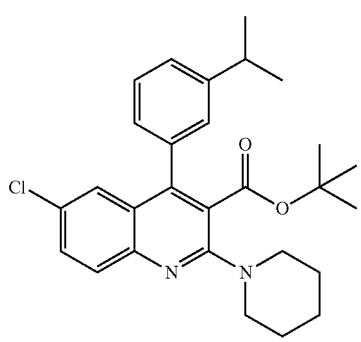 [SMILES: CC(C)c1cccc(-c2c(C(=O)OC(C)(C)C)c(N3CCCCC3)nc3ccc(Cl)cc23)c1]

The title compound was prepared in analogy to example 79 step A from 6-chloro-4-(3-isopropyl-phenyl)-2-trifluoromethanesulfonyloxy-quinoline-3-carboxylic acid tert-butyl ester (prepared as described in example 78 step C, 250 mg, 0.47 mmol) and piperidine (0.093 ml, 0.94 mmol). Yellow solid (140 mg, 64%). LC-MS (ESI): 465 (M+H)⁺.

Step B: 6-Chloro-4-(3-isopropyl-phenyl)-2-piperidin-1-yl-quinoline-3-carboxylic acid

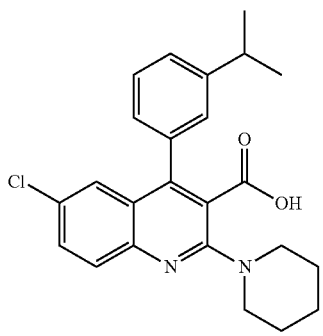 [SMILES: CC(C)c1cccc(-c2c(C(=O)O)c(N3CCCCC3)nc3ccc(Cl)cc23)c1]

The title compound was prepared in analogy to example 78 step E from 6-chloro-4-(3-isopropyl-phenyl)-2-piperidin-1-yl-quinoline-3-carboxylic acid tert-butyl ester (75 mg, 0.16 mmol) and 4N HCl in dioxane. Pale yellow solid (58 mg, 88%). LC-MS (ESI): 409 (M+H)⁺.

Example 81

6-Chloro-2-dimethylamino-4-(3-isopropyl-phenyl)-quinoline-3-carboxylic acid

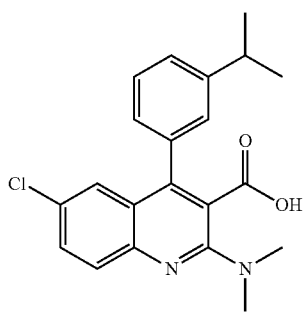 [SMILES: CC(C)c1cccc(-c2c(C(=O)O)c(N(C)C)nc3ccc(Cl)cc23)c1]

Step A: 6-Chloro-2-dimethylamino-4-(3-isopropyl-phenyl)-quinoline-3-carboxylic acid tert-butyl ester

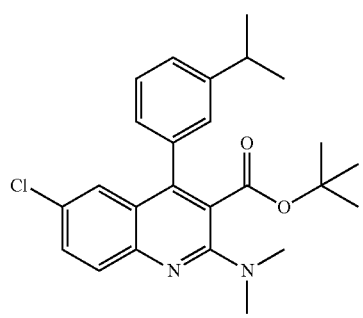 [SMILES: CC(C)c1cccc(-c2c(C(=O)OC(C)(C)C)c(N(C)C)nc3ccc(Cl)cc23)c1]

The title compound was prepared in analogy to example 79 step A from 6-chloro-4-(3-isopropyl-phenyl)-2-trifluoromethanesulfonyloxy-quinoline-3-carboxylic acid tert-butyl ester (prepared as described in example 78 step C, 250 mg, 0.47 mmol) and dimethylamine (2M solution in THF, 2 ml, 2.36 mmol). Pale yellow solid (130 mg, 65%). LC-MS (ESI): 425 (M+H)⁺.

Step B: 6-Chloro-2-dimethylamino-4-(3-isopropyl-phenyl)-quinoline-3-carboxylic acid

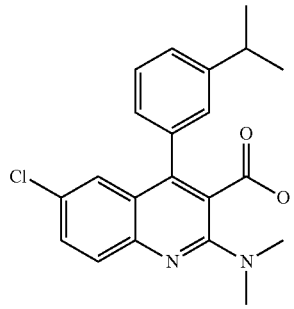 [SMILES: CC(C)c1cccc(-c2c(C(=O)O)c(N(C)C)nc3ccc(Cl)cc23)c1]

The title compound was prepared in analogy to example 78 step E from 6-chloro-2-dimethylamino-4-(3-isopropyl-phenyl)-quinoline-3-carboxylic acid tert-butyl ester (75 mg, 0.18 mmol) and 4N HCl in dioxane. Off white solid (45 mg, 69%). LC-MS (ESI): 369 (M+H)⁺.

Example 82

6-Chloro-4-(3-isopropyl-phenyl)-2-(2,2,2-trifluoro-1-methyl-ethoxy)-quinoline-3-carboxylic acid

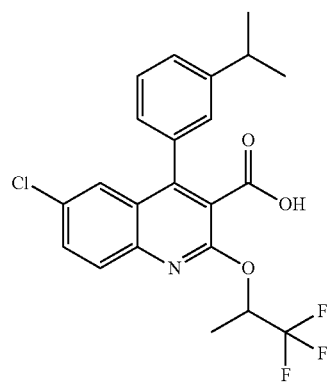 [SMILES: CC(C)c1cccc(-c2c(C(=O)O)c(OC(C)C(F)(F)F)nc3ccc(Cl)cc23)c1]

Step A: 6-Chloro-4-(3-isopropyl-phenyl)-2-(2,2,2-trifluoro-1-methyl-ethoxy)-quinoline-3-carboxylic acid tert-butyl ester

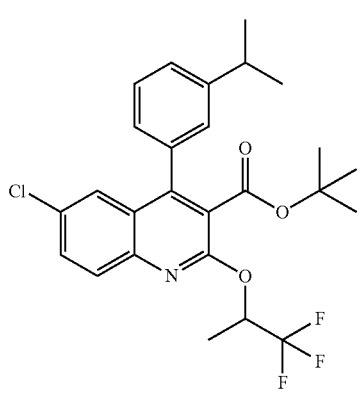 [SMILES: CC(C)c1cccc(-c2c(C(=O)OC(C)(C)C)c(OC(C)C(F)(F)F)nc3ccc(Cl)cc23)c1]

The title compound was prepared in analogy to example 79 step A from 6-chloro-4-(3-isopropyl-phenyl)-2-trifluoromethanesulfonyloxy-quinoline-3-carboxylic acid tert-butyl ester (prepared as described in example 78 step C, 250 mg, 0.47 mmol) and 1,1,1-trifluoro-propan-2-ol (64.57 mg, 0.57 mmol). Off white solid (100 mg, 43%). LC-MS (ESI): 494 (M+H)+.

Step B: 6-Chloro-4-(3-isopropyl-phenyl)-2-(2,2,2-trifluoro-1-methyl-ethoxy)-quinoline-3-carboxylic acid

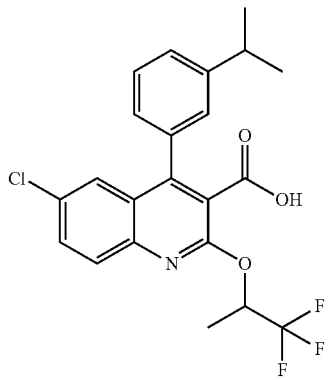 [SMILES: CC(C)c1cccc(-c2c(C(=O)O)c(OC(C)C(F)(F)F)nc3ccc(Cl)cc23)c1]

The title compound was prepared in analogy to example 78 step E from 6-chloro-4-(3-isopropyl-phenyl)-2-(2,2,2-trifluoro-1-methyl-ethoxy)-quinoline-3-carboxylic acid tert-butyl ester (70 mg, 0.14 mmol) and 4N HCl in dioxane. Off white solid (44 mg, 71%). LC-MS (ESI): 438 (M+H)+.

Example 83

6-Chloro-4-(2-chloro-benzyl)-2-isopropyl-8-methoxy-quinoline-3-carboxylic acid

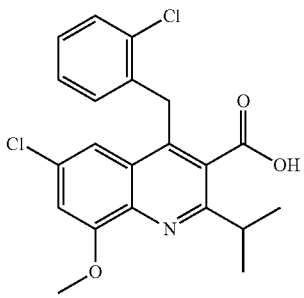 [SMILES: COc1cc(Cl)cc2c(Cc3ccccc3Cl)c(C(=O)O)c(C(C)C)nc12]

Step A: 4-Chloro-2-iodo-6-methoxy-phenylamine

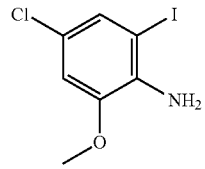

To a solution of 4-chloro-2-methoxy-phenylamine (600 mg, 3.81 mmol) in ethanol (12 ml) at 50° C. was added a solution of silver sulphate (2.14 g, 6.85 mmol) and iodine (967 mg, 3.81 mmol) in ethanol (8 ml). The resulting reaction mixture was stirred at 50° C. for 4 h. After cooling at 25° C., reaction mixture was filtered through a bed of celite and the filtrate was diluted with EtOAc (30 ml). The organic phase was washed with aqueous Na2S2O3 solution (2×15 ml), and brine (10 ml), dried over anhydrous Na2SO4, filtered, and evaporated off in vacuo. The crude residue was purified by flash column chromatography (2% EtOAc in hexane) to afford 4-chloro-2-iodo-6-methoxy-phenylamine (160 mg, 15%) as brown sticky liquid. GC-MS: 283 (M).

Step B: 4-Chloro-2-(2-chloro-phenylethynyl)-6-methoxy-phenylamine

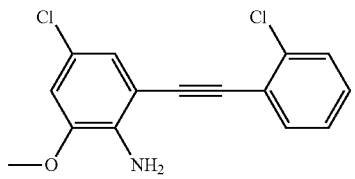

The title compound was prepared in analogy to example 10 step A from 4-chloro-2-iodo-6-methoxy-phenylamine (300 mg, 1.06 mmol) and 1-chloro-2-ethynyl-benzene (174 mg, 1.27 mmol). Brown solid (220 mg, 71%). LC-MS (ESI): 292 (M+H)+.

Step C: 6-Chloro-4-(2-chloro-benzyl)-2-isopropyl-8-methoxy-quinoline-3-carboxylic acid ethyl ester

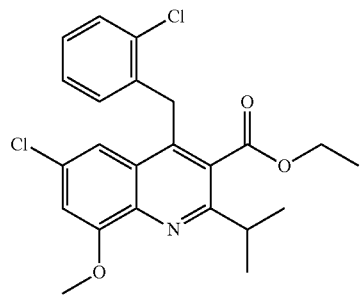 [SMILES: CCOC(=O)c1c(C(C)C)nc2c(OC)cc(Cl)cc2c1Cc1ccccc1Cl]

The title compound was prepared in analogy to example 10 step B from 4-chloro-2-(2-chloro-phenylethynyl)-6-methoxy-phenylamine (200 mg, 0.68 mmol) and 4-methyl-3-oxo-pentanoic acid ethyl ester (0.166 ml, 1.03 mmol). Brown solid (45 mg, 15%). LC-MS (ESI): 432 (M+H)+.

Step D: 6-Chloro-4-(2-chloro-benzyl)-2-isopropyl-8-methoxy-quinoline-3-carboxylic acid

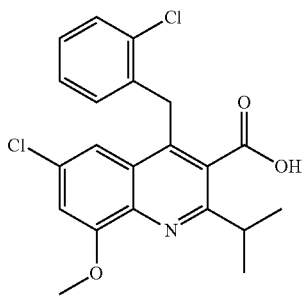 [SMILES: COc1cc(Cl)cc2c(Cc3ccccc3Cl)c(C(=O)O)c(C(C)C)nc12]

The title compound was prepared in analogy to example 6 step B from a mixture of 6-chloro-4-(2-chloro-benzyl)-2- isopropyl-8-methoxy-quinoline-3-carboxylic acid ethyl ester (20 mg, 0.05 mmol) and 1N NaOH in ethanol. Off white solid (5 mg, 27%). LC-MS (ESI): 404 (M+H)⁺.

Example 84

6-Chloro-4-(2-chloro-benzyl)-2-isopropyl-8-methoxy-quinoline-3-carboxylic acid

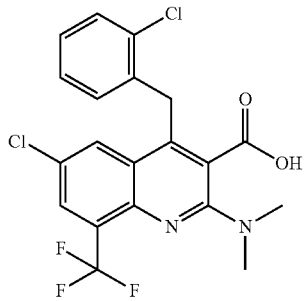 [SMILES: CN(C)c1nc2c(C(F)(F)F)cc(Cl)cc2c(Cc2ccccc2Cl)c1C(=O)O]

Step A:
4-Chloro-2-iodo-6-trifluoromethyl-phenylamine

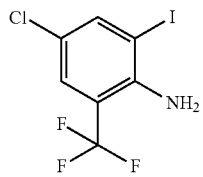 [SMILES: Nc1c(I)cc(Cl)cc1C(F)(F)F]

The title compound was prepared in analogy to example 76 step A from 4-chloro-2-trifluoromethyl-phenylamine (1 g, 5.11 mmol) and N-iodo succinimide (1.73 g, 7.67 mmol). Off white solid. (1.64 g, 88%). GC-MS: 321 (M).

Step B: 4-Chloro-2-(2-chloro-phenylethynyl)-6-trifluoromethyl-phenylamine

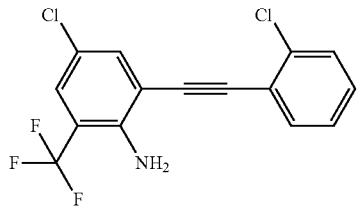 [SMILES: Nc1c(C#Cc2ccccc2Cl)cc(Cl)cc1C(F)(F)F]

The title compound was prepared in analogy to example 10 step A from 4-chloro-2-iodo-6-trifluoromethyl-phenylamine (1.5 g, 4.67 mmol) and 1-chloro-2-ethynyl-benzene (766 mg, 5.6 mmol). Brown solid (1.05 g, 68%). LC-MS (ESI): 328 (M−H)⁻.

Step C: N-[4-Chloro-2-(2-chloro-phenylethynyl)-6-trifluoromethyl-phenyl]-malonamic acid ethyl ester

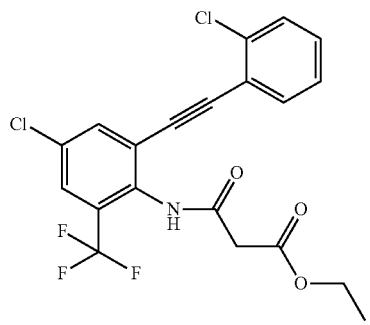 [SMILES: CCOC(=O)CC(=O)Nc1c(C#Cc2ccccc2Cl)cc(Cl)cc1C(F)(F)F]

The title compound was prepared in analogy to example 29 step A from 4-chloro-2-(2-chloro-phenylethynyl)-6-trifluoromethyl-phenylamine and chlorocarbonyl-acetic acid ethyl ester. Off white solid (1.2 g, 45%) LC-MS (ESI): 444 (M+H)⁺.

Step D: 6-Chloro-4-(2-chloro-benzyl)-2-oxo-8-trifluoromethyl-1,2-dihydro-quinoline-3-carboxylic acid ethyl ester

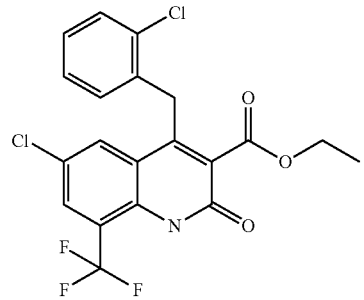 [SMILES: CCOC(=O)c1c(Cc2ccccc2Cl)c2cc(Cl)cc(C(F)(F)F)c2[nH]c1=O]

The title compound was prepared in analogy to example 29 step B from N-[4-chloro-2-(2-chloro-phenylethynyl)-6-trifluoromethyl-phenyl]-malonamic acid ethyl ester (1 g, 2.25 mmol) and NaH (140 mg, 3.38 mmol) in DMSO (10 ml). Off white solid (450 mg, 45%). LC-MS (ESI): 444 (M+H)⁺.

Step E: 6-Chloro-4-(2-chloro-benzyl)-2-trifluoromethanesulfonyloxy-8-trifluoromethyl-quinoline-3-carboxylic acid ethyl ester

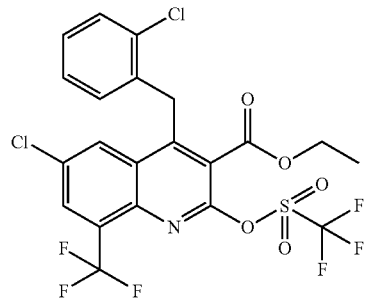 [SMILES: CCOC(=O)c1c(OS(=O)(=O)C(F)(F)F)nc2c(C(F)(F)F)cc(Cl)cc2c1Cc1ccccc1Cl]

The title compound was prepared in analogy to example 29 step C from 6-chloro-4-(2-chloro-benzyl)-2-oxo-8-trifluoromethyl-1,2-dihydro-quinoline-3-carboxylic acid ethyl ester (200 mg, 0.45 mmol) and N-phenylbis(trifluoromethanesulfonimide) (241 mg, 0.68 mmol). Pale yellow solid (85 mg, 33%). LC-MS (ESI): 576 (M+H)⁺.

Step F: 6-Chloro-4-(2-chloro-benzyl)-2-dimethyl-amino-8-trifluoromethyl-quinoline-3-carboxylic acid ethyl ester

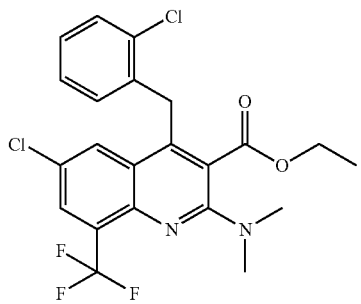 [SMILES: CCOC(=O)c1c(N(C)C)nc2c(C(F)(F)F)cc(Cl)cc2c1Cc1ccccc1Cl]

The title compound was prepared in analogy to example 29 step D from 6-chloro-4-(2-chloro-benzyl)-2-trifluoromethanesulfonyloxy-8-trifluoromethyl-quinoline-3-carboxylic acid ethyl ester (80 mg, 0.14 mmol) and dimethylamine (3 ml, 2M solution in THF). Off white solid (45 mg, 69%). LC-MS (ESI): 471 (M+H)$^+$ Step G: 6-Chloro-4-(2-chloro-benzyl)-2-dimethyl-amino-8-trifluoromethyl-quinoline-3-carboxylic acid

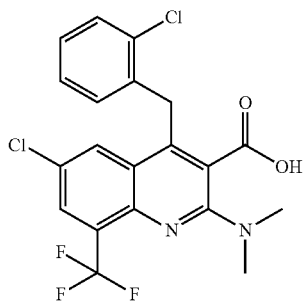 [SMILES: CN(C)c1nc2c(C(F)(F)F)cc(Cl)cc2c(Cc2ccccc2Cl)c1C(=O)O]

The title compound was prepared in analogy to example 12 step B from a mixture of 6-chloro-4-(2-chloro-benzyl)-2-dimethylamino-8-trifluoromethyl-quinoline-3-carboxylic acid ethyl ester (50 mg, 0.106 mmol) and 1N NaOH in ethanol. Pale yellow solid (22 mg, 47%). LC-MS (ESI): 441 (M–H)$^-$.

Example 85

5-(6-Chloro-4-phenyl-2-piperidin-1-yl-quinolin-3-yl)-3H-[1,3,4]oxadiazole-2-thione

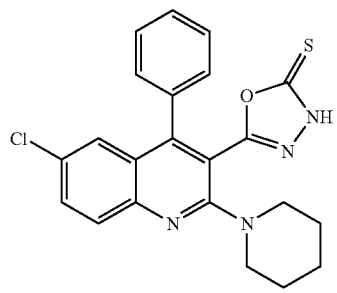

6-Chloro-4-phenyl-2-piperidin-1-yl-quinoline-3-carboxylic acid hydrazide (prepared as described in example 77 step E) (35 mg, 82.7 μmol, Eq: 1.00) and 1,1'-thiocarbonyl-diimidazole (17.7 mg, 99.2 μmol, Eq: 1.2) were dissolved in THF (1.00 ml). Then triethylamine (11.7 mg, 16.1 μl, 116 μmol, Eq: 1.4) was added and the mixture was warmed to 50° C. for 72 h. Water was added and the mixture was extracted with ethyl acetate (3×). The combined extracts were washed with water and brine, dried with Na$_2$SO$_4$ and evaporated. The remaining residue was purified by column chromatography (silica gel, DCM/EtOAc 97:3) to afford the title compound as yellow solid (28 mg). MS (ESI): 423.1 (M+H)$^+$.

Example 86

6-Chloro-4-(2-chloro-benzyl)-2-diethylamino-quinoline-3-carboxylic acid

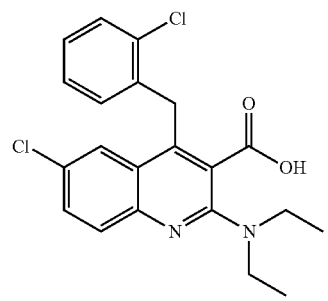 [SMILES: CCN(CC)c1nc2ccc(Cl)cc2c(Cc2ccccc2Cl)c1C(=O)O]

Step A: 6-Chloro-4-(2-chloro-benzyl)-2-diethyl-amino-quinoline-3-carboxylic acid ethyl ester

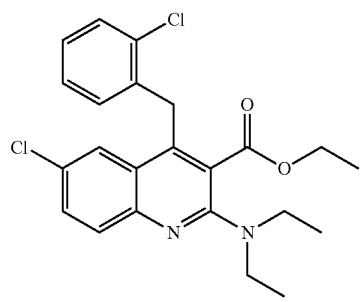 [SMILES: CCOC(=O)c1c(N(CC)CC)nc2ccc(Cl)cc2c1Cc1ccccc1Cl]

This compound was prepared in analogy to example 29 step D from 6-chloro-4-(2-chloro-benzyl)-2-trifluoromethanesulfonyloxy-quinoline-3-carboxylic acid ethyl ester (prepared as described in example 29 step C, 100 mg, 0.2 mmol) and diethyl amine (0.047 ml, 0.39 mmol). Pale yellow solid (52 mg, 61%). LC-MS (ESI): 431 (M+H)$^+$.

Step B: 6-Chloro-4-(2-chloro-benzyl)-2-diethyl-amino-quinoline-3-carboxylic acid

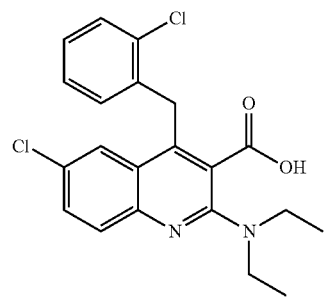 [SMILES: CCN(CC)c1nc2ccc(Cl)cc2c(Cc2ccccc2Cl)c1C(=O)O]

The title compound was prepared in analogy to example 12 step B from a mixture of 6-chloro-4-(2-chloro-benzyl)-2-diethylamino-quinoline-3-carboxylic acid ethyl ester (50 mg, 0.116 mmol) and 1N NaOH. Pale yellow solid (32 mg, 68%). LC-MS (ESI): 403 (M+H)+.

Example 87

6-Chloro-4-(2-chloro-benzyl)-2-pyrrolidin-1-yl-quinoline-3-carboxylic acid

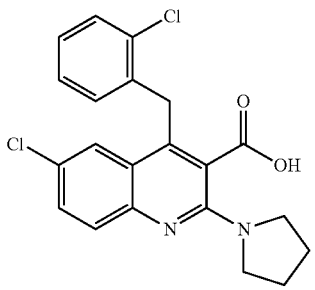 [SMILES: O=C(O)c1c(N2CCCC2)nc2ccc(Cl)cc2c1Cc1ccccc1Cl]

Step A: 6-Chloro-4-(2-chloro-benzyl)-2-pyrrolidin-1-yl-quinoline-3-carboxylic acid ethyl ester

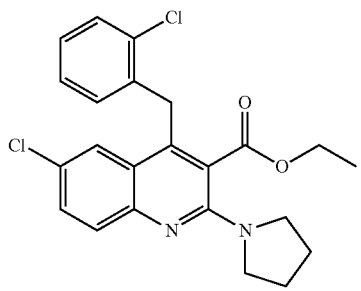 [SMILES: CCOC(=O)c1c(N2CCCC2)nc2ccc(Cl)cc2c1Cc1ccccc1Cl]

This compound was prepared in analogy to example 29 step D from 6-chloro-4-(2-chloro-benzyl)-2-trifluoromethanesulfonyloxy-quinoline-3-carboxylic acid ethyl ester (prepared as described in example 29 step C, 100 mg, 0.2 mmol) and pyrrolidine (0.032 ml, 0.39 mmol). Pale yellow solid (60 mg, 71%). LC-MS (ESI): 429 (M+H)+.

Step B: 6-Chloro-4-(2-chloro-benzyl)-2-pyrrolidin-1-yl-quinoline-3-carboxylic acid

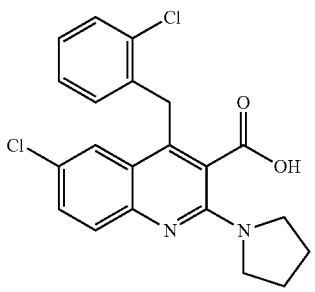 [SMILES: O=C(O)c1c(N2CCCC2)nc2ccc(Cl)cc2c1Cc1ccccc1Cl]

The title compound was prepared in analogy to example 12 step B from 6-chloro-4-(2-chloro-benzyl)-2-pyrrolidin-1-yl-quinoline-3-carboxylic acid ethyl ester (50 mg, 0.117 mmol) and 1N NaOH. Pale yellow solid (13 mg, 28%). LC-MS (ESI): 401 (M+H)+.

Example 88

6-Chloro-4-(2-chloro-benzyl)-2-piperidin-1-yl-quinoline-3-carboxylic acid

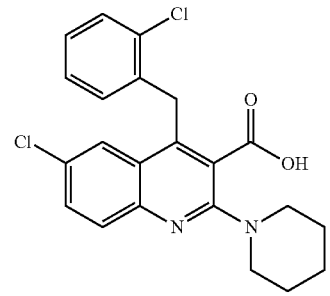 [SMILES: O=C(O)c1c(N2CCCCC2)nc2ccc(Cl)cc2c1Cc1ccccc1Cl]

Step A: 6-Chloro-4-(2-chloro-benzyl)-2-piperidin-1-yl-quinoline-3-carboxylic acid ethyl ester

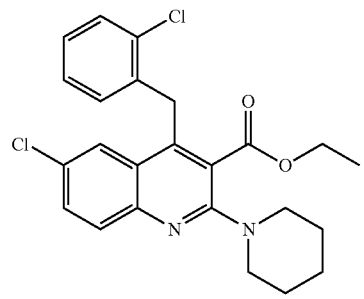 [SMILES: CCOC(=O)c1c(N2CCCCC2)nc2ccc(Cl)cc2c1Cc1ccccc1Cl]

This compound was prepared in analogy to example 29 step D from 6-chloro-4-(2-chloro-benzyl)-2-trifluoromethanesulfonyloxy-quinoline-3-carboxylic acid ethyl ester (prepared as described in example 29 step C, 100 mg, 0.2 mmol) and piperidine (0.039 ml, 0.39 mmol). Pale yellow solid (52 mg, 60%). LC-MS (ESI): 443 (M+H)+.

Step B: 6-Chloro-4-(2-chloro-benzyl)-2-piperidin-1-yl-quinoline-3-carboxylic acid

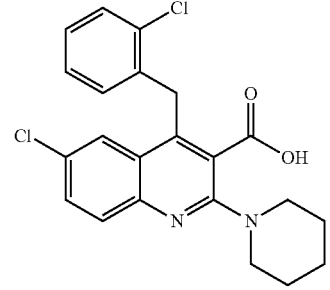 [SMILES: O=C(O)c1c(N2CCCCC2)nc2ccc(Cl)cc2c1Cc1ccccc1Cl]

The title compound was prepared in analogy to example 12 step B from 6-chloro-4-(2-chloro-benzyl)-2-piperidin-1-yl-quinoline-3-carboxylic acid ethyl ester (50 mg, 0.113 mmol) and 1N NaOH. Pale yellow solid (35 mg, 75%). LC-MS (ESI): 415 (M+H)+.

Example 89

6-Chloro-2-piperidin-1-yl-4-(2-trifluoromethyl-benzyl)-quinoline-3-carboxylic acid

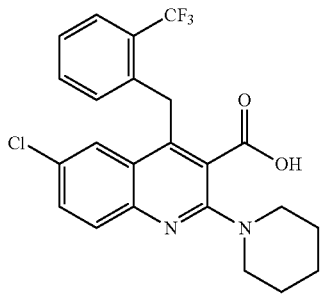 [SMILES: O=C(O)c1c(N2CCCCC2)nc2ccc(Cl)cc2c1Cc1ccccc1C(F)(F)F]

Step A: 4-Chloro-2-(2-trifluoromethyl-phenylethynyl)-phenylamine

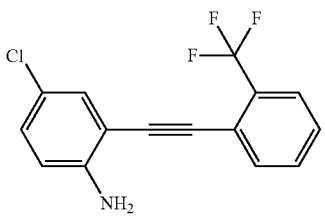 [SMILES: Nc1ccc(Cl)cc1C#Cc1ccccc1C(F)(F)F]

The title compound was prepared in analogy to example 10 step A from 4-chloro-2-iodoaniline (500 mg, 1.97 mmol) and 1-ethynyl-2-(trifluoromethyl)benzene (330 µl, 2.37 mmol). Off white solid. Rf 0.3 (1:9 Ethyl acetate:heptane) as an intense blue spot under UV light.

Step B: N-[4-Chloro-2-(2-trifluoromethyl-phenyl-ethynyl)-phenyl]-malonamic acid ethyl ester

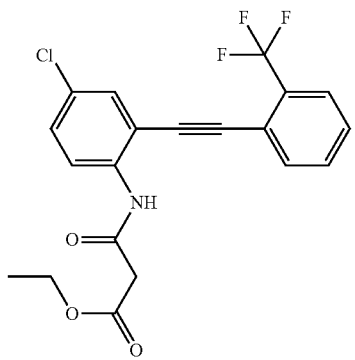 [SMILES: CCOC(=O)CC(=O)Nc1ccc(Cl)cc1C#Cc1ccccc1C(F)(F)F]

The title compound was prepared in analogy to example 29 step A from 4-chloro-2-((2-(trifluoromethyl)phenyl)ethynyl)aniline (200 mg, 0.68 mmol) and chlorocarbonyl-acetic acid ethyl ester (128 µl, 1.01 mmol). Off white solid (213 mg, 77%). MS (ESI): 410 (M+H)+.

Step C: 6-Chloro-2-oxo-4-(2-trifluoromethyl-benzyl)-1,2-dihydro-quinoline-3-carboxylic acid ethyl ester

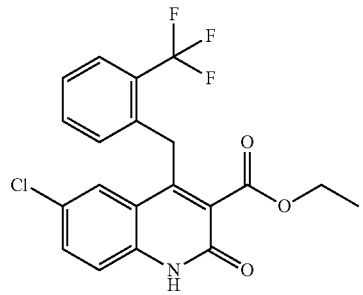 [SMILES: CCOC(=O)c1c(Cc2ccccc2C(F)(F)F)c2cc(Cl)ccc2[nH]c1=O]

The title compound was prepared in analogy to example 29 step B from N-[4-chloro-2-(2-trifluoromethyl-phenyl-ethynyl)-phenyl]-malonamic acid ethyl ester (213 mg, 0.52 mmol) and NaH (31.2 mg, 0.78 mmol) in DMSO. Off white solid (95 mg, 45%). MS (ESI): 410 (M+H)+.

Step D: 6-Chloro-2-piperidin-1-yl-4-(2-trifluoromethyl-benzyl)-quinoline-3-carboxylic acid ethyl ester

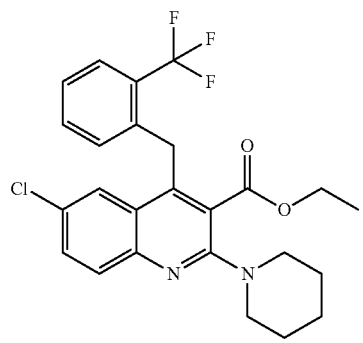 [SMILES: CCOC(=O)c1c(N2CCCCC2)nc2ccc(Cl)cc2c1Cc1ccccc1C(F)(F)F]

The title compound was prepared in analogy to example 29 step D from crude 6-chloro-2-methanesulfonyloxy-4-(2-trifluoromethyl-benzyl)-quinoline-3-carboxylic acid ethyl ester (prepared in analogy to example 29 step C) and piperidine. Off white solid. MS (ESI): 477 (M+H)+.

Step E: 6-Chloro-2-piperidin-1-yl-4-(2-trifluoromethyl-benzyl)-quinoline-3-carboxylic acid

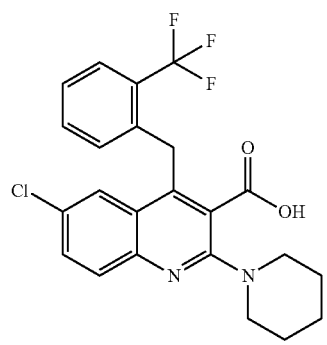 [SMILES: O=C(O)c1c(N2CCCCC2)nc2ccc(Cl)cc2c1Cc1ccccc1C(F)(F)F]

The title compound was prepared in analogy to example 12 step B from a mixture of 6-chloro-2-piperidin-1-yl-4-(2- trifluoromethyl-benzyl)-quinoline-3-carboxylic acid ethyl ester and 1N NaOH in ethanol. Pale yellow solid. MS (ESI): 449 (M+H)+.

Example 90

6-Chloro-4-(2-chloro-benzyl)-2-isopropoxy-quinoline-3-carboxylic acid

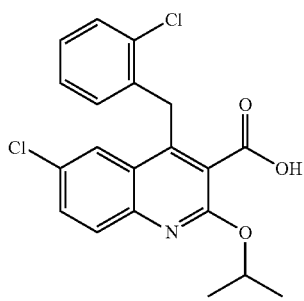 [SMILES: CC(C)Oc1nc2ccc(Cl)cc2c(Cc2ccccc2Cl)c1C(=O)O]

Step A: 6-Chloro-4-(2-chloro-benzyl)-2-isopropoxy-quinoline-3-carboxylic acid ethyl ester

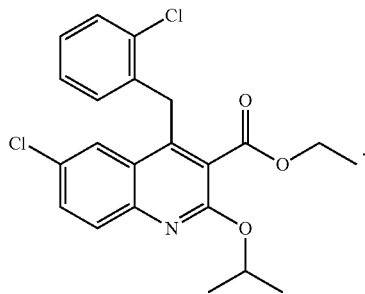 [SMILES: CCOC(=O)c1c(OC(C)C)nc2ccc(Cl)cc2c1Cc1ccccc1Cl]

This compound was prepared in analogy to example 29 step D from 6-chloro-4-(2-chloro-benzyl)-2-trifluoromethanesulfonyloxy-quinoline-3-carboxylic acid ethyl ester (prepared as described in example 29 step C) and propan-2-ol. Off white solid. LC-MS (ESI): 418 (M+H)+.

Step B: 6-Chloro-4-(2-chloro-benzyl)-2-isopropoxy-quinoline-3-carboxylic acid

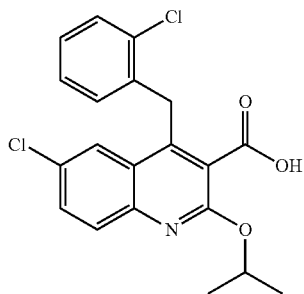 [SMILES: CC(C)Oc1nc2ccc(Cl)cc2c(Cc2ccccc2Cl)c1C(=O)O]

The title compound was prepared in analogy to example 12 step B from 6-chloro-4-(2-chloro-benzyl)-2-isopropoxy-quinoline-3-carboxylic acid ethyl ester and 1N NaOH. Off white solid. LC-MS (ESI): 390 (M+H)+.

Example 91

6-Chloro-4-(3-chloro-phenyl)-2-diethylamino-quinoline-3-carboxylic acid

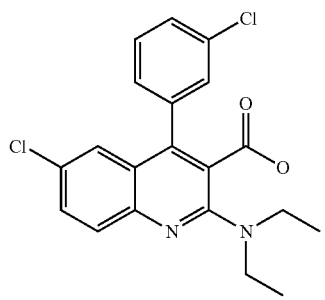 [SMILES: CCN(CC)c1nc2ccc(Cl)cc2c(-c2cccc(Cl)c2)c1C(=O)O]

Step A: (2-Amino-5-chloro-phenyl)-(3-chloro-phenyl)-methanone

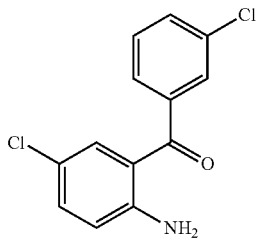 [SMILES: Nc1ccc(Cl)cc1C(=O)c1cccc(Cl)c1]

To the stirred solution of 2-amino-5-chloro-benzonitrile (500 mg, 3.28 mmol) in diethyl ether (10 ml) was added 3-chloro phenyl magnesium bromide (freshly prepared 1M solution in ether, 10 ml, 9.83 mmol) drop wise at 0° C. and the resulting reaction mixture was refluxed for 1 h. Then the mixture was stirred for 16 h at 25° C., cooled to 5° C. and quenched with water followed by 2 N HCl solution (20 ml). The reaction mixture was stirred at 45° C. for 5 h and then the pH of the reaction mixture was adjusted to 8-9 with 2N aqueous NaOH solution. The mixture was extracted with diethyl ether (3×30 ml) and the combined organic extracts were washed with brine (25 ml), dried over sodium sulfate and concentrated in vacuo to give a crude residue which was purified by flash column chromatography (5% ethyl acetate in hexane) to yield (2-amino-5-chloro-phenyl)-(3-chloro-phenyl)-methanone (550 mg, 63%) as a yellow solid. LC-MS (ESI): 266 (M+H)+.

Step B: 6-Chloro-4-(3-chloro-phenyl)-2-hydroxy-quinoline-3-carboxylic acid tert-butyl ester

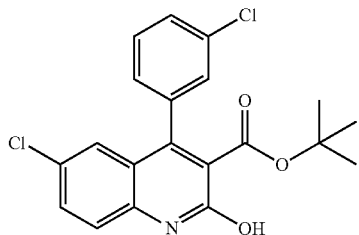 [SMILES: CC(C)(C)OC(=O)c1c(O)nc2ccc(Cl)cc2c1-c1cccc(Cl)c1]

A mixture of (2-amino-5-chloro-phenyl)-(3-chloro-phenyl)-methanone (550 mg, 2.07 mmol), KOH (58 mg, 1.03 mmol) and malonic acid di-tert-butyl ester (0.7 ml, 3.1 mmol) was placed in a sealed tube, and the resulting reaction mixture was stirred at 110° C. for 16 h. After cooling, the reaction mixture was purified by flash column chromatography (20-30% ethyl acetate in hexane) to give 6-chloro-4-(3-chloro-phenyl)-2-hydroxy-quinoline-3-carboxylic acid tert-butyl ester (410 mg, 51%) as an off white solid. LC-MS (ESI): 390 (M+H)$^+$.

Step C: 6-Chloro-4-(3-chloro-phenyl)-2-trifluoromethanesulfonyloxy-quinoline-3-carboxylic acid tert-butyl ester

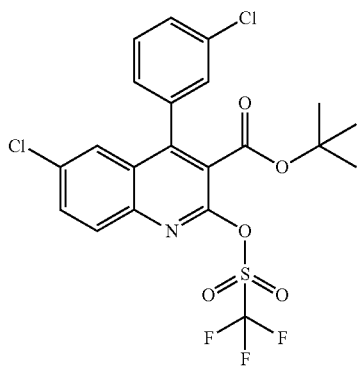 [SMILES: CC(C)(C)OC(=O)c1c(OS(=O)(=O)C(F)(F)F)nc2ccc(Cl)cc2c1-c1cccc(Cl)c1]

To the stirred solution of 6-chloro-4-(3-chloro-phenyl)-2-hydroxy-quinoline-3-carboxylic acid tert-butyl ester (500 mg, 1.28 mmol) in DMF (7 ml) was added NaH (60%, 77 mg, 1.92 mmol) portion wise at 0° C. and the resulting reaction mixture was stirred at 25° C. for 1.5 h. The reaction mixture was cooled to 0° C. and a solution of N-phenylbis(trifluoromethanesulfonimide) (686 mg, 1.92 mmol) in DMF (3 ml) was added drop wise. The reaction mixture was stirred for 3 h at 25° C. and monitored by TLC and LCMS. The reaction mixture was quenched with saturated aqueous ammonium chloride (25 ml) and extracted with ethyl acetate (3×50 ml). The separated organic layer was washed with brine (20 ml), dried over sodium sulfate and concentrated in vacuo to give a crude residue which was purified by flash column chromatography (1-2% ethyl acetate in hexane) to yield 6-chloro-4-(3-chloro-phenyl)-2-trifluoromethanesulfonyloxy-quinoline-3-carboxylic acid tert-butyl ester (475 mg, 71%) as an off white solid. LC-MS (ESI): 522 (M+H)$^+$.

Step D: 6-Chloro-4-(3-chloro-phenyl)-2-diethylamino-quinoline-3-carboxylic acid tert-butyl ester

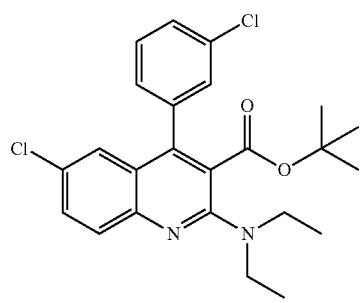 [SMILES: CCN(CC)c1nc2ccc(Cl)cc2c(-c2cccc(Cl)c2)c1C(=O)OC(C)(C)C]

To a stirred solution of diethyl amine (0.059 ml, 0.57 mmol) in THF (5 ml) was added K$_2$CO$_3$ (159 mg, 1.15 mmol) and 6-chloro-4-(3-chloro-phenyl)-2-diethylamino-quinoline-3-carboxylic acid tert-butyl ester (150 mg, 0.29 mmol) at 25° C. The resulting reaction mixture was stirred at 70° C. for 3 h. After cooling the reaction mixture to room temperature the mixture was diluted with water (10 ml) and extracted with ethyl acetate (3×25 ml). The separated organic layer was washed with brine (10 ml), dried over sodium sulfate and concentrated in vacuo to afford a crude residue which was purified by column chromatography eluting with 3% ethyl acetate in hexane to give 6-chloro-4-(3-chloro-phenyl)-2-diethylamino-quinoline-3-carboxylic acid tert-butyl ester (100 mg, 78% yield) as a pale yellow solid. LC-MS (ESI): 445 (M+H)$^+$.

Step E: 6-Chloro-4-(3-chloro-phenyl)-2-diethylamino-quinoline-3-carboxylic acid

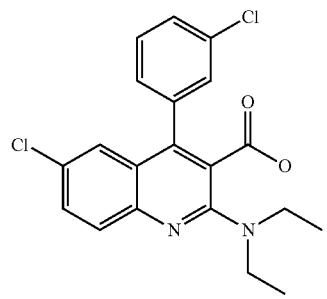 [SMILES: CCN(CC)c1nc2ccc(Cl)cc2c(-c2cccc(Cl)c2)c1C(=O)O]

A solution of 6-chloro-4-(3-chloro-phenyl)-2-diethylamino-quinoline-3-carboxylic acid tert-butyl ester (60 mg, 0.13 mmol) in 3 ml of 4M HCl solution in dioxane was heated to reflux and stirred for 4 h. The reaction mixture was cooled to room temperature and concentrated in vacuo. The crude residue was diluted with ethyl acetate (25 ml) and washed with brine (5 ml). The organic layer was dried over anhydrous sodium sulphate and concentrated in vacuo to yield 6-chloro-4-(3-chloro-phenyl)-2-diethylamino-quinoline-3-carboxylic acid (45 mg, 86%) as a pale yellow solid. LC-MS (ESI): 389 (M+H)$^+$.

Example 92

6-Chloro-4-(3-chloro-phenyl)-2-pyrrolidin-1-yl-quinoline-3-carboxylic acid

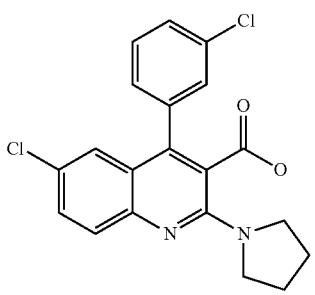 [SMILES: O=C(O)c1c(N2CCCC2)nc2ccc(Cl)cc2c1-c1cccc(Cl)c1]

Step A: 6-Chloro-4-(3-chloro-phenyl)-2-pyrrolidin-1-yl-quinoline-3-carboxylicacid tert-butyl ester

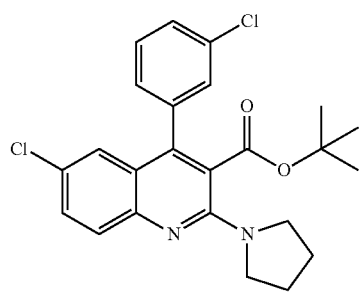 [SMILES: CC(C)(C)OC(=O)c1c(N2CCCC2)nc2ccc(Cl)cc2c1-c1cccc(Cl)c1]

To a stirred solution of pyrrolidine (0.047 ml, 0.58 mmol) in DMSO (5 ml) was added $K_2CO_3$ (159 mg, 1.15 mmol) and 6-chloro-4-(3-chloro-phenyl)-2-trifluoromethanesulfonyloxy-quinoline-3-carboxylic acid tert-butyl ester (prepared as described in example 91 step C, 150 mg, 0.29 mmol) at room temperature. The resulting reaction mixture was stirred at 90° C. for 3 h. After cooling, the reaction mixture was diluted with water (15 ml) and extracted with ethyl acetate (3×30 ml). The separated organic layer was washed with brine (15 ml), dried over sodium sulfate and concentrated under vacuum to give a crude residue which was purified by column chromatography eluting with 5-10% ethyl acetate in hexane to yield 6-chloro-4-(3-chloro-phenyl)-2-pyrrolidin-1-yl-quinoline-3-carboxylic acid tert-butyl ester (90 mg, 71% yield) as a pale yellow solid. LC-MS (ESI): 443 $(M+H)^+$.

Step B: 6-Chloro-4-(3-chloro-phenyl)-2-pyrrolidin-1-yl-quinoline-3-carboxylicacid

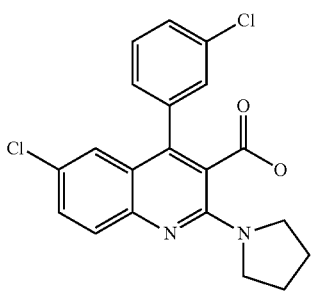 [SMILES: O=C(O)c1c(N2CCCC2)nc2ccc(Cl)cc2c1-c1cccc(Cl)c1]

The title compound was prepared in analogy to example 91 step E from 6-chloro-4-(3-chloro-phenyl)-2-pyrrolidin-1-yl-quinoline-3-carboxylic acid tert-butyl ester (70 mg, 0.16 mmol) and 4N HCl in dioxane. Off white solid (44 mg, 72%). LC-MS (ESI): 387 $(M+H)^+$.

Example 93

6-Chloro-4-(3-chloro-phenyl)-2-piperidin-1-yl-quinoline-3-carboxylic acid

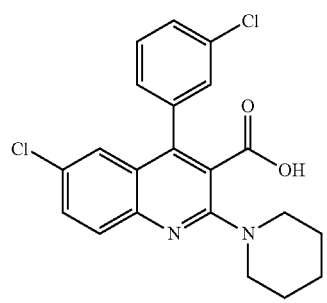 [SMILES: O=C(O)c1c(N2CCCCC2)nc2ccc(Cl)cc2c1-c1cccc(Cl)c1]

Step A: 6-Chloro-4-(3-chloro-phenyl)-2-piperidin-1-yl-quinoline-3-carboxylic acid tert-butyl ester

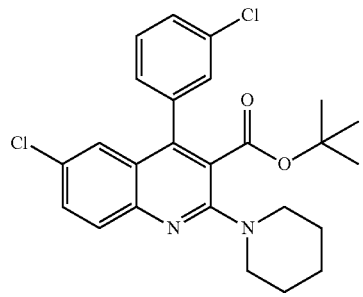 [SMILES: CC(C)(C)OC(=O)c1c(N2CCCCC2)nc2ccc(Cl)cc2c1-c1cccc(Cl)c1]

The title compound was prepared in analogy to example 92 step A from 6-chloro-4-(3-chloro-phenyl)-2-trifluoromethanesulfonyloxy-quinoline-3-carboxylic acid tert-butyl ester (prepared as described in example 91 step C, 150 mg, 0.29 mmol) and piperidine (0.057 ml, 0.58 mmol). Pale yellow solid (95 mg, 72%). LC-MS (ESI): 457 $(M+H)^+$.

Step B: 6-Chloro-4-(3-chloro-phenyl)-2-piperidin-1-yl-quinoline-3-carboxylic acid

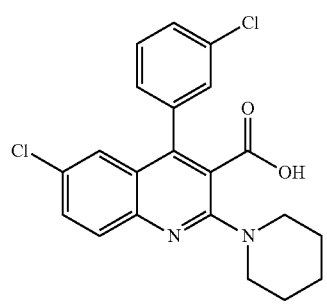 [SMILES: O=C(O)c1c(N2CCCCC2)nc2ccc(Cl)cc2c1-c1cccc(Cl)c1]

The title compound was prepared in analogy to example 91 step E from 6-chloro-4-(3-chloro-phenyl)-2-piperidin-1- yl-quinoline-3-carboxylic acid tert-butyl ester (70 mg, 0.15 mmol) and 4N HCl in dioxane. Off white solid (40 mg, 65%). LC-MS (ESI): 401 (M+H)+.

Example 94

6-Chloro-4-(3-chloro-phenyl)-2-dimethylamino-quinoline-3-carboxylic acid

Step A: 6-Chloro-4-(3-chloro-phenyl)-2-dimethyl-amino-quinoline-3-carboxylic acid tert-butyl ester

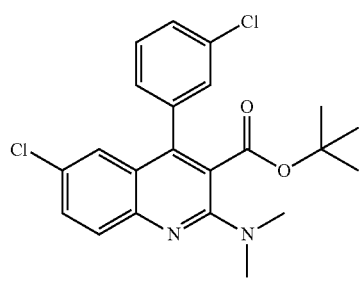 [SMILES: CN(C)c1nc2ccc(Cl)cc2c(-c2cccc(Cl)c2)c1C(=O)OC(C)(C)C]

The title compound was prepared in analogy to example 91 step D from 6-chloro-4-(3-chloro-phenyl)-2-trifluoromethanesulfonyloxy-quinoline-3-carboxylic acid tert-butyl ester (prepared as described in example 91 step C, 150 mg, 0.29 mmol) and dimethylamine (2M solution in THF, 1 ml, 2 mmol). Pale yellow solid (85 mg, 71%). LC-MS (ESI): 417 (M+H)+.

Step B: 6-Chloro-4-(3-chloro-phenyl)-2-dimethyl-amino-quinoline-3-carboxylic acid

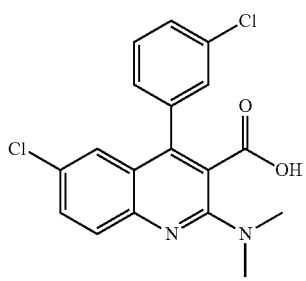 [SMILES: CN(C)c1nc2ccc(Cl)cc2c(-c2cccc(Cl)c2)c1C(=O)O]

The title compound was prepared in analogy to example 91 step E from 6-chloro-4-(3-chloro-phenyl)-2-dimethyl-amino-quinoline-3-carboxylic acid tert-butyl ester (70 mg, 0.17 mmol) and 4N HCl in dioxane. Off white solid (41 mg, 68%). LC-MS (ESI): 361 (M+H)+.

Example 95

6-Chloro-4-(2-chloro-benzyl)-2-(2,2,2-trifluoro-1-methyl-ethoxy)-quinoline-3-carboxylic acid

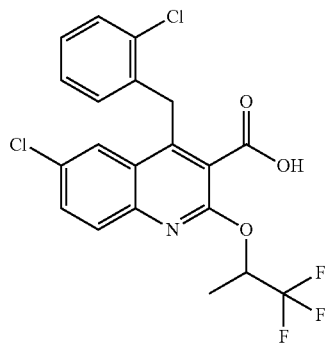 [SMILES: CC(Oc1nc2ccc(Cl)cc2c(Cc2ccccc2Cl)c1C(=O)O)C(F)(F)F]

Step A: 6-Chloro-4-(2-chloro-benzyl)-2-(2,2,2-trifluoro-1-methyl-ethoxy)-quinoline-3-carboxylic acid ethyl ester

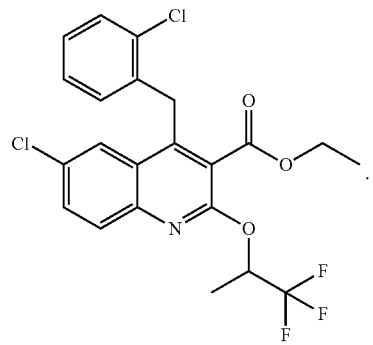 [SMILES: CCOC(=O)c1c(OC(C)C(F)(F)F)nc2ccc(Cl)cc2c1Cc1ccccc1Cl]

This compound was prepared in analogy to example 29 step D from 6-chloro-4-(2-chloro-benzyl)-2-trifluoromethanesulfonyloxy-quinoline-3-carboxylic acid ethyl ester (prepared as described in example 29 step C, 75 mg, 0.15 mmol) and 1,1,1-trifluoro-propan-2-ol (0.026 ml, 0.2 mmol). Off white solid (10 mg, 14%). LC-MS (ESI): 472 (M+H)+.

Step B: 6-Chloro-4-(2-chloro-benzyl)-2-(2,2,2-trifluoro-1-methyl-ethoxy)-quinoline-3-carboxylic acid

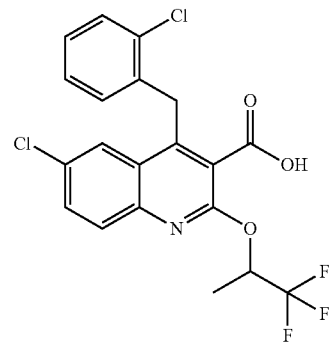 [SMILES: CC(Oc1nc2ccc(Cl)cc2c(Cc2ccccc2Cl)c1C(=O)O)C(F)(F)F]

The title compound was prepared in analogy to example 12 step B from 6-chloro-4-(2-chloro-benzyl)-2-(2,2,2-trifluoro-1-methyl-ethoxy)-quinoline-3-carboxylic acid ethyl ester (35 mg, 0.074 mmol) and 1N NaOH. Pale brown solid (21 mg, 64%). LC-MS (ESI): 442 (M+H)+.

Example 96

6-Chloro-4-(3-chloro-phenyl)-2-(2,2,2-trifluoro-1-methyl-ethoxy)-quinoline-3-carboxylic acid

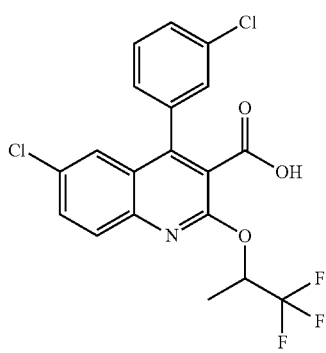 [SMILES: CC(Oc1nc2ccc(Cl)cc2c(-c2cccc(Cl)c2)c1C(=O)O)C(F)(F)F]

Step A: 6-Chloro-4-(3-chloro-phenyl)-2-(2,2,2-trifluoro-1-methyl-ethoxy)-quinoline-3-carboxylic acid tert-butyl ester

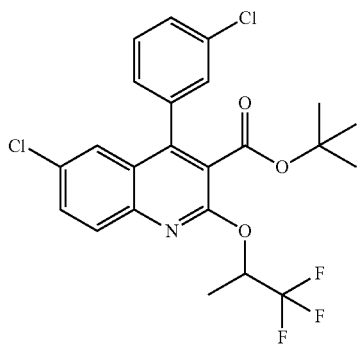 [SMILES: CC(Oc1nc2ccc(Cl)cc2c(-c2cccc(Cl)c2)c1C(=O)OC(C)(C)C)C(F)(F)F]

The title compound was prepared in analogy to example 92 step A from 6-chloro-4-(3-chloro-phenyl)-2-trifluoromethanesulfonyloxy-quinoline-3-carboxylic acid tert-butyl ester (prepared as described in example 91 step C, 150 mg, 0.29 mmol) and 1,1,1-trifluoro-propan-2-ol (0.052 ml, 0.58 mmol). Sticky pale yellow liquid (70 mg, 50%). LC-MS (ESI): 486 (M+H)+.

Step B: 6-Chloro-4-(3-chloro-phenyl)-2-(2,2,2-trifluoro-1-methyl-ethoxy)-quinoline-3-carboxylic acid

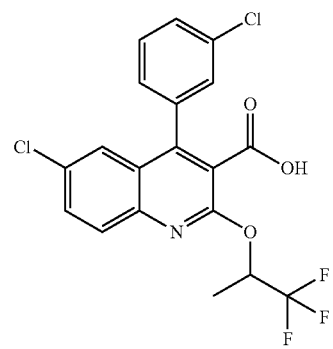 [SMILES: CC(Oc1nc2ccc(Cl)cc2c(-c2cccc(Cl)c2)c1C(=O)O)C(F)(F)F]

The title compound was prepared in analogy to example 91 step E from 6-chloro-4-(3-chloro-phenyl)-2-(2,2,2-trifluoro-1-methyl-ethoxy)-quinoline-3-carboxylic acid tert-butyl ester (60 mg, 0.12 mmol) and 4N HCl in dioxane. Off white solid (21 mg, 40%). LC-MS (ESI): 428 (M−H)−.

Example 97

6-Chloro-4-(3-chloro-phenyl)-2-isopropoxy-quinoline-3-carboxylic acid

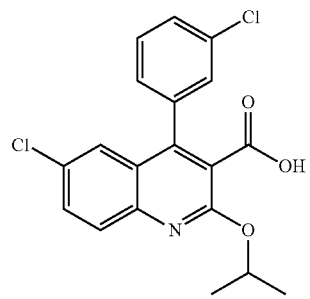 [SMILES: CC(C)Oc1nc2ccc(Cl)cc2c(-c2cccc(Cl)c2)c1C(=O)O]

Step A: 6-Chloro-4-(3-chloro-phenyl)-2-isopropoxy-quinoline-3-carboxylic acid tert-butyl ester

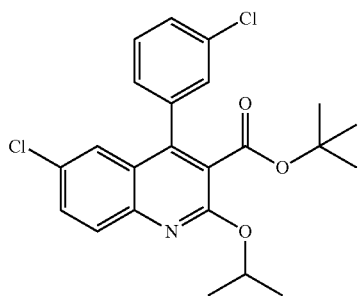 [SMILES: CC(C)Oc1nc2ccc(Cl)cc2c(-c2cccc(Cl)c2)c1C(=O)OC(C)(C)C]

To the stirred solution of 6-chloro-4-(3-chloro-phenyl)-2-hydroxy-quinoline-3-carboxylic acid tert-butyl ester (prepared as described in example 91 step B, 400 mg, 1.02 mmol) in 8 ml DMF was added NaH (60%, 65 mg, 1.54 mmol) portion wise at 0° C. and the resulting reaction mixture was stirred for 30 min at 25° C. Then the reaction mixture was cooled to 0° C. and a solution of 2-bromo-propane (0.192 ml, 2.05 mmol) was added dropwise in 2 ml DMF. The reaction mixture was stirred for 16 h at 50° C. and then quenched with saturated aqueous ammonium chloride solution (10 ml). Subsequently the mixture was diluted with water (25 ml) and extracted with ethyl acetate (3×60 ml). The organic phases were combined and was washed with brine (25 ml), dried over sodium sulfate and concentrated in vacuo to give a crude residue which was purified by column chromatography eluting with 2% ethyl acetate in hexane to yield 6-chloro-4-(3-chloro-phenyl)-2-isopropoxy-quinoline-3-carboxylic acid tert-butyl ester (290 mg, 65% yield) as an off white solid. LC-MS (ESI): 432 (M+H)$^+$.

Step B: 6-Chloro-4-(3-chloro-phenyl)-2-isopropoxy-quinoline-3-carboxylic acid

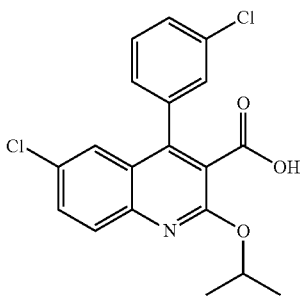

To the stirred solution of 6-chloro-4-(3-chloro-phenyl)-2-isopropoxy-quinoline-3-carboxylic acid tert-butyl ester (100 mg, 0.23 mmol) in DCM (4 ml) was added 0.2 ml TFA and reaction mixture was refluxed for 16 h. After cooling, the volatiles were removed under vacuum and the reaction mixture was diluted with ethyl acetate (40 ml) and washed with NaHCO$_3$ solution (10 ml). The separated organic layer was washed with brine (7 ml), dried over sodium sulfate and concentrated in vacuo to give a crude residue which was purified by flash column chromatography (100% ethyl acetate) to afford 6-chloro-4-(3-chloro-phenyl)-2-isopropoxy-quinoline-3-carboxylic acid (14 mg, 16%) as an off white solid. LC-MS (ESI): 374 (M–H)$^-$.

Example 98

[6-Chloro-4-(3-isopropyl-phenyl)-3-(1H-tetrazol-5-yl)-quinolin-2-yl]-diethyl-amine

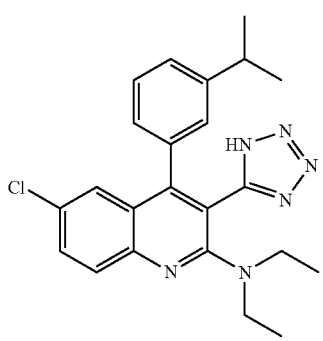 [SMILES: CCN(CC)c1nc2ccc(Cl)cc2c(-c2cccc(C(C)C)c2)c1-c1nnn[nH]1]

Step A: 6-Chloro-4-hydroxy-2-oxo-1,2-dihydro-quinoline-3-carbonitrile

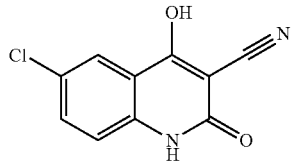 [SMILES: N#Cc1c(O)c2cc(Cl)ccc2[nH]c1=O]

A solution of 6-chloro-1,2-dihydro-4H-3,1-benzoxazine-2,4-дione (2 g, 10.1 mmol, Eq: 1.00), ethyl cyanoacetate (1.15 g, 1.08 ml, 10.1 mmol, Eq: 1.00) and triethylamine (14.5 g, 20.0 ml, 143 mmol, Eq: 14.2) in DMF (1.00 ml) was stirred at RT for 65 h. Then 1N HCl was added and the reaction mixture was extracted with ethyl acetate (3×). The combined extracts were washed brine. An off-white solid precipitated and was filtered off (337 mg). MS (ESI): 219.1 (M–H)$^-$.

Step B: Trifluoro-methanesulfonic acid 6-chloro-3-cyano-2-oxo-1,2-dihydro-quinolin-4-yl ester

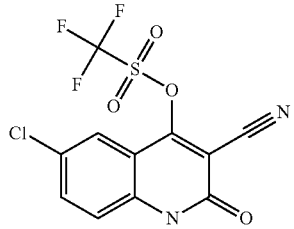 [SMILES: N#Cc1c(OS(=O)(=O)C(F)(F)F)c2cc(Cl)ccc2[nH]c1=O]

Sodium hydride (55% in mineral oil, 514 mg, 11.8 mmol, Eq: 1.3) was added to a solution of 6-chloro-4-hydroxy-2-oxo-1,2-dihydro-quinoline-3-carbonitrile (2 g, 9.07 mmol, Eq: 1.00) in DMF (20 ml) and the resulting suspension was stirred for 30 min at RT. Then a solution of 1,1,1-trifluoro-N-phenyl-N-(trifluoromethylsulfonyl)methanesulfonamide (4.21 g, 11.8 mmol, Eq: 1.3) in DMF (20 ml) was added and the reaction mixture was stirred at RT for 2 h. Then water was added and the mixture was extracted with ethyl acetate (3×). The combined organic layers were washed with water (3×) and brine, dried with Na$_2$SO$_4$ and evaporated. The remaining residue was purified by column chromatography (silica gel, EtOAc) to afford the title compound as white solid (1.38 g). MS (ESI): 352.9 (M+H)$^+$.

Step C: 6-Chloro-4-(3-isopropyl-phenyl)-2-oxo-1,2-dihydro-quinoline-3-carbonitrile

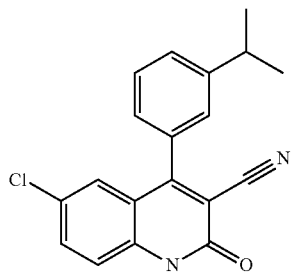 [SMILES: CC(C)c1cccc(-c2c(C#N)c(=O)[nH]c3ccc(Cl)cc23)c1]

A mixture of trifluoro-methanesulfonic acid 6-chloro-3-cyano-2-oxo-1,2-dihydro-quinolin-4-yl ester (400 mg, 1.13 mmol, Eq: 1.00), 3-isopropylphenylboronic acid (223 mg, 1.36 mmol, Eq: 1.2), potassium phosphate tribasic (361 mg, 1.7 mmol, Eq: 1.5) and tetrakis(triphenylphosphine)palladium (0) (65.5 mg, 56.7 µmol, Eq: 0.05) in dioxane (8.00 ml) was heated to 100° C. for 4 h. The reaction mixture was cooled to RT, diluted with sat. NH$_4$Cl solution and extracted with ethyl acetate (2×). The combined extracts were washed with sat. NH$_4$Cl solution and brine, dried with Na$_2$SO$_4$ and evaporated. Diethylether was added to the remaining red solid and the mixture was stirred for 2 h. Then the orange solid was filtered off (222 mg). MS (ESI): 323.2 (M+H)$^+$.

Step D: 2,6-Dichloro-4-(3-isopropyl-phenyl)-quinoline-3-carbonitrile

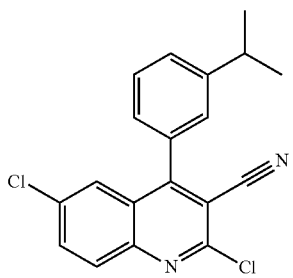 [SMILES: CC(C)c1cccc(-c2c(C#N)c(Cl)nc3ccc(Cl)cc23)c1]

A mixture of 6-chloro-4-(3-isopropyl-phenyl)-2-oxo-1,2-dihydro-quinoline-3-carbonitrile (142 mg, 440 µmol, Eq: 1.00) and phosphorus oxychloride (2.02 g, 1.23 ml, 13.2 mmol, Eq: 30) was heated to reflux for 3 h. The reaction mixture was then poured into water and extracted with DCM (3×). The combined organic layers were washed with water and brine, dried with Na$_2$SO$_4$ and evaporated to afford the title compound (126 mg, light yellow solid). MS (ESI): 343.1 (M+H)$^+$.

Step E: 6-Chloro-2-diethylamino-4-(3-isopropyl-phenyl)-quinoline-3-carbonitrile

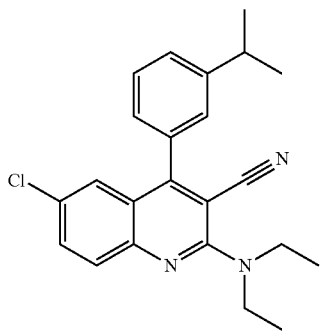 [SMILES: CCN(CC)c1nc2ccc(Cl)cc2c(-c2cccc(C(C)C)c2)c1C#N]

A mixture of 2,6-dichloro-4-(3-isopropyl-phenyl)-quinoline-3-carbonitrile (128 mg, 375 µmol, Eq: 1.00), diethylamine (54.9 mg, 78.4 µl, 750 µmol, Eq: 2) and triethylamine (114 mg, 157 µl, 1.13 mmol, Eq: 3) in DMF (1 ml) was heated first to 120° C. for 20 min and then to 180° C. for additional 20 min in a microwave. Then water was added and the mixture was extracted with ethyl acetate (3×). The combined extracts were washed with water and brine, dried with Na$_2$SO$_4$ and evaporated. The remaining residue was purified by column chromatography (silica gel, heptane/EtOAc 90:10 to 85:15) to afford the title compound as yellow oil (128 mg). MS (ESI): 377.1 (M−H)$^-$.

Step F: [6-Chloro-4-(3-isopropyl-phenyl)-3-(1H-tetrazol-5-yl)-quinolin-2-yl]-diethyl-amine

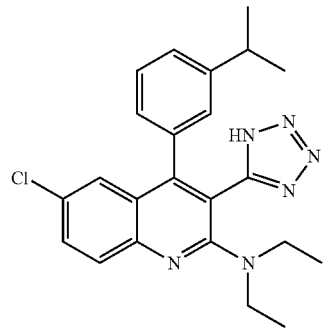 [SMILES: CCN(CC)c1nc2ccc(Cl)cc2c(-c2cccc(C(C)C)c2)c1-c1nnn[nH]1]

The title compound was prepared in analogy to example 27 step D from 6-chloro-2-diethylamino-4-(3-isopropyl-phenyl)-quinoline-3-carbonitrile. Off-white solid. MS (ESI): 421.2 (M+H)$^+$.

Example 99

[6-Chloro-4-(3-isopropyl-phenyl)-3-(1H-tetrazol-5-yl)-quinolin-2-yl]-ethyl-methyl-amine

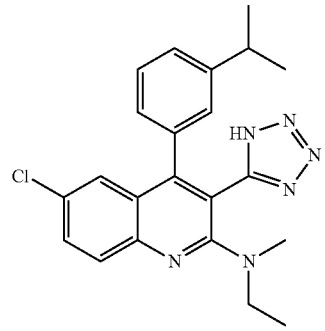 [SMILES: CCN(C)c1nc2ccc(Cl)cc2c(-c2cccc(C(C)C)c2)c1-c1nnn[nH]1]

Step A: 6-Chloro-2-(ethyl-methyl-amino)-4-(3-isopropyl-phenyl)-quinoline-3-carbonitrile

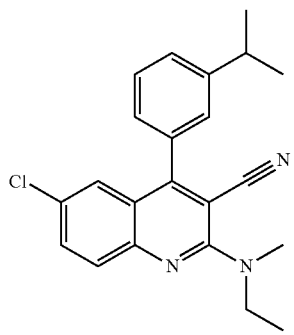 [SMILES: CCN(C)c1nc2ccc(Cl)cc2c(-c2cccc(C(C)C)c2)c1C#N]

The title compound was prepared in analogy to example 98 step E from 2,6-dichloro-4-(3-isopropyl-phenyl)-quinoline-3-carbonitrile (prepared as described in example 98 step D) and ethyl-methyl-amine. Light yellow oil. MS (ESI): 364.2 (M+H)+.

Step B: [6-Chloro-4-(3-isopropyl-phenyl)-3-(1H-tetrazol-5-yl)-quinolin-2-yl]-ethyl-methyl-amine

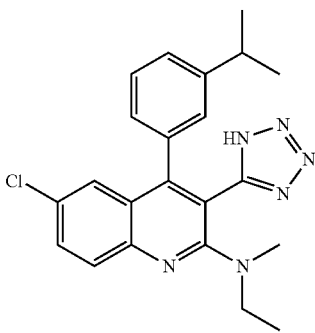 [SMILES: CCN(C)c1nc2ccc(Cl)cc2c(-c2cccc(C(C)C)c2)c1-c1nnn[nH]1]

The title compound was prepared in analogy to example 27 step D from 6-chloro-2-(ethyl-methyl-amino)-4-(3-isopropyl-phenyl)-quinoline-3-carbonitrile. Light yellow solid. MS (ESI): 405.4 (M−H)−.

Example 100

6-Chloro-8-fluoro-4-phenyl-2-(piperidin-1-yl)-3-(2H-tetrazol-5-yl)quinoline

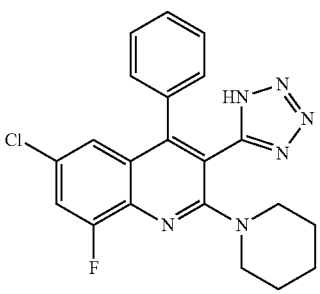 [SMILES: Fc1cc(Cl)cc2c(-c3ccccc3)c(-c3nnn[nH]3)c(N3CCCCC3)nc12]

Step A:
2-Amino-3-fluoro-N-methoxy-N-methyl-benzamide

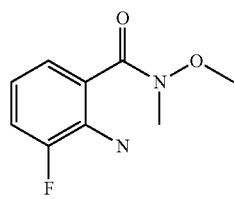

To a suspension of N,O-dimethylhydroxylamine hydrochloride (703 mg, 7.21 mmol) in ethanol (5.4 ml) and water (0.6 ml) was added triethylamine (729 mg, 1.00 ml, 7.21 mmol) and the mixture was stirred for 10 min at room temperature. Then 8-fluoro-1H-benzo[d][1,3]oxazine-2,4-dione (870 mg, 4.8 mmol) and additional ethanol (2 ml) were added and the reaction mixture was heated to reflux for 3.5 h. After cooling to room temperature, the mixture was poured onto ice/saturated NaHCO3-solution, extracted with EtOAc and the combined extracts were washed with water and brine, dried with Na2SO4 and evaporated. The remaining residue was purified by column chromatography (silica gel, heptane/EtOAc 80:20-70:30) to afford the title compound (765 mg, 80%) as light brown oil. MS (ESI): 199.2 (M+H)+.

Step B: 2-Amino-5-chloro-3-fluoro-N-methoxy-N-methyl-benzamide

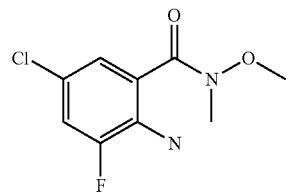

To a solution of 2-amino-3-fluoro-N-methoxy-N-methyl-benzamide (765 mg, 3.86 mmol) in acetic acid (18 ml) was added 1,3-dichloro-5,5-dimethylimidazolidine-2,4-dione (783 mg, 2.7 mmol) at room temperature. The orange solution was stirred over night and was then poured carefully onto ice/saturated NaHCO3-solution. The mixture was extracted with EtOAc and the combined extracts were washed with brine, dried with Na2SO4 and evaporated. The remaining residue was purified by column chromatography (silica gel, heptane/EtOAc 90:10-80:20) to afford the title compound (544 mg, 61%) as light brown solid. MS (ESI): 233.0 (M+H)+.

Step C: (2-Amino-5-chloro-3-fluoro-phenyl)-phenyl-methanone

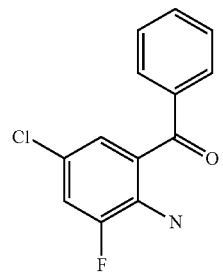 [SMILES: Nc1c(F)cc(Cl)cc1C(=O)c1ccccc1]

To a solution of 2-amino-5-chloro-3-fluoro-N-methoxy-N-methyl-benzamide (250 mg, 1.07 mmol) in diethyl ether (5 ml) was added phenylmagnesium bromide (2.69 ml, 1M in THF, 2.69 mmol) dropwise at 0° C. The resulting mixture was stirred for 2.5 h at 0° C. and the quenched by addition of saturated NH4Cl solution. The mixture was extracted with EtOAc and the combined organic extracts were washed with brine, dried with Na2SO4 and evaporated. The remaining residue was purified by column chromatography (silica gel, heptane/EtOAc 98:2-95:5) to afford the title compound (189 mg, 70%) as yellow solid. MS (ESI): 250.2 (M+H)+.

Step D: 6-Chloro-8-fluoro-2-oxo-4-phenyl-1,2-dihydro-quinoline-3-carbonitrile

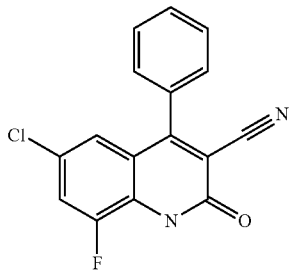 [SMILES: N#Cc1c(-c2ccccc2)c2cc(Cl)cc(F)c2[nH]c1=O]

2-Cyanoacetic acid (140 mg, 1.65 mmol) was co-evaporated with toluene two times and then suspended in dichloromethane (3 ml). One drop of DMF was added followed by dropwise addition of oxalyl chloride (304 mg, 206 µl, 2.4 mmol) at 0° C. The reaction mixture was stirred for 15 min at 0° C. and for another 2.5 h at room temperature. The solvent was then removed and the remaining residue was co-evaporated two times with dichloromethane. The residue was again dissolved in dichloromethane (3 ml) and a solution of (2-amino-5-chloro-3-fluoro-phenyl)-phenyl-methanone (374 mg, 1.5 mmol) and triethylamine (152 mg, 209 µl, 1.5 mmol) in dichloromethane (3 ml) was added dropwise at 0° C. The mixture was stirred at room temperature overnight. Then triethylamine (227 mg, 313 µl, 2.25 mmol) was added dropwise and the reaction mixture was stirred for 2 h before dichloromethane and water were added and the phases were separated. The aqueous layer was extracted with dichloromethane and the combined organic layers were washed with water and brine, dried with Na₂SO₄ and evaporated. The remaining residue was purified by column chromatography (silica gel, heptane/EtOAc 80:20-45:55) to afford the title compound (146 mg, 33%) as white solid. MS (ESI): 299.3 (M+H)⁺.

Step E: Trifluoro-methanesulfonic acid 6-chloro-3-cyano-8-fluoro-4-phenyl-quinolin-2-yl ester

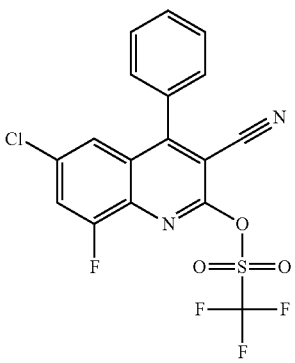 [SMILES: N#Cc1c(OS(=O)(=O)C(F)(F)F)nc2c(F)cc(Cl)cc2c1-c1ccccc1]

A solution of 6-chloro-8-fluoro-2-oxo-4-phenyl-1,2-dihydro-quinoline-3-carbonitrile (135 mg, 0.452 mmol) in DMF (2.5 ml) was added dropwise to a suspension of sodium hydride (25.7 mg, 55% in mineral oil, 0.588 mmol) in DMF (0.8 ml) at room temperature. The suspension was stirred for 45 min and then a solution of 1,1,1-trifluoro-N-phenyl-N-(trifluoromethylsulfonyl)methanesulfonamide (210 mg, 0.588 mmol) in DMF (2.5 ml) was added dropwise. The reaction mixture was stirred for 2 d. then a saturated NH₄Cl solution was added and the mixture was extracted with dichloromethane. The combined organic layers were washed with water and brine, dried with Na₂SO₄ and evaporated. The remaining residue was purified by column chromatography (silica gel, heptane/EtOAc 95:5-70:30) to afford the title compound (195 mg, 100%) as yellow solid.

Step F: 6-Chloro-8-fluoro-4-phenyl-2-piperidin-1-yl-quinoline-3-carbonitrile

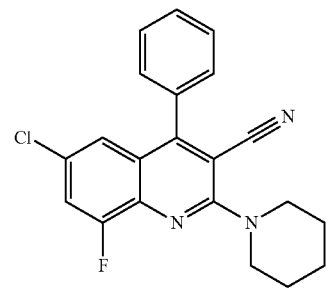 [SMILES: N#Cc1c(N2CCCCC2)nc2c(F)cc(Cl)cc2c1-c1ccccc1]

A mixture of trifluoro-methanesulfonic acid 6-chloro-3-cyano-8-fluoro-4-phenyl-quinolin-2-yl ester (189 mg, 0.439 mmol), piperidine (150 mg, 174 µl, 1.76 mmol) and potassium carbonate (121 mg, 0.878 mmol) in THF (6 ml) was heated to 70° C. for 60 min. The yellow suspension was cooled to room temperature, diluted with water and extracted with EtOAc. The combined organic layers were washed with brine, dried with Na₂SO₄ and evaporated. The remaining residue was triturated with dichloromethane and the off-white solid was filtered off. The filtrate was evaporated and the remaining residue was purified by column chromatography (silica gel, heptane/EtOAc 98:2-95:5) to afford the title compound (60 mg, 37%) as yellow solid. MS (ESI): 366.4 (M+H)⁺.

Step G: 6-Chloro-8-fluoro-4-phenyl-2-(piperidin-1-yl)-3-(2H-tetrazol-5-yl)quinoline

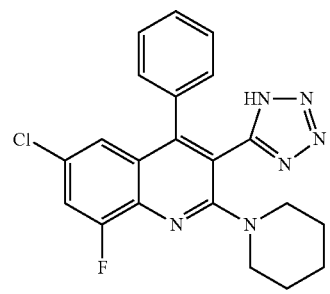 [SMILES: Fc1cc(Cl)cc2c(-c3ccccc3)c(-c3nnn[nH]3)c(N3CCCCC3)nc12]

The title compound was prepared in analogy to example 27 step D from 6-chloro-8-fluoro-4-phenyl-2-piperidin-1-yl-quinoline-3-carbonitrile. Light yellow solid. MS (ESI): 409.4 (M+H)⁺.

Example 101

6-Chloro-2-(pentan-3-yl)-4-phenyl-3-(1H-tetrazol-5-yl)quinoline

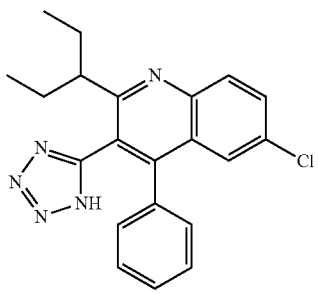 [SMILES: CCC(CC)c1nc2ccc(Cl)cc2c(-c2ccccc2)c1-c1nnn[nH]1]

Step A: 4-Ethyl-3-oxo-hexanenitrile

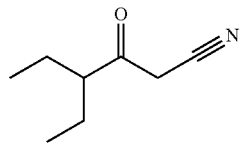

To a solution of n-butyllithium (56.6 ml, 1.6M solution in hexane, 90.6 mmol) in THF (60 ml) was added a solution of acetonitrile (3.71 g, 4.73 ml, 90.5 mmol) in THF (12 ml) slowly at a temperature between −78° C. and −70° C. Then a solution of ethyl 2-ethylbutanoate (6.52 g, 7.5 ml, 45.2 mmol) in THF (17 ml) was added and the reaction mixture was stirred for 1 h at −78° C. and for 1.5 h at −45° C. Then cold 2M HCl was added carefully to adjust the pH to 7. The mixture was extracted with DCM and the combined extracts were dried with MgSO$_4$ and evaporated. The crude material was purified by chromatography (silica gel, heptane/EtOAc 9:1) to afford the title compound (6.29 g, 100%) as light yellow oil. MS (ESI): 138.3 (M−H)$^-$.

Step B: 6-Chloro-2-(1-ethyl-propyl)-4-phenyl-quinoline-3-carbonitrile

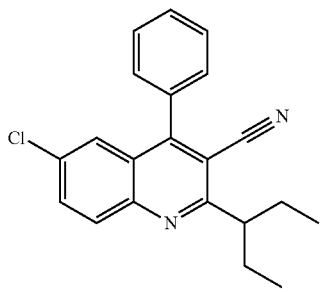

A solution of (2-amino-5-chlorophenyl)(phenyl)methanone (700 mg, 3.02 mmol), 4-ethyl-3-oxo-hexanenitrile (505 mg, 3.63 mmol) and methanesulfonic acid (290 mg, 196 µl, 3.02 mmol) in toluene (40 ml) was stirred for 5 min at room temperature and then heated to reflux using a Dean-Stark-trap to remove water. After 2.5 h the mixture was cooled to room temperature, washed with saturated NaHCO$_3$ solution and water and was evaporated. n-Heptane was added to the remaining residue and the off-white precipitate that formed was filtered off. The precipitate was again dissolved in EtOAc and the solution was washed with saturated NaHCO$_3$ solution and water and was evaporated to yield the title compound (461 mg, 46%) as yellow solid. The filtrate was concentrated and the remaining residue was purified by column chromatography (silica gel, heptane/EtOAc 100:0-0:100) to afford a second batch of the title compound (347 mg, 34%) as yellow solid. MS (ESI): 335.1 (M+H)$^+$.

Step C: 6-Chloro-2-(pentan-3-yl)-4-phenyl-3-(1H-tetrazol-5-yl)quinoline

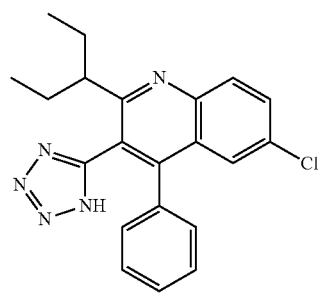 [SMILES: CCC(CC)c1nc2ccc(Cl)cc2c(-c2ccccc2)c1-c1nnn[nH]1]

The title compound was prepared in analogy to example 27 step D from 6-chloro-2-(1-ethyl-propyl)-4-phenyl-quinoline-3-carbonitrile. White solid. MS (ESI): 378.5 (M+H)$^+$.

Example 102

4-Phenyl-2-(piperidin-1-yl)-3-(1H-tetrazol-5-yl)-6-(trifluoromethyl)quinoline

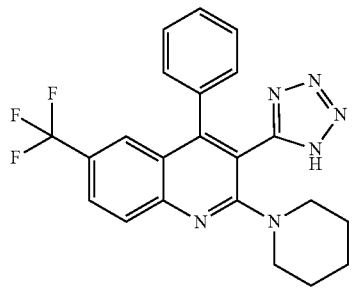 [SMILES: FC(F)(F)c1ccc2nc(N3CCCCC3)c(-c3nnn[nH]3)c(-c3ccccc3)c2c1]

Step A: 4-Phenyl-3-(1H-tetrazol-5-yl)-6-trifluoromethyl-1H-quinolin-2-one

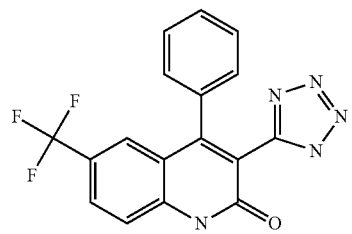 [SMILES: O=c1[nH]c2ccc(C(F)(F)F)cc2c(-c2ccccc2)c1-c1nnn[nH]1]

(2-Amino-5-(trifluoromethyl)phenyl)(phenyl)methanone (300 mg, 1.13 mmol) and 2-(1H-tetrazol-5-yl)acetic acid (145 mg, 1.13 mmol) were suspended in ethyl acetate (10 ml). Then 1-propanephosphonic acid cyclic anhydride (2.02 g, 1.89 ml, 50% solution in EtOAc, 3.18 mmol) was added and the mixture was heated to 50° C. overnight. Then water was added at room temperature and the resulting precipitate was filtered, washed with water and heptane and dried at 50° C. and 15 mbar to afford the title compound (380 mg, 94%) as yellow solid. MS (ESI): 356.5 (M−H)⁻.

Step B: 2-Chloro-4-phenyl-3-(1H-tetrazol-5-yl)-6-trifluoromethyl-quinoline

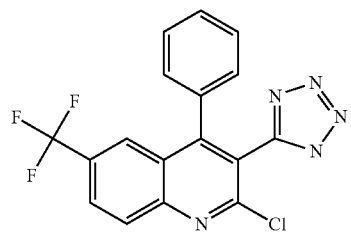 [SMILES: FC(F)(F)c1ccc2nc(Cl)c(-c3nnn[nH]3)c(-c3ccccc3)c2c1]

4-Phenyl-3-(1H-tetrazol-5-yl)-6-trifluoromethyl-1H-quinolin-2-one (160 mg, 448 µmol) was twice co-evaporated with toluene (5 ml). Then toluene (5 ml), phosphorus oxychloride (446 mg, 271 µl, 2.91 mmol) and N,N-diisopropylethylamine (72.3 mg, 97.8 µl, 560 µmol) were added and the mixture was heated to 70° C. for 5 h. Then all volatiles were removed and toluene (5 ml) was added and evaporated twice. Then ethanol (5 ml) was added and evaporated. Water and methanol were added to the remaining residue and the solid was filtered off and dried to obtain the title compound (107 mg, 64%) as brown solid. MS (ESI): 374.3 (M−H)⁻.

Step C: 4-Phenyl-2-(piperidin-1-yl)-3-(1H-tetrazol-5-yl)-6-(trifluoromethyl)quinoline

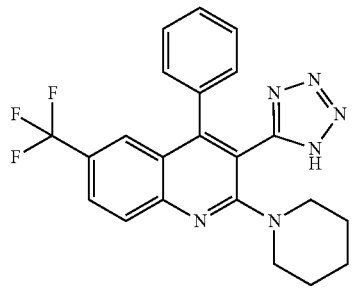 [SMILES: FC(F)(F)c1ccc2nc(N3CCCCC3)c(-c3nnn[nH]3)c(-c3ccccc3)c2c1]

A mixture of 2-chloro-4-phenyl-3-(1H-tetrazol-5-yl)-6-trifluoromethyl-quinoline (105 mg, 279 µmol), piperidine (47.6 mg, 55.3 µl, 559 µmol) and triethylamine (84.8 mg, 117 µl, 838 µmol) in DMA (2 ml) was heated to 100° C. in a sealed tube. After 4 h 0.1N HCl was added at room temperature and the mixture was extracted with EtOAc. The combined organic layers were washed with 0.1N HCl and brine and dried with Na₂SO₄. The remaining brown oil was purified by chromatography (silica gel, DCM/MeOH 98:2 to 95:5). The product fractions were concentrated and the remaining solid was dissolved in EtOAc, filtered through silica gel and evaporated. The remaining residue was finally purified by preparative thin-layer chromatography (DCM/ MeOH 95:5) to obtain the title compound (22 mg, 18%) as light yellow solid. MS (ESI): 425.4 (M+H)⁺.

Example 103

Diethyl-[4-phenyl-3-(2H-tetrazol-5-yl)-6-trifluoromethyl-quinolin-2-yl]-amine

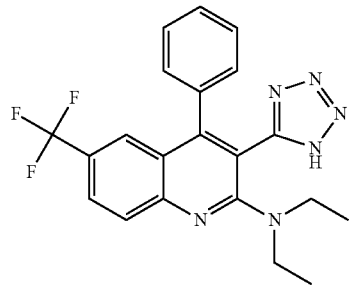 [SMILES: CCN(CC)c1nc2ccc(C(F)(F)F)cc2c(-c2ccccc2)c1-c1nnn[nH]1]

The title compound was prepared in analogy to example 102 step C from 2-chloro-4-phenyl-3-(1H-tetrazol-5-yl)-6-trifluoromethyl-quinoline (prepared as described in example 102 step B) and diethylamine. Light yellow solid. MS (ESI): 413.4 (M+H)⁺.

Example 104

6-Chloro-2-cyclobutyl-4-phenyl-3-(1H-tetrazol-5-yl)quinoline

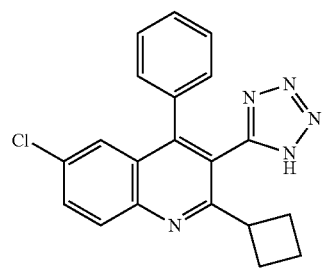 [SMILES: Clc1ccc2nc(C3CCC3)c(-c3nnn[nH]3)c(-c3ccccc3)c2c1]

Step A: 3-Cyclobutyl-3-oxo-propionitrile

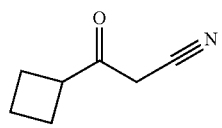

The title compound was prepared in analogy to example 101 step A from cyclobutanecarboxylic acid ethyl ester and acetonitrile. Light yellow oil.

Step B: 6-Chloro-2-cyclobutyl-4-phenyl-quinoline-3-carbonitrile

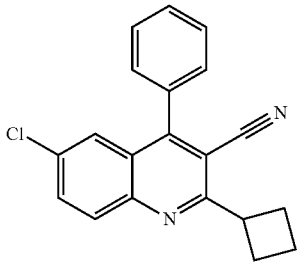 [SMILES: N#Cc1c(C2CCC2)nc2ccc(Cl)cc2c1-c1ccccc1]

The title compound was prepared in analogy to example 101 step B from (2-amino-5-chlorophenyl)(phenyl)methanone and 3-cyclobutyl-3-oxo-propionitrile. Light yellow powder. MS (ESI): 319.3 (M+H)+.

Step C: 6-Chloro-2-cyclobutyl-4-phenyl-3-(1H-tetrazol-5-yl)quinoline

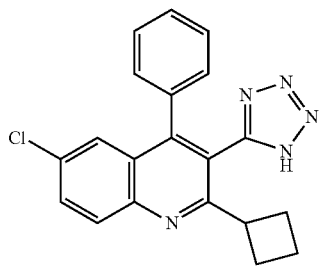 [SMILES: Clc1ccc2nc(C3CCC3)c(-c3nnn[nH]3)c(-c3ccccc3)c2c1]

The title compound was prepared in analogy to example 27 step D from 6-chloro-2-cyclobutyl-4-phenyl-3-(1H-tetrazol-5-yl)quinoline. Off-white solid. MS (ESI): 362.4 (M+H)+.

Example 105

6-Chloro-2-cyclopentyl-7-fluoro-4-phenyl-3-(2H-tetrazol-5-yl)quinoline

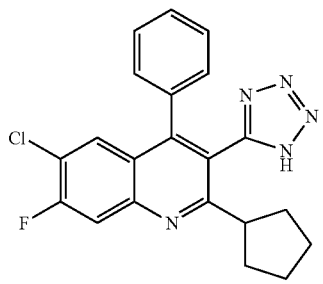 [SMILES: Fc1cc2nc(C3CCCC3)c(-c3nnn[nH]3)c(-c3ccccc3)c2cc1Cl]

Step A: 3-Cyclopentyl-3-oxo-propionitrile

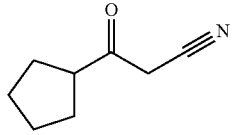

To a suspension of sodium hydride (1.87 g, 55% in mineral oil, 42.9 mmol) in THF (10 ml) was added a solution of methyl cyclopentanecarboxylate (5 g, 39.0 mmol) and acetonitrile (1.92 g, 2.45 ml, 46.8 mmol) in THF (3 ml) dropwise at 70° C. The mixture was heated to 70° C. overnight, then cooled to room temperature, diluted with 1N HCl and extracted with EtOAc. The combined organic layers were washed with water and brine, dried with $Na_2SO_4$ and evaporated. The remaining residue was purified by column chromatography (silica gel, heptane/EtOAc 95:5-85:15) to afford the title compound (4105 mg, 77%) as light yellow liquid.

Step B: 4-Chloro-5-fluoro-2-iodo-phenylamine

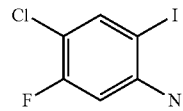

Iodine chloride (20.6 ml, 1M solution in DCM, 20.6 mmol) was added dropwise to a solution of 4-chloro-3-fluoroaniline (2 g, 13.7 mmol) in methanol (35 ml) at 0° C. and the reaction mixture was stirred for 1 h at room temperature. Volatiles were removed under reduced pressure, water was added and the mixture was extracted with dichloromethane. The combined organic layers were washed with water, dried with $Na_2SO_4$ and evaporated. The remaining residue was purified by chromatography with three consecutive columns (silica gel, heptane/EtOAc 98:2-93:7 and twice heptane/EtOAc 98:2-95:5) to obtain the title compound (2.51 g, 67%) as dark red solid. MS (ESI): 272.1 (M+H)+.

Step C: 2-Amino-5-chloro-4-fluoro-benzonitrile

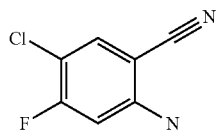 [SMILES: N#Cc1cc(Cl)c(F)cc1N]

A solution of 4-chloro-5-fluoro-2-iodo-phenylamine (2.5 g, 9.21 mmol) and copper (I) cyanide (1.65 g, 18.4 mmol) in DMA (45 ml) was heated to 130° C. overnight. Most of the DMA was removed under reduced pressure and the remaining residue was diluted with EtOAc and dichloromethane. The slurry was filtered and the filter cake was washed with dichloromethane and EtOAc. The filtrate was concentrated and the remaining residue was purified by column chromatography (silica gel, heptane/EtOAc 98:2-85:15) to afford the title compound (1232 mg, 78%) as light red solid. MS (ESI): 169.2 (M−H)−.

Step D: (2-Amino-5-chloro-4-fluoro-phenyl)-phenyl-methanone

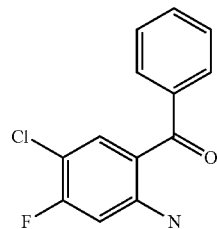 [SMILES: Nc1cc(F)c(Cl)cc1C(=O)c1ccccc1]

A solution of phenylmagnesium bromide (7.18 ml, 3M solution in diethyl ether, 21.5 mmol) in diethyl ether (15 ml) was added to a solution of 2-amino-5-chloro-4-fluoro-benzonitrile (1225 mg, 7.18 mmol) in diethyl ether (20 ml) at 0° C. The reaction mixture was then stirred at reflux for 2 h, cooled to room temperature and quenched carefully by addition of 2N HCl (~40 ml). The mixture was heated to 55° C. for 3 h and then cooled to room temperature again. 3N NaOH (~20 ml) was added carefully at 0° C. to adjust the pH to 9. The mixture was extracted with EtOAc and the combined extracts were washed with brine, dried with Na$_2$SO$_4$ and evaporated. The remaining residue was purified by column chromatography (silica gel, heptane/EtOAc 95:5-90:10) to afford the title compound (1667 mg, 93%) as yellow solid. MS (ESI): 250.3 (M+H)$^+$.

Step E: 6-Chloro-2-cyclopentyl-7-fluoro-4-phenyl-quinoline-3-carbonitrile

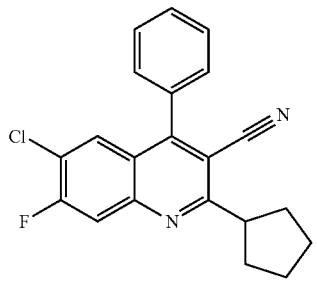 [SMILES: N#Cc1c(C2CCCC2)nc2cc(F)c(Cl)cc2c1-c1ccccc1]

The title compound was prepared in analogy to example 101 step B from (2-amino-5-chloro-4-fluoro-phenyl)-phenyl-methanone and 3-cyclopentyl-3-oxo-propionitrile. Off-white solid. MS (ESI): 351.4 (M+H)$^+$.

Step F: 6-Chloro-2-cyclopentyl-7-fluoro-4-phenyl-3-(2H-tetrazol-5-yl)quinoline

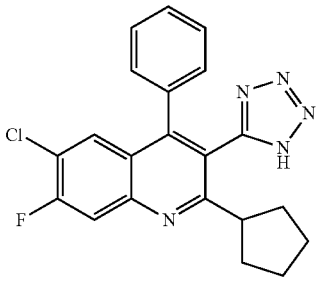 [SMILES: Fc1cc2nc(C3CCCC3)c(-c3nnn[nH]3)c(-c3ccccc3)c2cc1Cl]

The title compound was prepared in analogy to example 27 step D from 6-chloro-2-cyclopentyl-7-fluoro-4-phenyl-quinoline-3-carbonitrile. Off-white solid. MS (ESI): 394.4 (M+H)$^+$.

Example 106

6-Chloro-7-fluoro-2-(pentan-3-yl)-4-phenyl-3-(2H-tetrazol-5-yl)quinoline

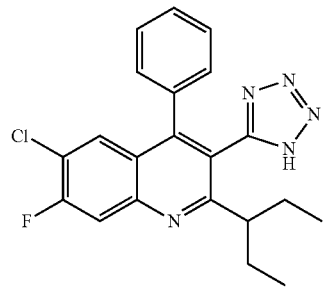 [SMILES: CCC(CC)c1nc2cc(F)c(Cl)cc2c(-c2ccccc2)c1-c1nnn[nH]1]

Step A: 6-Chloro-2-(1-ethyl-propyl)-7-fluoro-4-phenyl-quinoline-3-carbonitrile

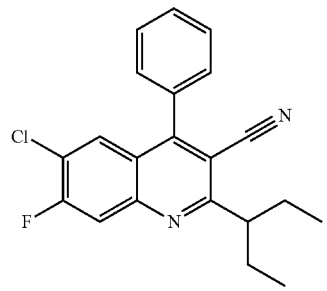

The title compound was prepared in analogy to example 101 step B from (2-amino-5-chloro-4-fluoro-phenyl)-phenyl-methanone (prepared as described in example 105 step D) and 4-ethyl-3-oxo-hexanenitrile (prepared as described in example 101 step A). Off-white solid. MS (ESI): 353.4 (M+H)$^+$.

Step B: 6-Chloro-7-fluoro-2-(pentan-3-yl)-4-phenyl-3-(2H-tetrazol-5-yl)quinoline

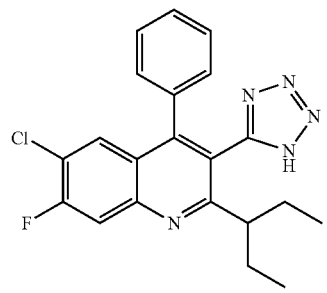

The title compound was prepared in analogy to example 27 step D from 6-chloro-2-(1-ethyl-propyl)-7-fluoro-4-phenyl-quinoline-3-carbonitrile. White solid. MS (ESI): 396.5 (M+H)$^+$.

Example 107

6-Chloro-7-fluoro-4-phenyl-2-(piperidin-1-yl)-3-(2H-tetrazol-5-yl)quinoline

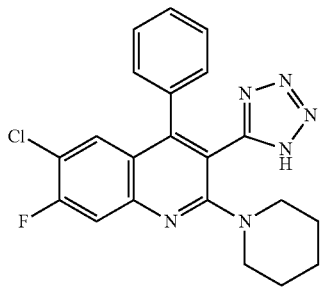 [SMILES: Fc1cc2nc(N3CCCCC3)c(-c3nnn[nH]3)c(-c3ccccc3)c2cc1Cl]

Step A: 6-Chloro-7-fluoro-4-phenyl-3-(1H-tetrazol-5-yl)-1H-quinolin-2-one

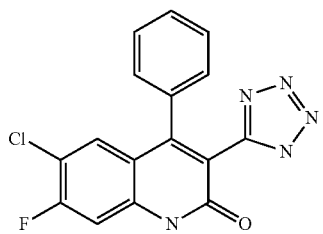 [SMILES: O=c1[nH]c2cc(F)c(Cl)cc2c(-c2ccccc2)c1-c1nnn[nH]1]

The title compound was prepared in analogy to example 102 step A from (2-amino-5-chloro-4-fluoro-phenyl)-phenyl-methanone (prepared as described in example 105 step D) and 2-(1H-tetrazol-5-yl)acetic acid. Off-white solid. MS (ESI): 342.4 (M+H)$^+$.

Step B: 2,6-Dichloro-7-fluoro-4-phenyl-3-(1H-tetrazol-5-yl)-quinoline

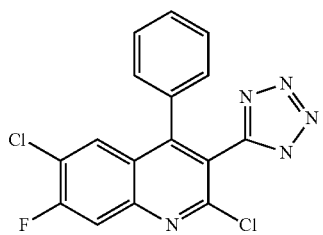 [SMILES: Fc1cc2nc(Cl)c(-c3nnn[nH]3)c(-c3ccccc3)c2cc1Cl]

The title compound was prepared in analogy to example 102 step B from 6-chloro-7-fluoro-4-phenyl-3-(1H-tetrazol-5-yl)-1H-quinolin-2-one. Light brown solid. MS (ESI): 360.2 (M+H)$^+$.

Step C: 6-Chloro-7-fluoro-4-phenyl-2-(piperidin-1-yl)-3-(2H-tetrazol-5-yl)quinoline

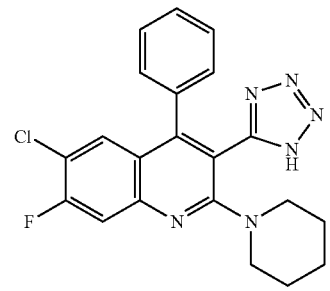 [SMILES: Fc1cc2nc(N3CCCCC3)c(-c3nnn[nH]3)c(-c3ccccc3)c2cc1Cl]

The title compound was prepared in analogy to example 102 step C from 2,6-dichloro-7-fluoro-4-phenyl-3-(1H-tetrazol-5-yl)-quinoline and piperidine. Off-white solid. MS (ESI): 409.5 (M+H)$^+$.

Example 108

6-Chloro-N,N-diethyl-7-fluoro-4-phenyl-3-(2H-tetrazol-5-yl)quinolin-2-amine

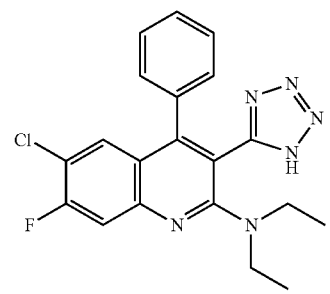 [SMILES: CCN(CC)c1nc2cc(F)c(Cl)cc2c(-c2ccccc2)c1-c1nnn[nH]1]

The title compound was prepared in analogy to example 102 step C from 2,6-dichloro-7-fluoro-4-phenyl-3-(1H-tetrazol-5-yl)-quinoline (prepared as described in example 107 step B) and diethylamine. Light brown solid. MS (ESI): 397.4 (M+H)$^+$.

Example 109

6-Chloro-4-(3-chlorophenyl)-2-(pentan-3-yl)-3-(1H-tetrazol-5-yl)quinoline

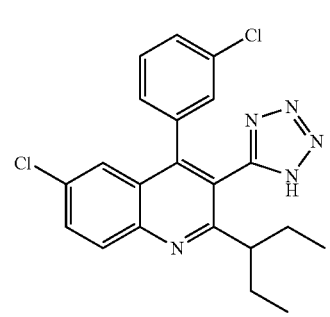

Step A: 6-Chloro-4-(3-chloro-phenyl)-2-(1-ethyl-propyl)-quinoline-3-carbonitrile

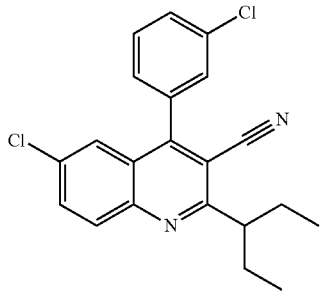 [SMILES: CCC(CC)c1nc2ccc(Cl)cc2c(-c2cccc(Cl)c2)c1C#N]

The title compound was prepared in analogy to example 101 step B from (2-amino-5-chloro-phenyl)-(3-chloro-phenyl)-methanone (prepared as described in example 91 step A) and 4-ethyl-3-oxo-hexanenitrile (prepared as described in example 101 step A). Light yellow oil. MS (ESI): 369.3 (M+H)$^+$.

Step B: 6-Chloro-4-(3-chlorophenyl)-2-(pentan-3-yl)-3-(1H-tetrazol-5-yl)quinoline

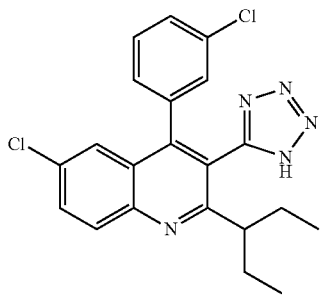 [SMILES: CCC(CC)c1nc2ccc(Cl)cc2c(-c2cccc(Cl)c2)c1-c1nnn[nH]1]

The title compound was prepared in analogy to example 27 step D from 6-chloro-4-(3-chloro-phenyl)-2-(1-ethyl-propyl)-quinoline-3-carbonitrile. Off-white foam. MS (ESI): 412.3 (M+H)$^+$.

Example 110

6-Chloro-2-cyclohexyl-4-phenyl-3-(1H-tetrazol-5-yl)quinoline

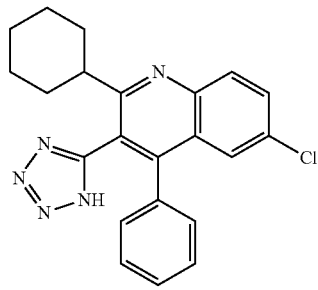 [SMILES: Clc1ccc2nc(C3CCCCC3)c(-c3nnn[nH]3)c(-c3ccccc3)c2c1]

Step A: 3-Cyclohexyl-3-oxo-propionitrile

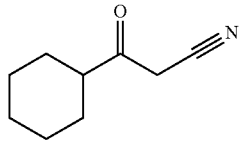 [SMILES: N#CCC(=O)C1CCCCC1]

The title compound was prepared in analogy to example 105 step A from cyclohexanecarboxylic acid methyl ester and acetonitrile. Yellow liquid. MS (ESI): 150.2 (M–H)$^-$.

Step B: 6-Chloro-2-cyclohexyl-4-phenyl-quinoline-3-carbonitrile

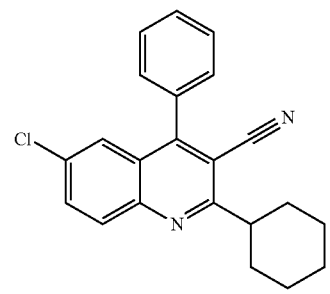 [SMILES: N#Cc1c(C2CCCCC2)nc2ccc(Cl)cc2c1-c1ccccc1]

The title compound was prepared in analogy to example 101 step B from (2-amino-5-chlorophenyl)(phenyl)methanone and 3-cyclohexyl-3-oxo-propionitrile. Colorless solid.

Step C: 6-Chloro-2-cyclohexyl-4-phenyl-3-(1H-tetrazol-5-yl)quinoline

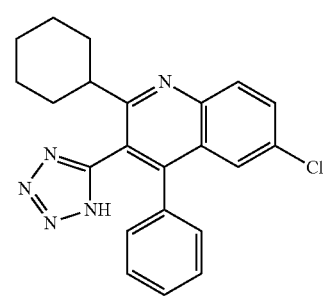 [SMILES: Clc1ccc2nc(C3CCCCC3)c(-c3nnn[nH]3)c(-c3ccccc3)c2c1]

The title compound was prepared in analogy to example 27 step D from 6-chloro-2-cyclohexyl-4-phenyl-quinoline-3-carbonitrile. Off-white solid. MS (ESI): 390.4 (M+H)$^+$.

Example 111

6-Chloro-4-(3-chlorophenyl)-2-cyclobutyl-3-(1H-tetrazol-5-yl)quinoline

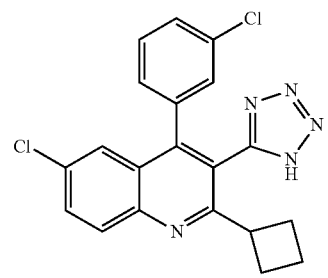 [SMILES: Clc1cccc(-c2c(-c3nnn[nH]3)c(C3CCC3)nc3ccc(Cl)cc23)c1]

Step A: 6-Chloro-4-(3-chloro-phenyl)-2-cyclobutyl-quinoline-3-carbonitrile

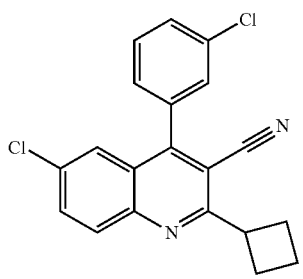 [SMILES: N#Cc1c(C2CCC2)nc2ccc(Cl)cc2c1-c1cccc(Cl)c1]

The title compound was prepared in analogy to example 101 step B from (2-amino-5-chloro-phenyl)-(3-chloro-phenyl)-methanone (prepared as described in example 91 step A) and 3-cyclobutyl-3-oxo-propionitrile (prepared as described in example 104 step A). Yellow foam. MS (ESI): 353.3 (M+H)$^+$.

Step B: 6-Chloro-4-(3-chlorophenyl)-2-cyclobutyl-3-(1H-tetrazol-5-yl)quinoline

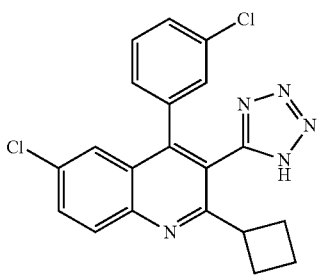 [SMILES: Clc1cccc(-c2c(-c3nnn[nH]3)c(C3CCC3)nc3ccc(Cl)cc23)c1]

The title compound was prepared in analogy to example 27 step D from 6-chloro-4-(3-chloro-phenyl)-2-cyclobutyl-quinoline-3-carbonitrile. Off-white solid. MS (ESI): 396.4 (M+H)$^+$.

Example 112

2-(Pentan-3-yl)-4-phenyl-3-(2H-tetrazol-5-yl)-6-(trifluoromethyl)quinoline

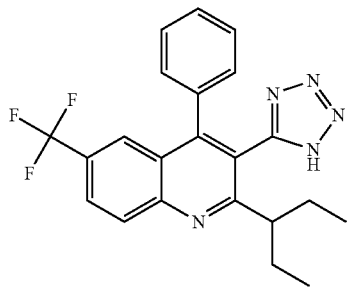 [SMILES: CCC(CC)c1nc2ccc(C(F)(F)F)cc2c(-c2ccccc2)c1-c1nnn[nH]1]

Step A: 2-(1-Ethyl-propyl)-4-phenyl-6-trifluoromethyl-quinoline-3-carbonitrile

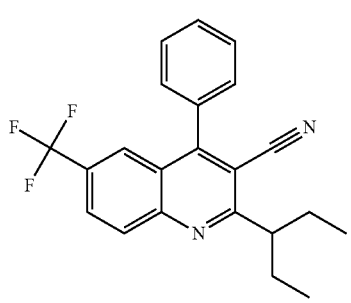 [SMILES: CCC(CC)c1nc2ccc(C(F)(F)F)cc2c(-c2ccccc2)c1C#N]

The title compound was prepared in analogy to example 101 step B from (2-amino-5-trifluoromethyl-phenyl)-phenyl-methanone and 4-ethyl-3-oxo-hexanenitrile (prepared as described in example 101 step A). Off-white solid. MS (ESI): 369.4 (M+H)$^+$.

Step B: 2-(Pentan-3-yl)-4-phenyl-3-(2H-tetrazol-5-yl)-6-(trifluoromethyl)quinoline

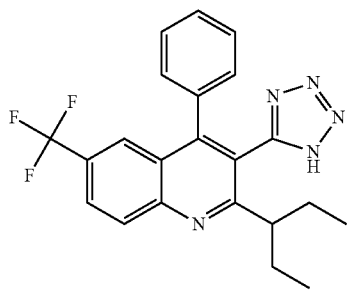 [SMILES: CCC(CC)c1nc2ccc(C(F)(F)F)cc2c(-c2ccccc2)c1-c1nnn[nH]1]

The title compound was prepared in analogy to example 27 step D from 2-(1-ethyl-propyl)-4-phenyl-6-trifluoromethyl-quinoline-3-carbonitrile. White solid. MS (ESI): 412.4 (M+H)$^+$.

Example 113

2-Cyclopentyl-4-phenyl-3-(2H-tetrazol-5-yl)-6-(trifluoromethyl)quinoline

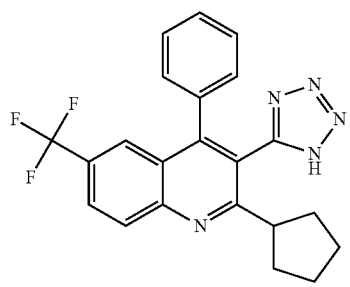 [SMILES: FC(F)(F)c1ccc2nc(C3CCCC3)c(-c3nnn[nH]3)c(-c3ccccc3)c2c1]

Step A: 2-Cyclopentyl-4-phenyl-6-trifluoromethyl-quinoline-3-carbonitrile

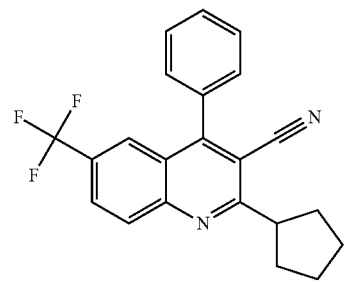 [SMILES: N#Cc1c(C2CCCC2)nc2ccc(C(F)(F)F)cc2c1-c1ccccc1]

The title compound was prepared in analogy to example 101 step B from (2-amino-5-trifluoromethyl-phenyl)-phenyl-methanone and 3-cyclopentyl-3-oxo-propionitrile (prepared as described in example 105 step A). White solid. MS (ESI): 367.4 (M+H)+.

Step B: 2-Cyclopentyl-4-phenyl-3-(2H-tetrazol-5-yl)-6-(trifluoromethyl)quinoline

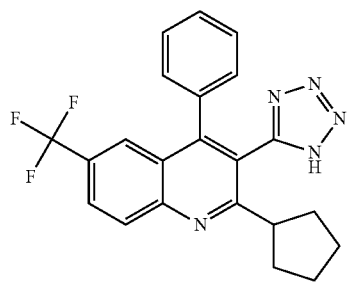 [SMILES: FC(F)(F)c1ccc2nc(C3CCCC3)c(-c3nnn[nH]3)c(-c3ccccc3)c2c1]

The title compound was prepared in analogy to example 27 step D from 2-cyclopentyl-4-phenyl-6-trifluoromethyl-quinoline-3-carbonitrile. White solid. MS (ESI): 410.5 (M+H)+.

Example 114

6-Chloro-2-cyclohexyl-7-fluoro-4-phenyl-3-(2H-tetrazol-5-yl)quinoline

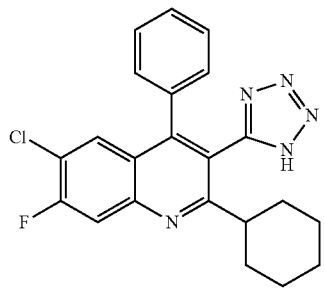 [SMILES: Fc1cc2nc(C3CCCCC3)c(-c3nnn[nH]3)c(-c3ccccc3)c2cc1Cl]

Step A: 6-Chloro-2-cyclohexyl-7-fluoro-4-phenyl-quinoline-3-carbonitrile

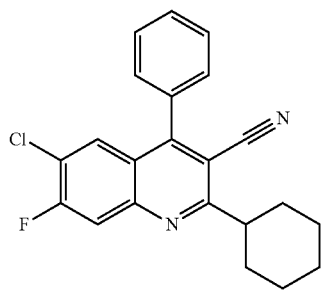 [SMILES: N#Cc1c(C2CCCCC2)nc2cc(F)c(Cl)cc2c1-c1ccccc1]

The title compound was prepared in analogy to example 101 step B from (2-amino-5-chloro-4-fluoro-phenyl)-phenyl-methanone (prepared as described in example 105 step D) and 3-cyclohexyl-3-oxo-propionitrile (prepared as described in example 110 step A). Off-white solid. MS (ESI): 365.4 (M+H)+.

Step B: 6-Chloro-2-cyclohexyl-7-fluoro-4-phenyl-3-(2H-tetrazol-5-yl)quinoline

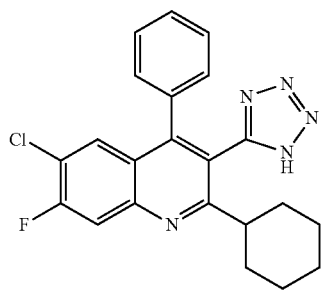 [SMILES: Fc1cc2nc(C3CCCCC3)c(-c3nnn[nH]3)c(-c3ccccc3)c2cc1Cl]

The title compound was prepared in analogy to example 27 step D from 6-chloro-2-cyclohexyl-7-fluoro-4-phenyl-quinoline-3-carbonitrile. White solid. MS (ESI): 408.5 (M+H)+.

Example 115

2-Cyclohexyl-4-phenyl-3-(2H-tetrazol-5-yl)-6-(trifluoromethyl)quinoline

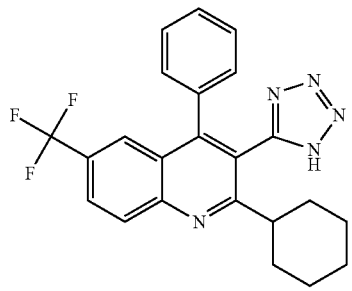 [SMILES: FC(F)(F)c1ccc2nc(C3CCCCC3)c(-c3nnn[nH]3)c(-c3ccccc3)c2c1]

Step A: 2-Cyclohexyl-4-phenyl-6-trifluoromethyl-quinoline-3-carbonitrile

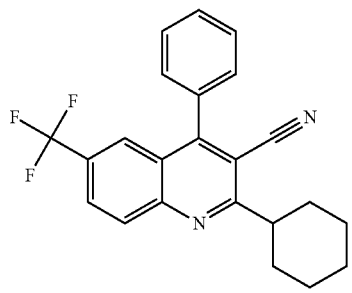 [SMILES: N#Cc1c(C2CCCCC2)nc2ccc(C(F)(F)F)cc2c1-c1ccccc1]

The title compound was prepared in analogy to example 101 step B from (2-amino-5-trifluoromethyl-phenyl)-phenyl-methanone and 3-cyclohexyl-3-oxo-propionitrile (prepared as described in example 110 step A). Off-white solid. MS (ESI): 381.4 (M+H)+.

Step B: 2-Cyclohexyl-4-phenyl-3-(2H-tetrazol-5-yl)-6-(trifluoromethyl)quinoline

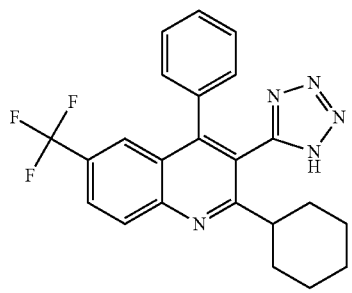 [SMILES: FC(F)(F)c1ccc2nc(C3CCCCC3)c(-c3nnn[nH]3)c(-c3ccccc3)c2c1]

The title compound was prepared in analogy to example 27 step D from 2-cyclohexyl-4-phenyl-6-trifluoromethyl-quinoline-3-carbonitrile. White solid. MS (ESI): 424.5 (M+H)+.

Example 116

6-Chloro-4-(3-chlorophenyl)-2-isopropyl-3-(1H-tetrazol-5-yl)quinoline

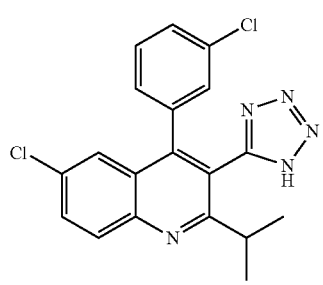 [SMILES: CC(C)c1nc2ccc(Cl)cc2c(-c2cccc(Cl)c2)c1-c1nnn[nH]1]

Step A: 6-Chloro-4-(3-chloro-phenyl)-2-isopropyl-quinoline-3-carbonitrile

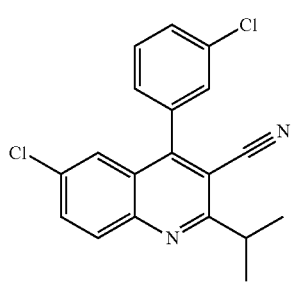 [SMILES: CC(C)c1nc2ccc(Cl)cc2c(-c2cccc(Cl)c2)c1C#N]

The title compound was prepared in analogy to example 101 step B from (2-amino-5-chloro-phenyl)-(3-chloro-phenyl)-methanone (prepared as described in example 91 step A) and 4-methyl-3-oxo-pentanenitrile. Light yellow solid. MS (ESI): 341.3 (M+H)+.

Step B: 6-Chloro-4-(3-chlorophenyl)-2-isopropyl-3-(1H-tetrazol-5-yl)quinoline

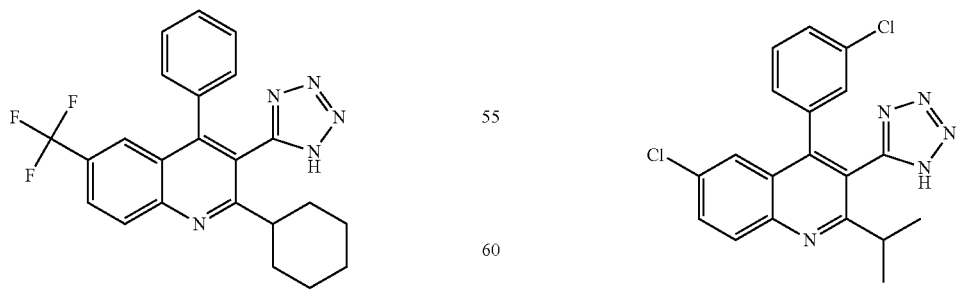

The title compound was prepared in analogy to example 27 step D from 6-chloro-4-(3-chloro-phenyl)-2-isopropyl-quinoline-3-carbonitrile. Colorless solid. MS (ESI): 384.3 (M+H)+.

Example 117

6-Chloro-4-(3-chlorophenyl)-2-cyclopropyl-3-(1H-tetrazol-5-yl)quinoline

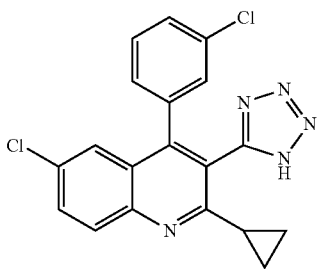 [SMILES: Clc1cccc(-c2c(-c3nnn[nH]3)c(C3CC3)nc3ccc(Cl)cc23)c1]

Step A: 6-Chloro-4-(3-chloro-phenyl)-2-cyclopropyl-quinoline-3-carbonitrile

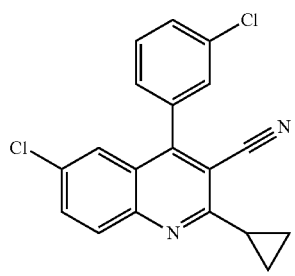 [SMILES: N#Cc1c(C2CC2)nc2ccc(Cl)cc2c1-c1cccc(Cl)c1]

The title compound was prepared in analogy to example 101 step B from (2-amino-5-chloro-phenyl)-(3-chloro-phenyl)-methanone (prepared as described in example 91 step A) and 3-cyclopropyl-3-oxo-propionitrile. Light yellow solid. MS (ESI): 339.3 (M+H)$^+$.

Step B: 6-Chloro-4-(3-chlorophenyl)-2-cyclopropyl-3-(1H-tetrazol-5-yl)quinoline

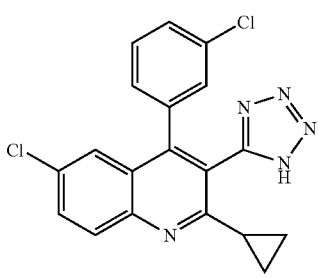

The title compound was prepared in analogy to example 27 step D from 6-chloro-4-(3-chloro-phenyl)-2-cyclopropyl-quinoline-3-carbonitrile. Off-white solid. MS (ESI): 382.3 (M+H)$^+$.

Example 118

6-Chloro-2-(3,3-difluoropiperidin-1-yl)-7-fluoro-4-phenyl-3-(2H-tetrazol-5-yl)quinoline

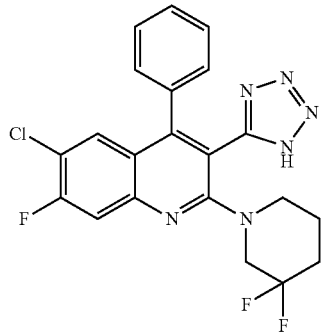 [SMILES: Fc1cc2nc(N3CCCC(F)(F)C3)c(-c3nnn[nH]3)c(-c3ccccc3)c2cc1Cl]

The title compound was prepared in analogy to example 102 step C from 2,6-dichloro-7-fluoro-4-phenyl-3-(1H-tetrazol-5-yl)-quinoline (prepared as described in example 107 step B), 3,3-difluoro-piperidine hydrochloride and triethylamine. Off-white solid. MS (ESI): 445.4 (M+H)$^+$.

Example 119

6-Chloro-2-(3,3-difluoroazetidin-1-yl)-7-fluoro-4-phenyl-3-(2H-tetrazol-5-yl)quinoline

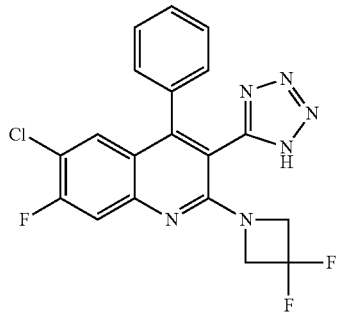 [SMILES: Fc1cc2nc(N3CC(F)(F)C3)c(-c3nnn[nH]3)c(-c3ccccc3)c2cc1Cl]

The title compound was prepared in analogy to example 102 step C from 2,6-dichloro-7-fluoro-4-phenyl-3-(1H-tetrazol-5-yl)-quinoline (prepared as described in example 107 step B), 3,3-difluoroazetidine hydrochloride and triethylamine. Light brown solid. MS (ESI): 417.4 (M+H)$^+$.

Example 120

1-(6-Chloro-4-phenyl-3-(2H-tetrazol-5-yl)quinolin-2-yl)piperidin-2-one

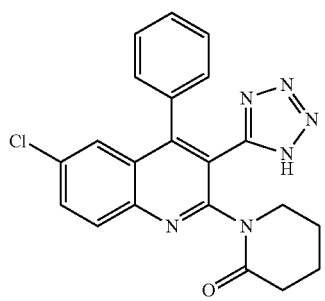 [SMILES: O=C1CCCCN1c1nc2ccc(Cl)cc2c(-c2ccccc2)c1-c1nnn[nH]1]

Step A: 6-Chloro-2-(2-oxo-piperidin-1-yl)-4-phenyl-quinoline-3-carbonitrile

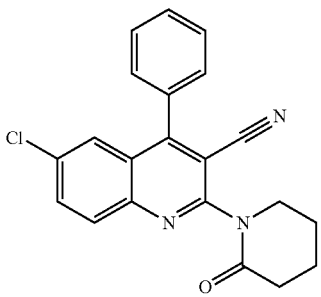 [SMILES: N#Cc1c(N2CCCCC2=O)nc2ccc(Cl)cc2c1-c1ccccc1]

To a suspension of sodium hydride (31.5 mg, 55% in mineral oil, 0.723 mmol) in toluene (4 ml) was added piperidin-2-one (133 mg, 1.34 mmol) followed by 2,6-dichloro-4-phenyl-quinoline-3-carbonitrile (prepared as described in example 27 step B) (200 mg, 0.669 mmol) and the mixture was heated to 100° C. for 6 h. The reaction mixture was cooled to room temperature, diluted with water and extracted twice with DCM and twice with EtOAc. The combined extracts were washed with brine, dried with Na$_2$SO$_4$ and evaporated. The remaining residue was triturated with cold diethyl ether to afford the title compound (157 mg, 62%) as light yellow solid. MS (ESI): 362.3 (M+H)$^+$.

Step B: 1-(6-Chloro-4-phenyl-3-(2H-tetrazol-5-yl)quinolin-2-yl)piperidin-2-one

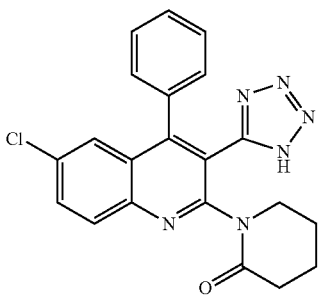 [SMILES: O=C1CCCCN1c1nc2ccc(Cl)cc2c(-c2ccccc2)c1-c1nnn[nH]1]

The title compound was prepared in analogy to example 27 step D from 6-chloro-2-(2-oxo-piperidin-1-yl)-4-phenyl-quinoline-3-carbonitrile. Off-white solid. MS (ESI): 405.4 (M+H)$^+$.

Example 121

7-Methoxy-2-(pentan-3-yl)-4-phenyl-3-(1H-tetrazol-5-yl)quinoline

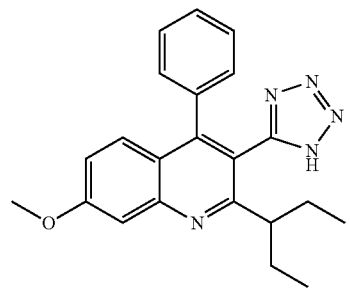 [SMILES: CCC(CC)c1nc2cc(OC)ccc2c(-c2ccccc2)c1-c1nnn[nH]1]

Step A: (2-Amino-4-methoxy-phenyl)-phenyl-methanone

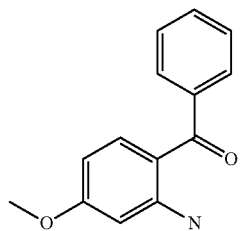 [SMILES: COc1ccc(C(=O)c2ccccc2)c(N)c1]

A solution of phenylmagnesium bromide (6.75 ml, 3M solution in diethyl ether, 20.2 mmol) in diethyl ether (15 ml) was added dropwise to a solution of 2-amino-4-methoxy-benzonitrile (1000 mg, 6.75 mmol) in diethyl ether (20 ml) at 0° C. The resulting suspension was heated to reflux for 2 h. The mixture was then cooled to 0° C. and 2N HCl (40 ml) was added very carefully. After complete addition, the mixture was heated to 55° C. for 2 h. Then 3N NaOH (~20 ml) was added at 0° C. to adjust the pH to 9. The mixture was extracted with EtOAc and the combined organic extracts were washed with brine, dried with Na$_2$SO$_4$ and evaporated. The remaining residue was purified by column chromatography (silica gel, heptane/EtOAc 85:15-70:30) to afford the title compound (1300 mg, 85%) as yellow solid. MS (ESI): 228.4 (M+H)$^+$.

Step B: 2-(1-Ethyl-propyl)-7-methoxy-4-phenyl-quinoline-3-carbonitrile

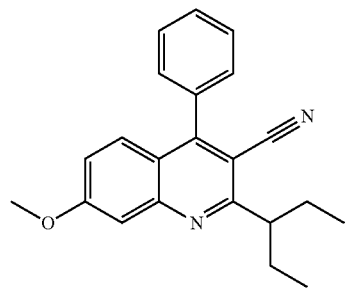 [SMILES: CCC(CC)c1nc2cc(OC)ccc2c(-c2ccccc2)c1C#N]

The title compound was prepared in analogy to example 101 step B from (2-amino-4-methoxy-phenyl)-phenyl-methanone and 4-ethyl-3-oxo-hexanenitrile (prepared as described in example 101 step A). Colorless oil. MS (ESI): 331.4 (M+H)$^+$.

Step C: 7-Methoxy-2-(pentan-3-yl)-4-phenyl-3-(1H-tetrazol-5-yl)quinoline

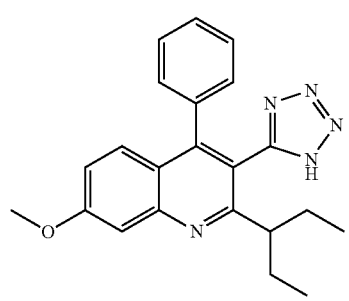 [SMILES: CCC(CC)c1nc2cc(OC)ccc2c(-c2ccccc2)c1-c1nnn[nH]1]

The title compound was prepared in analogy to example 27 step D from 2-(1-ethyl-propyl)-7-methoxy-4-phenyl-quinoline-3-carbonitrile. Light yellow solid. MS (ESI): 374.5 (M+H)+.

Example 122

2-Cyclopentyl-7-methoxy-4-phenyl-3-(1H-tetrazol-5-yl)quinoline

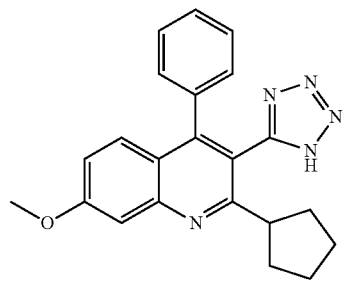 [SMILES: COc1ccc2c(-c3ccccc3)c(-c3nnn[nH]3)c(C3CCCC3)nc2c1]

Step A: 2-Cyclopentyl-7-methoxy-4-phenyl-quinoline-3-carbonitrile

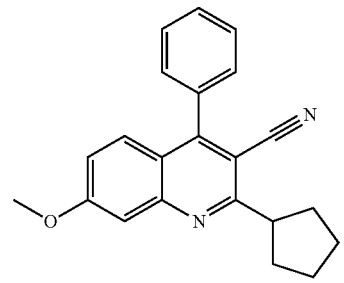 [SMILES: COc1ccc2c(-c3ccccc3)c(C#N)c(C3CCCC3)nc2c1]

The title compound was prepared in analogy to example 101 step B from (2-amino-4-methoxy-phenyl)-phenyl-methanone (prepared as described in example 121 step A) and 3-cyclopentyl-3-oxo-propionitrile (prepared as described in example 105 step A). White solid. MS (ESI): 329.4 (M+H)+.

Step B: 2-Cyclopentyl-7-methoxy-4-phenyl-3-(1H-tetrazol-5-yl)quinoline

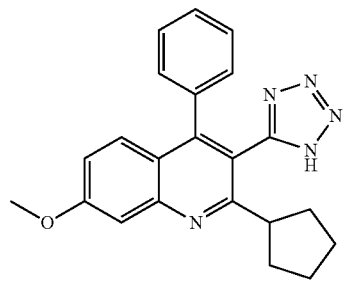 [SMILES: COc1ccc2c(-c3ccccc3)c(-c3nnn[nH]3)c(C3CCCC3)nc2c1]

The title compound was prepared in analogy to example 27 step D from 2-cyclopentyl-7-methoxy-4-phenyl-quinoline-3-carbonitrile. Light yellow solid. MS (ESI): 372.4 (M+H)+.

Example 123

7-Methoxy-4-phenyl-2-(piperidin-1-yl)-3-(2H-tetrazol-5-yl)quinoline

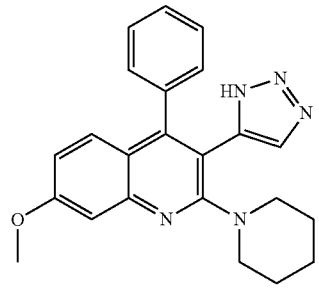 [SMILES: COc1ccc2c(-c3ccccc3)c(-c3cnn[nH]3)c(N3CCCCC3)nc2c1]

Step A: 7-Methoxy-2-oxo-4-phenyl-1,2-dihydro-quinoline-3-carbonitrile

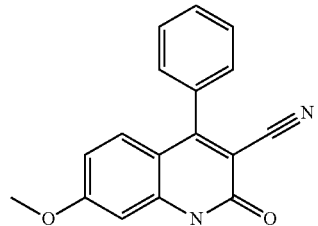 [SMILES: COc1ccc2c(-c3ccccc3)c(C#N)c(=O)[nH]c2c1]

A solution of (2-amino-4-methoxy-phenyl)-phenyl-methanone (400 mg, 1.76 mmol) and ethyl 2-cyanoacetate (239 mg, 225 µl) in toluene (6 ml) containing catalytic amounts of piperidine (15.0 mg, 17.4 µl) was pumped at a flow rate of 0.42 ml min$^{-1}$ (residence time 40 min) through a steel reactor coil (volume=17 ml) that was heated to 300° C. The reaction mixture was evaporated to dryness and the remaining solid was triturated with CH$_2$Cl$_2$/heptane 2:1 for 3 h. The solid was filtrated off and washed two times with CH$_2$Cl$_2$/heptane 1:1 to give the title compound (140 mg, 29%) as off-white solid. MS (ESI): 277.4 (M+H)+.

Step B: 2-Chloro-7-methoxy-4-phenyl-quinoline-3-carbonitrile

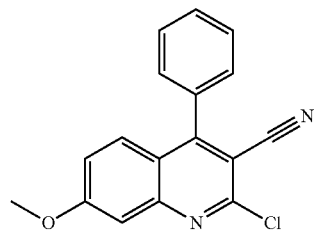 [SMILES: COc1ccc2c(-c3ccccc3)c(C#N)c(Cl)nc2c1]

The title compound was prepared in analogy to example 27 step B from 7-methoxy-2-oxo-4-phenyl-1,2-dihydro-quinoline-3-carbonitrile. White solid. MS (ESI): 295.4 (M+H)⁺.

Step C: 7-Methoxy-4-phenyl-2-piperidin-1-yl-quinoline-3-carbonitrile

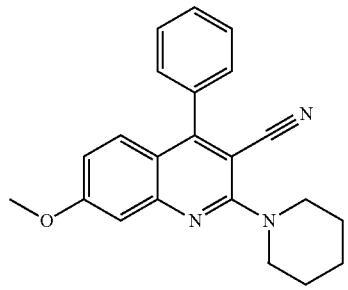 [SMILES: COc1ccc2c(-c3ccccc3)c(C#N)c(N3CCCCC3)nc2c1]

The title compound was prepared in analogy to example 27 step C from 2-chloro-7-methoxy-4-phenyl-quinoline-3-carbonitrile and piperidine. Light yellow solid. MS (ESI): 344.5 (M+H)⁺.

Step D: 7-Methoxy-4-phenyl-2-(piperidin-1-yl)-3-(2H-tetrazol-5-yl)quinolone

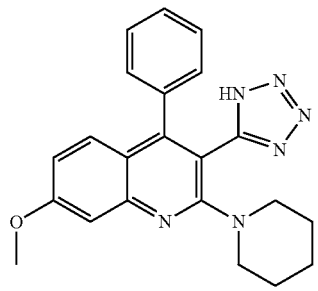 [SMILES: COc1ccc2c(-c3ccccc3)c(-c3nnn[nH]3)c(N3CCCCC3)nc2c1]

The title compound was prepared in analogy to example 27 step D from 7-Methoxy-4-phenyl-2-piperidin-1-yl-quinoline-3-carbonitrile. Off-white solid. MS (ESI): 387.5 (M+H)⁺.

Example 124

1-(6-Chloro-4-phenyl-3-(2H-tetrazol-5-yl)quinolin-2-yl)pyrrolidin-2-one

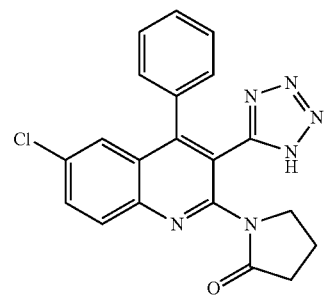 [SMILES: O=C1CCCN1c1nc2ccc(Cl)cc2c(-c2ccccc2)c1-c1nnn[nH]1]

Step A: 6-Chloro-2-(2-oxo-pyrrolidin-1-yl)-4-phenyl-quinoline-3-carbonitrile

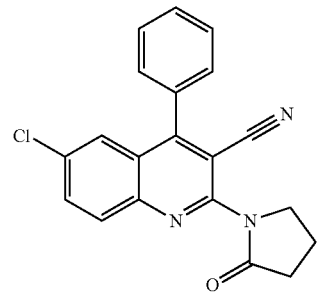 [SMILES: N#Cc1c(N2CCCC2=O)nc2ccc(Cl)cc2c1-c1ccccc1]

The title compound was prepared in analogy to example 120 step A from 2,6-dichloro-4-phenyl-quinoline-3-carbonitrile (prepared as described in example 27 step B) and pyrrolidin-2-one. Yellow solid. MS (ESI): 348.4 (M+H)⁺.

Step B: 1-(6-Chloro-4-phenyl-3-(2H-tetrazol-5-yl)quinolin-2-yl)pyrrolidin-2-one

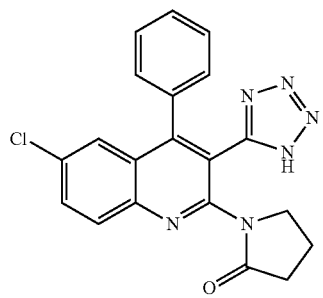 [SMILES: O=C1CCCN1c1nc2ccc(Cl)cc2c(-c2ccccc2)c1-c1nnn[nH]1]

The title compound was prepared in analogy to example 27 step D from 6-chloro-2-(2-oxo-pyrrolidin-1-yl)-4-phenyl-quinoline-3-carbonitrile. Off-white solid. MS (ESI): 391.4 (M+H)⁺.

Example 125

2-Cyclopentyl-4-(2-methylpyridin-4-yl)-3-(2H-tetrazol-5-yl)-6-(trifluoromethyl)quinoline

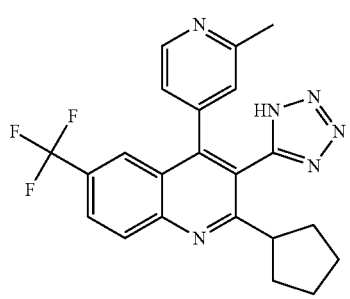 [SMILES: Cc1cc(-c2c(-c3nnn[nH]3)c(C3CCCC3)nc3ccc(C(F)(F)F)cc23)ccn1]

Step A: 6-Trifluoromethyl-1H-benzo[d][1,3]oxazine-2,4-dione

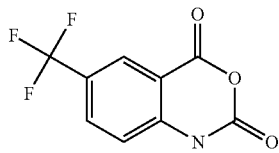 [SMILES: O=c1[nH]c2ccc(C(F)(F)F)cc2c(=O)o1]

To a suspension of 2-amino-5-(trifluoromethyl)benzoic acid (2 g, 9.75 mmol) in acetonitrile (10.0 ml) was added pyridine (2.31 g, 2.37 ml, 29.2 mmol) and a solution of triphosgene (1.74 g, 5.85 mmol) in acetonitrile (10.0 ml) at 50° C. The reaction mixture was stirred for 2 h at 50° C. Then additional triphosgene (579 mg, 1.95 mmol) was added and heating to 50° C. was continued overnight. The solvent was removed and water was added. The mixture was extracted with EtOAc and the combined extracts were washed with water and brine, dried with $Na_2SO_4$ and evaporated. The remaining residue was triturated in dichloromethane for 3 h. The solid was filtrated off and washed two times with dichloromethane to afford the crude title compound (1.53 g, 45%) as off-white solid. MS (ESI): 230.3 (M−H)+.

Step B: 2-Cyclopentyl-4-hydroxy-6-trifluoromethyl-quinoline-3-carbonitrile

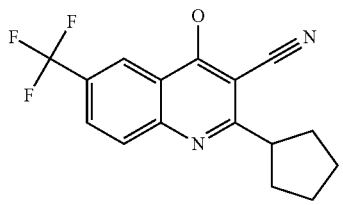 [SMILES: N#Cc1c(C2CCCC2)nc2ccc(C(F)(F)F)cc2c1O]

A mixture of 6-trifluoromethyl-1H-benzo[d][1,3]oxazine-2,4-dione (1.5 g, 4.22 mmol), 3-cyclopentyl-3-oxopropanenitrile (579 mg, 4.22 mmol), triethylamine (5.98 g, 8.23 ml, 59.1 mmol) and DMF (638 µl) was stirred for 72 h at room temperature. 1N HCl was added and the reaction mixture was extracted with EtOAc. The combined extracts were washed with brine, dried with $Na_2SO_4$ and evaporated. The remaining residue was triturated in EtOAc (8 ml) for 3 h. The solid was filtrated off and washed two times with EtOAc to afford the title compound (421 mg, 24%) as white solid. MS (ESI): 307.5 (M+H)+.

Step C: 4-Bromo-2-cyclopentyl-6-trifluoromethyl-quinoline-3-carbonitrile

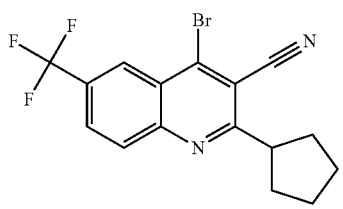 [SMILES: N#Cc1c(C2CCCC2)nc2ccc(C(F)(F)F)cc2c1Br]

To a solution of 2-cyclopentyl-4-hydroxy-6-trifluoromethyl-quinoline-3-carbonitrile (200 mg, 490 µmol) in DMF (2.00 ml) was added phosphorus tribromide (1.47 ml, 1.47 mmol) dropwise at 0° C. The reaction mixture was allowed to reach room temperature and stirring was continued for 20 h. The mixture was concentrated in vacuo and the remaining residue was poured on water. The mixture was extracted with EtOAc and the combined extracts were dried with $Na_2SO_4$ and evaporated. The resulting yellow solid was purified by column chromatography (silica gel, dichloromethane) to afford the title compound (139 mg, 77%) as white solid. MS (ESI): 369.5 (M+H)+.

Step D: 2-Cyclopentyl-4-(2-methyl-pyridin-4-yl)-6-trifluoromethyl-quinoline-3-carbonitrile

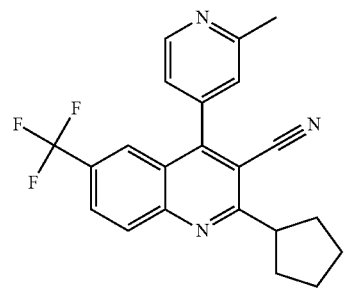 [SMILES: Cc1cc(-c2c(C#N)c(C3CCCC3)nc3ccc(C(F)(F)F)cc23)ccn1]

A suspension of 4-bromo-2-cyclopentyl-6-trifluoromethyl-quinoline-3-carbonitrile (130 mg, 352 µmol), 2-methylpyridine-4-boronic acid pinacol ester (92.6 mg, 423 µmol), cesium carbonate (103 mg, 317 µmol) and tetrakis(triphenylphosphine)palladium (0) (40.7 mg, 35.2 µmol) in DMF (5.2 ml) was heated to 90° C. for 16 h. The reaction mixture was poured on water and extracted with EtOAc. The combined extracts were washed with water and brine, dried with $Na_2SO_4$ and evaporated. The remaining solid was purified by column chromatography (silica gel, n-heptane/EtOAc 4:1) to afford the title compound (20 mg, 15%) as off-white solid. MS (ESI): 382.6 (M+H)+.

Step E: 2-Cyclopentyl-4-(2-methyl-pyridin-4-yl)-3-(2H-tetrazol-5-yl)-6-trifluoromethyl-quinoline

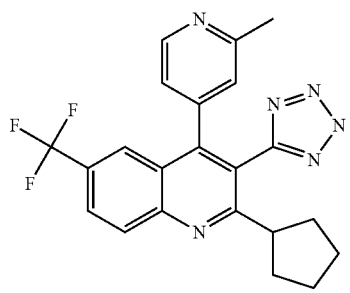 [SMILES: Cc1cc(-c2c(-c3nn[nH]n3)c(C3CCCC3)nc3ccc(C(F)(F)F)cc23)ccn1]

The title compound was prepared in analogy to example 27 step D from 2-cyclopentyl-4-(2-methyl-pyridin-4-yl)-6-trifluoromethyl-quinoline-3-carbonitrile. Off-white solid. MS (ESI): 425.6 (M+H)+.

Example 126

6-Chloro-2-cyclohexyl-4-(2-methyl-pyridin-4-yl)-3-(2H-tetrazol-5-yl)-quinoline

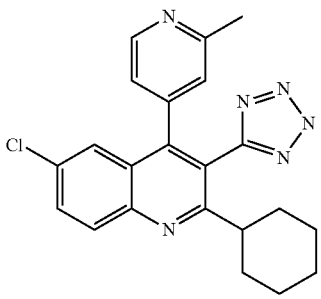 [SMILES: Cc1cc(-c2c(-c3nn[nH]n3)c(C3CCCCC3)nc3ccc(Cl)cc23)ccn1]

Step A: 2-Methyl-isonicotinonitrile

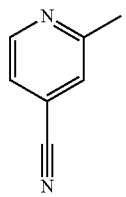

A solution of 2-chloroisonicotinonitrile (2 g, 14.4 mmol), trimethylaluminum (7.94 ml, 15.9 mmol) and tetrakis(triphenylphosphine)palladium (0) (367 mg, 318 µmol) in dioxane (20.0 ml) was heated to reflux for 4 h. The reaction mixture was poured on 1N HCl and extracted two times with EtOAc. The aqueous layer was basified with 3N NaOH and extracted with EtOAc. The combined organic extracts were dried with $Na_2SO_4$ and evaporated. The remaining solid was purified by column chromatography (silica gel, dichloromethane/EtOAc 95:5) to afford the title compound (980 mg, 57%) as white solid. $^1$H NMR (CDCl$_3$, 300 MHz): 2.64 (s, 3H), 7.34 (d, J=5.05 Hz 1H), 7.40 (s, 1H), 8.68 (d, J=5.05 Hz, 1H).

Step B: (2-Amino-5-chloro-phenyl)-(2-methyl-pyridin-4-yl)-methanone

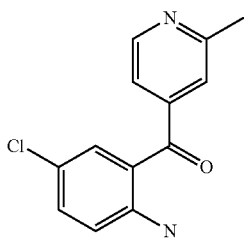 [SMILES: Cc1cc(C(=O)c2cc(Cl)ccc2N)ccn1]

To a solution of boron trichloride (9.35 ml, 9.35 mmol) in 1,1,2,2-tetrachloroethane at 0° C. was added 4-chloroaniline (1.19 g, 9.35 mmol) and the mixture was stirred for 30 minutes. 2-methyl-isonicotinonitrile (920 mg, 7.79 mmol) and aluminum chloride (1.14 g, 8.57 mmol) were added successively and the mixture was heated to reflux for 20 h. The reaction mixture was cooled to 0° C., 2N HCl (20 ml) was added and the mixture was heated to 80° C. for 30 minutes.

The mixture was basified with 3N NaOH and extracted with EtOAc. The combined extracts were washed with brine, dried with $Na_2SO_4$ and evaporated. The remaining solid was purified by column chromatography (silica gel, dichloromethane/EtOAc 95:5 to 100:0) to afford the title compound (390 mg, 20%) as yellow solid. MS (ESI): 247.4 (M+H)$^+$.

Step C: 6-Chloro-2-cyclohexyl-4-(2-methyl-pyridin-4-yl)-quinoline-3-carbonitrile

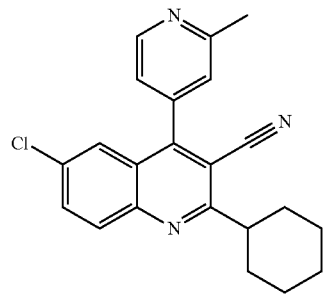 [SMILES: Cc1cc(-c2c(C#N)c(C3CCCCC3)nc3ccc(Cl)cc23)ccn1]

The title compound was prepared in analogy to example 101 step B from (2-amino-5-chloro-phenyl)-(2-methyl-pyridin-4-yl)-methanone and 3-cyclohexyl-3-oxo-propionitrile (prepared as described in example 110 step A). White solid. MS (ESI): 362.5 (M+H)$^+$.

Step D: 6-Chloro-2-cyclohexyl-4-(2-methyl-pyridin-4-yl)-3-(2H-tetrazol-5-yl)-quinoline

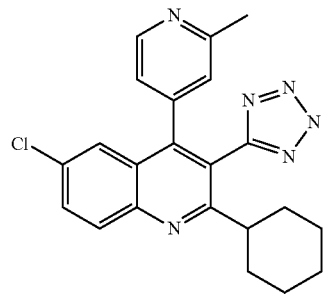 [SMILES: Cc1cc(-c2c(-c3nn[nH]n3)c(C3CCCCC3)nc3ccc(Cl)cc23)ccn1]

The title compound was prepared in analogy to example 27 step D from 6-chloro-2-cyclohexyl-4-(2-methyl-pyridin-4-yl)-quinoline-3-carbonitrile. Off-white solid. MS (ESI): 405.5 (M+H)$^+$.

Example 127

6-Chloro-2-cyclopentyl-4-(2-methyl-pyridin-4-yl)-3-(2H-tetrazol-5-yl)-quinoline

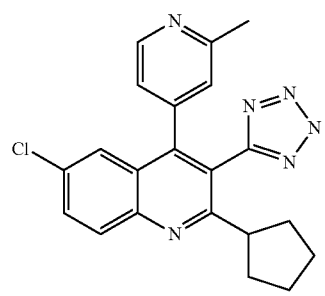 [SMILES: Cc1cc(-c2c(-c3nn[nH]n3)c(C3CCCC3)nc3ccc(Cl)cc23)ccn1]

Step A: 6-Chloro-2-cyclopentyl-4-(2-methyl-pyridin-4-yl)-quinoline-3-carbonitrile

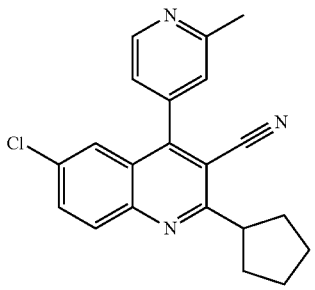 [SMILES: Cc1cc(-c2c(C#N)c(C3CCCC3)nc3ccc(Cl)cc23)ccn1]

The title compound was prepared in analogy to example 101 step B from (2-amino-5-chloro-phenyl)-(2-methyl-pyridin-4-yl)-methanone (prepared in analogy to example 126 step B) and 3-cyclopentyl-3-oxo-propionitrile (prepared as described in example 105 step A). White solid. MS (ESI): 348.4 (M+H)$^+$.

Step B: 6-Chloro-2-cyclopentyl-4-(2-methyl-pyridin-4-yl)-3-(2H-tetrazol-5-yl)-quinoline

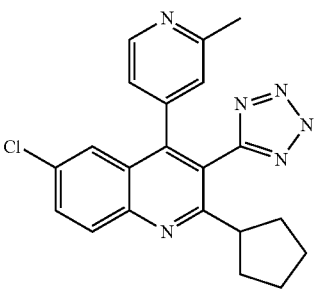 [SMILES: Cc1cc(-c2c(-c3nn[nH]n3)c(C3CCCC3)nc3ccc(Cl)cc23)ccn1]

The title compound was prepared in analogy to example 27 step D from 6-chloro-2-cyclopentyl-4-(2-methyl-pyridin-4-yl)-3-(2H-tetrazol-5-yl)-quinoline. Off white solid. MS (ESI): 391.5 (M+H)$^+$.

Example 128

6-Chloro-4-(2-methylpyridin-4-yl)-2-(pentan-3-yl)-3-(2H-tetrazol-5-yl)quinoline

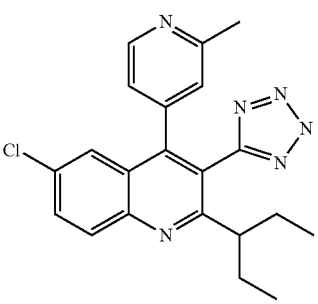 [SMILES: CCC(CC)c1nc2ccc(Cl)cc2c(-c2ccnc(C)c2)c1-c1nn[nH]n1]

Step A: 6-Chloro-2-(1-ethyl-propyl)-4-(2-methylpyridin-4-yl)-quinoline-3-carbonitrile

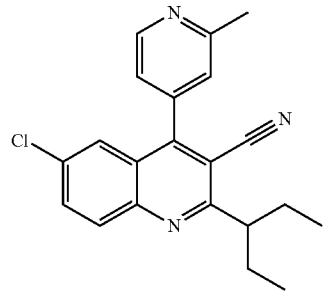 [SMILES: CCC(CC)c1nc2ccc(Cl)cc2c(-c2ccnc(C)c2)c1C#N]

The title compound was prepared in analogy to example 101 step B from (2-amino-5-chloro-phenyl)-(2-methyl-pyridin-4-yl)-methanone (prepared in analogy to example 126 step B) and 4-ethyl-3-oxo-hexanenitrile (prepared as described in example 101 step A). Yellow solid. MS (ESI): 350.5 (M+H)$^+$.

Step B: 6-Chloro-4-(2-methylpyridin-4-yl)-2-(pentan-3-yl)-3-(2H-tetrazol-5-yl)-quinoline

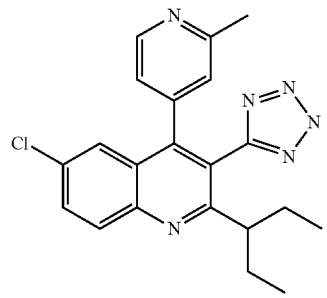 [SMILES: CCC(CC)c1nc2ccc(Cl)cc2c(-c2ccnc(C)c2)c1-c1nn[nH]n1]

The title compound was prepared in analogy to example 27 step D from 6-chloro-2-(1-ethyl-propyl)-4-(2-methylpyridin-4-yl)-quinoline-3-carbonitrile. White solid. MS (ESI): 393.5 (M+H)$^+$.

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound according to formula (I),

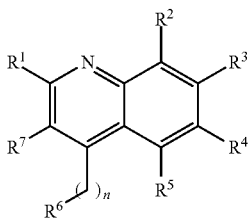

wherein $R^1$ is selected from the group consisting of alkyl, haloalkyl, cycloalkyl, halocycloalkyl, haloalkoxy, cycloalkoxy, halocycloalkoxy, hydroxyalkyl, heterocycloalkyl, substituted heterocycloalkyl, substituted amino, aminocarbonyl or substituted aminocarbonyl, wherein substituted heterocycloalkyl is substituted with one to three substituents independently selected from the group consisting of oxo, halogen, alkyl, cycloalkyl and haloalkyl, and wherein substituted amino and substituted aminocarbonyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl, with the proviso that $R^1$ is not methyl or ethyl;

$R^2$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^3$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^4$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^5$ is selected from the group consisting of hydrogen, halogen, alkyl, haloalkyl, cycloalkyl, halocycloalkyl, alkoxy, haloalkoxy, cycloalkoxy, halocycloalkoxy, nitro, cyano, amino, aminoalkyl, substituted amino and substituted aminoalkyl, wherein substituted amino and substituted aminoalkyl are substituted on the nitrogen atom with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^6$ is selected from the group consisting of phenyl, substituted phenyl, pyridinyl and substituted pyridinyl, wherein substituted phenyl and substituted pyridinyl are substituted with one to three substituent independently selected from the group consisting of alkyl, cycloalkyl, alkylcycloalkyl, cycloalkylalkyl, cycloalkylalkoxy, cycloalkylalkoxyalkyl, cycloalkoxy, cycloalkoxyalkyl, alkylcycloalkylalkyl, halocycloalkyl, halocycloalkylalkyl, halogen, cyano, haloalkyl, hydroxy, hydroxyalkyl, alkoxy, alkoxyalkyl, haloalkoxy, hydroxyalkoxy, alkoxyalkoxy, alkoxyalkoxyalkyl, hydroxyhaloalkyl, amino and substituted amino, wherein substituted amino is substituted with one to two substituents independently selected from the group consisting of alkyl, cycloalkyl, haloalkyl, alkylcycloalkyl, cycloalkylalkyl, alkylcycloalkylalkyl, hydroxyalkyl and alkoxyalkyl;

$R^7$ is selected from the group consisting of —COOH, 3H-[1,3,4]oxadiazol-2-on-5-yl, 3H-[1,3,4]oxadiazole-2-thion-5-yl, 4H-[1,2,4]oxadiazol-5-on-3-yl, 4H-[1,2,4]oxadiazole-5-thion-3-yl, 3H-[1,2,3,5]oxathiadiazole-2-oxide-4-yl, 4H-[1,2,4]thiadiazol-5-on-3-yl, isoxazol-3-ol-5-yl, 5-alkylisoxazol-3-ol-4-yl, 5-cycloalkylisoxazol-3-ol-4-yl, furazan-3-ol-4-yl, 5-alkylsulfonylamino-[1,3,4]oxadiazol-2-yl, 5-cycloalkylsulfonylamino-[1,3,4]oxadiazol-2-yl, 5-alkylsulfonylamino-2H-[1,2,4]triazol-3-yl, 5-cycloalkylsulfonylamino-2H-[1,2,4]triazol-3-yl, 5-alkylisothiazol-3-ol-4-yl, 5-cycloalkylisothiazol-3-ol-4-yl, [1,2,5]thiadiazol-3-ol-4-yl, 1,4-dihydro-tetrazol-5-on-1-yl, 2H-tetrazol-5-ylcarbamoyl, 2H-tetrazole-5-carbonyl, [1,2,4]oxadiazolidine-3,5-dion-2-y, 4H-[1,2,4]oxadiazol-5-on-3-yl, 2,4-dihydro-[1,2,4]triazol-3-on-5-sulfanyl, 4H-[1,2,4]triazole-3-sulfanyl, 4H-[1,2,4]triazole-3-sulfinyl, 4H-[1,2,4]triazole-3-sulfonyl, 4-alkyl-pyrazol-1-ol-5-yl, 4-cycloalkyl-pyrazol-1-ol-5-yl, 4-alkyl-[1,2,3]triazol-1-ol-5-yl, 4-cycloalkyl-[1,2,3]triazol-1-ol-5-yl, 5-alkyl-imidazol-1-ol-2-yl, 5-cycloalkyl-imidazol-1-ol-2-yl, 4-alkyl-imidazol-1-ol-5-yl, 4-cycloalkyl-imidazol-1-ol-5-yl, 4-alkyl-1,1-dioxo-1%-[1,2,5]thiadiazolidin-3-on-5-yl, 4,4-dialkyl-1,1-dioxo-1$\lambda^6$-[1,2,5]thiadiazolidin-3-on-5-yl, 4-cycloalkyl-1,1-dioxo-1$\lambda^6$-[1,2,5]thiadiazolidin-3-on-5-yl, 4,4-dicycloalkyl-1,1-dioxo-1$\lambda^6$1,2,5]thiadiazolidin-3-on-5-yl, thiazolidine-2,4-dion-5-yl, oxazolidine-2,4-dion-5-yl, 3-[1-Hydroxy-meth-(E)-ylidene]-pyrrolidine-2,4-dion-1-yl, 3-[1-Hydroxy-meth-(Z)-ylidene]-pyrrolidine-2,4-dion-1-yl, 5-methyl-4-hydroxy-5H-furan-2-on-3-yl, 5,5-dialkyl-4-hydroxy-5H-furan-2-on-3-yl, 5-cycloalkyl-4-hydroxy-5H-furan-2-on-3-yl, 5,5-dicycloalkyl-4-hydroxy-5H-furan-2-on-3-yl, 3-hydroxy-cyclobut-3-ene-1,2-dion-4-yl and 3-hydroxy-cyclobut-3-ene-1,2-dion-4-amino; and n is zero or 1;
with the proviso that at least one of $R^2$, $R^3$, $R^4$ and $R^5$ is different from hydrogen and that said compound is not 6-methoxy-4-phenyl-2-trifluoromethyl-quinoline-3-carboxylic acid or 4-(3,4-dimethoxy-phenyl)-2-hydroxymethyl-6,7-dimethoxy-quinoline-3-carboxylic acid; or a pharmaceutically acceptable salt thereof.

2. The compound according to claim 1, wherein $R^1$ is selected from the group consisting of alkyl, haloalkyl, cycloalkyl, haloalkoxy, cycloalkoxy, hydroxyalkyl, heterocycloalkyl, substituted heterocycloalkyl, substituted amino and substituted aminocarbonyl, wherein substituted heterocycloalkyl is substituted with one to three substituents independently selected from the group consisting of oxo, halogen and alkyl, and wherein substituted amino and substituted aminocarbonyl are substituted on the nitrogen atom with one to two substituents independently selected from the group consisting of alkyl, hydroxyalkyl and alkoxyalkyl, with the proviso that $R^1$ is not methyl or ethyl.

3. The compound according to claim 1, wherein $R^1$ is selected from the group consisting of heterocycloalkyl, substituted heterocycloalkyl and substituted amino, wherein substituted heterocycloalkyl is substituted with one alkyl, and wherein substituted amino is substituted on the nitrogen atom with two alkyl.

4. The compound according to claim 1, wherein $R^1$ is piperidinyl or methylpyrrolidinyl.

5. The compound according to claim 1, wherein $R^1$ is substituted amino, wherein substituted amino is substituted on the nitrogen atom with one to two alkyl.

6. The compound according to claim 1, wherein $R^2$ is selected from the group consisting of hydrogen, halogen, alkyl, haloalkyl, alkoxy and substituted amino, wherein substituted amino is substituted on the nitrogen atom with one to two alkyl.

7. The compound according to claim 1, wherein $R^2$ is hydrogen or halogen.

8. The compound according to claim 1, wherein $R^3$ is selected from the group consisting of hydrogen, alkoxy and halogen.

9. The compound according to claim 1, wherein $R^3$ is hydrogen.

10. The compound according to claim 1, wherein $R^4$ is selected from the group consisting of hydrogen, halogen, alkyl, nitro and cyano.

11. The compound according to claim 1, wherein $R^4$ is halogen.

12. The compound according to claim 1, wherein $R^5$ is hydrogen.

13. The compound according to claim 1, wherein $R^6$ is phenyl or phenyl substituted with one to three substituent independently selected from the group consisting of alkyl, halogen, haloalkyl, alkoxy and haloalkoxy.

14. The compound according to claim 1, wherein $R^6$ is pyridinyl or pyridinyl substituted with one to three substituents independently selected from the group consisting of alkyl, halogen, haloalkyl, alkoxy and haloalkoxy.

15. The compound according to claim 1, wherein $R^7$ is selected from the group consisting of —COOH, 3H-[1,3,4]oxadiazol-2-on-5-yl, 3H-[1,3,4]oxadiazole-2-thion-5-yl, 4H-[1,2,4]oxadiazol-5-on-3-yl, 4H-[1,2,4]oxadiazole-5-thion-3-yl, 3H-[1,2,3,5]oxathiadiazole-2-oxide-4-yl and 4H-[1,2,4]thiadiazol-5-on-3-yl.

16. The compound according to claim 1, wherein $R^7$ is selected from the group consisting of —COOH, 3H-[1,3,4]oxadiazol-2-on-5-yl and 3H-[1,3,4]oxadiazole-2-thion-5-yl.

17. The compound according to claim 1, wherein $R^7$ is —COOH.

18. The compound according to claim 1, selected from the group consisting of
6-Chloro-2-cyclopropyl-4-phenyl-quinoline-3-carboxylic acid;
6-Chloro-2-isopropyl-4-phenyl-quinoline-3-carboxylic acid;
6-Chloro-4-phenyl-2-piperidin-1-yl-quinoline-3-carboxylic acid;
6-Chloro-4-(3-chloro-phenyl)-2-cyclopropyl-quinoline-3-carboxylic acid;
7-Chloro-4-(2-fluoro-phenyl)-2-isopropyl-quinoline-3-carboxylic acid;
7-Chloro-2-cyclopropyl-4-(2-fluoro-phenyl)-quinoline-3-carboxylic acid;
6-Chloro-2-methylcarbamoyl-4-phenyl-quinoline-3-carboxylic acid;
6-Chloro-4-(2-chloro-benzyl)-2-cyclopropyl-quinoline-3-carboxylic acid;
6-Chloro-4-phenyl-2-(2,2,2-trifluoro-ethoxy)-quinoline-3-carboxylic acid;
6-Chloro-2-morpholin-4-yl-4-phenyl-quinoline-3-carboxylic acid;
6-Chloro-2-cyclopropyl-4-(2-trifluoromethyl-benzyl)-quinoline-3-carboxylic acid;
6-Chloro-4-(2-chloro-benzyl)-2-isopropyl-quinoline-3-carboxylic acid;
and pharmaceutically acceptable salts thereof.

19. The compound according to claim 1, selected from the group consisting of
6-Chloro-2-cyclopentyloxy-4-phenyl-quinoline-3-carboxylic acid;
6-Chloro-2-(4,4-difluoro-piperidin-1-yl)-4-phenyl-quinoline-3-carboxylic acid;
6,7-Dichloro-2-cyclopropyl-4-phenyl-quinoline-3-carboxylic acid;
6-Chloro-2-cyclopropyl-8-methyl-4-phenyl-quinoline-3-carboxylic acid;
6-Chloro-2-isopropyl-4-(3-trifluoromethoxy-phenyl)-quinoline-3-carboxylic acid;
6,8-Dichloro-4-phenyl-2-piperidin-1-yl-quinoline-3-carboxylic acid;
6,8-Dichloro-4-phenyl-2-pyrrolidin-1-yl-quinoline-3-carboxylic acid;
6,8-Dichloro-2-dimethylamino-4-phenyl-quinoline-3-carboxylic acid;
6,8-Dichloro-2-diethylamino-4-phenyl-quinoline-3-carboxylic acid;
6,7-Dichloro-4-phenyl-2-piperidin-1-yl-quinoline-3-carboxylic acid;
6,7-Dichloro-4-phenyl-2-pyrrolidin-1-yl-quinoline-3-carboxylic acid;
6-Chloro-4-(2-chloro-benzyl)-2-dimethylamino-quinoline-3-carboxylic acid;
6-Chloro-2-hydroxymethyl-4-phenyl-quinoline-3-carboxylic acid;
and pharmaceutically acceptable salts thereof.

20. The compound according to claim 1, selected from the group consisting of
6-Chloro-2-isopropyl-4-(3-isopropyl-phenyl)-quinoline-3-carboxylic acid;
6-Chloro-4-(3-ethoxy-phenyl)-2-isopropyl-quinoline-3-carboxylic acid;
6-Chloro-2-isopropyl-4-(3-trifluoromethyl-phenyl)-quinoline-3-carboxylic acid;

6-Chloro-4-phenyl-2-(2,2,2-trifluoro-ethyl)-quinoline-3-carboxylic acid;
6-Chloro-4-(3-chloro-4-fluoro-phenyl)-2-isopropyl-quinoline-3-carboxylic acid;
6-Chloro-2-cyclopentyl-4-phenyl-quinoline-3-carboxylic acid;
6-Chloro-4-phenyl-2-pyrrolidin-1-yl-quinoline-3-carboxylic acid;
6-Chloro-2-(2-oxo-pyrrolidin-1-yl)-4-phenyl-quinoline-3-carboxylic acid;
6-Chloro-2-isopropyl-4-(2-methoxy-benzyl)-quinoline-3-carboxylic acid;
6-Chloro-8-methyl-4-phenyl-2-piperidin-1-yl-quinoline-3-carboxylic acid;
6-Chloro-8-methyl-4-phenyl-2-pyrrolidin-1-yl-quinoline-3-carboxylic acid;
6-Chloro-2-(isopropyl-methyl-amino)-4-phenyl-quinoline-3-carboxylic acid;
8-Ethyl-4-phenyl-2-piperidin-1-yl-quinoline-3-carboxylic acid;
6-Chloro-2-diethylamino-8-methyl-4-phenyl-quinoline-3-carboxylic acid;
6,8-Dichloro-2-(isopropyl-methyl-amino)-4-phenyl-quinoline-3-carboxylic acid;
and pharmaceutically acceptable salts thereof.

21. The compound according to claim 1, selected from the group consisting of
6-Chloro-2-[(2-hydroxy-ethyl)-methyl-amino]-4-phenyl-quinoline-3-carboxylic acid;
8-Ethyl-4-phenyl-2-pyrrolidin-1-yl-quinoline-3-carboxylic acid;
2-Dimethylamino-8-ethyl-4-phenyl-quinoline-3-carboxylic acid;
6-Chloro-2-[(2-methoxy-ethyl)-methyl-amino]-4-phenyl-quinoline-3-carboxylic acid;
6,8-Dichloro-2-(ethyl-methyl-amino)-4-phenyl-quinoline-3-carboxylic acid;
6,8-Dichloro-2-(2-methyl-pyrrolidin-1-yl)-4-phenyl-quinoline-3-carboxylic acid;
6-Chloro-2-diethylamino-4-phenyl-quinoline-3-carboxylic acid;
6-Chloro-4-phenyl-2-(2,2,2-trifluoro-1-methyl-ethoxy)-quinoline-3-carboxylic acid;
6-Ethyl-8-methyl-4-phenyl-2-piperidin-1-yl-quinoline-3-carboxylic acid;
6-Chloro-2-(ethyl-methyl-amino)-8-methyl-4-phenyl-quinoline-3-carboxylic acid;
6-Chloro-8-methyl-2-(2-methyl-pyrrolidin-1-yl)-4-phenyl-quinoline-3-carboxylic acid;
6,8-Dichloro-2-(4,4-difluoro-piperidin-1-yl)-4-phenyl-quinoline-3-carboxylic acid;
6-Chloro-2-((4,4-difluoro-piperidin-1-yl)-8-methyl-4-phenyl-quinoline-3-carboxylic acid;
6-Cyano-8-methyl-4-phenyl-2-piperidin-1-yl-quinoline-3-carboxylic acid;
and pharmaceutically acceptable salts thereof.

22. The compound according to claim 1, selected from the group consisting of
6-Chloro-4-(2-chloro-benzyl)-2-dimethylamino-8-fluoro-quinoline-3-carboxylic acid;
6-Chloro-4-(2-chloro-benzyl)-2,8-bis-dimethylamino-quinoline-3-carboxylic acid;
6-Chloro-4-(2-chloro-benzyl)-8-fluoro-2-methylamino-quinoline-3-carboxylic acid;
6-Ethyl-8-methyl-2-(2-methyl-pyrrolidin-1-yl)-4-phenyl-quinoline-3-carboxylic acid;
6-Ethyl-2-(ethyl-methyl-amino)-8-methyl-4-phenyl-quinoline-3-carboxylic acid;
6-Cyano-2-(ethyl-methyl-amino)-8-methyl-4-phenyl-quinoline-3-carboxylic acid;
6-Chloro-4-(2-chloro-benzyl)-2-(2,2,2-trifluoro-ethyl)-quinoline-3-carboxylic acid;
6-Chloro-2-isopropyl-4-(2-trifluoromethoxy-benzyl)-quinoline-3-carboxylic acid;
6,8-Dichloro-4-(3-chloro-4-fluoro-phenyl)-2-isopropyl-quinoline-3-carboxylic acid;
6,8-Dichloro-4-(3-ethoxy-phenyl)-2-isopropyl-quinoline-3-carboxylic acid;
6,8-Dichloro-2-isopropyl-4-(3-isopropyl-phenyl)-quinoline-3-carboxylic acid;
6-Chloro-4-(2-chloro-benzyl)-2-(ethyl-methyl-amino)-8-fluoro-quinoline-3-carboxylic acid;
and pharmaceutically acceptable salts thereof.

23. The compound according to claim 1, selected from the group consisting of
6-Chloro-4-(2-chloro-benzyl)-2-isopropyl-8-methyl-quinoline-3-carboxylic acid;
5-(6-Chloro-4-phenyl-2-piperidin-1-yl-quinolin-3-yl)-3H-[1,3,4]oxadiazol-2-one;
6-Chloro-2-diethylamino-4-(3-isopropyl-phenyl)-quinoline-3-carboxylic acid;
6-Chloro-4-(3-isopropyl-phenyl)-2-pyrrolidin-1-yl-quinoline-3-carboxylic acid;
6-Chloro-4-(3-isopropyl-phenyl)-2-piperidin-1-yl-quinoline-3-carboxylic acid;
6-Chloro-2-dimethylamino-4-(3-isopropyl-phenyl)-quinoline-3-carboxylic acid;
6-Chloro-4-(3-isopropyl-phenyl)-2-(2,2,2-trifluoro-1-methyl-ethoxy)-quinoline-3-carboxylic acid;
6-Chloro-4-(2-chloro-benzyl)-2-isopropyl-8-methoxy-quinoline-3-carboxylic acid;
6-Chloro-4-(2-chloro-benzyl)-2-dimethylamino-8-trifluoromethyl-quinoline-3-carboxylic acid;
5-(6-Chloro-4-phenyl-2-piperidin-1-yl-quinolin-3-yl)-3H-[1,3,4]oxadiazole-2-thione;
6-Chloro-4-(2-cloro-benzyl)-2-diethylamino-quinoline-3-carboxylic acid;
6-Chloro-4-(2-chloro-benzyl)-2-pyrrolidin-1-yl-quinoline-3-carboxylic acid;
6-Chloro-4-(2-chloro-benzyl)-2-piperidin-1-yl-quinoline-3-carboxylic acid;
6-Chloro-2-piperidin-1-yl-4-(2-trifluoromethyl-benzyl)-quinoline-3-carboxylic acid;
and pharmaceutically acceptable salts thereof.

24. The compound according to claim 1, selected from the group consisting of
6-Chloro-4-(3-chloro-phenyl)-2-diethylamino-quinoline-3-carboxylic acid;
6-Chloro-4-(3-chloro-phenyl)-2-pyrrolidin-1-yl-quinoline-3-carboxylic acid;
6-Chloro-4-(3-chloro-phenyl)-2-piperidin-1-yl-quinoline-3-carboxylic acid;
6-Chloro-4-(3-chloro-phenyl)-2-dimethylamino-quinoline-3-carboxylic acid;
6-Chloro-4-(2-chloro-benzyl)-2-(2,2,2-trifluoro-1-methyl-ethoxy)-quinoline-3-carboxylic acid;
6-Chloro-4-(3-chloro-phenyl)-2-(2,2,2-trifluoro-1-methyl-ethoxy)-quinoline-3-carboxylic acid;
and pharmaceutically acceptable salts thereof.

25. The compound according to claim 1, selected from the group consisting of
6-Chloro-4-phenyl-2-piperidin-1-yl-quinoline-3-carboxylic acid;

6,8-Dichloro-2-(2-methyl-pyrrolidin-1-yl)-4-phenyl-quinoline-3-carboxylic acid;

5-(6-Chloro-4-phenyl-2-piperidin-1-yl-quinolin-3-yl)-3H-[1,3,4]oxadiazole-2-thione;

6-Chloro-4-(2-chloro-benzyl)-2-diethylamino-quinoline-3-carboxylic acid;

6-Chloro-4-(3-chloro-phenyl)-2-diethylamino-quinoline-3-carboxylic acid;

and pharmaceutically acceptable salts thereof.

26. A pharmaceutical composition, comprising a compound according to claim 1, or a pharmaceutically acceptable salt thereof, and a therapeutically inert carrier.

* * * * *